United States Patent [19]
Mandel et al.

[11] Patent Number: 6,110,672
[45] Date of Patent: Aug. 29, 2000

[54] PERIPHERAL NERVOUS SYSTEM SPECIFIC SODIUM CHANNELS, DNA ENCODING THEREFOR, CRYSTALLIZATION, X-RAY DIFFRACTION, COMPUTER MOLECULAR MODELING, RATIONAL DRUG DESIGN, DRUG SCREENING, AND METHODS OF MAKING AND USING THEREOF

[75] Inventors: Gail Mandel, Stony Brook; Simon Halegoua, Belle Terre, both of N.Y.

[73] Assignee: Research Foundation of State University of New York, The SUNY at Stony Brook, Albany, N.Y.

[21] Appl. No.: 08/836,325

[22] PCT Filed: Nov. 2, 1995

[86] PCT No.: PCT/US95/14251

§ 371 Date: May 2, 1997

§ 102(e) Date: May 2, 1997

[87] PCT Pub. No.: WO96/14077

PCT Pub. Date: May 17, 1996

Related U.S. Application Data

[63] Continuation-in-part of application No. 08/482,401, Jun. 7, 1995, abandoned, which is a continuation-in-part of application No. 08/334,029, Nov. 2, 1994, abandoned.

[51] Int. Cl.$^7$ .............................. C12Q 1/68; C07N 21/00; C07N 15/12; C07N 15/85; C07N 15/86

[52] U.S. Cl. ........................ 435/6; 435/91.41; 435/320.1; 435/325; 435/455; 536/23.1; 536/23.2; 536/23.5; 536/24.3; 536/24.31

[58] Field of Search ................................ 424/93.2; 435/6, 435/91.41, 455, 320.1, 325; 514/44; 536/23.1, 23, 23.5, 24.3, 24.31

[56] References Cited

U.S. PATENT DOCUMENTS 5,356,777 10/1994 Hoffman et al. ............................ 435/6

FOREIGN PATENT DOCUMENTS

WO 90/09391 8/1990 WIPO.

OTHER PUBLICATIONS

Beckh, S., "Differential expression of sodium channel mRNAs in rat peripheral nervous system and innervated tissues," *FEBS Lett.* 262:317–322 (1990).

Donahue, L.M. et al., "Segregation of Na$^+$–Channel Gene Expression during Neuronal–Glial Branching of a Rat PNS–Derived Stem Cell Line, RT4–AC," *Devel. Bio.* 147:415–424 (1991).

Ahmed et al., Primary structure, chromosomal localization, and functional expression of a voltage–gated sodium channel from human brain, *Proc. Natl. Acad. Sci. USA* 89(17):8220–4 (Sep., 1992).

Alonso & Llinás, Subthreshold Na$^+$–dependent theta–like rhythmicity in stellate cells of entorhinal cortex layer II, *Nature* 342:175–77 (Nov. 9., 1989).

Auld et al., A Rat Brain Na$^+$ Channel α Subunit with Novel Gating Properties, *Neuron* 1:449–461 (Aug., 1988).

Barres et al., Glial and Neuronal Forms of the Voltage–Dependent Sodium Channel: Characteristics and Cell–Type Distribution, *Neuron* 2:1375–1388 (Apr., 1989).

Bossu & Feltz, Patch–Clamp Study of the Tetrodotoxin–Resistant Sodium Current in Group C Sensory Neurones, *Neurosci. Lett.* 51:241–246 (1984).

Chen et al., Chimeric study of sodium channels from rat skeletal and cardiac muscle, *FEBS Lett.* 309(3):253–7 (Sep., 1992).

Cooperman et al., Modulation of sodium–channel mRNA levels in rat skeletal muscle, *Proc. Natl. Acad. Sci. USA* 84:8721–8725 (Dec., 1987).

Gautron et al., The glial voltage–gated sodium channel: Cell– and tissue–specific mRNA expression, *Proc. Natl. Acad. Sci. USA* 89:7272–6 (Aug., 1992).

George & Brismar, Primary Structure of the Adult Human Skeletal Muscle Voltage–Dependent Sodium Channel, *Ann. Neurol.* 31(2):131–7 (Feb., 1992).

George et al., Genomic Organization of the Human Skeletal Muscle Sodium Channel Gene, *Genomics* 15:598–606 (1993).

George et al., Molecular cloning of an atypical voltage–gated sodium channel expressed in human heart and uterus: Evidence for a distinct gene family, *Proc. Natl. Acad. Sci. USA* 89:4893–4897 (Jun., 1992).

Gilly & Brismar, Properties of Appropriately and Inappropriately Expressed Sodium Channels in Squid Giant Axon and Its Somata, *J. Neurosci.* 9:1362–1374 (Apr., 1989).

Gilly Wm.F., Threshold channels—a novel type of sodium channels in squid giant axon, *Nature* 309:448–450 (May 31, 1984).

Gordon et al., Tissue–specific expression of the R$_I$ and R$_{II}$ sodium channel subtypes, *Proc. Natl. Acad. Sci. USA* 84:8682–8686 (Dec., 1987).

Halegoua et al., Dissecting the Mode of Action of a Neuronal Growth Factor, *Curr. Top. Microbiol. Immunol.* 165:119–170 (1991).

Ikeda et al., Na$^+$ and Ca$^{2+}$ Currents of Acutely Isolated Adult Rat Nodose Ganglion Cells, *J. Neurophysiol.* 55:527–539 (Mar., 1986).

Isom et al., Primary Structure and Functional Expression of the β$_1$ Subunit of the Rat Brain Sodium Channel, *Science* 256:839–42 (May 8, 1992).

(List continued on next page.)

*Primary Examiner*—Scott D. Priebe
*Attorney, Agent, or Firm*—Sterne, Kessler, Goldstein & Fox P.L.L.C.

[57] ABSTRACT

Cloning, expression, viral and delivery vectors and hosts which contain nucleic acid coding for at least one peripheral nervous system specific (PNS) sodium channel peptide (SCP), isolated PNS SCP, and compounds and compositions and methods, are provided, for isolating, crystallizing, x-ray analysing molecular modeling, rational drug designing, selecting, making and using therapeutic or diagnostic agents or ligands having at least one peripheral nervous system specific (PNS) sodium channel (SC) modulating activity.

15 Claims, 35 Drawing Sheets

OTHER PUBLICATIONS

Joho et al., Toxin and kinetic profile of rat brain type III sodium channels expressed in Xenopus oocytes, *Mol. Brain. Res.* 7:105–113(1990).

Jones St. W., Sodium Currents in Dissociated Bull–Frog Sympathetic Neurones, *J. Physiol.* 389:605–627 (1987).

Kallen et al., Primary Structure and Expression of a Sodium Channel Characteristic of Denervated and Immature Rat Skeletal Muscle, *Neuron* 4:233–242 (Feb., 1990).

Kayano et al., Primary structure of rat brain sodium channel III deduced from the cDNA sequence, *FEBS Lett.* 228(1):187–194 (Feb., 1988).

Klugbauer, N. et al., "Structure and Funtional Expression of a New Member of the Tetrodotoxin–Sensitive Voltage –Activated Sodium Channel Family from Human Neuroendocrine Cells," *EMBO J.* 14(16):1084–1090 (Mar. 1995).

Kostyuk et al., Ionic Currents in the Somatic Membrane of Rat Dorsal Root Ganglion Neurons–I. Sodium Currents, *Neuroscience* 6(12):2423–2430 (1981).

Llinás et al., Electrophysiological Properties of In Vitro Purkinje Cell Dendrites in Mammalian Cerebellar Slices, *J. Physiol.* 305:197–213 (1980).

Mandel et al., Selective induction of brain type II $Na^+$ channels by nerve growth factor, *Proc. Natl. Acad. Sci. USA* 85:924–928 (Feb., 1988).

Mandel G., Tissue–Specific Expression of the Voltage–Sensitive Sodium Channel, *J. Membrane Biol.* 125:193–205 (1992).

Maue et al., Neuron–Specific Expression of the Rat Brain Type II Sodium Channel Gene Is Directed by Upstream Regulatory Elements, *Neuron* 4:223–231 (Feb., 1990).

McClatchey et al., The cloning and expression of a sodium channel β1–subunit cDNA from human brain, *Hum. Mol. Genet.* 2(6):745–9 (1993).

Moorman et al., Fast and Slow Gating of Sodium Channels Encoded by a Single mRNA, *Neuron* 4:243–252 (Feb., 1990).

Noda et al., Existence of distinct sodium channel messenger RNAs in rat brain, *Nature* 320:188–192 (Mar. 13, 1986).

Noda et al., Expression of functional sodium channels from cloned cDNA, *Nature* 322:826–828 (Aug. 28, 1986).

Ragsdale et al., Inhibition of $Na^+$ Channels by the Novel Blocker PD85,639, *Mol. Pharmacol.* 43(6):949–54 (1993).

Rogart et al., Molecular cloning of a putative tetrodotoxin–resistant rat heart $Na^+$ channel isoform, *Proc. Natl. Acad. Sci. USA* 86:8170–8174 (Oct., 1989).

Sheng et al., Molecular Cloning and Functional Analysis of the Promoter of Rat Skeletal Muscle Voltage–Sensitive Sodium Channel Subtype 2 (rSkM2): Evidence for Muscle–Specific Nuclear Protein Binding to the Core Promoter, *DNA Cell. Biol.* 13(1):9–23 (1994).

Sills et al., Expression of Diverse $Na^+$ Channel Messenger RNAs in Rat Myocardium, *J. Clin. Invest.* 84:331–336 (Jul., 1989).

Trimmer et al., Regulation of Muscle Sodium Channel Transcripts during Development and in Response to Denervation, *Dev. Biol.* 142:360–367 (1990).

Trimmer et al., Primary Structure and Functional Expression of a Mammalian Skeletal Muscle Sodium Channel, *Neuron* 3:33–49 (Jul., 1989).

Lipkind, G.M. and Fozzard, H.A., "A Structural Model of the Tetrodotoxin and Saxitoxin Binding Site of the $Na^+$ Channel," *Biophys. J.* 66:1–13 (1994).

Marshall, E., "Gene Therapy's Growing Pains," *Science* 269:1050–1055 (1995).

Sansom, M.S.P. and Kerr, I.D., "Influenza virus $M_2$ protein: a molecular modelling study of the ion channel," *Prot. Eng.* 6(1):65–74 (1993).

Wakamatsu, K. et al., "Structure–Activity Relationships of μ–Conotoxin GIIIA: Structure Determination of Active and Inactive Sodium Channel Blocker Peptides by NMR and Simulated Annealing Calculations," *Biochem.* 31:12577–12584 (1992).

Orkin et al., "Report and recommendations of the panel to assess the NIH investment in research on gene therapy", issued by the U.S. National Institutes of Health, Dec. 1995.

Gewirtz et al., "Facilitating oligonucleotide delivery: helping antsense deliver on its promise", Proc. Natl. Acad. Sci. USA, 93: 3161–3163, Apr. 1996.

James, "Towards gene–inhibition therapy: a review of progress and prospects in the field of antiviral antisense nucleic acids and ribozymes", Antiviral Chemistry & Chemotherapy, 2(4): 191–214, 1991.

Christofferson et al., "Ribozymes as human therapeutic agents", J. Med. Chem. 38(12): 2023–2037, Jun. 1995.

Berkner, "Expression of heterologous sequences in adenoviral vectors", Curr. Top. Microbiol. Immunol. 158: 39–67, 1992.

```
        ATAGTTGAAACACTGGTTTGAAAGCTTCATGATCCTGCTTCTCATGATCGTTCTCAGCAGTGGAGCTCTGGCTTTTGAA          75
PN1      I V E H   S W F E   S F I V   L M I L L S S G A L A F E
TYPE 11  I V E H   N W F E   T F I V   L M I L L S S G A L A F E
                                       ——IIS1——

GATATCTATATTGAAAAGAAAAAGACCATTAAGATATTATCTGAGTAGTGCTGACAAGATATTCACTTACATCTTC         150
         D I Y I E K K K T I K I I L E Y A D K I F T Y I F

ATTCTGGAAATGCTTCTAAAATGGTCCCATATGGGTATAAAACATATTTCACTAATGCCTGGTGTTGCTGGAC           225
         I L E M L L K W V A Y G Y K T Y F T N A W C W L D

TTCTTAATTGTTGATGTGTCTCTAGTTACTTTAGTAGCCAACACTCTTGGCTACTCAGACCTTGGCCCCATTAAA         300
         F L I V D V S L V T L V A N T L G Y S D L G P I K

TCTCTACGGACACTGAGGGCCCTAAGACCCTTGTCTAGATTTGAAGGAATGAGGGTAGTGGTCAAC                   375
         S L R T L R A L R P L R A L S R F E G M R V V V N
                                           F E G M R V
                                           ————YJI————

GCACTCATAGGAGCAATCCCTTCCATCATGAACGTGCTTCTCGTGTGCCTTATATTCTGGCTAATATTTAGCATC         450
         A L I G A I P S I M N V L L V C L I F W L I F S I
```

FIG.1A

```
ATGGGAGTCAATCTGTTTGCTGGCAAGTTCTATGAGTGTGTCAACACCACCGATGGTCACGATTTCCTACATCT   525
 M  G  V  N  L  F  A  G  K  F  Y  E  C  V  N  T  T  D  G  S  R  F  P  T  S

CAAGTTGCAAACCGTTCTGAGTGTTTGCCCGATGAACGTTAGTGGAAATGTGCGATGGAAAAACCTGAAAGTA   600
 Q  V  A  N  R  S  E  C  F  A  L  M  N  V  S  G  N  V  R  W  K  N  L  K  V

AACTTCGACAACGTTGGGCTTGGTTACCTGTCGCCTTCAAGTTGCAACATTCAAGGGCTGGATGGATATTATG   675
 N  F  D  N  V  G  L  G  Y  L  S  L  L  Q  V  A  T  F  K  G  W  M  D  I  M

TATGCAGCAGTTGACTCTGTTAATGTAAATGAACAGCCCAAATACCGAATACAGTCTCTACATGTACATTTACTTT   750
 Y  A  A  V  D  S  V  N  V  N  E  Q  P  K  Y  E  Y  S  L  Y  M  Y  I  Y  F
                                                 YOIC

GTCATCTTCATCATCTTCGGCTCATTCTTCACGTTGAACCTGTTCATTGGTGTCATAGATAATTTCAACCAA   825
 V  I  F  I  I  F  G  S  F  F  T  L  N  L  F  I  G  V  I  I  D  N  F  N  Q

CAGAAAAAAGCTTGGAGGTCAAGATATCTTTATGACAGAAGAACAGAAGAAATACTATAATGCAATGAAGAAG   900
 Q  K  K  K  L  G  G  Q  D  I  F  M  T  E  E  Q  K  K  Y  Y  N  A  M  K  K

CTTGGGTCCAAAAAACCACAAAAACCAATTCCAAGGCCAGGGAACAAATTCCAAGGATGTATATTTGAC   969
 L  G  S  K  K  P  Q  K  P  I  P  R  P  G  N  K  F  Q  G  C  I  F  D
```

FIG.1B

SCG DRG
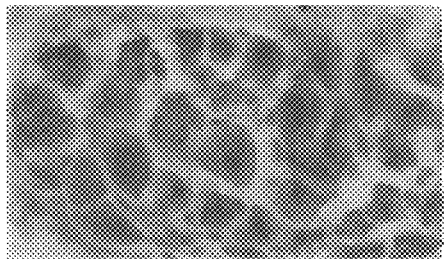 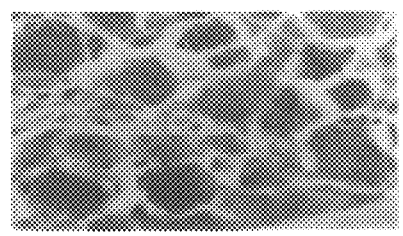
PN1
FIG.4A  FIG.4B
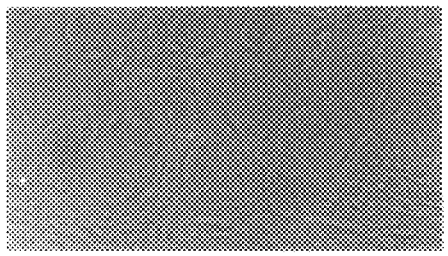 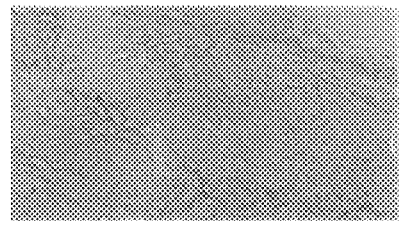
PN1
(unlabeled)
FIG.4C  FIG.4D
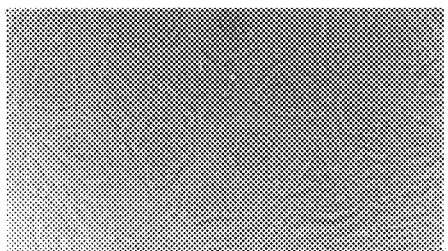 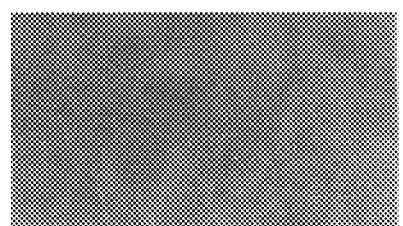
Type II
FIG.4E  FIG.4F

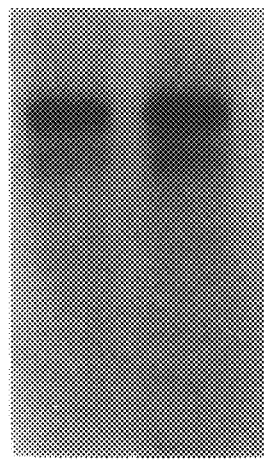 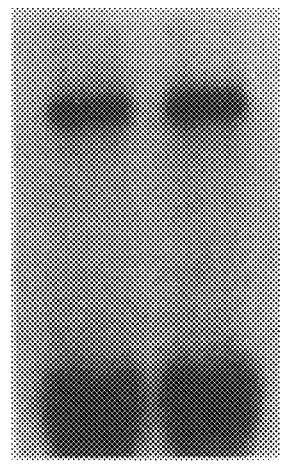 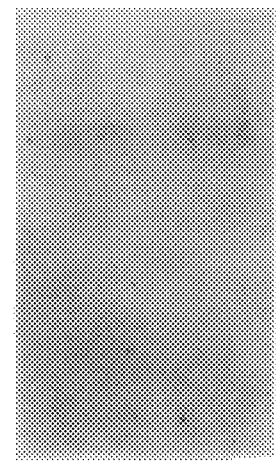
FIG.5

```
               10         20         30         40         50
          1234567890 1234567890 1234567890 1234567890 1234567890
          AGGAACCTTG TGGTCCTGAA CCTGTTTCTG GCTCTTTTGC TGAGTTCCTT   50
           R  N  L   V  V  L  N  L  F  L   A  L  L    S  S  F
          TAGTTCTGAC AATCTTACAG CAATTGAGGA AGACACCGAT GCAAACAACC  100
           S  S  D   N  L  T   A  I  E  E  D  T  D   A  N  N  L
          TCCAGATCGC AGTGGCCAGA ATTAAGAGGG GAATCAATTA CGTGAAACAG  150
            Q  I  A  V  A  R    I  K  R  G   I  N  Y   V  K  Q
          ACCCTGCGTG AATTCATTCT AAAATCATTT TCCAAAAAGC CAAAGGGCTC  200
           T  L  R  E   F  I  L   K  S  F   S  K  K  P  K  G  S
          CAAGGACACA AAACGAACAG CAGATCCCAA CAACAAGAAA GAAAACTATA  250
           K  D  T    K  R  T   A  D  P  N   N  K  K   E  N  Y  I
          TTTCAAACCG TACCCTTGCG GAGATGAGCA AGGATCACAA TTTCCTCAAA  300
           S  N  R   T  L  A   E  M  S  K  D  H  N    F  L  K
          GAAAAGGATA GGATCAGTGG TTATGGCAGC AGTCTAGACA AAAGCTTTAT  350
           E  K  D  R   I  S  G   Y  G  S   S  L  D  K   S  F  M
          GGATGAAAAT GATTACCAGT CCTTTATCCA TAACCCCAGC CTCACAGTGA  400
           D  E  N    D  Y  Q  S   F  I  H   N  P  S   L  T  V  T
          CAGTGCCAAT TGCACCTGGG GAGTCTGATT TGGAGATTAT GAACACAGAA  450
           V  P  I   A  P  G   E  S  D  L   E  I  M   N  T  E
          GAGCTTAGCA GTGACTCAGA CAGTGACTAC AGCAAAGAGA AACGGAACCG  500
           E  L  S  S   D  S  D   S  D  Y   S  K  E  K   R  N  R
          ATCAAGCTCT TCTGAGTGCA GCACTGTTGA CAACCCTCTG CCAGGAGAAG  550
           S  S  S    S  E  C  S   T  V  D   N  P  L   P  G  E  E
          AGGAGGCTGA AGCAGAGCCC GTAAACGCAG ATGAGCCTGA AGCCTGCTTT  600
           E  A  E   A  E  P    V  N  A  D  E  P  E    A  C  F
          ACAGATGGTT GTGTGAGGAG ATTTCCATGC TGCCAAGTTA ATGTAGACTC  650
           T  D  G  C   V  R  R   F  P  C  C  Q  V  N   V  D  S
          TGGGAAAGGG AAAGTTTGGT GGACCATCAG GAAGACGTGC TACAGGATAG  700
           G  K  G   K  V  W  W   T  I  R   K  T  C    Y  R  I  V
          TTGAACACAG CTGGTTTGAA AGCTTCATCG TTCTCATGAT CCTGCTCAGC  750
            E  H  S  W  F  E  S   F  I  V  L  M  I   L  L  S
          AGTGGAGCTC TGGCTTTTGA AGATATCTAT ATTGAAAAGA AAAAGACCAT  800
           S  G  A  L   A  F  E   D  I  Y    I  E  K  K   K  T  I
          TAAGATTATC CTGGAGTATG CTGACAAGAT ATTCACCTAC ATCTTCATTC  850
           K  I  I   L  E  Y  A   D  K  I    F  T  Y   I  F  I  L
          TGGAAATGCT TCTAAAATGG GTCGCATATG GGTATAAAAC ATATTTCACT  900
           E  M  L   L  K  W   V  A  Y  G   Y  K  T   Y  F  T
          AATGCCTGGT GTTGGCTGGA CTTCTTAATT GTTGATGTGT CTCTAGTTAC  950
           N  A  W  C   W  L  D   F  L  I   V  D  V  S   L  V  T
```

FIG. 7A

```
           10         20         30         40         50
   1234567890 1234567890 1234567890 1234567890 1234567890
   TTTAGTAGCC AACACTCTTG GCTACTCAGA CCTTGGCCCC ATTAAATCTC 1000
    L V A     N T L G    Y S D      L G P      I K S L
   TACGGACACT GAGGGCCCTA AGACCCCTAA GAGCCTTGTC TAGATTTGAA 1050
    R T L     R A L      R P L R    A L S      R F E
   GGAATGAGGG TAGTGGTCAA CGCACTCATA GGAGCAATCC CTTCCATCAT 1100
    G M R V   V V N      A L I      G A I P    S I M
   GAACGTGCTT CTCGTGTGCC TTATATTCTG GCTAATATTT AGCATCATGG 1150
    N V L     L V C L    I F W      L I F      S I M G
   GAGTCAATCT GTTTGCTGGC AAGTTCTATG AGTGTGTCAA CACCACCGAT 1200
    V N L     F A G      K F Y E    C V N      T T D
   GGGTCACGAT TTCCTACATC TCAAGTTGCA AACCGTTCTG AGTGTTTTGC 1250
    G S R F   P T S      Q V A      N R S E    C F A
   CCTGATGAAC GTTAGTGGAA ATGTGCGATG GAAAAACCTG AAAGTAAACT 1300
    L M N     V S G N    V R W      K N L      K V N F
   TCGACAACGT TGGGCTTGGT TACCTGTCGC TGCTTCAAGT TGCAACATTC 1350
    D N V     G L G      Y L S L    L Q V      A T F
   AAGGGCTGGA TGGATATTAT GTATGCAGCA GTTGACTCTG TTAATGTAAA 1400
    K G W M   D I M      Y A A      V D S V    N V N
   TGAACAGCCG AAATACGAAT ACAGTCTCTA CATGTACATT TACTTTGTCA 1450
    E Q P     K Y E Y    S L Y      M Y I      Y F V I
   TCTTCATCAT CTTCGGCTCA TTCTTCACGT TGAACCTGTT CATTGGTGTC 1500
    F I I     F G S      F F T L    N L F      I G V
   ATCATAGATA ATTTCAACCA ACAGAAAAAA AAGCTTGGAG GTCAAGATAT 1550
    I I D N   F N Q      Q K K      K L G G    Q D I
   CTTTATGACA GAAGAACAGA AGAAATACTA TAATGCAATG AAGAAGCTTG 1600
    F M T     E E Q K    K Y Y      N A M      K K L G
   GGTCCAAAAA ACCACAAAAA CCAATTCCAA GGCCAGGGAA CAAATTCCAA 1650
    S K K     P Q K      P I P R    P G N      K F Q
   GGATGTATAT TTGACTTAGT GACAAACCAA GCTTTTGATA TCACCATCAT 1700
    G C I F   D L V      T N Q      A F D I    T I M
   GGTTCTTATA TGCCTCAACA TGGTAACCAT GATGGTAGAA AAAGAGGGGC 1750
    V L I     C L N M    V T M      M V E      K E G Q
   AAACTGAGTA CATGGATTAT GTTTTACACT GGATCAACAT GGTCTTCATT 1800
    T E Y     M D Y      V L H W    I N M      V F I
   ATCCTGTTCA CTGGGGAGTG TGTGCTGAAG CTAATCTCCC TCAGACATTA 1850
    I L F T   G E C      V L K      L I S L    R H Y
   CTACTTCACT GTGGGTTGGA ACATTTTGTA TTTTGTGGTA GTGATCCTCT 1900
    Y F T     V G W      N I L Y    F V V      V I L S
```

FIG. 7B

```
              10         20         30         40         50
         1234567890 1234567890 1234567890 1234567890 1234567890
         CCATTGTAGG AATGTTTCTC GCTGAGATGA TAGAGAAGTA TTTCGTGTCC 1950
          I V G      M F L      A E M I    E K Y      F V S
         CCTACCCTGT TCCGAGTCAT CCGCCTGGCC AGGATTGGAC GAATCCTACG 2000
          P T L F    R V I      R L A      R I G R    I L R
         CCTGATCAAA GGCGCCAAGG GGATCCGCAC TCTGCTCTTT GCTTTGATGA 2050
          L I K      G A K G    I R T      L L F      A L M M
         TGTCCCTTCC TGCGCTGTTC AACATCGGCC TCCTGCTTTT CCTGGTCATG 2100
          S L P      A L F      N I G L    L L F      L V M
         TTCATCTACG CCATCTTTGG GATGTCCAAC TTTGCCTACG TTAAAAAGGA 2150
          F I Y A    I F G      M S N      F A Y V    K K E
         GGCTGGAATT AATGACATGT TCAACTTTGA GACTTTTGGC AACAGCATGA 2200
          A G I      N D M F    N F E      T F G      N S M I
         TCTGCTTGTT CCAAATCACC ACCTCTGCCG GCTGGGACGG ACTGCTGGCC 2250
          C L F      Q I T      T S A G    W D G      L L A
         CCCATCCTCA ACAGCGCACC TCCCGACTGT GACCCTAAAA AAGTTCACCC 2300
          P I L N    S A P      P D C      D P K K    V H P
         AGGAAGTTCA GTGGAAGGGG ACTGTGGGAA CCCATCCGTG GGATTTTTT  2350
          G S S      V E G D    C G N      P S V      G I F Y
         ACTTTGTCAG CTACATCATC ATATCCTTCC TGGTGGTGGT GAACATGTAC 2400
          F V S      Y I I      I S F L    V V V      N M Y
         ATCGCTGTCA TCCTGGAGAA CTTCAGCGTC GCCACCGAAG AGAGCACTGA 2450
          I A V I    L E N      F S V      A T E E    S T E
         GCCTCTGAGT GAGGACGACT TTGAGATGTT CTACGAGGTC TGGGAGAAGT 2500
          P L S      E D D F    E M F      Y E V      W E K F
         TCGACCCTGA CGCCACTCAG TTCATAGAGT TCTGCAAGCT CTCTGACTTT 2550
          D P D      A T Q      F I E F    C K L      S D F
         GCAGCTGCCC TGGATCCTCC CCTCCTCATC GCAAAGCCAA ACAAAGTCCA 2600
          A A A L    D P P      L L I      A K P N    K V Q
         GCTCATTGCC ATGGACCTGC CCATGGTGAG TGGAGACCGC ATCCACTGCC 2650
          L I A      M D L P    M V S      G D R      I H C L
         TGGACATCTT GTTTGCTTTT ACAAAGCGGG TCCTGGGTGA GGGTGGAGAG 2700
          D I L      F A F      T K R V    L G E      G G E
         ATGGATTCTC TTCGTTCACA GATGGAAGAA AGGTTCATGT CAGCCAATCC 2750
          M D S L    R S Q      M E E      R F M S    A N P
         TTCTAAAGTG TCCTATGAAC CCATCACGAC CACACTGAAG AGAAAACAAG 2800
          S K V      S Y E P    I T T      T L K      R K Q E
         AGGAGGTGTC CGCGACTATC ATTCAGCGTG CTTACAGACG GTATCGCCTC 2850
          E V S      A T I      I Q R A    Y R R      Y R L
```

FIG. 7C

```
          10         20         30         40         50
 1234567890 1234567890 1234567890 1234567890 1234567890
AGACAACACG TCAAGAATAT ATCGAGTATA TACATAAAAG ATGGAGACAG 2900
 R  Q  H  V   K  N  I   S  S  I   Y  I  K  D   G  D  R
GGATGATGAT TTGCCCAATA AAGAAGATAC AGTTTTTGAT AACGTGAACG 2950
 D  D  D   L  P  N  K   E  D  T   V  F  D   N  V  N  E
AGAACTCAAG TCCGGAAAAG ACAGATGTAA CTGCCTCAAC CATCTCGCCA 3000
  N  S  S   P  E  K   T  D  V  T   A  S  T   I  S  P
CCTTCCTATG ACAGTGTCAC AAAGCCAGAT CAA                   3033
 P  S  Y  D  S  V  T   K  P  D   Q
```

FIG. 7D

```
PN1     T
RNSCPIIR T  MARSVLVPPG  PDSFRFFTRE  SLAAIEQRIA  EEKAKRPKQE  RKDEDDENGP  50
CONSENSUS   ..........  ..........  ..........  ..........  ..........  50

PN1     T
RNSCPIIR T  KPNSDLEAGK  SLPFIYGDIP  PEMVSEPLED  LDPYYINKKT  FIVLNKGKAI  100
CONSENSUS   ..........  ..........  ..........  ..........  ..........  100

PN1     T
RNSCPIIR T  SRFSATSALY  ILTPFNPIRK  LAIKILVHSL  FNVLIMCTIL  TNCVFMTMSN  150
CONSENSUS   ..........  ..........  ..........  ..........  ..........  150

PN1     T
RNSCPIIR T  PPDWTKNVEY  TFTGIYTFES  LIKILARGFC  LEDFTFLRNP  WNWLDFTVIT  200
CONSENSUS   ..........  ..........  ..........  ..........  ..........  200

PN1     T
RNSCPIIR T  FAYVTEFVNL  GNVSALRTFR  VLRALKTISV  IPGLKTIVGA  LIQSVKKLSD  250
CONSENSUS   ..........  ..........  ..........  ..........  ..........  250

PN1     T
RNSCPIIR T  VMILTVFCLS  VFALIGLQLF  MGNLRNKCLQ  WPPDNSTFEI  NITSFFNNSL  300
CONSENSUS   ..........  ..........  ..........  ..........  ..........  300

PN1     T
RNSCPIIR T  DWNGTAFNRT  VNMFNWDEYI  EDKSHFYFLE  GQNDALLCGN  SSDAGQCPEG  350
CONSENSUS   ..........  ..........  ..........  ..........  ..........  350

PN1     T
RNSCPIIR T  YICVKAGRNP  NYGYTSFDTF  SWAFLSLFRL  MTQDFWENLY  QLTLRAAGKT  400
CONSENSUS   ..........  ..........  ..........  ..........  ..........  400

PN1     T
RNSCPIIR T  YMIFFVLVIF  LGSFYLINLI  LAVVAMAYEE  QNQATLEEAE  QKEAEFQQML  450
CONSENSUS   ..........  ..........  ..........  ..........  ..........  450

PN1     T
RNSCPIIR T  EQLKKQQEEA  QAAAAAASAE  SRDFSGAGGI  GVFSESSSVA  SKLSSKSEKE  500
CONSENSUS   ..........  ..........  ..........  ..........  ..........  500
```

FIG. 8A

| | | | | | | |
|---|---|---|---|---|---|---|
| PN1 T | ---------- | ---------- | ---------- | ---------- | ---------- | |
| RNSCPIIR T | LKNRRKKKKQ | KEQAGEEEKE | DAVRKSASED | SIRKKGFQFS | LEGSRLTYEK | 550 |
| CONSENSUS | .......... | .......... | .......... | .......... | .......... | 550 |
| | | | | | | |
| PN1 T | ---------- | ---------- | ---------- | ---------- | ---------- | |
| RNSCPIIR T | RFSSPHQSLL | SIRGSLFSPR | RNSRASLFNF | KGRVKDIGSE | NDFADDEHST | 600 |
| CONSENSUS | .......... | .......... | .......... | .......... | .......... | 600 |
| | | | | | | |
| PN1 T | ---------- | ---------- | ---------- | ---------- | ---------- | |
| RNSCPIIR T | FEDNDSRRDS | LFVPHRHGER | RPSNVSQASR | ASRGIPTLPM | NGKMHSAVDC | 650 |
| CONSENSUS | .......... | .......... | .......... | .......... | .......... | 650 |
| | | | | | | |
| PN1 T | ---------- | ---------- | ---------- | ---------- | ---------- | |
| RNSCPIIR T | NGVVSLVGGP | SALTSPVGQL | LPEGTTTETE | IRKRRSSSYH | VSMDLLEDPS | 700 |
| CONSENSUS | .......... | .......... | .......... | .......... | .......... | 700 |
| | | | | | | |
| PN1 T | ---------- | ---------- | ---------- | ---------- | ---------- | |
| RNSCPIIR T | RQRAMSMASI | LTNTMEELEE | SRQKCPPCWY | KFANMCLIWD | CCKPWLKVKH | 750 |
| CONSENSUS | .......... | .......... | .......... | .......... | .......... | 750 |
| | | | | | | |
| PN1 T | ---------- | ---------- | ---------- | ---------- | ---------- | |
| RNSCPIIR T | VVNLVVMDPF | VDLAITICIV | LNTLFMAMEH | YPMTEQFSSV | LSVGNLVFTG | 800 |
| CONSENSUS | .......... | .......... | .......... | .......... | .......... | 800 |
| | | | | | | |
| PN1 T | ---------- | ---------- | ---------- | ---------- | ---------- | |
| RNSCPIIR T | IFTAEMFLKI | IAMDPYYYFQ | EGWNIFDGFI | VSLSLMELGL | ANVEGLSVLR | 850 |
| CONSENSUS | .......... | .......... | .......... | .......... | .......... | 850 |
| | | | | | | |
| PN1 T | ---------- | ---------- | ---------- | ---------- | ---------- | |
| RNSCPIIR T | SFRLLRVFKL | AKSWPTLNML | IKIIGNSVGA | LGNLTLVLAI | IVFIFAVVGM | 900 |
| CONSENSUS | .......... | .......... | .......... | .......... | .......... | 900 |
| | | | | | | |
| PN1 T | ---------- | ---------- | ---------- | ---------- | -----R---- | 1 |
| RNSCPIIR T | QLFGKSYKEC | VCKISNDCEL | PRWHMHHFFH | SFLIVFRVLC | GEWIETMWDC | 950 |
| CONSENSUS | .......... | .......... | .......... | .......... | ......R... | 950 |
| | | | | | | |
| PN1 T | ---------- | ---------- | NLVVLNLFLA | LLLSSFSSDN | LIAIEEDTDA | 31 |
| RNSCPIIR T | MEVAGQTMCL | TVFMMVMVIG | NLVVLNLFLA | LLLSSFSSDN | LAATDDDNEM | 1000 |
| CONSENSUS | .......... | .......... | NLVVLNLFLA | LLLSSFSSDN | L.A..D.... | 1000 |

FIG.8B

| | | |
|---|---|---|
| PN1 T | NNLQIAVARI KRGINYVKQT LREFILKSES KKPKGSKDTK RTADPNNKKE | 81 |
| RNSCPIIR T | NNLQIAVGRM QKGIDFVKRK IREFICKAEV RKQKALDEIK PLEDLNNKKD | 1050 |
| CONSENSUS | NNLQIAV.R. ..GI..VK.. .REFI.K.E. .K.K.....K ...D.NNKK. | 1050 |
| | | |
| PN1 T | NYISNRTLAE MSKDHNFLKE KD-RISGYGS SLDKSFMDEN DYQSFIHNPS | 130 |
| RNSCPIIR T | SCISNHTTIE IGKDLNYLKD GNGTTSGIGS SVEKYVVDES DYMSFINNPS | 1100 |
| CONSENSUS | ..ISN.T..E ..KD.N.LK. .....SG.GS S..K...DE. DY.SFI.NPS | 1100 |
| | | |
| PN1 T | LTVTVPIAPG ESDLEIMNTE ELSSDSDSDY SKEKRNRSSS SEQSTVDNPL | 180 |
| RNSCPIIR T | LTVTVPIALG ESDFENLNTE EFSSESDMEE SKEKLNATSS SEGSTVDIGA | 1150 |
| CONSENSUS | LTVTVPIA.G ESD.E..NTE E.SS.SD... SKEK.N..SS SE.STVD... | 1150 |
| | | |
| PN1 T | PGE-EEAEAE PVNADEPEAC FTDCVRRFP CCQVNVDSGK GKVWWTIRKT | 229 |
| RNSCPIIR T | PAEGEQPEAE PEESLEPEAC FTEDCVRKFK CCQISIEEGK GKLWWNLRKT | 1200 |
| CONSENSUS | P.E.E..EAE P...EPEAC FT..CVR.F. CCQ......GK GK.WW..RKT | 1200 |
| | | |
| PN1 T | CYRIVEHSWF ESFIVLMILL SSGALAFEDI YIEKKKTIKI ILEYADKIFT | 279 |
| RNSCPIIR T | CYKIVEHNWF EIFIVFMILL SSGALAFEDI YIEQRKTIKT MLEYADKVFT | 1250 |
| CONSENSUS | CY.IVEH.WF E.FIV.MILL SSGALAFEDI YIE..KTTK. .LEYADK.FT | 1250 |
| | | |
| PN1 T | YIFILEMLLK WVAYGYKTYF TNAWCWLDFL IVDVSLVILV ANILGYSCLG | 329 |
| RNSCPIIR T | YIFILEMLLK WVAYGFQMYF TNAWCWLDFL IVDVSLVSLT ANALGYSELG | 1300 |
| CONSENSUS | YIFILEMLLK WVAYG...YF TNAWCWLDFL IVDVSLV.L. AN.LGYS.LG | 1300 |
| | | |
| PN1 T | PIKSLRTLRA LRPLRALSRF EGMRVVVNAL IGAIPSIMNV LLVCLIFWLI | 379 |
| RNSCPIIR T | AIKSLRTLRA LRPLRALSRF EGMRVVVNAL LGAIPSIMNV LLVCLIFWLI | 1350 |
| CONSENSUS | .IKSLRTLRA LRPLRALSRF EGMRVVVNAL .GAIPSIMNV LLVCLIFWLI | 1350 |
| | | |
| PN1 T | FSIMGVNLFA GKFYECINTT DGSRFPTSQV ANRSECFALM NVSGNVRWKN | 429 |
| RNSCPIIR T | FSIMGVNLFA GKFYHCINYT IGEMFDVSVV NNYSECQALI ESNQTARWKN | 1400 |
| CONSENSUS | FSIMGVNLFA GKFY.C.N.T .G.F..S.V .N.SEC.AL. ......RWKN | 1400 |
| | | |
| PN1 T | LKVNFDNVGL GYLSLLQVAT FKGWMDIMYA AVDSVNVNEQ PKYEYSLYMY | 479 |
| RNSCPIIR T | VKVNFDNVGL GYLSLLQVAT FKGWMDIMYA AVDSRNVELQ PKYEDNLYMY | 1450 |
| CONSENSUS | .KVNFDNVGL GYLSLLQVAT FKGWMDIMYA AVDS.NV..Q PKYE...LYMY | 1450 |
| | | |
| PN1 T | IYFVIFIIFG SFFTLNLFIG VIIDNFNQQK KKLGGQDIFM TEEQKKYYNA | 529 |
| RNSCPIIR T | LYFVIFIIFG SFFTLNLFIG VIIDNFNQQK KKFGGQDIFM TEEQKKYYNA | 1500 |
| CONSENSUS | .YFVIFIIFG SFFTLNLFIG VIIDNFNQQK KK.GGQDIFM TEEQKKYYNA | 1500 |

FIG.8C

```
PN1      T       MKKLGSKKPQ KPIPRPGNKF QGCIFDLVTN QAFDIIIMML  ICLNMVTMMV   579
RNSCPIIR T       MKKLGSKKPQ KPIPRPANKF QGMVFDFVTK QVFDISIMIL  ICLNMVTMMV  1550
CONSENSUS        MKKLGSKKPQ KPIPRP.NKF QG..FD.VT. Q.FDI.IM.L  ICLNMVTMMV  1550

PN1      T       EKICQTEYMD YVLHWINMVF IILFTGECVL KLISLRHYYF TMGWNILYFV   629
RNSCPIIR T       ETDDQSQEMT NILYWINLVF IMLFTGECVL KLISLRHYYF TIGWNIFDFV  1600
CONSENSUS        E...Q...M. .L.WIN.VF I.LFTGECVL KLISLRHYYF T.GWNI..FV   1600

PN1      T       VVILSIVGMF LAEMIEKYFV SPTLFRVIRL ARIGRILRLI KGAKGIRTLL   679
RNSCPIIR T       VVILSIVGMF LAELIEKYFV SPTLFRVIRL ARIGRILRLI KGAKGIRTLL  1650
CONSENSUS        VVILSIVGMF LAE.IEKYFV SPTLFRVIRL ARIGRILRLI KGAKGIRTLL  1650

PN1      T       FALMMSLPAL FNIGLLLFLV MFIYAIFGMS NFAYVKKEAG INDMFNFETF   729
RNSCPIIR T       FALMMSLPAL FNIGLLLFLV MFIYAIFGMS NFAYVKREVG IDDMFNFETF  1700
CONSENSUS        FALMMSLPAL FNIGLLLFLV MFIYAIFGMS NFAYVK.E.G I.DMFNFETF  1700

PN1      T       GNSMICLFQI TTSAGWDGLL APILNSAPPD CDPKKVHPGS SVEGDCGNPS   779
RNSCPIIR T       GNSMICLFQI TTSAGWDGLL APILNSGPPD CDPEKDHPGS SVKGDCGNPS  1750
CONSENSUS        GNSMICLFQI TTSAGW.GLL APILNS.PPD CDP.K.HPGS SV.GDCGNPS  1750

PN1      T       VGIFYFVSYI IISFLVVVNM YIAVILENES VATEESIEPL SEDDFEMEYE   829
RNSCPIIR T       VGIFFFVSYI IISFLVVVNM YIAVILENES VATEESAEPL SEDDFEMEYE  1800
CONSENSUS        VGIF.FVSYI IISFLVVVNM YIAVILENES VATEES.EPL SEDDFEMEYE  1800

PN1      T       VWEKEDPDAT QFIEFCKLSD FAAALDPPLL IAKPNKVQLI AMDLPMVSGD   879
RNSCPIIR T       VWEKFDPDAT QFIEFCKLSD FAAALDPPLL IAKPNKVQLI AMDLPMVSGD  1850
CONSENSUS        VWEK.DPDAT QFIEFCKLSD FAAALDPPLL IAKPNKVQLI AMDLPMVSGD  1850

PN1      T       RIHCLDILFA FTKRVLGEGG EMDSLRSQME ERFMSANPSK VSYEPITTTL   929
RNSCPIIR T       RIHCLDILFA FTKRVLGESG EMDALRIQME ERFMASNPSK VSYEPITTTL  1900
CONSENSUS        RIHCLDILFA FTKRVLGE.G EMD.LR.QME EREM..NPSK VSYEPITTTL  1900

PN1      T       KRKQEEVSAT IIQRAYRRYR LRQHVKNISS IYIKDGDRDD D-LPNKEDTV   978
RNSCPIIR T       KRKQEEVSAI VIQRAYRRYL LKQKVKKVSS IYKKDKGKED FGTPIKEDII  1950
CONSENSUS        KRKQEEVSA. .IQRAYRRY. L.Q.VK..SS IY.KD...D. .P.KED..   1950

PN1      T       FDNVNENSSP EKTDVTASTI SPPSYDSVTK FDQ--------- ---------   1011
RNSCPIIR T       TDKLNENSTP EKTDVTPSTT SPPSYDSVTK FEKEKFEKDK SEKEDKGKDI  2000
CONSENSUS        .D..NENS.P EKTDVT.ST. SPPSYDSVTK F......... ..........  2000

PN1      T       -----                                                    1011
RNSCPIIR T       RESKK                                                    2005
CONSENSUS        .....                                                    2005
```

FIG.8D

```
GTCGCCTCAT CCTGAGCAGA CTGGAAACAG ACTCCGTGCA GGCCTCGCCC GCGCTCCAGT    60
TGCGACTGTA GGGTTTTCAT TCCTGCCCAC TGCGCAGACT GGGCTGAGCT AGCCTGGGTA   120
TCCACGATTC GCGACTCGTA GTAACAGGCA CTCTGAGCAA CAGGATTTCA GAGAAAGAAG   180
CAGAGGCAAG AAAGAAGCCT GGGGAGAGAG GAAGACTTTC CTTGGATCAG ACTCCGCAGG   240
TGCACACACC GGGTGGGCAT GATCCGTGGG GCCAGGCCTC TTAGGTAAGG AGTCAAAGGG   300
GAAATAAAAC ATACAGGATG AAAAGATGGC GATGCTGCCT CCTCCAGGAC CTCAGAGTTT   360
CGTTCACTTC ACAAAACAGT CCCTTGCCCT CATTGAACAG CGTATTTCTG AAGAAAAAGC   420
CAAGGAACAC AAAGACGAAA AGAAAGATGA TGAGGAAGAA GGCCCCAAGC CCAGCAGTGA   480
CTTGGAAGCT GGGAAACAGC TCCCCTTCAT CTATGGAGAC ATTCCCCCTG GAATGGTGTC   540
AGAGCCCCTG GAGGACCTGG ACCCATACTA TGCTGACAAA AAAACTTTTA TAGTATTGAA   600
CAAAGGGAAA GCAATCTTCC GTTTCAACGC CACCCCTGCT TTGTACATGC TGTCTCCCTT   660
CAGTCCTCTA AGAAGAATAT CTATTAAGAT CTTAGTGCAC TCCTTATTCA GCATGCTAAT   720
CATGTGCACA ATTCTGACGA ACTGCATATT CATGACCTTG AGCAACCCTC AGAATGGAC    780
CAAAAATGTA GGGTACACTT TTACTGGGAT ATATACTTTT GAATCACTCA TAAAAATCCT   840
TGCAAGAGGC TTTTGCGTGG GAGAATTCAC CTTCCTCCGT GACCCTTGGA ACTGGCTGGA   900
CTTTGTTGTC ATTGTTTTTG CGTATTTAAC AGAATTTGTA AACCTAGGCA ATGTTTCAGC   960
TCTTCGAACT TTCAGAGTCT TGAGAGCTTT GAAAACTATT TCTGTAATCC CAGGACTAAA  1020
GACCATCGTG GGGGCCCTGA TCCAGTCAGT GAAGAAGCTC TCTGACGTCA TGATCCTCAC  1080
TGTGTTCTGT CTCAGTGTGT TTGCACTAAT TGGACTACAG CTGTTTATGG CAACTTGAA   1140
GCATAAATGT TTCAGGAAGG AACTCGAAGA GAATGAAACA TTAGAAAGTA TCATGAATAC  1200
TGCTGAGAGT GAAGAAGAAT TGAAAAAATA TTTTTATTAC TTGGAGGGAT CCAAAGATGC  1260
TCTACTCTGC GGCTTCAGCA CAGATTCAGG GCAGTGTCCA GAAGGCTACA TCTGTGTGAA  1320
GGCTGGCAGA AACCCGGATT ATGGCTACAC GAGCTTTGAC ACATTCAGCT GGGCCTTCTT  1380
GGCCTTGTTT CGGCTAATGA CTCAGGACTA CTGGGAGAAC CTTTACCAAC AGACTCTGCG  1440
TGCTGCTGGC AAAACCTACA TGATTTTCTT TGTCGTGGTT ATTTTCTGG GCTCCTTTTA   1500
CCTGATAAAC TTGATCCTGG CTGTGGTAGC CATGGCGTAT GAGGAACAGA ACCAGGCCAA  1560
CATCGAAGAA GCTAAACAGA AAGAGTTAGA ATTTCAGCAG ATGTTAGACC GACTCAAAAA  1620
GGAGCAGGAA GAAGCTGAGG CGATCGCTGC AGCTGCTGCT GAGTTCACGA GTATAGGGCG  1680
GAGCAGGATC ATGGGACTCT CTGAGAGCTC TTCAGAAACC TCCAGGCTGA GCTCAAAGAG  1740
TGCCAAGGAG AGAAGAAACC GAAGAAAGAA AAAGAAACAG AAGATGTCCA GTGGCGAGGA  1800
AAAGGGTGAC GATGAGAAGC TGTCCAAGTC AGGATCAGAG GAAAGCATCC GAAAGAAAAG  1860
CTTCCATCTC GGTGTGGAAG GCACCACCG GACCCGGGAA AAGAGGCTGT CCACCCCCAA  1920
CCAGTCGCCA CTCAGCATTC GCGGGTCCCT GTTTTCTGCC AGGCGCAGCA GCAGGACGAG  1980
TCTCTTCAGT TTTAAGGGGC GAGGAAGAGA TCTGGGATCT GAGACAGAAT CGCTGATGA   2040
TGAGCATAGC ATTTTTGGAG ACAACGAGAG CAGAAGGGGT TCACTATTCG TACCCCATAG  2100
ACCCCGGGAG CGGCGCAGCA GTAACATCAG TCAGGCCAGT AGGTCCCCGC CAGTGCTACC  2160
GGTGAACGGG AAGATGCACA GTGCAGTGGA CTGCAATGGA GTCGTGTCGC TTGTTGATGG  2220
ACCCTCAGCC CTCATGCTCC CCAATGGACA GCTTCTTCCA GAGGTGATAA TAGATAAGGC  2280
AACTTCCGAC GACAGCGGCA CGACTAATCA GATGCGCAAA AAAAGGCTCT CTAGTTCTTA  2340
CTTCTTGTCT GAGGACATGC TGAATGACCC GCATCTCAGG CAAAGGGCCA TGAGCAGGGC  2400
GAGCATACTG ACCAACACTG TGGAAGAACT TGAAGAATCT AGACAAAAAT GTCACCAGTT  2460
GTTGTACAGA TTTGCTCACA CATTTTTAAT CTGGAATTGC TCTCCATATT GGATAAAATT  2520
```

FIG. 9A

```
CAAAAAGCTC ATCTATTTTA TTGTGATGGA TCCTTTTGTA GATCTTGCAA TTACCATTTG 2580
CATAGTTTTA AACACCTTAT TTATGGCTAT GGAGCACCAC CCAATGACTG AAGAATTCAA 2640
AAATGTCCTT GCAGTGGGGA ACTTGATCTT TACAGGGATC TTCGCAGCTG AAATGGTACT 2700
GAAGTTAATA GCCATGGACC CCTATGAGTA TTTCCAAGTA GGGTGGAATA TTTTTGACAG 2760
CCTAATTGTG ACGCTGAGTT TGATAGAGCT TTTCCTAGCA GATGTGGAAG GATTATCAGT 2820
TCTGCGGTCA TTCAGATTGC TCCGAGTCTT CAAGTTGGCA AAGTCCTGGC CCACACTGAA 2880
CATGCTCATT AAGATCATCG GCAACTCGGT GGGCGCACTG GGCAACCTGA CCCTGGTGCT 2940
GGCCATCATC GTCTTCATTT TTGCCGTGGT CGGCATGCAG CTGTTTGGAA AGAGCTACAA 3000
GGAGTGTGTC TGCAAGATCA ATGTGGACTG CAAGCTGCCG CGCTGGCACA TGAACGACTT 3060
CTTCCACTCC TTCCTCATCG TGTTCCGAGT GCTGTGTGGG GAGTGGATAG AGACCATGTG 3120
GGACTGCATG GAGGTCGCGG GCCAGACCAT GTGCCTTATT GTTTACATGA TGGTCATGGT 3180
GATTGGGAAC CTTGTGGTCC TGAACCTGTT TCTGGCTCTT TTGCTGAGTT CCTTTAGTTC 3240
TGACAATCTT ACAGCAATTG AGGAAGACAC CGATGCAAAC AACCTCCAGA TCGCAGTGGC 3300
CAGAATTAAG AGGGGAATCA ATTACGTGAA ACAGACCCTG CGTGAATTCA TTCTAAAATC 3360
ATTTTCCAAA AAGCCAAAGG CTCCAAGGA CACAAAACGA ACAGCAGATC CAACAACAA 3420
GAAAGAAAAC TATATTTCAA ACCGTACCCT TGCGGAGATG AGCAAGGATC ACAATTTCCT 3480
CAAAGAAAAG GATAGGATCA GTGGTTATGG CAGCAGTCTA GACAAAAGCT TTATGGATGA 3540
AAATGATTAC CAGTCCTTTA TCCATAACCC CAGCCTCACA GTGACAGTGC CAATTGCACC 3600
TGGGGAGTCT GATTTGGAGA TTATGAACAC AGAAGAGCTT AGCAGTGACT CAGACAGTGA 3660
CTACAGCAAA GAGAAACGGA ACCGATCAAG CTCTTCTGAG TGCAGCACTG TTGACAACCC 3720
TCTGCCAGGA GAAGAGGAGG CTGAAGCAGA GCCCGTAAAC GCAGATGAGC CTGAAGCCTG 3780
CTTTACAGAT GGTTGTGTGA GGAGATTTCC ATGCTGCCAA GTTAATGTAG ACTCTGGGAA 3840
AGGGAAAGTT TGGTGGACCA TCAGGAAGAC GTGCTACAGG ATAGTTGAAC ACAGCTGGTT 3900
TGAAAGCTTC ATCGTTCTCA TGATCCTGCT CAGCAGTGGA GCTCTGGCTT TTGAAGATAT 3960
CTATATTGAA AAGAAAAAGA CCATTAAGAT TATCCTGGAG TATGCTGACA AGATATTCAC 4020
CTACATCTTC ATTCTGGAAA TGCTTCTAAA ATGGGTCGCA TATGGGTATA AAACATATTT 4080
CACTAATGCC TGGTGTTGGC TGGACTTCTT AATTGTTGAT GTGTCTCTAG TTACTTTAGT 4140
AGCCAACACT CTTGGCTACT CAGACCTTGG CCCCATTAAA TCTCTACGGA CACTGAGGGC 4200
CCTAAGACCC CTAAGAGCCT TGTCTAGATT TGAAGGAATG AGGGTAGTGG TCAACGCACT 4260
CATAGGAGCA ATCCCTTCCA TCATGAACGT GCTTCTCGTG TGCCTTATAT TCTGGCTAAT 4320
ATTTAGCATC ATGGGAGTCA ATCTGTTTGC TGGCAAGTTC TATGAGTGTG TCAACACCAC 4380
CGATGGGTCA CGATTTCCTA CATCTCAAGT TGCAAACCGT TCTGAGTGTT TTGCCCTGAT 4440
GAACGTTAGT GGAAATGTGC GATGGAAAAA CCTGAAAGTA AACTTCGACA ACGTTGGGCT 4500
TGGTTACCTG TCGCTGCTTC AAGTTGCAAC ATTCAAGGGC TGGATGGATA TTATGTATGC 4560
AGCAGTTGAC TCTGTTAATG TAAATGAACA GCCGAAATAC GAATACAGTC TCTACATGTA 4620
CATTTACTTT GTCATCTTCA TCATCTTCGG CTCATTCTTC ACGTTGAACC TGTTCATTGG 4680
TGTCATCATA GATAATTTCA ACCAACAGAA AAAAAAGCTT GGAGGTCAAG ATATCTTTAT 4740
GACAGAAGAA CAGAAGAAAT ACTATAATGC AATGAAGAAG CTTGGGTCCA AAAAACCACA 4800
AAAACCAATT CCAAGGCCAG GGAACAAATT CCAAGGATGT ATATTTGACT TAGTGACAAA 4860
CCAAGCTTTT GATATCACCA TCATGGTTCT TATATGCCTC AACATGGTAA CCATGATGGT 4920
AGAAAAAGAG GGGCAAACTG AGTACATGGA TTATGTTTTA CACTGGATCA ACATGGTCTT 4980
```

FIG. 9B

```
CATTATCCTG TTCACTGGGG AGTGTGTGCT GAAGCTAATC TCCCTCAGAC ATTACTACTT  5040
CACTGTGGGT TGGAACATTT TGTATTTTGT GGTAGTGATC CTCTCCATTG TAGGAATGTT  5100
TCTCGCTGAG ATGATAGAGA AGTATTTCGT GTCCCCTACC CTGTTCCGAG TCATCCGCCT  5160
GGCCAGGATT GGACGAATCC TACGCCTGAT CAAAGGCGCC AAGGGGATCC GCACTCTGCT  5220
CTTTGCTTTG ATGATGTCCC TTCCTGCGCT GTTCAACATC GGCCTCCTGC TTTTCCTGGT  5280
CATGTTCATC TACGCCATCT TTGGGATGTC CAACTTTGCC TACGTTAAAA AGGAGGCTGG  5340
AATTAATGAC ATGTTCAACT TTGAGACTTT TGGCAACAGC ATGATCTGCT TGTTCCAAAT  5400
CACCACCTCT GCCGGCTGGG ACGGACTGCT GGCCCCATC CTCAACAGCG CACCTCCCGA  5460
CTGTGACCCT AAAAAAGTTC ACCCAGGAAG TTCAGTGGAA GGGGACTGTG GAACCCATC  5520
CGTGGGGATT TTTTACTTTG TCAGCTACAT CATCATATCC TTCCTGGTGG TGGTGAACAT  5580
GTACATCGCT GTCATCCTGG AGAACTTCAG CGTCGCCACC GAAGAGAGCA CTGAGCCTCT  5640
GAGTGAGGAC GACTTTGAGA TGTTCTACGA GGTCTGGGAG AAGTTCGACC CTGACGCCAC  5700
TCAGTTCATA GAGTTCTGCA AGCTCTCTGA CTTTGCAGCT GCCCTGGATC CTCCCCTCCT  5760
CATCGCAAAG CCAAACAAAG TCCAGCTCAT TGCCATGGAC CTGCCCATGG TGAGTGGAGA  5820
CCGCATCCAC TGCCTGGACA TCTTGTTTGC TTTTACAAAG CGGGTCCTGG GTGAGGGTGG  5880
AGAGATGGAT TCTCTTCGTT CACAGATGGA AGAAAGGTTC ATGTCAGCCA ATCCTTCTAA  5940
AGTGTCCTAT GAACCCATCA CGACCACACT GAAGAGAAAA CAAGAGGAGG TGTCCGCGAC  6000
TATCATTCAG CGTGCTTACA GACGGTATCG CCTCAGACAA CACGTCAAGA ATATATCGAG  6060
TATATACATA AAAGATGGAG ACAGGGATGA TGATTTGCCC AATAAAGAAG ATACAGTTTT  6120
TGATAACGTG AACGAGAACT CAAGTCCGGA AAAGACAGAT GTAACTGCCT CAACCATCTC  6180
GCCACCTTCC TATGACAGTG TCACAAAGCC AGATCAAGAG AAATATGAAA CAGACAAAAC  6240
AGAGAAGGAA GACAAAGAGA AAGATGAAAG CAGGAAATAG AGCTTTGGTT TTGATACACT  6300
GTTGACAGCC TGTGAAGGTT GACTCACTCG TGTTAGTAAG ACTCTTTTAC GGAGGTCTAT  6360
CCAAACTCTT TTATCAAAAA TTCTCAAGGC AGCACAGCCA TTAGCTCTGA TCCAACGAGG  6420
CAGAGGGCAG CATTTACACA TGGCTATGTT TT                                6452
```

FIG. 9C

```
MAMLPPPGPQ SFVHFTKQSL ALIEQRISEE KAKEHKDEKK DDEEEGPKPS   50
SDLEAGKQLP FIYGDIPPGM VSEPLEDLDP YYADKKTFIV LNKGKAIFRF  100
NATPALYMLS PFSPLRRISI KILVHSLFSM LIMCTILTNC IFMTLSNPPE  150
WTKNVGYTFT GIYTFESLIK ILARGFCVGE FTFLRDPWNW LDFVVIVFAY  200
LTEFVNLGNV SALRTFRVLR ALKTISVIPG LKTIVGALIQ SVKKLSDVMI  250
LTVFCLSVFA LIGLQLFMGN LKHKCFRKEL EENETLESIM NTAESEEELK  300
KYFYYLEGSK DALLCGFSTD SGQCPEGYIC VKAGRNPDYG YTSFDTFSWA  350
FLALFRLMTQ DYWENLYQQT LRAAGKTYMI FFVVVIFLGS FYLINLILAV  400
VAMAYEEQNQ ANIEEAKQKE LEFQQMLDRL KKEQEEAEAI AAAAAEFTSI  450
GRSRIMGLSE SSSETSRLSS KSAKERRNRR KKKKQKMSSG EEKGDDEKLS  500
KSGSEESIRK KSFHLGVEGH HRTREKRLST PNQSPLSIRG SLFSARRSSR  550
TSLFSFKGRG RDLGSETEFA DDEHSIFGDN ESRRGSLFVP HRPRERRSSN  600
ISQASRSPPV LPVNGKMHSA VDCNGVVSLV DGPSALMLPN GQLLPEVIID  650
KATSDDSGTT NQMRKKRLSS SYFLSEDMLN DPHLRQRAMS RASILTNTVE  700
ELEESRQKCH QLLYRFAHTF LIWNCSPYWI KFKKLIYFIV MDPFVDLAIT  750
ICIVLNTLFM AMEHHPMTEE FKNVLAVGNL IFTGIFAAEM VLKLIAMDPY  800
EYFQVGWNIF DSLIVTLSLI ELFLADVEGL SVLRSFRLLR VFKLAKSWPT  850
LNMLIKIIGN SVGALGNLTL VLAIIVFIFA VVGMQLFGKS YKECVCKINV  900
DCKLPRWHMN DFFHSFLIVF RVLCGEWIET MWDCMEVAGQ TMCLIVYMMV  950
MVIGNLVVLN LFLALLLSSF SSDNLTAIEE DTDANNLQIA VARIKRGINY 1000
VKQTLREFIL KSFSKKPKGS KDTKRTADPN NKKENYISNR TLAEMSKDHN 1050
FLKEKDRISG YGSSLDKSFM DENDYQSFIH NPSLTVTVPI APGESDLEIM 1100
NTEELSSDSD SDYSKEKRNR SSSSECSTVD NPLPGEEEAE AEPVNADEPE 1150
ACFTDGCVRR FPCCQVNVDS GKGKVWWTIR KTCYRIVEHS WFESFIVLMI 1200
LLSSGALAFE DIYIEKKKTI KIILEYADKI FTYIFILEML LKWVAYGYKT 1250
YFTNAWCWLD FLIVDVSLVT LVANTLGYSD LGPIKSLRTL RALRPLRALS 1300
RFEGMRVVVN ALIGAIPSIM NVLLVCLIFW LIFSIMGVNL FAGKFYECVN 1350
TTDGSRFPTS QVANRSECFA LMNVSGNVRW KNLKVNFDNV GLGYLSLLQV 1400
ATFKGWMDIM YAAVDSVNVN EQPKYEYSLY MYIYFVIFII FGSFFTLNLF 1450
IGVIIDNFNQ QKKKLGGQDI FMTEEQKKYY NAMKKLGSKK PQKPIPRPGN 1500
KFQGCIFDLV TNQAFDITIM VLICLNMVTM MVEKEGQTEY MDYVLHWINM 1550
VFIILFTGEC VLKLISLRHY YFTVGWNILY FVVVILSIVG MFLAEMIEKY 1600
FVSPTLFRVI RLARIGRILR LIKGAKGIRT LLFALMMSLP ALFNIGLLLF 1650
LVMFIYAIFG MSNFAYVKKE AGINDMFNFE TFGNSMICLF QITTSAGWDG 1700
LLAPILNSAP PDCDPKKVHP GSSVEGDCGN PSVGIFYFVS YIIISFLVVV 1750
NMYIAVILEN FSVATEESTE PLSEDDFEMF YEVWEKFDPD ATQFIEFCKL 1800
SDFAAALDPP LLIAKPNKVQ LIAMDLPMVS GDRIHCLDIL FAFTKRVLGE 1850
GGEMDSLRSQ MEERFMSANP SKVSYEPITT TLKRKQEEVS ATIIQRAYRR 1900
YRLRQHVKNI SSIYIKDGDR DDDLPNKEDT VFDNVNENSS PEKTDVTAST 1950
ISPPSYDSVT KPDQEKYETD KTEKEDKEKD ESRK                 1984
```

FIG. 10

```
RATPN1    1  MAMLPPPGPQSFVHFTKQSLALIEQRISEEKAKEHKDEKKDDEEEGPKPSSDLEAGKQLPF
             ||||||||||||||||||||||||||  |  ||  |  |||||  ||  ||||||||||||
HUMPN1A      MAMLPPPGPQSFVHFTKQSLALIEQRIXEXKXKEXKXEKKDDXEEXPKPSSDLEAGKQLPF
HUMPN1B      MAMLPPPGPQSFVHFTKQSLALIEQRIAERKSKEPKEEKKDDDEEAPKPSSDLEAGKQLPF
HUMPN1C      MAMLPPPGPQSFVHFTKQSLALIEQRI-E-K-KE-K-EKKDD-EE-PKPSSDLEAGKQLPF
HUMPN1D      MAMLPPPGPQSFVHFTKQSLALIEQRISEEKAKEHKDEKKDDEEEGPKPSSDLEAGKQLPF

RATPN1   62  IYGDIPPGMVSEPLEDLDPYYADKKTFIVLNKGKAIFRFNATPALYMLSPFSPLRRISIKI
             |||||||||||||||||||||||||||||||||  |||||||||||||||||||||||||
HUMPN1A      IYGDIPPGMVSEPLEDLDPYYADKKTFIVLNKGKXIFRFNATPALYMLSPFSPLRRISIKI
HUMPN1B      IYGDIPPGMVSEPLEDLDPYYADKKTFIVLNKGKAIFRFNATPALYMLSPFSPLRRISIKI
HUMPN1C      IYGDIPPGMVSEPLEDLDPYYADKKTFIVLNKGK-IFRFNATPALYMLSPFSPLRRISIKI
HUMPN1D      IYGDIPPGMVSEPLEDLDPYYADKKTFIVLNKGKAIFRFNATPALYMLSPFSPLRRISIKI

RATPN1  123  LVHSLFSMLIMCTILTNCIFMTLSNPPEWTKNVGYTFTGIYTFESLIKILARGFCVGEFTF
             |||||||||||||||||||||||||   |||  |||||  ||||||||||||||||||||
HUMPN1A      LVHSLFSMLIMCTILTNCIFMTXXNPPXWTKNVXYTFTGIYTFESLXKILARGFCVGEFTF
HUMPN1B      LVHSLFSMLIMCTILTNCIFMTMNNPPDWTKNVGYTFTGIYTFESLVKILARGFCVGEFTF
HUMPN1C      LVHSLFSMLIMCTILTNCIFMT--NPP-WTKNV-YTFTGIYTFESL-KILARGFCVGEFTF
HUMPN1D      LVHSLFSMLIMCTILTNCIFMTLSNPPEWTKNVGYTFTGIYTFESLIKILARGFCVGEFTF

RATPN1  184  LRDPWNWLDFVVIVFAYLTEFVNLGNVSALRTFRVLRALKTISVIPGLKTIVGALIQSVKK
             ||||||||||||||||||||||||||||||||||||||||||||||||||||||||||||
HUMPN1A      LRDPWNWLDFVVIVFAYLTEFVNLGNVSALRTFRVLRALKTISVIPGLKTIVGALIQSVKK
HUMPN1B      LRDPWNWLDFVVIVFAYLTEFVNLGNVSALRTFRVLRALKTISVIPGLKTIVGALIQSVKK
HUMPN1C      LRDPWNWLDFVVIVFAYLTEFVNLGNVSALRTFRVLRALKTISVIPGLKTIVGALIQSVKK
HUMPN1D      LRDPWNWLDFVVIVFAYLTEFVNLGNVSALRTFRVLRALKTISVIPGLKTIVGALIQSVKK

RATPN1  245  LSDVMILTVFCLSVFALIGLQLFMGNLKHKCFRKELEENETLESIMNTAESEEELKKYFYY
             |||||||||||||||||||||||||||||||||  || |||||||||| |||    |||||
HUMPN1A      LSDVMILTVFCLSVFALIGLQLFMGNLKHKCFRXXLEXNETLESIMNTXESEEXXXKYFYY
HUMPN1B      LSDVMILTVFCLSVFALIGLQLFMGNLKHKCFRNSLENNETLESIMNTLESEEDFRKYFYY
HUMPN1C      LSDVMILTVFCLSVFALIGLQLFMGNLKHKCFR--LE-NETLESIMNT-ESEE---KYFYY
HUMPN1D      LSDVMILTVFCLSVFALIGLQLFMGNLKHKCFRKELEENETLESIMNTAESEEELKKYFYY

RATPN1  306  LEGSKDALLCGFSTDSGQCPEGYICVKAGRNPDYGYTSFDTFSWAFLALFRLMTQDYWENL
             ||||||||||||||||||||||||   ||| |||||||||||||||||||||||||||||
HUMPN1A      LEGSKDALLCGFSTDSGQCPEGYXCVKXGRNPDYGYTSFDTFSWAFLALFRLMTQDYWENL
HUMPN1B      LEGSKDALLCGFSTDSGQCPEGYTCVKIGRNPDYGYTSFDTFSWAFLALFRLMTQDYWENL
HUMPN1C      LEGSKDALLCGFSTDSGQCPEGY-CVK-GRNPDYGYTSFDTFSWAFLALFRLMTQDYWENL
HUMPN1D      LEGSKDALLCGFSTDSGQCPEGYICVKAGRNPDYGYTSFDTFSWAFLALFRLMTQDYWENL
```

FIG. 11A

```
RATPN1   367  YQQTLRAAGKTYMIFFVVVIFLGSFYLINLILAVVAMAYEEQNQANIEEAKQKELEFQQML
              ||||||||||||||||||||||||||||||||||||||||||||||||||||||||||||
HUMPN1A       YQQTLRAAGKTYMIFFVVVIFLGSFYLINLILAVVAMAYEEQNQANIEEAKQKELEFQQML
HUMPN1B       YQQTLRAAGKTYMIFFVVVIFLGSFYLINLILAVVAMAYEEQNQANIEEAKQKELEFQQML
HUMPN1C       YQQTLRAAGKTYMIFFVVVIFLGSFYLINLILAVVAMAYEEQNQANIEEAKQKELEFQQML
HUMPN1D       YQQTLRAAGKTYMIFFVVVIFLGSFYLINLILAVVAMAYEEQNQANIEEAKQKELEFQQML

RATPN1   428  DRLKKEQEEAEAIAAAAAEFTSIGRSRIMGLSESSSETSRLSSKSAKERRNRRKKKKQK M
              |||||||||||||||||||    |||   ||||||||||||| |||||||||||||| ||
HUMPN1A       DRLKKEQEEAEAIAAAAAEXTSIXRSRIMGLSESSSETSXLSSKSAKERRNRRKKKXQKKX
HUMPN1B       DRLKKEQEEAEAIAAAAAEYTSIRRSRIMGLSESSSETSKLSSKSAKERRNRRKKKNQKKL
HUMPN1C       DRLKKEQEEAEAIAAAAAE-TSI-RSRIMGLSESSSETS-LSSKSAKERRNRRKKK-QK-
HUMPN1D       DRLKKEQEEAEAIAAAAAEFTSIGRSRIMGLSESSSETSRLSSKSAKERRNRRKKKKQKXM

RATPN1   488  SSGEEKGDDEKLSKSGSEESIRKKSFHLGVEGHHRTREKRLSTPNQSPLSIRGSLFSARRS
              |||||||| ||||||  || |||  |||||||||   |||||||||||||||||||||||
HUMPN1A       SSGEEKGDXEKLSKSXSEXSIRXKSFHLGVEGHXRXXEKRLSTPNQSPLSIRGSLFSARRS
HUMPN1B       SSGEEKGDAEKLSKSESEDSIRRKSFHLGVEGHRRAHEKRLSTPNQSPLSIRGSLFSARRS
HUMPN1C       SSGEEKGD-EKLSKS-SE-SIR-KSFHLGVEGH-R--EKRLSTPNQSPLSIRGSLFSARRS
HUMPN1D       SSGEEKGDDEKLSKSGSEESIRKKSFHLGVEGHHRTREKRLSTPNQSPLSIRGSLFSARRS

RATPN1   549  SRTSLFSFKGRGRDLGSETEFADDEHSIFGDNESRRGSLFVPHRPRERRSSNISQASRSPP
              |||||||||||||| ||||||||||||||||||||||||||||| |||||||||||||||
HUMPN1A       SRTSLFSFKGRGRDIGSETEFADDEHSIFGDNESRRGSLFVPHRPQERRSSNISQASRSPP
HUMPN1B       SRTSLFSFKGRGRDLGSETEFADDEHSIFGDNESRRGSLFVPHRPRERRSSNISQASRSPP
HUMPN1C       SRTSLFSFKGRGRD-GSETEFADDEHSIFGDNESRRGSLFVPHRP-ERRSSNISQASRSPP
HUMPN1D       SRTSLFSFKGRGRDLGSETEFADDEHSIFGDNESRRGSLFVPHRPRERRSSNISQASRSPP

RATPN1   610  VLPVNGKMHSAVDCNGVVSLVDGPSALMLPNGQLLPEVIIDKATSDDSGTTNQMRKKRLSS
              |||||||||||||||||||||||| ||||||||||||           |||||  ||| |
HUMPN1A       XLPVNGKMHSAVDCNGVVSLVDGXSALMLPNGQLLPEXXXXXXXXXXXXGTTNQXXKKRXXS
HUMPN1B       MLPVNGKMHSAVDCNGVVSLVDGRSALMLPNGQLLPE----------GTTNQIHKKRRCS
HUMPN1C       -LPVNGKMHSAVDCNGVVSLVDG-SALMLPNGQLLPE----------GTTNQ--KKR--S
HUMPN1D       VLPVNGKMHSAVDCNGVVSLVDGPSALMLPNGQLLPEVIIDKATSDDSGTTNQMRKKRLSS

RATPN1   671  SYFLSEDMLNDPHLRQRAMSRASILTNTVEELEESRQKCHQLLYRFAHTFLIWNCSPYWIK
              || |||||||||  |||||||||||||||||||||||||    |||||  |||||||||||
HUMPN1A       SYXLSEDMLNDPXLRQRAMSRASILTNTVEELEESRQKCXXXXYRFAHXFLIWNCSPYWIK
HUMPN1B       SYLLSEDMLNDPNLRQRAMSRASILTNTVEELEESRQKCPPWWYRFAHKFLIWNCSPYWIK
HUMPN1C       SY-LSEDMLNDP-LRQRAMSRASILTNTVEELEESRQKC----YRFAH-FLIWNCSPYWIK
HUMPN1D       SYFLSEDMLNDPHLRQRAMSRASILTNTVEELEESRQKCHQLLYRFAHTFLIWNCSPYWIK
```

FIG. 11B

```
RATPN1    732  FKKLIYFIVMDPFVDLAITICIVLNTLFMAMEHHPMTEEFKNVLAVGNLIFTGIFAAEMVL
               |||  ||||||||||||||||||||||||||||||||||||||||  || ||||||||||
HUMPN1A        FKKXIYFIVMDPFVDLAITICIVLNTLFMAMEHHPMTEEFKNVLAXGNLXFTGIFAAEMVL
HUMPN1B        FKKCIYFIVMDPFVDLAITICIVLNTLFMAMEHHPMTEEFKNVLAIGNLVFTGIFAAEMVL
HUMPN1C        FKK-IYFIVMDPFVDLAITICIVLNTLFMAMEHHPMTEEFKNVLA-GNL-FTGIFAAEMVL
HUMPN1D        FKKLIYFIVMDPFVDLAITICIVLNTLFMAMEHHPMTEEFKNVLAVGNLIFTGIFAAEMVL

RATPN1    793  KLIAMDPYEYFQVGWNIFDSLIVTLSLIELFLADVEGLSVLRSFRLLRVFKLAKSWPTLNM
               |||||||||||||||||||||||||| |||||||||||||||||||||||||||||||||
HUMPN1A        KLIAMDPYEYFQVGWNIFDSLIVTLSLXELFLADVEGLSVLRSFRLLRVFKLAKSWPTLNM
HUMPN1B        KLIAMDPYEYFQVGWNIFDSLIVTLSLVELFLADVEGLSVLRSFRLLRVFKLAKSWPTLNM
HUMPN1C        KLIAMDPYEYFQVGWNIFDSLIVTLSL-ELFLADVEGLSVLRSFRLLRVFKLAKSWPTLNM
HUMPN1D        KLIAMDPYEYFQVGWNIFDSLIVTLSLIELFLADVEGLSVLRSFRLLRVFKLAKSWPTLNM

RATPN1    854  LIKIIGNSVGALGNLTLVLAIIVFIFAVVGMQLFGKSYKECVCKINVDCKLPRWHMNDFFH
               |||||||||||||||||||||||||||||||||||||||||||||| || ||||||||||
HUMPN1A        LIKIIGNSVGALGNLTLVLAIIVFIFAVVGMQLFGKSYKECVCKINXDCXLPRWHMNDFFH
HUMPN1B        LIKIIGNSVGALGNLTLVLAIIVFIFAVVGMQLFGKSYKECVCKINDDCTLPRWHMNDFFH
HUMPN1C        LIKIIGNSVGALGNLTLVLAIIVFIFAVVGMQLFGKSYKECVCKIN-DC-LPRWHMNDFFH
HUMPN1D        LIKIIGNSVGALGNLTLVLAIIVFIFAVVGMQLFGKSYKECVCKINVDCKLPRWHMNDFFH

RATPN1    915  SFLIVFRVLCGEWIETMWDCMEVAGQTMCLIVYMMVMVIGNLVVLNLFLALLLSSFSSDNL
               ||||||||||||||||||||||||||| ||||||||||||||||||||||||||||||||
HUMPN1A        SFLIVFRVLCGEWIETMWDCMEVAGQXMCLIVYMMVMVIGNLVVLNLFLALLLSSFSSDNL
HUMPN1B        SFLIVFRVLCGEWIETMWDCMEVAGQAMCLIVYMMVMVIGNLVVLNLFLALLLSSFSSDNL
HUMPN1C        SFLIVFRVLCGEWIETMWDCMEVAGQ-MCLIVYMMVMVIGNLVVLNLFLALLLSSFSSDNL
HUMPN1D        SFLIVFRVLCGEWIETMWDCMEVAGQTMCLIVYMMVMVIGNLVVLNLFLALLLSSFSSDNL

RATPN1    976  TAIEEDTDANNLQIAVARIKRGINYVKQTLREFILKSFSKKPKGSKDTKRTADPNNKKENY
               ||||||  |||||||||  |||  |||||||||||||| ||||||| |        ||||||
HUMPN1A        TAIEEDXDANNLQIAVXRIKXGINYVKQTLREFILKXFSKKPKXSXXXXXXXDXNXKKENY
HUMPN1B        TAIEEDPDANNLQIAVTRIKKGINYVKQTLREFILKAFSKKPKISREIRQAEDLNTKKENY
HUMPN1C        TAIEED-DANNLQIAV-RIK-GINYVKQTLREFILK-FSKKPK-S-------D-N-KKENY
HUMPN1D        TAIEEDTDANNLQIAVARIKRGINYVKQTLREFILKSFSKKPKGSKDTKRTADPNNKKENY

RATPN1   1037  ISNRTLAEMSKDHNFLKEKDRISGYGSSLDKSFMDENDYQSFIHNPSLTVTVPIAPGESDL
               |||  ||||||| ||||||||  |||  ||  ||    |  ||||||||||||||||||||
HUMPN1A        ISNXTLAEMSKXHNFLKEKDXISGXGSSXDKXXMXXXDXQSFIHNPSLTVTVPIAPGESDL
HUMPN1B        ISNMTLAEMSKGHNFLKEKDKISGFGSSVDKHLMEDSDGQSFIHNPSLTVTVPIAPGESDL
HUMPN1C        ISN-TLAEMSK-HNFLKEKD-ISG-GSS-DK--M---D-QSFIHNPSLTVTVPIAPGESDL
HUMPN1D        ISNRTLAEMSKDHNFLKEKDRISGYGSSLDKSFMDENDYQSFIHNPSLTVTVPIAPGESDL
```

FIG. 11C

```
RATPN1  1098  EIMNTEELSSDSDSDYSKEKRNRSSSSECSTVDNPLPGE EEAEAEPVNADEPEACFTDGC
              | || |||||||||| |||   ||||||||||||||||||| |||||||| | |||||||||||
HUMPN1A        EXMNXEELSSDSDSXYSKXXXNRSSSSECSTVDNPLPGEGEEAEAEPXNXDEPEACFTDGC
HUMPN1B        ENMNAEELSSDSDSEYSKVRLNRSSSSECSTVDNPLPGEGEEAEAEPMNSDEPEACFTDGC
HUMPN1C        E-MN-EELSSDSDS-YSK---NRSSSSECSTVDNPLPGEGEEAEAEP-N-DEPEACFTDGC
HUMPN1D        EIMNTEELSSDSDSDYSKEKRNRSSSSECSTVDNPLPGEXEEAEAEPVNADEPEACFTDGC

RATPN1  1158  VRRFPCCQVNVDSGKGKVWWTIRKTCYRIVEHSWFESFIVLMILLSSGALAFEDIYIEKKK
              |||| ||||||  ||||| ||  ||||| ||||||||||||||||||||||||||||| ||
HUMPN1A        VRRFXCCQVNXXSGKGKXWWXIRKTCYXIVEHSWFESFIVLMILLSSGALAFEDIYIEXKK
HUMPN1B        VRRFSCCQVNIESGKGKIWWNIRKTCYKIVEHSWFESFIVLMILLSSGALAFEDIYIERKK
HUMPN1C        VRRF-CCQVN--SGKGK-WW-IRKTCY-IVEHSWFESFIVLMILLSSGALAFEDIYIE-KK
HUMPN1D        VRRFPCCQVNVDSGKGKVWWTIRKTCYRIVEHSWFESFIVLMILLSSGALAFEDIYIEKKK

RATPN1  1219  TIKIILEYADKIFTYIFILEMLLKWVAYGYKTYFTNAWCWLDFLIVDVSLVTLVANTLGYS
              |||||||||||||||||||||||||| |||||||||||||||||||||||||||||||||
HUMPN1A        TIKIILEYADKIFTYIFILEMLLKWXAYGYKTYFTNAWCWLDFLIVDVSLVTLVANTLGYS
HUMPN1B        TIKIILEYADKIFTYIFILEMLLKWIAYGYKTYFTNAWCWLDFLIVDVSLVTLVANTLGYS
HUMPN1C        TIKIILEYADKIFTYIFILEMLLKW-AYGYKTYFTNAWCWLDFLIVDVSLVTLVANTLGYS
HUMPN1D        TIKIILEYADKIFTYIFILEMLLKWVAYGYKTYFTNAWCWLDFLIVDVSLVTLVANTLGYS

RATPN1  1280  DLGPIKSLRTLRALRPLRALSRFEGMRVVVNALIGAIPSIMNVLLVCLIFWLIFSIMGVNL
              ||||||||||||||||||||||||||||||||||||||||||||||||||||||||||||
HUMPN1A        DLGPIKSLRTLRALRPLRALSRFEGMRVVVNALIGAIPSIMNVLLVCLIFWLIFSIMGVNL
HUMPN1B        DLGPIKSLRTLRALRPLRALSRFEGMRVVVNALIGAIPSIMNVLLVCLIFWLIFSIMGVNL
HUMPN1C        DLGPIKSLRTLRALRPLRALSRFEGMRVVVNALIGAIPSIMNVLLVCLIFWLIFSIMGVNL
HUMPN1D        DLGPIKSLRTLRALRPLRALSRFEGMRVVVNALIGAIPSIMNVLLVCLIFWLIFSIMGVNL

RATPN1  1341  FAGKFYECVNTTDGSRFPTSQVANRSECFALMNVSGNVRWKNLKVNFDNVGLGYLSLLQVA
              |||||||| |||||||||  || |||||||||||| ||||||||||||||||||||||||
HUMPN1A        FAGKFYECXNTTDGSRFPXSQVXNRSECFALMNVSXNVRWKNLKVNFDNVGLGYLSLLQVA
HUMPN1B        FAGKFYECINTTDGSRFPASQVPNRSECFALMNVSQNVRWKNLKVNFDNVGLGYLSLLQVA
HUMPN1C        FAGKFYEC-NTTDGSRFP-SQV-NRSECFALMNVS-NVRWKNLKVNFDNVGLGYLSLLQVA
HUMPN1D        FAGKFYECVNTTDGSRFPTSQVANRSECFALMNVSGNVRWKNLKVNFDNVGLGYLSLLQVA

RATPN1  1402  TFKGWMDIMYAAVDSVNVNEQPKYEYSLYMYIYFVIFIIFGSFFTLNLFIGVIIDNFNQQK
              ||||| |||||||||||| |||||||||||||||||| ||||||||||||||||||||||
HUMPN1A        TFKGWXXIMYAAVDSVNVXXQPKYEYSLYMYIYFVXFIIFGSFFTLNLFIGVIIDNFNQQK
HUMPN1B        TFKGWTIIMYAAVDSVNVDKQPKYEYSLYMYIYFVVFIIFGSFFTLNLFIGVIIDNFNQQK
HUMPN1C        TFKGW--IMYAAVDSVNV--QPKYEYSLYMYIYFV-FIIFGSFFTLNLFIGVIIDNFNQQK
HUMPN1D        TFKGWMDIMYAAVDSVNVNEQPKYEYSLYMYIYFVIFIIFGSFFTLNLFIGVIIDNFNQQK
```

FIG. 11D

```
RATPN1   1463 KKLGGQDIFMTEEQKKYYNAMKKLGSKKPQKPIPRPGNKFQGCIFDLVTNQAFDITIMVLI
              |||||||||||||||||||||||||||||||||||||| |||||||||||||| |||||
HUMPN1A        KKLGGQDIFMTEEQKKYYNAMKKLGSKKPQKPIPRPGNKXQGCIFDLVTNQAFDIXIMVLI
HUMPN1B        KKLGGQDIFMTEEQKKYYNAMKKLGSKKPQKPIPRPGNKIQGCIFDLVTNQAFDISIMVLI
HUMPN1C        KKLGGQDIFMTEEQKKYYNAMKKLGSKKPQKPIPRPGNK-QGCIFDLVTNQAFDI-IMVLI
HUMPN1D        KKLGGQDIFMTEEQKKYYNAMKKLGSKKPQKPIPRPGNKFQGCIFDLVTNQAFDITIMVLI

RATPN1   1524 CLNMVTMMVEKEGQTEYMDYVLHWINMVFIILFTGECVLKLISLRHYYFTVGWNILYFVVV
              |||||||||||||   |  || ||| ||||||||||||||||||||||||||||  ||||
HUMPN1A        CLNMVTMMVEKEGQXXXMXXVLXWINXVFIILFTGECVLKLISLRHYYFTVGWNIXXFVVV
HUMPN1B        CLNMVTMMVEKEGQSQHMTEVLYWINVVFIILFTGECVLKLISLRHYYFTVGWNIFDFVVV
HUMPN1C        CLNMVTMMVEKEGQ---M--VL-WIN-VFIILFTGECVLKLISLRHYYFTVGWNI--FVVV
HUMPN1D        CLNMVTMMVEKEGQTEYMDYVLHWINMVFIILFTGECVLKLISLRHYYFTVGWNILYFVVV

RATPN1   1585 ILSIVGMFLAEMIEKYFVSPTLFRVIRLARIGRILRLIKGAKGIRTLLFALMMSLPALFNI
              | ||||||||  || |||||||||||||||||||||| ||||||||||||||||||||||
HUMPN1A        IXSIVGMFLAXXIEXYFVSPTLFRVIRLARIGRILRLXKGAKGIRTLLFALMMSLPALFNI
HUMPN1B        IISIVGMFLADLIETYFVSPTLFRVIRLARIGRILRLVKGAKGIRTLLFALMMSLPALFNI
HUMPN1C        I-SIVGMFLA--IE-YFVSPTLFRVIRLARIGRILRL-KGAKGIRTLLFALMMSLPALFNI
HUMPN1D        ILSIVGMFLAEMIEKYFVSPTLFRVIRLARIGRILRLIKGAKGIRTLLFALMMSLPALFNI

RATPN1   1646 GLLLFLVMFIYAIFGMSNFAYVKKEAGINDMFNFETFGNSMICLFQITTSAGWDGLLAPIL
              ||||||||||||||||||||||||| ||||||||||||||||||||||||||||||||||
HUMPN1A        GLLLFLVMFIYAIFGMSNFAYVKKEXGINDMFNFETFGNSMICLFQITTSAGWDGLLAPIL
HUMPN1B        GLLLFLVMFIYAIFGMSNFAYVKKEDGINDMFNFETFGNSMICLFQITTSAGWDGLLAPIL
HUMPN1C        GLLLFLVMFIYAIFGMSNFAYVKKE-GINDMFNFETFGNSMICLFQITTSAGWDGLLAPIL
HUMPN1D        GLLLFLVMFIYAIFGMSNFAYVKKEAGINDMFNFETFGNSMICLFQITTSAGWDGLLAPIL

RATPN1   1707 NSAPPDCDPKKVHPGSSVEGDCGNPSVGIFYFVSYIIISFLVVVNMYIAVILENFSVATEE
              || |||||||||||||||||||||||||||||||||||||||||||||||||||||||||
HUMPN1A        NSXPPDCDPKKVHPGSSVEGDCGNPSVGIFYFVSYIIISFLVVVNMYIAVILENFSVATEE
HUMPN1B        NSKPPDCDPKKVHPGSSVEGDCGNPSVGIFYFVSYIIISFLVVVNMYIAVILENFSVATEE
HUMPN1C        NS-PPDCDPKKVHPGSSVEGDCGNPSVGIFYFVSYIIISFLVVVNMYIAVILENFSVATEE
HUMPN1D        NSAPPDCDPKKVHPGSSVEGDCGNPSVGIFYFVSYIIISFLVVVNMYIAVILENFSVATEE

RATPN1   1768 STEPLSEDDFEMFYEVWEKFDPDATQFIEFCKLSDFAAALDPPLLIAKPNKVQLIAMDLPM
              ||||||||||||||||||||||||||||||| ||||||||||||||||||||||||||||
HUMPN1A        STEPLSEDDFEMFYEVWEKFDPDATQFIEFXKLSDFAAALDPPLLIAKPNKVQLIAMDLPM
HUMPN1B        STEPLSEDDFEMFYEVWEKFDPDATQFIEFSKLSDFAAALDPPLLIAKPNKVQLIAMDLPM
HUMPN1C        STEPLSEDDFEMFYEVWEKFDPDATQFIEF-KLSDFAAALDPPLLIAKPNKVQLIAMDLPM
HUMPN1D        STEPLSEDDFEMFYEVWEKFDPDATQFIEFCKLSDFAAALDPPLLIAKPNKVQLIAMDLPM
```

FIG. 11E

```
RATPN1    1829  VSGDRIHCLDILFAFTKRVLGEGGEMDSLRSQMEERFMSANPSKVSYEPITTTLKRKQEEV
                ||||||||||||||||||||||| |||||||||||||||||||||||||||||||||| |
HUMPN1A         VSGDRIHCLDILFAFTKRVLGEXGEMDSLRSQMEERFMSANPSKVSYEPITTTLKRKQEXV
HUMPN1B         VSGDRIHCLDILFAFTKRVLGESGEMDSLRSQMEERFMSANPSKVSYEPITTTLKRKQEDV
HUMPN1C         VSGDRIHCLDILFAFTKRVLGE-GEMDSLRSQMEERFMSANPSKVSYEPITTTLKRKQE-V
HUMPN1D         VSGDRIHCLDILFAFTKRVLGEGGEMDSLRSQMEERFMSANPSKVSYEPITTTLKRKQEEV

RATPN1    1890  SATIIQRAYRRYRLRQHVKNISSIYIKDGDRDDDLPNKEDTVFDNVNENSSPEKTDVTAST
                |||  |||||||||||  ||||||||||||||| | |  ||||||||||||||||| | ||
HUMPN1A         SATXIQRAYRRYRLRQXVKNISSIYIKDGDRDDDLXNKXDXXFDNVNENSSPEKTDXTXST
HUMPN1B         SATVIQRAYRRYRLRQNVKNISSIYIKDGDRDDDLLNKKDMAFDNVNENSSPEKTDATSST
HUMPN1C         SAT-IQRAYRRYRLRQ-VKNISSIYIKDGDRDDDL-NK-D--FDNVNENSSPEKTD-T-ST
HUMPN1D         SATIIQRAYRRYRLRQHVKNISSIYIKDGDRDDDLPNKEDTVFDNVNENSSPEKTDVTAST

RATPN1    1951  ISPPSYDSVTKPDQEKYETDKTEKEDKEKD  ESRK-    1985
                 |||||||||||| |||| | |||||| ||   || ||
HUMPN1A         XSPPSYDSVTKPDXEKYEXDXTEKEDKXKDSKESXKX
HUMPN1B         TSPPSYDSVTKPDKEKYEQDRTEKEDKGKDSKESKK-
HUMPN1C         -SPPSYDSVTKPD-EKYE-D-TEKEDK-KDSKES-K-
HUMPN1D         ISPPSYDSVTKPDQEKYETDKTEKEDKEKDXXESRKX
```

FIG. 11F

```
CTCTTATGTG AGGAGCTGAA GAGGAATTAA AATATACAGG ATGAAAAGAT      50
GGCAATGTTG CCTCCCCCAG GACCTCAGAG CTTTGTCCAT TTCACAAAAC     100
AGTCTCTTGC CCTCATTGAA CAACGCATTG CTGAAAGAAA ATCAAAGGAA     150
CCCAAAGAAG AAAAGAAAGA TGATGATGAA GAAGCCCCAA AGCCAAGCAG     200
TGACTTGGAA GCTGGCAAAC AACTGCCCTT CATCTATGGG GACATTCCTC     250
CCGGCATGGT GTCAGAGCCC CTGGAGGACT TGGACCCCTA CTATGCAGAC     300
AAAAAGACTT TCATAGTATT GAACAAAGGG AAAACAATCT TCCGTTTCAA     350
TGCCACACCT GCTTTATATA TGCTTTCTCC TTTCAGTCCT CTAAGAAGAA     400
TATCTATTAA GATTTTAGTA CACTCCTTAT TCAGCATGCT CATCATGTGC     450
ACTATTCTGA CAAACTGCAT ATTTATGACC ATGAATAACC CGCCGGACTG     500
GACCAAAAAT GTCGAGTACA CTTTTACTGG AATATATACT TTTGAATCAC     550
TTGTAAAAAT CCTTGCAAGA GGCTTCTGTG TAGGAGAATT CACTTTTCTT     600
CGTGACCCGT GGAACTGGCT GGATTTTGTC GTCATTGTTT TTGCGTATTT     650
AACAGAATTT GTAAACCTAG GCAATGTTTC AGCTCTTCGA ACTTTCAGAG     700
TATTGAGAGC TTTGAAAACT ATTTCTGTAA TCCCAGGCCT GAAGACAATT     750
GTAGGGGCTT TGATCCAGTC AGTGAAGAAG CTTTCTGATG TCATGATCCT     800
GACTGTGTTC TGTCTGAGTG TGTTTGCACT AATTGGACTA CAGCTGTTCA     850
TGGGAAACCT GAAGCATAAA TGTTTTCGAA ATTCACTTGA AAATAATGAA     900
ACATTAGAAA GCATAATGAA TACCCTAGAG AGTGAAGAAG ACTTTAGAAA     950
ATATTTTTAT TACTTGGAAG GATCCAAAGA TGCTCTCCTT TGTGGTTTCA    1000
GCACAGATTC AGGTCAGTGT CCAGAGGGGT ACACCTGTGT GAAAATTGGC    1050
AGAAACCCTG ATTATGGCTA CACGAGCTTT GACACTTTCA GCTGGGCCTT    1100
CTTAGCCTTG TTTAGGCTAA TGACCCAAGA TTACTGGGAA AACCTTTACC    1150
AACAGACGCT GCGTGCTGCT GGCAAAACCT ACATGATCTT CTTTGTCGTA    1200
GTGATTTTCC TGGGCTCCTT TTATCTAATA AACTTGATCC TGGCTGTGGT    1250
TGCCATGGCA TATGAAGAAC AGAACCAGGC AAACATTGAA GAAGCTAAAC    1300
AGAAAGAATT AGAATTTCAA CAGATGTTAG ACCGTCTTAA AAAAGAGCAA    1350
GAAGAAGCTG AGGCAATTGC AGCGGCAGCG CTGAATATA CAAGTATTAG    1400
GAGAAGCAGA ATTATGGGCC TCTCAGAGAG TTCTTCTGAA ACATCCAAAC    1450
TGAGCTCTAA AAGTGCTAAA GAAAGAAGAA ACAGAAGAAA GAAAAAGAAT    1500
CAAAAGAAGC TCTCCAGTGG AGAGGAAAAG GGAGATGCTG AGAAATTGTC    1550
GAAATCAGAA TCAGAGGACA GCATCAGAAG AAAAAGTTTC CACCTTGGTG    1600
TCGAAGGGCA TAGGCGAGCA CATGAAAAGA GGTTGTCTAC CCCCAATCAG    1650
TCACCACTCA GCATTCGTGG CTCCTTGTTT TCTGCAAGGC GAAGCAGCAG    1700
AACAAGTCTT TTTAGTTTCA AAGGCAGAGG AAGAGATATA GGATCTGAGA    1750
CTGAATTTGC CGATGATGAG CACAGCATTT TTGGAGACAA TGAGAGCAGA    1800
AGGGGCTCAC TGTTTGTGCC CCACAGACCC CAGGAGCGAC GCAGCAGTAA    1850
CATCAGCCAA GCCAGTAGGT CCCCACCAAT GCTGCCGGTG AACGGGAAAA    1900
TGCACAGTGC TGTGGACTGC AACGGTGTGG TCTCCCTGGT TGATGGACGC    1950
TCAGCCCTCA TGCTCCCCAA TGGACAGCTT CTGCCAGAGG GCACGACCAA    2000
TCAAATACAC AAGAAAAGGC GTTGTAGTTC CTATCTCCTT TCAGAGGATA    2050
```

FIG. 13A

```
TGCTGAATGA TCCCAACCTC AGACAGAGAG CAATGAGTAG AGCAAGCATA    2100
TTAACAAACA CTGTGGAAGA ACTTGAAGAG TCCAGACAAA AATGTCCACC    2150
TTGGTGGTAC AGATTTGCAC ACAAATTCTT GATCTGGAAT TGCTCTCCAT    2200
ATTGGATAAA ATTCAAAAAG TGTATCTATT TTATTGTAAT GGATCCTTTT    2250
GTAGATCTTG CAATTACCAT TTGCATAGTT TTAAACACAT TATTTATGGC    2300
TATGGAACAC CACCCAATGA CTGAGGAATT CAAAAATGTA CTTGCTATAG    2350
GAAATTTGGT CTTTACTGGA ATCTTTGCAG CTGAAATGGT ATTAAAACTG    2400
ATTGCCATGG ATCCATATGA GTATTTCCAA GTAGGCTGGA ATATTTTTGA    2450
CAGCCTTATT GTGACTTTAA GTTTAGTGGA GCTCTTTCTA GCAGATGTGG    2500
AAGGATTGTC AGTTCTGCGA TCATTCAGAC TGCTCCGAGT CTTCAAGTTG    2550
GCAAAATCCT GGCCAACATT GAACATGCTG ATTAAGATCA TTGGTAACTC    2600
AGTAGGGGCT CTAGGTAACC TCACCTTAGT GTTGGCCATC ATCGTCTTCA    2650
TTTTTGCTGT GGTCGGCATG CAGCTCTTTG GTAAGAGCTA CAAAGAATGT    2700
GTCTGCAAGA TCAATGATGA CTGTACGCTC CCACGGTGGC ACATGAACGA    2750
CTTCTTCCAC TCCTTCCTGA TTGTGTTCCG CGTGCTGTGT GGAGAGTGGA    2800
TAGAGACCAT GTGGGACTGT ATGGAGGTCG CTGGTCAAGC TATGTGCCTT    2850
ATTGTTTACA TGATGGTCAT GGTCATTGGA AACCTGGTGG TCCTAAACCT    2900
ATTTCTGGCC TTATTATTGA GCTCATTTAG TTCAGACAAT CTTACAGCAA    2950
TTGAAGAAGA CCCTGATGCA AACAACCTCC AGATTGCAGT GACTAGAATT    3000
AAAAAGGGAA TAAATTATGT GAAACAAACC TTACGTGAAT TTATTCTAAA    3050
AGCATTTTCC AAAAAGCCAA AGATTTCCAG GGAGATAAGA CAAGCAGAAG    3100
ATCTGAATAC TAAGAAGGAA AACTATATTT CTAACCATAC ACTTGCTGAA    3150
ATGAGCAAAG GTCACAATTT CCTCAAGGAA AAAGATAAAA TCAGTGGTTT    3200
TGGAAGCAGC GTGGACAAAC ACTTGATGGA AGACAGTGAT GGTCAATCAT    3250
TTATTCACAA TCCCAGCCTC ACAGTGACAG TGCCAATTGC ACCTGGGGAA    3300
TCCGATTTGG AAAATATGAA TGCTGAGGAA CTTAGCAGTG ATTCGGATAG    3350
TGAATACAGC AAAGTGAGAT TAAACCGGTC AAGCTCCTCA GAGTGCAGCA    3400
CAGTTGATAA CCCTTTGCCT GGAGAAGGAG AAGAAGCAGA GGCTGAACCT    3450
ATGAATTCCG ATGAGCCAGA GGCCTGTTTC ACAGATGGTT GTGTACGGAG    3500
GTTCTCATGC TGCCAAGTTA ACATAGAGTC AGGGAAAGGA AAAATCTGGT    3550
GGAACATCAG GAAAACCTGC TACAAGATTG TTGAACACAG TTGGTTTGAA    3600
AGCTTCATTG TCCTCATGAT CCTGCTCAGC AGTGGTGCCC TGGCTTTTGA    3650
AGATATTTAT ATTGAAAGGA AAAAGACCAT TAAGATTATC CTGGAGTATG    3700
CAGACAAGAT CTTCACTTAC ATCTTCATTC TGGAAATGCT TCTAAAATGG    3750
ATAGCATATG GTTATAAAAC ATATTTCACC AATGCCTGGT GTTGGCTGGA    3800
TTTCCTAATT GTTGATGTTT CTTTGGTTAC TTTAGTGGCA AACACTCTTG    3850
GCTACTCAGA TCTTGGCCCC ATTAAATCCC TTCGGACACT GAGAGCTTTA    3900
AGACCTCTAA GAGCCTTATC TAGATTTGAA GGAATGAGGG TCGTTGTGAA    3950
TGCACTCATA GGAGCAATTC CTTCCATCAT GAATGTGCTA CTTGTGTGTC    4000
TTATATTCTG GCTGATATTC AGCATCATGG GAGTAAATTT GTTTGCTGGC    4050
```

FIG. 13B

```
AAGTTCTATG AGTGTATTAA CACCACAGAT GGGTCACGGT TTCCTGCAAG    4100
TCAAGTTCCA AATCGTTCCG AATGTTTTGC CCTTATGAAT GTTAGTCAAA    4150
ATGTGCGATG GAAAAACCTG AAAGTGAACT TTGATAATGT CGGACTTGGT    4200
TACCTATCTC TGCTTCAAGT TGCAACTTTT AAGGGATGGA CGATTATTAT    4250
GTATGCAGCA GTGGATTCTG TTAATGTAGA CAAGCAGCCC AAATATGAAT    4300
ATAGCCTCTA CATGTATATT TATTTTGTCG TCTTTATCAT CTTTGGGTCA    4350
TTCTTCACTT TGAACTTGTT CATTGGTGTC ATCATAGATA ATTTCAACCA    4400
ACAGAAAAAG AAGCTTGGAG GTCAAGACAT CTTTATGACA GAAGAACAGA    4450
AGAAATACTA TAATGCAATG AAAAAGCTGG GGTCCAAGAA GCCACAAAAG    4500
CCAATTCCTC GACCAGGGAA CAAAATCCAA GGATGTATAT TTGACCTAGT    4550
GACAAATCAA GCCTTTGATA TTAGTATCAT GGTTCTTATC TGTCTCAACA    4600
TGGTAACCAT GATGGTAGAA AAGGAGGGTC AAAGTCAACA TATGACTGAA    4650
GTTTTATATT GGATAAATGT GGTTTTTATA ATCCTTTTCA CTGGAGAATG    4700
TGTGCTAAAA CTGATCTCCC TCAGACACTA CTACTTCACT GTAGGATGGA    4750
ATATTTTTGA TTTTGTGGTT GTGATTATCT CCATTGTAGG TATGTTTCTA    4800
GCTGATTTGA TTGAAACGTA TTTTGTGTCC CCTACCCTGT TCCGAGTGAT    4850
CCGTCTTGCC AGGATTGGCC GAATCCTACG TCTAGTCAAA GGAGCAAAGG    4900
GGATCCGCAC GCTGCTCTTT GCTTTGATGA TGTCCCTTCC TGCGTTGTTT    4950
AACATCGGCC TCCTGCTCTT CCTGGTCATG TTCATCTACG CCATCTTTGG    5000
AATGTCCAAC TTTGCCTATG TTAAAAAGGA AGATGGAATT AATGACATGT    5050
TCAATTTTGA GACCTTTGGC AACAGTATGA TTTGCCTGTT CCAAATTACA    5100
ACCTCTGCTG GCTGGGATGG ATTGCTAGCA CCTATTCTTA ACAGTAAGCC    5150
ACCCGACTGT GACCCAAAAA AAGTTCATCC TGGAAGTTCA GTTGAAGGAG    5200
ACTGTGGTAA CCCATCTGTT GGAATATTCT ACTTTGTTAG TTATATCATC    5250
ATATCCTTCC TGGTTGTGGT GAACATGTAC ATTGCAGTCA TACTGGAGAA    5300
TTTTAGTGTT GCCACTGAAG AAAGTACTGA ACCTCTGAGT GAGGATGACT    5350
TTGAGATGTT CTATGAGGTT TGGGAGAAGT TTGATCCCGA TGCGACCCAG    5400
TTTATAGAGT TCTCTAAACT CTCTGATTTT GCAGCTGCCC TGGATCCTCC    5450
TCTTCTCATA GCAAAACCCA ACAAAGTCCA GCTCATTGCC ATGGATCTGC    5500
CCATGGTTAG TGGTGACCGG ATCCATTGTC TTGACATCTT ATTTGCTTTT    5550
ACAAAGCGTG TTTTGGGTGA GAGTGGGGAG ATGGATTCTC TTCGTTCACA    5600
GATGGAAGAA AGGTTCATGT CTGCAAATCC TTCCAAAGTG TCCTATGAAC    5650
CCATCACAAC CACACTAAAA CGGAAACAAG AGGATGTGTC TGCTACTGTC    5700
ATTCAGCGTG CTTATAGACG TTACCGCTTA AGGCAAAATG TCAAAAATAT    5750
ATCAAGTATA TACATAAAAG ATGGAGACAG AGATGATGAT TTACTCAATA    5800
AAAAAGATAT GGCTTTTGAT AATGTTAATG AGAACTCAAG TCCAGAAAAA    5850
ACAGATGCCA CTTCATCCAC CACCTCTCCA CCTTCATATG ATAGTGTAAC    5900
AAAGCCAGAC AAAGAGAAAT ATGAACAAGA CAGAACAGAA AAGGAAGACA    5950
AAGGGAAAGA CAGCAAGGAA AGCAAAAAAT AGAGCTTCAT TTTTGATATA    6000
TTGTTTACAG CCTGTGAAAG TGATTTATTT GTGTTAATAA AACTCTTTTG    6050
```

FIG. 13C

```
AGGAAGTCTA TGCCAAAATC CTTTTTATCA AAATATTCTC GAAGGCAGTG    6100
CAGTCACTAA CTCTGATTTC CTAAGAAAGG TGGGCAGCAT TAGCAGATGG    6150
TTATTTTTGC ACTGATGATT CTTTAAGAAT CGTAAGAGAA CTCTGTAGGA    6200
ATTATTGATT ATAGCATACA AAAGTGATTG ATTCAGTTTT TTGGTTTTTA    6250
ATAAATCAGA AGACCATGTA GAAAACTTTT ACATCTGCCT TGTCATCTTT    6300
TCACAGGATT GTAATTAGTC TTGTTTCCCA TGTAAATAAA CAACACACGC    6350
ATACAGAAAA AAAAAAAAAA A                                   6371
```

FIG. 13D

```
CTCTTATGTG AGGAGCTGAA GAGGAATTAA AATATACAGG ATGAAAAGAT    50
GGCAATGTTG CCTCCCCCAG GACCTCAGAG CTTTGTCCAT TTCACAAAAC   100
AGTCTCTTGC CCTCATTGAA CAACGCATTG CTGAAAGAAA ATCAAAGGAA   150
CCCAAAGAAG AAAAGAAAGA TGATGATGAA GAAGCCCCAA AGCCAAGCAG   200
TGACTTGGAA GCTGGCAAAC AACTGCCCTT CATCTATGGG GACATTCCTC   250
CCGGCATGGT GTCAGAGCCC CTGGAGGACT TGGACCCCTA CTATGCAGAC   300
AAAAAGACTT TCATAGTATT GAACAAAGGG AAAACAATCT TCCGTTTCAA   350
TGCCACACCT GCTTTATATA TGCTTTCTCC TTTCAGTCCT CTAAGAAGAA   400
TATCTATTAA GATTTTAGTA CACTCCTTAT TCAGCATGCT CATCATGTGC   450
ACTATTCTGA CAAACTGCAT ATTTATGACC ATGAATAACC CGCCGGACTG   500
GACCAAAAAT GTCGAGTACA CTTTTACTGG AATATATACT TTTGAATCAC   550
TTGTAAAAAT CCTTGCAAGA GGCTTCTGTG TAGGAGAATT CACTTTTCTT   600
CGTGACCCGT GGAACTGGCT GGATTTTGTC GTCATTGTTT TTGCGTATTT   650
AACAGAATTT GTAAACCTAG GCAATGTTTC AGCTCTTCGA ACTTTCAGAG   700
TATTGAGAGC TTTGAAAACT ATTTCTGTAA TCCCAGGCCT GAAGACAATT   750
GTAGGGGCTT TGATCCAGTC AGTGAAGAAG CTTTCTGATG TCATGATCCT   800
GACTGTGTTC TGTCTGAGTG TGTTTGCACT AATTGGACTA CAGCTGTTCA   850
TGGGAAACCT GAAGCATAAA TGTTTTCGAA ATTCACTTGA AAATAATGAA   900
ACATTAGAAA GCATAATGAA TACCCTAGAG AGTGAAGAAG ACTTTAGAAA   950
ATATTTTTAT TACTTGGAAG GATCCAAAGA TGCTCTCCTT TGTGGTTTCA  1000
GCACAGATTC AGGTCAGTGT CCAGAGGGGT ACACCTGTGT GAAAATTGGC  1050
AGAAACCCTG ATTATGGCTA CACGAGCTTT GACACTTTCA GCTGGGCCTT  1100
CTTAGCCTTG TTTAGGCTAA TGACCCAAGA TTACTGGGAA AACCTTTACC  1150
AACAGACGCT GCGTGCTGCT GGCAAAACCT ACATGATCTT CTTTGTCGTA  1200
GTGATTTTCC TGGGCTCCTT TTATCTAATA AACTTGATCC TGGCTGTGGT  1250
TGCCATGGCA TATGAAGAAC AGAACCAGGC AAACATTGAA GAAGCTAAAC  1300
AGAAAGAATT AGAATTTCAA CAGATGTTAG ACCGTCTTAA AAAAGAGCAA  1350
GAAGAAGCTG AGGCAATTGC AGCGGCAGCG GCTGAATATA CAAGTATTAG  1400
GAGAAGCAGA ATTATGGGCC TCTCAGAGAG TTCTTCTGAA ACATCCAAAC  1450
TGAGCTCTAA AAGTGCTAAA GAAAGAAGAA ACAGAAGAAA GAAAAAGAAT  1500
CAAAAGAAGC TCTCCAGTGG AGAGGAAAAG GGAGATGCTG AGAAATTGTC  1550
GAAATCAGAA TCAGAGGACA GCATCAGAAG AAAAAGTTTC CACCTTGGTG  1600
TCGAAGGGCA TAGGCGAGCA CATGAAAAGA GGTTGTCTAC CCCCAATCAG  1650
TCACCACTCA GCATTCGTGG CTCCTTGTTT TCTGCAAGGC GAAGCAGCAG  1700
AACAAGTCTT TTTAGTTTCA AAGGCAGAGG AAGAGATATA GGATCTGAGA  1750
CTGAATTTGC CGATGATGAG CACAGCATTT TTGGAGACAA TGAGAGCAGA  1800
AGGGGCTCAC TGTTTGTGCC CCACAGACCC CAGGAGCGAC GCAGCAGTAA  1850
CATCAGCCAA GCCAGTAGGT CCCCACCAAT GCTGCCGGTG AACGGGAAAA  1900
TGCACAGTGC TGTGGACTGC AACGGTGTGG TCTCCCTGGT TGATGGACGC  1950
TCAGCCCTCA TGCTCCCCAA TGGACAGCTT CTGCCAGAGG TGATAATAGA  2000
```

FIG. 14A

```
TAAGACAACT TCTGATGACA GCGGCACGAC CAATCAAATA CACAAGAAAA    2050
GGCGTTGTAG TTCCTATCTC CTTTCAGAGG ATATGCTGAA TGATCCCAAC    2100
CTCAGACACA GAGCAATGAG TAGAGCAAGC ATATTAACAA ACACTGTGGA    2150
AGAACTTGAA GAGTCCAGAC AAAAATGTCC ACCTTGGTGG TACAGATTTG    2200
CACACAAATT CTTGATCTGG AATTGCTCTC CATATTGGAT AAAATTCAAA    2250
AAGTGTATCT ATTTTATTGT AATGGATCCT TTTGTAGATC TTGCAATTAC    2300
CATTTGCATA GTTTTAAACA CATTATTTAT GGCTATGGAA CACCACCCAA    2350
TGACTGAGGA ATTCAAAAAT GTACTTGCTA TAGGAAATTT GGTCTTTACT    2400
GGAATCTTTG CAGCTGAAAT GGTATTAAAA CTGATTGCCA TGGATCCATA    2450
TGAGTATTTC CAAGTAGGCT GGAATATTTT TGACAGCCTT ATTGTGACTT    2500
TAAGTTTAGT GGAGCTCTTT CTAGCAGATG TGGAAGGATT GTCAGTTCTG    2550
CGATCATTCA GACTGCTCCG AGTCTTCAAG TTGGCAAAAT CCTGGCCAAC    2600
ATTGAACATG CTGATTAAGA TCATTGGTAA CTCAGTAGGG GCTCTAGGTA    2650
ACCTCACCTT AGTGTTGGCC ATCATCGTCT TCATTTTTGC TGTGGTCGGC    2700
ATGCAGCTCT TTGGTAAGAG CTACAAAGAA TGTGTCTGCA AGATCAATGA    2750
TGACTGTACG CTCCCACGGT GGCACATGAA CGACTTCTTC CACTCCTTCC    2800
TGATTGTGTT CCGCGTGCTG TGTGGAGAGT GGATAGAGAC CATGTGGGAC    2850
TGTATGGAGG TCGCTGGTCA AGCTATGTGC CTTATTGTTT ACATGATGGT    2900
CATGGTCATT GGAAACCTGG TGGTCCTAAA CCTATTTCTG GCCTTATTAT    2950
TGAGCTCATT TAGTTCAGAC AATCTTACAG CAATTGAAGA AGACCCTGAT    3000
GCAAACAACC TCCAGATTGC AGTGACTAGA ATTAAAAAGG GAATAAATTA    3050
TGTGAAACAA ACCTTACGTG AATTTATTCT AAAAGCATTT TCCAAAAAGC    3100
CAAAGATTTC CAGGGAGATA AGACAAGCAG AAGATCTGAA TACTAAGAAG    3150
GAAAACTATA TTTCTAACCA TACACTTGCT GAAATGAGCA AAGGTCACAA    3200
TTTCCTCAAG GAAAAAGATA AAATCAGTGG TTTTGGAAGC AGCGTGGACA    3250
AACACTTGAT GGAAGACAGT GATGGTCAAT CATTTATTCA CAATCCCAGC    3300
CTCACAGTGA CAGTGCCAAT TGCACCTGGG GAATCCGATT TGGAAAATAT    3350
GAATGCTGAG GAACTTAGCA GTGATTCGGA TAGTGAATAC AGCAAAGTGA    3400
GATTAAACCG GTCAAGCTCC TCAGAGTGCA GCACAGTTGA TAACCCTTTG    3450
CCTGGAGAAG GAGAAGAAGC AGAGGCTGAA CCTATGAATT CCGATGAGCC    3500
AGAGGCCTGT TTCACAGATG GTTGTGTACG GAGGTTCTCA TGCTGCCAAG    3550
TTAACATAGA GTCAGGGAAA GGAAAAATCT GGTGGAACAT CAGGAAAACC    3600
TGCTACAAGA TTGTTGAACA CAGTTGGTTT GAAAGCTTCA TTGTCCTCAT    3650
GATCCTGCTC AGCAGTGGTG CCCTGGCTTT TGAAGATATT TATATTGAAA    3700
GGAAAAAGAC CATTAAGATT ATCCTGGAGT ATGCAGACAA GATCTTCACT    3750
TACATCTTCA TTCTGGAAAT GCTTCTAAAA TGGATAGCAT ATGGTTATAA    3800
AACATATTTC ACCAATGCCT GGTGTTGGCT GGATTTCCTA ATTGTTGATG    3850
TTTCTTTGGT TACTTTAGTG GCAAACACTC TTGGCTACTC AGATCTTGGC    3900
CCCATTAAAT CCCTTCGGAC ACTGAGAGCT TTAAGACCTC TAAGAGCCTT    3950
ATCTAGATTT GAAGGAATGA GGGTCGTTGT GAATGCACTC ATAGGAGCAA    4000
```

FIG 14B

```
TTCCTTCCAT CATGAATGTG CTACTTGTGT GTCTTATATT CTGGCTGATA    4050
TTCAGCATCA TGGGAGTAAA TTTGTTTGCT GGCAAGTTCT ATGAGTGTAT    4100
TAACACCACA GATGGGTCAC GGTTTCCTGC AAGTCAAGTT CCAAATCGTT    4150
CCGAATGTTT TGCCCTTATG AATGTTAGTC AAAATGTGCG ATGGAAAAAC    4200
CTGAAAGTGA ACTTTGATAA TGTCGGACTT GGTTACCTAT CTCTGCTTCA    4250
AGTTGCAACT TTTAAGGGAT GGACGATTAT TATGTATGCA GCAGTGGATT    4300
CTGTTAATGT AGACAAGCAG CCCAAATATG AATATAGCCT CTACATGTAT    4350
ATTTATTTTG TCGTCTTTAT CATCTTTGGG TCATTCTTCA CTTTGAACTT    4400
GTTCATTGGT GTCATCATAG ATAATTTCAA CCAACAGAAA AAGAAGCTTG    4450
GAGGTCAAGA CATCTTTATG ACAGAAGAAC AGAAGAAATA CTATAATGCA    4500
ATGAAAAAGC TGGGGTCCAA GAAGCCACAA AAGCCAATTC CTCGACCAGG    4550
GAACAAAATC CAAGGATGTA TATTTGACCT AGTGACAAAT CAAGCCTTTG    4600
ATATTAGTAT CATGGTTCTT ATCTGTCTCA ACATGGTAAC CATGATGGTA    4650
GAAAAGGAGG GTCAAAGTCA ACATATGACT GAAGTTTTAT ATTGGATAAA    4700
TGTGGTTTTT ATAATCCTTT TCACTGGAGA ATGTGTGCTA AAACTGATCT    4750
CCCTCAGACA CTACTACTTC ACTGTAGGAT GGAATATTTT TGATTTTGTG    4800
GTTGTGATTA TCTCCATTGT AGGTATGTTT CTAGCTGATT TGATTGAAAC    4850
GTATTTTGTG TCCCCTACCC TGTTCCGAGT GATCCGTCTT GCCAGGATTG    4900
GCCGAATCCT ACGTCTAGTC AAAGGAGCAA AGGGGATCCG CACGCTGCTC    4950
TTTGCTTTGA TGATGTCCCT TCCTGCGTTG TTTAACATCG GCCTCCTGCT    5000
CTTCCTGGTC ATGTTCATCT ACGCCATCTT TGGAATGTCC AACTTTGCCT    5050
ATGTTAAAAA GGAAGATGGA ATTAATGACA TGTTCAATTT TGAGACCTTT    5100
GGCAACAGTA TGATTTGCCT GTTCCAAATT ACAACCTCTG CTGGCTGGGA    5150
TGGATTGCTA GCACCTATTC TTAACAGTAA GCCACCCGAC TGTGACCCAA    5200
AAAAAGTTCA TCCTGGAAGTT CAGTTGAAG GAGACTGTG GTAACCCATCT   5250
GTTGGAATAT TCTACTTTGT TAGTTATATC ATCATATCCT TCCTGGTTGT    5300
GGTGAACATG TACATTGCAG TCATACTGGA GAATTTTAGT GTTGCCACTG    5350
AAGAAAGTAC TGAACCTCTG AGTGAGGATG ACTTTGAGAT GTTCTATGAG    5400
GTTTGGGAGA AGTTTGATCC CGATGCGACC CAGTTTATAG AGTTCTCTAA    5450
ACTCTCTGAT TTTGCAGCTG CCCTGGATCC TCCTCTTCTC ATAGCAAAAC    5500
CCAACAAAGT CCAGCTCATT GCCATGGATC TGCCCATGGT TAGTGGTGAC    5550
CGGATCCATT GTCTTGACAT CTTATTTGCT TTTACAAAGC GTGTTTTGGG    5600
TGAGAGTGGG GAGATGGATT CTCTTCGTTC ACAGATGGAA GAAAGGTTCA    5650
TGTCTGCAAA TCCTTCCAAA GTGTCCTATG AACCCATCAC AACCACACTA    5700
AAACGGAAAC AAGAGGATGT GTCTGCTACT GTCATTCAGC GTGCTTATAG    5750
ACGTTACCGC TTAAGGCAAA ATGTCAAAAA TATATCAAGT ATATACATAA    5800
AAGATGGAGA CAGAGATGAT GATTTACTCA ATAAAAAAGA TATGGCTTTT    5850
GATAATGTTA ATGAGAACTC AAGTCCAGAA AAAACAGATG CCACTTCATC    5900
CACCACCTCT CCACCTTCAT ATGATAGTGT AACAAAGCCA GACAAAGAGA    5950
AATATGAACA AGACAGAACA GAAAAGGAAG ACAAAGGGAA AGACAGCAAG    6000
```

FIG. 14C

```
GAAAGCAAAA AATAGAGCTT CATTTTTGAT ATATTGTTTA CAGCCTGTGA    6050
AAGTGATTTA TTTGTGTTAA TAAAACTCTT TTGAGGAAGT CTATGCCAAA    6100
ATCCTTTTTA TCAAAATATT CTCGAAGGCA GTGCAGTCAC TAACTCTGAT    6150
TTCCTAAGAA AGGTGGGCAG CATTAGCAGA TGGTTATTTT TGCACTGATG    6200
ATTCTTTAAG AATCGTAAGA GAACTCTGTA GGAATTATTG ATTATAGCAT    6250
ACAAAAGTGA TTGATTCAGT TTTTTGGTTT TTAATAAATC AGAAGACCAT    6300
GTAGAAAACT TTTACATCTG CCTTGTCATC TTTTCACAGG ATTGTAATTA    6350
GTCTTGTTTC CCATGTAAAT AAACAACACA CGCATACAGA AAAAAAAAAA    6400
AAAA                                                     6404
```

FIG. 14D

PERIPHERAL NERVOUS SYSTEM SPECIFIC SODIUM CHANNELS, DNA ENCODING THEREFOR, CRYSTALLIZATION, X-RAY DIFFRACTION, COMPUTER MOLECULAR MODELING, RATIONAL DRUG DESIGN, DRUG SCREENING, AND METHODS OF MAKING AND USING THEREOF

CROSS-REFERENCE TO RELATED APPLICATIONS

This application is a continuation-in-part of U.S. application Ser. No. 08/482,401, filed Jun. 7, 1995 now abandoned, which is a continuation-in-part of U.S. application Ser. No. 08/334,029 filed Nov. 2, 1994 now abandoned, both of which disclosures are entirely incorporated herein by reference

STATEMENT AS TO RIGHTS TO INVENTIONS MADE UNDER FEDERALLY-SPONSORED RESEARCH AND DEVELOPMENT

The present invention was made with U.S. government support. Therefore, the U.S. government has certain rights in the invention.

FIELD OF THE INVENTION

The present invention is in the fields of biotechnology, protein purification and crystallization, x-ray diffraction analysis, three-dimensional computer molecular modeling, and rational drug design (RDD). The invention is directed to isolated peripheral nervous system (PNS) specific sodium channel proteins (SCPs) and encoding nucleic acid, as well as to compounds, compositions and methods for selecting, making and using therapeutic or diagnostic agents having sodium channel modulating activity. The present invention further provides three-dimensional computer modeling of the PNS SCP, and for RDD, based on the use of x-ray data and/or amino acid sequence data on computer readable media.

BACKGROUND OF THE INVENTION

Voltage-sensitive ion channels are a class of transmembrane proteins that provide a basis for cellular excitability, as the ability to transmit information via ion-generated membrane potentials. In response to changes in membrane potentials, these molecules mediate rapid ion flux through highly selective pores in a nerve cell membrane. If the channel density is high enough, a suitable regenerative depolarization results, termed the action potential.

The voltage-sensitive sodium channel is the ion channel most often responsible for generating the action potential in excitable cells. Although sodium-based action potentials in different excitable tissues look similar (Hille, B., In: *Ionic Channels of Excitable Membranes,* B. Hille, ed., Sinauer, Sunderland, Mass., (1984), pp. 70–71) recent electrophysiological studies indicate that sodium channels in different cells differ in both their structural and functional properties, and many sodium channels with distinct primary structures have now been identified. See, e.g. Mandel, *J. Membrane Biol.* 125:193–205 (1992).

Functionally distinct sodium channels have been described in a variety of neuronal cell types (Llinas et al., *J. Physiol.* 305:197–213 (1980); Kostyuk et al., *Neuroscience* 6:2423–2430 (1981); Bossu et al., *Neurosci. Lett.* 51:241–246 (1984) 1981; Gilly et al., *Nature* 309:448–450 (1984); French et al., *Neurosci. Lett.* 56:289–294 (1985); Ikeda et al., *J. Neurophysiol.* 55:527–539 (1986); Jones et al., *J. Physiol.* 389:605–627 (1987); Alonso & Llinas, 1989; Gilly et al., *J. Neurosci.* 9:1362–1374 (1989)) and in skeletal muscle (Gonoi et al., *J. Neurosci.* 5:2559–2564 (1985); Weiss et al., *Science* 233:361–364 (1986)). The kinetics of sodium currents in glia and neurons can also be distinguished (Barres et al., *Neuron* 2: 1375–1388 (1989)).

The type II and type III genes, expressed widely in the central nervous system (CNS), are expressed at very low levels in some cells in the PNS (Beckh, S., *FEBS Lett.* 262:317–322 (1990)). The type II and III mRNAs were barely detectable, by Northern blot analysis, in dorsal root ganglion (DRG), cranial nerves and sciatic nerves. On the other hand, type I mRNA was present in moderately high amounts in DRG and cranial nerve, but in low levels in sciatic nerve. A comparison of the amount of all three brain mRNAs, relative to total sodium channel mRNA detected with a conserved cDNA probe, suggested the presence of additional, as yet unidentified, sodium channel types in DRG neurons. Consistent with the mRNA studies, immunochemical studies showed that neither type I nor type II sodium channel alpha subunits made up a significant component of the total sodium channels in the superior cervical ganglion or sciatic nerve (Gordon et al., *Proc. Natl. Acad Sci. USA* 84:8682–8686 (1987)).

A population of neurons in vertebrate DRG has been identified electrophysiologically that contains, in addition to the more conventional channels, a distinct sodium channel type; this DRG channel has a $k_D$ for tetrodotoxin TTX approximately tenfold higher than the $k_D$ of sodium channels in either skeletal muscle or heart (Jones et al., *J. Physiol.* 389:605–627 (1987)).

The localization of different sodium channels to specific regions in the nervous system supports the possibility that cell-specific regulation of this gene family is at the transcriptional level. By analogy with other eukaryotic genes, distinct DNA elements can be present which mediate cell-specific and temporal regulation of individual sodium channel genes.

Studies of sodium channel gene regulation have been facilitated by the use of well-characterized cell lines, such as pheochromocytoma (PC12) cells, a popular cell model for neuronal differentiation (Green et al., *Proc. Natl. Acad Sci. USA* 73:2424–2428 (1976); Halegoua et al., *Curr. Top. Microbiol. Immunol.* 165:119–170 (1991)). In addition to extending neurites and initiating synthesis of certain neurotransmitters, NGF-treated PC12 cells acquire the ability to generate sodium-based action potentials (Dichter et al., *Nature* 268:501–504 (1977)). This ability is conferred by an increase in the density of functional sodium channels in the membranes of the NGF-treated cells (Rudy et al., *J. Neurosci.* 7:1613–1625 (1987); Mandel et al., *Proc. Natl. Acad. Sci. USA* 85:924–928 (1988); O'Lague et al., *Proc. Natl. Acad Sci. USA* 77:1701–1705 (1980)). Northern blot analysis revealed that undifferentiated PC12 cells contained a basal level of sodium channel mRNA which increased coincident with the increase in channel activity observed after treatment with NGF (Mandel et al., *Proc. Natl. Acad. Sci. USA* 85:924–928 (1988)).

There is a long standing need to diagnose and/or treat pathologies relating to impaired peripheral nervous system (PNS) nerve conduction associated with PNS injury or in genetic or other disease states, such as those involving lack of, or defects in, PNS sodium channels (SCs). In view of the possibility of cell or tissue specific sodium channels, the discovery and use of isolated PNS SCs and encoding nucleic acid would provide an opportunity to diagnose or treat such pathologies by either screening suitable PNS SC modulating drugs or molecules (e.g., analgesics), or by using recombinant PNS SCs for in situ or in vivo gene therapy to replace or supplement PNS SCs in at least one portion of the peripheral nervous system of a mammalian patient suffering from a PNS SC related pathology.

SUMMARY OF THE INVENTION

The present invention (hereinafter, "invention") provides peripheral nervous system specific (PNS) sodium channel peptides (SCPs), encoding nucleic acid, vectors, host cells and antibodies, as well as methods of making and using thereof, including recombinant expression, purification, cell-based drug screening, gene therapy, crystallization, X-ray diffraction analysis, as well as computer structure determination and rational drug design utilizing at least one PNS SCP amino acid sequence and/or x-ray diffraction data provided on computer readable media.

The invention also includes oligonucleotide probes specific for PNS SCP encoding sequences, as well as methods for dectection in a sample, where the probe is labeled. The invention further includes methods for producing a PNS SCP, comprising culturing a host in a culture medium, comprising a PNS SCP nucleic acid; and isolating the PNS SCP from said host or said culture medium.

The invention additionally includes an antibody which binds an epitope specific for a PNS SCP, as well as host cells which express the antibody. Diagnostic or therapeutic methods using the antibody are also included in the invention.

The invention further includes gene therapy methods and delivery vectors comprising nucleic acid encoding, or complementary to, at least one PNS SCP, and pharmaceutically acceptable compositions thereof.

The invention also includes gene therapy by methods that administer an antisense PNS SCP nucleic acid to an animal in amount effective to provide a PNS SC modulating effect, such as an analgesic effect.

The present invention further provides methods for purifying and crystallizing a PNS SCP that can be analyzed to obtain x-ray diffraction patterns of sufficiently high resolution to be useful for three-dimensional molecular modeling of the protein. The x-ray diffraction data, atomic coordinates, and/or amino acid sequences provided on computer readable medium, are modeled on computer systems, using methods of the invention, to generate secondary, tertiary and/or quaternary structures of a PNS SCP, which structures contribute to their overall three dimensional structure, as well as binding and active sites of the PNS SCP.

Molecular modeling methods and computer systems are also provided by the present invention for rational drug design (RDD). These drug design methods use computer modeling programs to find potential ligands or agents that are calculated to bind with sites or domains on the PNS SCP. Potential ligands or agents are then screened for modulating or binding activity. Such screening methods can be selected from assays for at least one biological activity of the protein, as associated with a PNS SCP-related pathology or trauma, according to known sodium channel assays. The resulting ligands provided by methods of the present invention are synthesized and are useful for treating, inhibiting or preventing at least one of PCS SCP-related pathology or trauma in a mammal.

Further objects, features, utilities, embodiments and/or advantages of the present invention will be apparent from the additional description provided herein.

BRIEF DESCRIPTION OF THE DRAWINGS

FIGS. 1A–B depicts a 323 amino acid and corresponding 969 nucleotide sequence of a PNS SCP as amino acids 233–555 of SEQ ID NO:2 and nucleotides 699–1665 of SEQ ID NO:1, as the primary structure of Domain III of the Peripheral Nerve type I (PN1) sodium channel alpha (α) subunit for both amino acid and DNA sequences. The single amino acid code is used to denote deduced amino acids. YJ1 and YOIC refer to the oligonucleotide primers used to obtain the initial PCR fragment of PN1 cDNA.

In FIG. 2(A), the probe used is pRB211 which encodes the highly conserved fourth repeated domain of the rat type II sodium channel. Both type H and PN1 mRNAs are detected with this probe. In FIG. 2(B), the probe used contains sequences specific for PN1. The levels of sodium channel mRNA are quantitated with reference to the amount of cyclophilin mRNA, as indicated. Control cells are PC 12 cells grown in the absence of NGF.

FIG. 3(A) presents a Northern blot analysis using equal amounts of RNA from tissues. PN1 mRNA is indicated by the dash. 28S refers to the 28S rRNA. The probe contains sequences specific for the PN1 gene. Note the absence of PN1 mRNA in skeletal muscle, cardiac muscle, and the low levels of PN1 mRNA in spinal cord. FIG. 3(B) shows RNAase protection analysis of PN1 mRNA. PN1 refers to the PN1 probe protected by mRNA from the different tissue samples. Actin refers to actin probe sequences protected by the same mRNA.

FIGS. 4A–F shows localization of PN1 mRNA in Superior Cervical Ganglion (SCG) and Dorsal Root Ganglion (DRG) tissues by in situ hybridization analysis. FIGS. 4A–4B represent neurons hybridized with a PN1-specific antisense RNA probe. FIGS. 4C–4D represent neurons hybridized with the radiolabeled PN1 probe in the presence of non-labeled PN1 competitor DNA. FIGS. 4E–4F represent tissue sections hybridized with an antisense type II probe.

FIG. 5 shows a blot analysis comparing Levels of PN1 and brain type I a subunit mRNA in SCG. The pRB11 conserved sodium channel probe detects both type II/IIA and PN1 transcripts.

FIG. 6(A) shows a representative autoradiogram of a Northern blot using radiolabeled antisense pRB211 RNA as probe. Postnatal days 7 (P7) to 42 (P42) are shown. FIG. 6(B) shows a plot of quantitation of the Northern blots showing a decrease in type I mRNA with time after birth.

FIGS. 7A–D show the deduced primary structure of cloned portion of PN1 a subunit cDNA as a partial 3033 nucleotide (SEQ ID NO:1) sequence and a partial 1011 amino acid (SEQ ID NO:2) sequence.

FIGS. 8A–D show a comparison of deduced primary amino acid sequences of PN1 (1–988 of SEQ ID NO:2) and brain type II/IIA α subunit (SEQ ID NO:7). A consensus sequence is also shown (SEQ ID NO:8)

FIGS. 9A–C show the entire DNA sequence for a rat PN1 PNS SCP(SEQ ID NO:9).

FIG. 10 shows the entire amino sequence for a rat PN1 PNS SCP (SEQ ID NO:10).

FIGS. 11A–F shows amino acid sequences for rat PN1 ("RATPN1") (SEQ ID NO:10) and two expected human PN1 sequences "HUMPN1A" (SEQ ID NO:11) "HUMPN1B" (SEQ ID NO:16) HUMPN1C (SEQ ID NO:15) and HUMPN1D (SEQ ID NO:12). Alternative sequences include those where "X" is 0, 1, 2, or 3 of the same or different amino acids, which can be optionally selected from Table 1 or Table 2.

FIGS. 13A–D shows a representative DNA sequence encoding a human PN1 (HUM PN1A) (SEQ ID NO:13)

FIGS. 14A–D shows a representative DNA sequence encoding a human PN1 (HUM PN1B) (SEQ ID NO:14)

DETAILED DESCRIPTION OF THE INVENTION

Figures 2A, 2B:
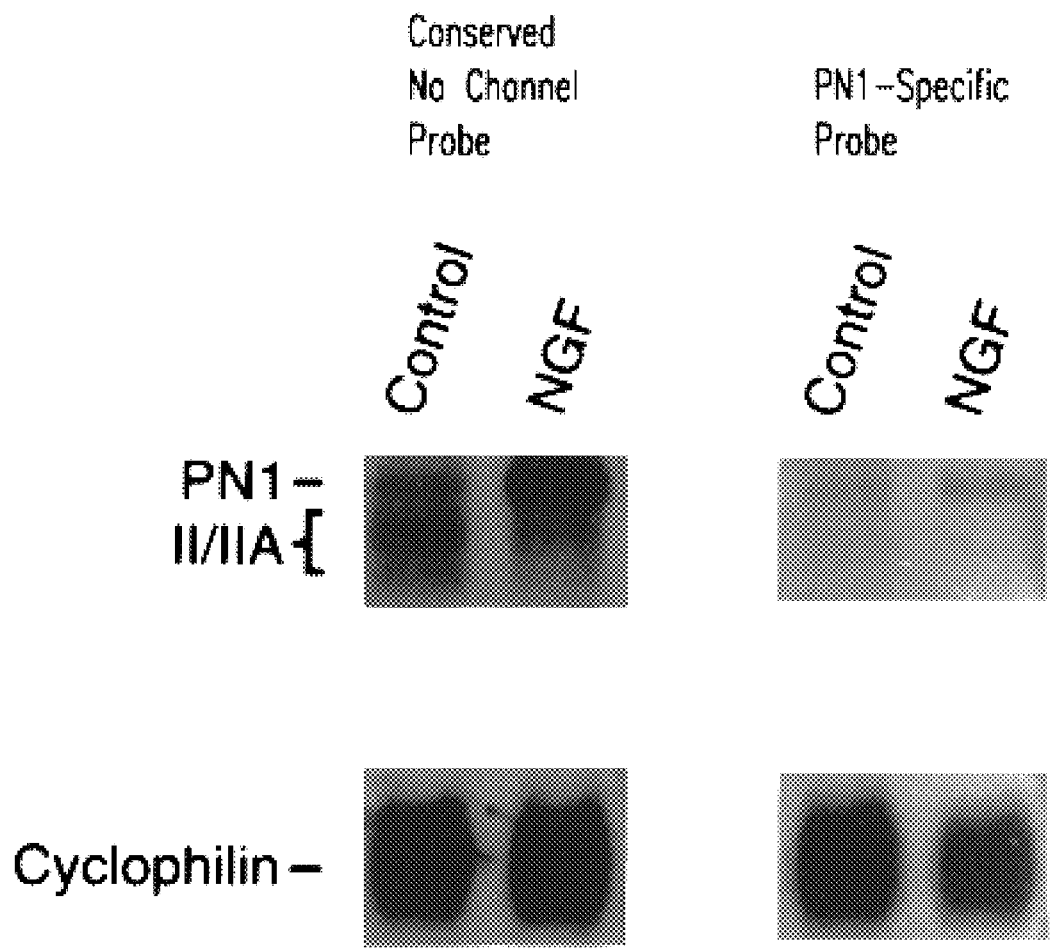
FIGS. 2A–B shows a Northern blot analysis of sodium channel α subunit mRNA in rat pheochromocytoma (PC12) cells treated with Nerve Growth Factor.

A need exists for modulating the activity of at least one peripheral nervous system specific (PNS) sodium channel (SCs). Such modulation could potentially provide analgesic or diagnostic agents for pain or pathologies associated with nerve conduction in the PNS.

Certain sodium channels—corresponding to PNS SCPs of the invention—are now discovered to be preferentially or selectively expressed in the peripheral nervous system (PNS). These sodium channels modulate peripheral nerve impulse conduction preferentially in the PNS. The present invention provides peripheral nervous system specific (PNS) sodium channel peptides (SCPs), encoding nucleic acid, vectors, host cells and antibodies, as well as methods of making and using thereof, including recombinant expression, purification, cell-based drug screening, gene therapy, crystallization, X-ray diffraction analysis, as well as computer structure determination and rational drug design utilizing at least one PNS SCP amino acid sequence and/or x-ray diffraction data provided on computer readable media.

A PNS sodium channel peptide (PNS SCP) can refer to any subset of a PNS sodium channel (SC) having SC activity, as a fragment, consensus sequence or repeating unit. A PNS SCP of the invention can be prepared by:

(a) recombinant DNA methods;
(b) proteolytic digestion of the intact molecule or a fragment thereof;
(c) chemical peptide synthesis methods well-known in the art; and/or
(d) by any other method capable of producing a PNS SCP and having a conformation similar to an active portion of a PNS SCP and having SC activity. The SC activity can be screened according to known screening assays for sodium channel activity, in vitro, in situ or in vivo. The minimum peptide sequence to have activity is based on the smallest unit containing or comprising a particular region, domain, consensus sequence, or repeating unit thereof, of at least one PNS SCP.

According to the invention, a PNS SCP includes an association of two or more polypeptide domains, such as transmembrane, pore lining domains, or fragments thereof, corresponding to a PNS SCP, such as 1–40 domains or any range or value therein. Transmembrane, cytoplasmic pore lining or other domains of a PNS SCP of the invention may have at least 74% homology, such as 74–100% overall homology or identity, or any range or value therein to one or more corresponding SC domains as described herein (e.g., as presented FIGS. 1, 7, 8, 10 or 11). As would be understood by one of ordinary skill in the art, the above configuration of domains are provided as part of a PNS SCP of the invention, such that a functional PNS SCP, when expressed in a suitable cell, is capable of transporting sodium ions across a lipid bilayer, a cell membrane or a membrane model. In intact cells having sufficient sodium channels, the cell can be capable of generating some form of an action potential, such as in a cell expressing at least one PNS SCP of the present invention. Such transport, as measured by suitable SC activity assays, establishes SC activity of one or more PNS SCPs of the invention.

Accordingly, a PNS SCP of the invention alternatively includes peptides having a portion of a SC amino acid sequence which substantially corresponds to at least one 20 to 2005 amino acid fragment and/or consensus sequence of a PNS SCP or group of PNS SCPs, wherein the PNS SCP has homology or identity of at least 74–99%, such as 88–99% (or any range or value therein, e.g., 87–99, 88–99, 89–99, 90–99, 91–99, 92–99, 93–99, 94–99, 95–99, 96–99, 97–99, or 98–99%) homology to at least one sequence or consensus sequence of FIGS. 1, 7, 8, 10 or 11. In one aspect, such a PNS SCP can maintain SC biological activity. It is preferred that a PNS SCP of the invention is not naturally occurring or is naturally occurring but is in a purified or isolated form which does not occur in nature. Preferably, a PNS SCP of the invention substantially corresponds to an set of domains of PN1, having at least 10 contiguous amino acids of FIGS. 1, 7, 8, 10 and 11, or at least 74% homology thereto.

Alternatively or additionally, a PNS SCP of the invention may comprise at least one domain corresponding to known sodium channel domains, such as rat brain or spinal cord SC domains, such as transmembrane domains, pore lining domains, cytoplasmic domains or extracellular domains, such as IIs6 (e.g., 1–3 to 14–17 (IIs6), 18–23 to 210–214 (cytoplasmic), 229–236 to 254–258 (IIIS1), 268–272 to 293–297 (IIIs2), 300–304 to 321–325 (IIIs3), 326–330 to 347–351 (IIIs4), 368–374 to 389–393 (IIIs5), 474–478 to 560–504 (IIs6), 553–559 to 577–583 (IVs1), 589–593 to 611–615 (IVs2), 619–623 to 642–646 (IVs3), 654–658 to 678–682 (IVs4), 690–694 to 711–715 (IVs5), 779–783 to 801–805 (IVs6), 348–352 to 368–372, 501–505 to 550–554, 233–555, 676–678 to 689–693, 554–557 to 941–945, or any range or value therein, corresponding to SEQ ID NO:2 as presented in FIGS. 7A–7D, or variants thereof as presented substitutions in Table 1 or Table 2, having 74–100% overall homology or any range or value therein. At least one of such domains are present in the PNS SCPs presented in FIGS. 11A–F, or fragments thereof, as non-limiting examples. Alternative domains are also encoded by DNA which hybridizes under stringent conditions to at least 30 contiguous nucleotides of FIGS. 1, 7, 9, 13 or 14, or having codons substituted therefor which encode the same amino acid as a particular codon. Additionally, phosphorylation (e.g., PKA and PKC) domains, as would be recognized by the those skilled in the art are also considered when providing a PNS SCP or encoding nucleic acid according to the invention.

Percent homology or identity can be determined, for example, by comparing sequence information using the GAP computer program, version 6.0, available from the University of Wisconsin Genetics Computer Group (UWGCG). The GAP program utilizes the alignment method of Needleman and Wunsch (J. Mol. Biol. 48:443 (1970), as revised by Smith and Waterman (i Adv. Appl. Math. 2:482 (1981). Briefly, the GAP program defines similarity as the number of aligned symbols (i.e., nucleotides or amino acids) which are similar, divided by the total number of symbols in the shorter of the two sequences. The preferred default parameters for the GAP program include: (1) a unitary comparison matrix (containing a value of 1 for identities and 0 for non-identities) and the weighted comparison matrix of Gribskov and Burgess, *Nucl. Acids Res.* 14:6745 (1986), as described by Schwartz and Dayhoff, eds., *ATLAS OF PROTEIN SEQUENCE AND STRUCTURE*, National Biomedical Research Foundation, pp. 353–358 (1979); (2) a penalty of 3.0 for each gap and an additional 0.10 penalty for each symbol in each gap; and (3) no penalty for end gaps. In a preferred embodiment, the peptide of the invention corresponds to a SC biologically active portion of SEQ ID NO:2, or variant thereof, e.g., as presented in FIGS. 11A–F.

Thus, one of ordinary skill in the art, given the teachings and guidance presented in the present specification, will know how to add, delete or substitute other amino acid residues in other positions of a SC to obtain a PNS SCP, including substituted, deletional or additional variants, e.g., with a substitution as presented in Tables 1 or 2 below.

A PNS SCP of the invention also includes a variant wherein at least one amino acid residue in the peptide has been conservatively replaced, added or deleted by at least one different amino acid. For a detailed description of protein chemistry and structure, See, e.g., Schulz, et al., *Principles of Protein Structure*, Springer-Verlag, New York, 1978, and Creighton, T. E., *Proteins: Structure and Molecular Properties*, W.H. Freeman & Co., San Francisco, 1983, which are hereby incorporated by reference. For a presentation of nucleotide sequence substitutions, such as codon preferences, see Ausubel et al, eds, *Current Protocols in Molecular Biology*, Greene Publishing Assoc., New York, N.Y. (1987, 1992, 1993, 1994, 1995) at §§ A.1.1–A.1.24, and Sambrook et al, *Molecular Cloning: A Laboratory Manual*, Second Edition, Cold Spring Harbor Press, Cold Spring Harbor, N.Y. (1989), at Appendices C and D.

Conservative substitutions of a PNS SCP of the invention includes a variant wherein at least one amino acid residue in the peptide has been conservatively replaced, added or deleted by at least one different amino acid. Such substitutions preferably are made in accordance with the following list as presented in Table 1, which substitutions can be determined by routine experimentation to provide modified structural and functional properties of a synthesized peptide molecule, while maintaining SC biological activity, as determined by known SC activity assays. In the context of the invention, the term PNS SCP or "substantially corresponding to" includes such substitutions.

TABLE 1

| Original Residue | Exemplary Substitution |
| --- | --- |
| Ala | Gly; Ser |
| Arg | Lys |
| Asn | Gln; His |
| Asp | Glu |
| Cys | Ser |
| Gln | Asn |
| Glu | Asp |
| Gly | Ala; Pro |
| His | Asn; Gln |
| Ile | Leu; Val |
| Leu | Ile; Val |
| Lys | Arg; Gln; Glu |
| Met | Leu; Tyr; Ile |
| Phe | Met; Leu; Tyr |
| Ser | Thr |
| Thr | Ser |

TABLE 1-continued

| Original Residue | Exemplary Substitution |
| --- | --- |
| Trp | Tyr |
| Tyr | Trp; Phe |
| Val | Ile; Leu |

Alternatively, another group of substitutions of PNS SCPs of the invention are those in which at least one amino acid residue in the protein molecule has been removed and a different residue added in its place according to the following Table 2. The types of substitutions which can be made in the protein or peptide molecule of the invention can be based on analysis of the frequencies of amino acid changes between a homologous protein of different species, such as those presented in Table 1-2 of Schulz et al., infra. Based on such an analysis, alternative conservative substitutions are defined herein as exchanges within one of the following five groups:

TABLE 2

1. Small aliphatic, nonpolar or slightly polar residues: Ala Ser, Thr (Pro, Gly);
2. Polar, negatively charged residues and their amnides: Asp. Asn, Glu, Gln;
3. Polar, positively charged residues:
   His, Arg, Lys;
4. Large aliphatic, nonpolar residues:
   Met, Leu, Ile, Val (Cys); and
5. Large aromatic residues: Phe, Tyr, Trp.

Most deletions and additions, and substitutions according to the invention are those which do not produce radical changes in the characteristics of the protein or peptide molecule. "Characteristics" is defined in a non-inclusive manner to define both changes in secondary structure, e.g. α-helix or β-sheet, as well as changes in physiological activity, e.g. in receptor binding assays.

Accordingly, based on the above examples of specific substitutions, alternative substitutions can be made by routine experimentation, to provide alternative PNS SCPs of the invention, e.g., by making one or more conservative substitutions of SC fragments which provide SC activity. However, when the exact effect of the substitution, deletion, or addition is to be confirmed, one skilled in the art will appreciate that the effect of at least one substitution, addition or deletion will be evaluated by at least one sodium channel activity screening assay, such as, but not limited to, immunoassays or bioassays, to confirm biological activity, such as, but not limited to, sodium channel activity.

Amino acid sequence variants of a PNS SCP of the invention can also be prepared by mutations in the DNA. Such variants include, for example, deletions from, or additions or substitutions of, residues within the amino acid sequence. Any combination of deletion, addition, and substitution can also be made to arrive at the final construct, provided that the final construct possesses some SC activity. Preferably improved SC activity is found over that of the non-variant peptide. Obviously, mutations that will be made in the DNA encoding the variant must not place the sequence out of reading frame and preferably will not create complementary regions that could produce secondary mRNA structure (see, e.g., EP Patent Application Publication No. 75,444; Ausubel, infra; Sambrook, infra). At the genetic level, these variants ordinarily are prepared by site-directed mutagenesis of nucleotides in the DNA encoding a PNS SCP, thereby producing DNA encoding the variant, and thereafter expressing the DNA in recombinant cell culture. The variants typically exhibit the same qualitative biological activity as the naturally occurring SC (see, e.g., Ausubel, infra; Sambrook, infra).

Once a PNS sodium channel structure or characteristics have been determined, PNS SCPs can be recombinantly or synthetically produced, or optionally purified, to provide commercially useful amounts of PNS SCPs for use in diagnostic or research applications, according to known method steps (see, e.g., Ausubel, infra, and Sambrook, infra, which references are herein entirely incorporated by reference).

A variety of methodologies known in the art can be utilized to obtain an isolated PNS SCP of the invention. In one embodiment, the peptide is purified from tissues or cells which naturally produce the peptide. Alternatively, the above-described isolated nucleic acid fragments could be used to expressed the PNS SCP protein in any organism. The samples of the invention include cells, protein extracts or membrane extracts of cells, or biological fluids. The sample will vary based on the assay format, the detection method and the nature of the tissues, cells or extracts used as the sample.

The cells and/or tissue can include, e.g., normal or pathologic animal cells or tissues, such as the peripheral nervous system, and extracts or cell cultures thereof, provided in vivo, in situ or in vitro, as cultured, passaged, non-passaged, transformed, recombinant, or isolated cells and/or tissues.

Any higher eukaryotic organism can be used as a source of at least one or PNS SCP of the invention, as long as the source organism naturally contains such a peptide. As used herein, "source organism" refers to the original organism from which the amino acid sequence of the peptide is derived, regardless of the organism the peptide is expressed in and/or ultimately isolated from. Preferred organisms as sources of at least one PNS SCP or encoding nucleic acid can be any vertebrate animal, such as mammals, birds, bony fish, electric eels, frogs and toads. Among mammals, the preferred recipients are mammals of the Orders Primata (including humans, apes and monkeys), Arteriodactyla (including horses, goats, cows, sheep, pigs), Rodenta (including mice, rats, rabbits, and hamsters), and Carnivora (including cats, and dogs). The most preferred source organisms are humans.

One skilled in the art can readily follow known methods for isolating proteins in order to obtain the peptide free of natural contaminants. These include, but are not limited to: immunochromotography, size-exclusion chromatography, HPLC, ion-exchange chromatography, and immunoaffinity chromatography. See, e.g., Ausubel, infra; Sambrook, infra; Colligan, infra.

Isolated Nucleic Acid Molecules Coding for PNS SCP Peptides In one embodiment, the present invention relates to an isolated nucleic acid molecule coding for a peptide having an amino acid sequence corresponding to novel PNS SCPs. In one preferred embodiment, the isolated nucleic acid molecule comprises a PNS SCP nucleotide sequence with greater than 70% overall identity or homology to at least a 60 nucleotide sequence present in SEQ ID NO:1 (preferably greater than 80%; more preferably greater than 90%, such as 70–99% any range or value therein). In another preferred embodiment, the isolated nucleic acid molecule comprises a PNS SCP nucleotide sequence corresponding to FIGS. 1, 7 or 9, or encoding at least one domain of FIGS. 1, 7, 8, 10 and 11.

Also included within the scope of this invention are the functional equivalents of the herein-described isolated nucleic acid molecules and derivatives thereof. For example, as presented above for PNS SCP amino acid sequences, the nucleic acid sequences depicted in SEQ ID NO:1 can be altered by substitutions, additions or deletions that provide for functionally equivalent molecules. Due to the degeneracy of nucleotide coding sequences, other DNA sequences which encode substantially the same amino acid sequence of a PNS SCP can be used in the practice of the invention. These include but are not limited to amino acid sequences encoding all or portions of PNS SCP amino acid sequence of FIGS. 1, 8, 10 and 11, which are altered by the substitution of different codons that encode a functionally equivalent amino acid residue within the sequence, thus producing a silent change.

Such functional alterations of a given nucleic acid sequence afford an opportunity to promote secretion and/or processing of heterologous proteins encoded by foreign nucleic acid sequences fused thereto. All variations of the nucleotide sequence of the PNS SCP gene and fragments thereof permitted by the genetic code are, therefore, included in this invention. See, e.g., Ausubel, infra; Sambrook, infra.

In addition, the nucleic acid sequence can comprise a nucleotide sequence which results from the addition, deletion or substitution of at least one nucleotide to the 5'-end and/or the 3'-end of a nucleic acid sequence corresponding to FIGS. 1, 7 or 9, or encoding at least a portion of FIGS. 1, 8, 10 or 11, or a variant thereof. Any nucleotide or polynucleotide can be used in this regard, provided that its addition, deletion or substitution does remove the sodium channel activity which is encoded by the nucleotide sequence. Moreover, the nucleic acid molecule of the invention can, as necessary, have restriction endonuclease recognition sites which do not remove the activity of the encoded PNS SCP.

Further, it is possible to delete codons or to substitute one or more codons by codons other than degenerate codons to produce a structurally modified peptide, but one which has substantially the same utility or activity of the peptide produced by the unmodified nucleic acid molecule. As recognized in the art, the two peptides are functionally equivalent, as are the two nucleic acid molecules which give rise to their production, even though the differences between the nucleic acid molecules are not related to degeneracy of the genetic code. See, e.g., Ausubel, infra; Sambrook, infra.

Isolation of Nucleic Acid In another aspect of the present invention, isolated nucleic acid molecules coding for peptides having amino acid sequences corresponding to PNS SCP are provided. In particular, the nucleic acid molecule can be isolated from a biological sample containing mammalian nucleic acid, as corresponding to a probe specific for a PNS SC obtained from a higher eukaryotic organism.

The nucleic acid molecule can be isolated from a biological sample containing nucleic acid using known techniques, such as but not limited to, primer amplification or cDNA cloning.

The nucleic acid molecule can be isolated from a biological sample containing genomic DNA or from a genomic library. Suitable biological samples include, but are not limited to, normal or pathologic animal cells or tissues, such as cerebrospinal fluid (CNS), peripheral nervous system (neurons, ganglion) and portions, cells of heart, smooth, skeletal or cardiac muscle, autonomic nervous system, and extracts or cell cultures thereof, provided in vivo, in situ or in vitro, as cultured, passaged, non-passaged, transformed, recombinant, or isolated cells and/or tissues. The method of obtaining the biological sample will vary depending upon the nature of the sample.

One skilled in the art will realize that a mammalian genome can be subject to slight allelic variations between individuals. Therefore, the isolated nucleic acid molecule is also intended to include allelic variations, so long as the sequence encodes a PNS SCP. When a PNS SCP allele does not encode the identical amino acid sequence to that found in FIGS. 1, 8, 10 or 11, or at least domain thereof, it can be isolated and identified as PNS SCP using the same techniques used herein, and especially nucleic acid amplification techniques to amplify the appropriate gene with primers based on the sequences disclosed herein. Such variations are presented, e.g., in FIG. 11 and in Tables 1 and 2.

The cloning of large cDNAs is the same (e.g., PN1 as a PNS SCP of the invention includes overlapping clones of about 13 kDa) but takes more routine experimentation, than smaller cDNAs. One useful method relies on cDNA bacteriophage library screening (see, e.g., Sambrook, infra, or Ausubel, infra). Probes for the screening are labeled, e.g., with random hexamers and Klenow enzyme (Pharmacia kit). If 5' cDNAs are not obtained with these approaches, a subcDNA library can be prepared in which a specific PN1 primers are used to prime the reverse transcript reaction in place of oligo dT or random primers. The cDNA sublibrary is then cloned into standard vectors such as lambda zap and screened using conventional techniques. This strategy was used previously (Noda et al. *Nature* 320:188–192 (1986); Noda et al., *Nature* 322:826–828 (1986)) to clone the brain type I and II sodium channel cDNAs. The construction of a full-length cDNA is performed by subcloning overlapping fragments into an expression vector (either prokaryotic or eukaryotic). This task is more difficult with large cDNAs because of the paucity of unique restriction sites, but routine restriction, cloning or PCR is used to join the fragments.

Synthesis of Nucleic Acid Isolated nucleic acid molecules of the present invention are also meant to include those chemically synthesized. For example, a nucleic acid molecule with the nucleotide sequence which codes for the expression product of a PNS SCP gene can be designed and, if necessary, divided into appropriate smaller fragments. Then an oligomer which corresponds to the nucleic acid molecule, or to each of the divided fragments, can be synthesized (e.g., of 10–6015 nucleotides or any range or value therein, such as 10–100 nucleotides). Such synthetic oligonucleotides can be prepared, for example, by known techniques (See, e.g., Ausubel, infra, or Sambrook, infra) or by using an automated DNA synthesizer.

A labeled oligonucleotide probe be derived synthetically or by cloning. If necessary, the 5'-ends of the oligomers can be phosphorylated using T4 polynucleotide kinase. Kinasing of single strands prior to annealing or for labeling can be achieved using an excess of the enzyme. If kinasing is for the labeling of probe, the ATP can contain high specific activity radioisotopes. Then, the DNA oligomer can be subjected to annealing and ligation with T4 ligase or the like.

A Nucleic Acid Probe for the Specific Detection of PNS SCP In another embodiment, the present invention relates to a nucleic acid probe of 15–6000 nucleotides for the specific detection of the presence of PNS SCP in a sample comprising the above-described nucleic acid molecules or at least a fragment thereof which binds under stringent conditions to a nucleic acid encoding at least one PNS SCP.

The nucleic acid probe can be used to screen an appropriate chromosomal or cDNA library by known hybridization method steps to obtain a PNS SCP encoding nucleic acid molecule of the invention. A chromosomal DNA or cDNA library can be prepared from appropriate cells according to recognized methods in the art (See, e.g., Ausubel, infra; Sambrook, infra).

In the alternative, organic chemical synthesis is carried out in order to obtain nucleic acid probes having nucleotide sequences which correspond to suitable portions of the amino acid sequence of the PNS SCP. Thus, the synthesized nucleic acid probes can be used as primers in nucleic acid amplification method steps.

The invention can thus provide methods for amplification of DNA and/or RNA using heat stable, cross-linked nucleotide primers, which cross linked primers of the invention to provide nucleic acid encoding PNS SCPs according to the invention.

Methods of amplification of RNA or DNA are well known in the art and can be used according to the invention without undue experimentation, based on the teaching and guidance presented herein. According to the invention, the use of nucleic acids encoding portions of PNS SCPs according to the invention, as amplification primers, allows for advantages over known amplification primers, due to the increase in sensitivity, selectivity and/or rate of amplification.

Known methods of DNA or RNA amplification include, but are not limited to polymerase chain reaction (PCR) and related amplification processes (see, e.g., U.S. Pat. Nos. 4,683,195, 4,683,202,4,800,159, 4,965,188, to Mullis et al.; 4,795,699 and 4,921,794 to Tabor et al; 5,142,033 to Innis; 5,122,464 to Wilson et al.; 5,091,310 to Innis; 5,066,584 to Gyllensten et al.; 4,889,818 to Gelfand et al.; 4,994,370 to Silver et al; 4,766,067 to Biswas; 4,656,134 to Ringold; 5,340,728 to Grosz et al.; 5,322,770 to Gelfand et al; 5,338,671 to Scalice et al; PCT WO 92/06200 to Cetus Corp.; PCT WO 94/14978 to Strack el al, which patent disclosures are entirely incorporated herein by reference) and RNA mediated amplification which uses antisense RNA to the target sequence as a template for double stranded DNA synthesis (U.S. Pat. No. 5,130,238 to Malek et al., with the tradename NASBA), the entire contents of which patents and references are herein entirely incorporated by reference. Reviews of the PCR are provided by Mullis (*Cold Spring Harbor Symp. Quant. Biol.* 51:263–273 (1986)); Saiki et al. (*Bio/Technology* 3:1008–1012 (1985)); and Mullis et al. (*Meth. Enzymol.* 155:335–350 (1987)). One skilled in the art can readily design such probes based on the sequence disclosed herein using methods such as computer alignment and sequence analysis known in the art. See, e.g. Ausubel, infra; Sambrook, infra.

The hybridization probes of the invention can be labeled by standard labeling techniques such as with a radiolabel, enzyme label, fluorescent label, biotin-avidin label, chemiluminescence, and any other known and suitable labels. After hybridization, the probes can be visualized using known methods. The nucleic acid probes of the invention include RNA, as well as DNA probes, such probes being generated using techniques known in the art (See, e.g., Ausubel, infra; Sambrook, infra). In one embodiment of the above described method, a nucleic acid probe is immobilized on a solid support. Examples of such solid supports include, but are not limited to, plastics such as polycarbonate, complex carbohydrates such as agarose and SEPHAROSE, and acrylic resins, such as polyacrylamide and latex beads. Techniques for coupling nucleic acid probes to such solid supports are well known in the art (See, e.g., Ausubel, infra; Sambrook, infra).

The test samples suitable for nucleic acid probing methods of the invention include, for example, cells or nucleic acid extracts of cells, or biological fluids. The sample used in the above-described methods will vary based on the assay format, the detection method and the nature of the tissues, cells or extracts to be assayed. Methods for preparing nucleic acid extracts of cells are well known in the art and can be readily adapted in order to obtain a sample which is compatible with the method utilized.

Methods for Detecting The Presence of PNS SCP Encoding Nucleic Acid in a Biological Sample. In another embodiment, the present invention relates to methods for detecting the presence of PNS SCP encoding nucleic acid in a sample. Such methods can comprise (a) contacting the sample with the above-described nucleic acid probe, under conditions such that hybridization occurs, and (b) detecting the presence of a labeled probe bound to the nucleic acid probe. One skilled in the art can select a suitable, labeled nucleic acid probe according to techniques known in the art as described above. Samples to be tested include, but are not limited to, RNA samples of mammalian tissue.

PNS SCP has been found to be expressed in peripheral nerve and dorsal root ganglion cells. Accordingly, PNS SCP probes can be used detect the presence of RNA from PN cells in such a biological sample. Further, altered expression levels of PNS SCP RNA in an individual, as compared to normal levels, can indicate the presence of disease. The PNS SCP probes can further be used to assay cellular activity in general and specifically in peripheral nervous system tissue.

A Kit for Detecting the Presence of PNS SCP in a Sample. In another embodiment, the present invention relates to a kit for detecting the presence of PNS SCP in a sample comprising at least one container having disposed therein the above-described nucleic acid probe. In a preferred embodiment, the kit further comprises other containers comprising one or more of the following: wash reagents and reagents capable of detecting the presence of bound nucleic acid probe. Examples of detection reagents include, but are not limited to radiolabeled probes, enzymatic labeled probes (horse radish peroxidase, alkaline phosphatase), and affinity labeled probes (biotin, avidin, or steptavidin) (See, e.g., Ausubel, infra; Sambrook, infra).

A compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (such as phosphate buffered saline, TRIS-buffers, and the like), and containers which contain the reagents used to detect the hybridized probe, bound antibody, amplified product, or the like.

One skilled in the art will readily recognize that the nucleic acid probes described in the invention can readily be incorporated into one of the established kit formats which are well known in the art.

DNA Constructs Comprising a PNS SCP Nucleic Acid Molecule and Hosts Containing These Constructs. A nucleic acid sequence encoding an PNS SCP of the invention can be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, e.g., by Ausubel el al., infra, and are well known in the art.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression as PNS SCPs or Ab fragments in recoverable amounts. The precise nature of the regulatory regions needed for gene expression can vary from organism to organism, as is well known in the analogous art. See, e.g., Sambrook, infra and Ausubel infra.

The invention accordingly encompasses the expression of an PNS SCP, in either prokaryotic or eukaryotic cells, although eukaryotic expression is preferred.

Preferred hosts are bacterial or eukaryotic hosts including bacteria, yeast, insects, fungi, bird and mammalian cells either in vivo, or in situ, or host cells of mammalian, insect, bird or yeast origin. It is preferred that the mammalian cell or tissue is of human, primate, hamster, rabbit, rodent, cow, pig, sheep, horse, goat, dog or cat origin, but any other mammalian cell can be used.

Eukaryotic hosts can include yeast, insects, fungi, and mammalian cells either in vivo, or in tissue culture. Preferred eukaryotic hosts can also include, but are not limited to insect cells, mammalian cells either in vivo, or in tissue culture. Preferred mammalian cells include Xenopus oocytes, HeLa cells, cells of fibroblast origin such as VERO or CHO-K1, or cells of lymphoid origin and their derivatives.

Mammalian cells provide post-translational modifications to protein molecules including correct folding or glycosylation at correct sites. Mammalian cells which can be useful as hosts include cells of fibroblast origin such as, but not limited to, NIH 3T3, VERO or CHO, or cells of lymphoid origin, such as, but not limited to, the hybridoma SP2/O-Ag14 or the murine myeloma P3-X63Ag8, hamster cell lines (e.g., CHO-K1 and progenitors, e.g., CHO-DUXB11) and their derivatives. One preferred type of mammalian cells are cells which are intended to replace the function of the genetically deficient cells in vivo. Neuronally derived cells are preferred for gene therapy of disorders of the nervous system. For a mammalian cell host, many possible vector systems are available for the expression of at least one PNS SCP. A wide variety of transcriptional and translational regulatory sequences can be employed, depending upon the nature of the host. The transcriptional and translational regulatory signals can be derived from viral sources, such as, but not limited to, adenovirus, bovine papilloma virus, Simian virus, or the like, where the regulatory signals are associated with a particular gene which has a high level of expression. Alternatively, promoters from mammalian expression products, such as, but not limited to, actin, collagen, myosin, protein production. See, Ausubel, infra,; Sanbrook, infra.

When live insects are to be used, silk moth caterpillars and baculoviral vectors are presently preferred hosts for large scale PNS SCP production according to the invention. Production of PNS SCPs in insects can be achieved, for example, by infecting the insect host with a baculovirus engineered to express at least one PNS SCP by methods known to those skilled in the related arts. See Ausubel et al, eds. *Current Protocols in Molecular Biology*, Wiley Interscience, §§16.8–16.11 (1987, 1992, 1993, 1994).

In a preferred embodiment, the introduced nucleotide sequence will be incorporated into a plasmid or viral vector capable of autonomous replication in the recipient host. Any of a wide variety of vectors can be employed for this purpose. See, e.g., Ausubel et al., infra, §§ 1.5, 1.10, 7.1, 7.3, 8.1, 9.6, 9.7, 13.4, 16.2, 16.6, and 16.8–16.11. Factors of importance in selecting a particular plasmid or viral vector include: the ease with which recipient cells that contain the vector can be recognized and selected from those recipient cells which do not contain the vector; the number of copies of the vector which are desired in a particular host; and whether it is desirable to be able to "shuttle" the vector between host cells of different species.

Different host cells have characteristic and specific mechanisms for the translational and post-translational processing and modification (e.g., glycosylation, cleavage) of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of the heterologous PNS SCP protein. Furthermore, different vector/host expression systems can effect processing reactions such as proteolytic cleavages to different extents.

As discussed above, expression of PNS SCP in eukaryotic hosts requires the use of eukaryotic regulatory regions. Such regions will, in general, include a promoter region sufficient to direct the initiation of RNA synthesis. See, e.g., Ausubel, infra; Sambrook, infra.

Once the vector or nucleic acid molecule containing the construct(s) has been prepared for expression, the DNA construct(s) can be introduced into an appropriate host cell by any of a variety of suitable means, i.e., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene molecule(s) results in the production of at least one PNS SCP. This can take place in the transformed cells as such, or following the induction of these cells to differentiate (for example, by administration of bromodeoxyuracil to neuroblastoma cells or the like).

Isolation of PNS SCP. The PNS SCP proteins or fragments of this invention can be obtained by expression from recombinant DNA as described above. Alternatively, a PNS SCP can be purified from biological material. If so desired, the expressed at least one PNS SCP can be isolated and purified in accordance with conventional method steps, such as extraction, precipitation, chromatography, affinity chromatography, electrophoresis, or the like. For example, cells expressing at least one PNS SCP in suitable levels can be collected by centrifugation, or with suitable buffers, lysed, and the protein isolated by column chromatography, for example, on DEAE-cellulose, phosphocellulose, polyribocytidylic acid-agarose, hydroxyapatite or by electrophoresis or immunoprecipitation. Alternatively, PNS SCPs can be isolated by the use of specific antibodies, such as, but not limited to, an PNS SCP or SC antibody. Such antibodies can be obtained by known method steps (see, e.g. Colligan, infra; Ausubel, infra.

For purposes of the invention, one method of purification which is illustrative, without being limiting, consists of the following steps. A first step in the purification of a PNS SCP includes extraction of the PNS SCP fraction from a biological sample, such as peripheral nerve tissue or dorsal root ganglia (DRG), in buffers, with or without solubilizing agents such as urea, formic acid, detergent, or thiocyanate. A second step includes subjecting the solubilized material to ion-exchange chromatography on Mono-Q or Mono-S columns (Pharmacia LKB Biotechnology, Inc; Piscataway, N.J.). Similarly, the solubilized material can be separated by any other process wherein molecules can be separated according to charge density, charge distribution and molecular size, for example. Elution of the PNS SCP from the ion-exchange resin are monitored by an immunoassay, such as M-IRMA, on each fraction. Immunoreactive peaks would are then dialyzed, lyophilized, and subjected to molecular sieve, or gel chromatography. In a third step, molecular sieve or gel chromatography is a type of partition chromatography in which separation is based on molecular size. Dextran, polyacrylamide, and agarose gels are commonly used for this type of separation. One useful gel for the invention is SEPHAROSE 12 (Pharmacia LKB Biotechnology, Inc.). However, other methods, known to those of skill in the art can be used to effectively separate molecules based on size. A fourth step in a purification protocol for a PNS SCP can include analyzing the immunoreactive peaks by sodium dodecyl sulfate-polyacrylamide gel electrophoresis (SDS-PAGE), a further gel chromatographic purification step, and staining, such as, for example, silver staining. A fifth step in a purification method can include subjecting the PNS SCP obtained after SDS-PAGE to affinity chromatography, or any other procedure based upon affinity between a substance to be isolated and a molecule to which it can specifically bind. For further purification of a PNS SCP, affinity chromatography on SEPHAROSE conjugated to anti-PNS SCP mAbs (specific mABs generated against substantially pure PNS SCP) can be used. Alternative methods, such as reverse-phase HPLC, or any other method characterized by rapid separation with good peak resolution are useful.

It will be appreciated that other purification steps can be substituted for the preferred method described above. Those of skill in the art will be able to devise alternate purification schemes without undue experimentation.

An Antibody Having Binding Affinity to a PNS SCP Peptide and a Hybridoma Containing the Antibody. In another embodiment, the invention relates to an antibody having binding affinity specifically to a PNS SCP peptide as described above or fragment thereof. Those which bind selectively to PNS SCP would be chosen for use in methods which could include, but should not be limited to, the analysis of altered PNS SCP expression in tissue containing PNS SCP.

The PNS SCP proteins of the invention can be used in a variety of procedures and methods, such as for the generation of antibodies, for use in identifying pharmaceutical compositions, and for studying DNA/protein interaction.

The PNS SCP peptide of the invention can be used to produce antibodies or hybridomas. One skilled in the art will recognize that if an antibody is desired, such a peptide would be generated as described herein and used as an immunogen.

The antibodies of the invention include monoclonal and polyclonal antibodies, as well as fragments of these antibodies. The invention further includes single chain antibodies. Antibody fragments which contain the idiotype of the molecule can be generated by known techniques.

The term "antibody" is meant to include polyclonal antibodies, monoclonal antibodies (mAbs), chimeric antibodies, anti-idiotypic (anti-Id) antibodies to antibodies that can be labeled in soluble or bound form, as well as fragments thereof provided by any known technique, such as, but not limited to enzymatic cleavage, peptide synthesis or recombinant techniques. Polyclonal antibodies are heterogeneous populations of antibody molecules derived from the sera of animals immunized with an antigen. A monoclonal antibody contains a substantially homogeneous population of antibodies specific to antigens, which population contains substantially similar epitope binding sites. MAbs can be obtained by methods known to those skilled in the art. See, e.g., Kohler and Milstein, *Nature* 256:495–497 (1975); U.S. Pat. No. 4,376,110; Ausubel et al, eds., *CURRENT PROTOCOLS IN MOLECULAR BIOLOGY*, Greene Publishing Assoc. and Wiley Interscience, N.Y., (1987, 1992); and Harlow and Lane *ANTIBODIES: A LABORATORY MANUAL* Cold Spring Harbor Laboratory (1988); Colligan et al., eds., *Current Protocols in Immunology,* Greene Publishing Assoc. and Wiley Interscience, N.Y., (1992, 1993), the contents of which references are incorporated entirely herein by reference. Such antibodies can be of any immunoglobulin class including IgG, IgM, IgE, IgA, GILD and any subclass thereof. A hybridoma producing a mAb of the invention can be cultivated in vitro, in situ or in vivo. Production of high titers of mAbs in vivo or in situ makes this the presently preferred method of production.

Chimeric antibodies are molecules different portions of which are derived from different animal species, such as those having variable region derived from a murine mAb and a human immunoglobulin constant region, which are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (Cabilly et al, *Proc. Natl. Acad Sci. USA* 81:3273–3277 (1984); Morrison et al., *Proc. Natl. Acad Sci. USA* 81:6851–6855 (1984); Boulianne et al., *Nature* 312:643–646 (1984); Cabilly et al., European Patent Application 125023; Neuberger et al., *Nature* 314:268–270 (1985); Taniguchi et al, European Patent Application 171 496; Morrison et al., European Patent Application 173 494; Neuberger el al., PCT Application WO 86/01533; Kudo et al, European Patent Application 184 187; Morrison et al, European Patent Application 173 494; Sahagan et al., *J. Immunol.* 137:1066–1074 (1986); Robinson et al., International Patent Publication No. PCT/US 86/02269; Liu et al., *Proc. Natl. Acad. Sci. USA* 84:3439–3443 (1987); Sun et al., *Proc. Natl. Acad. Sci. USA* 84:214–218 (1987); Better et al., *Science* 240:1041–1043 (1988); and Harlow, infra. These references are entirely incorporated herein by reference.

An anti-idiotypic (anti-id) antibody is an antibody which recognizes unique determinants generally associated with the antigen-binding site of an antibody. An Id antibody can be prepared by immunizing an animal of the same species and genetic type (e.g., mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference.

The anti-Id antibody can also be used as an "immunogen" to induce an immune response in yet another animal, producing a so-called anti-anti-Id antibody. The anti-anti-ld can be epitopically identical to the original mAb which induced the anti-Id. Thus, by using antibodies to the idiotypic determinants of a mAb, it is possible to identify other clones expressing antibodies of identical specificity.

Accordingly, mAbs generated against a PNS SCP of the invention can be used to induce anti-id antibodies in suitable animals, such as BALB/c mice. Spleen cells from such immunized mice are used to produce anti-Id hybridomas secreting anti-Id mAbs. Further, the anti-id mAbs can be coupled to a carrier such as keyhole limpet hemocyanin (KLH) and used to immunize additional BALB/c mice. Sera from these mice will contain anti-anti-Id antibodies that have the binding properties of the original mAb specific for a PNS SCP specific epitope. The anti-id mAbs thus have their own idiotypic epitopes, or "idiotopes" structurally similar to the epitope being evaluated.

The term "antibody" is also meant to include both intact molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and can have less non-specific tissue binding than an intact antibody (Wahl et al., *J. Nucl. Med.* 24:316–325 (1983)). It will be appreciated that Fab and F(ab')$_2$ and other fragments of the antibodies useful in the invention can be used for the detection and/or quantitation of a PNS SCP according to the methods disclosed herein for intact antibody molecules. Such fragments are typically produced by proteolytic cleavage, using enzymes such as papain (to produce Fab fragments) or pepsin (to produce F(ab')$_2$ fragments). An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen can have one, or more than one epitope. The specific reaction referred to above is meant to indicate that the antigen will react, in a highly selective manner, with its corresponding antibody and not with the multitude of other antibodies which can be evoked by other antigens.

Immunoassays. Antibodies of the invention, directed against a PNS SCP, can be used to detect or diagnose a PNS SC or a PNS SC-related pathologies. Screening methods are provided by the invention can include, e.g., immunoassays employing radioimmunoassay (RIA) or enzyme-linked immunosorbant assay (ELISA) methodologies, based on the production of specific antibodies (monoclonal or polyclonal) to a PNS SCP. For these assays, biological samples are obtained by, nerve biopsy, or other peripheral nervous system tissue sampling. For example, in one form of RIA, the substance under test is mixed with diluted antiserum in the presence of radiolabeled antigen. In this method, the concentration of the test substance will be inversely proportional to the amount of labeled antigen bound to the specific antibody and directly related to the amount of free labeled antigen. Other suitable screening methods will be readily apparent to those of skill in the art.

Furthermore, one skilled in the art can readily adapt currently available procedures, as well as the techniques, methods and kits disclosed above with regard to antibodies, to generate peptides capable of binding to a specific peptide sequence in order to generate rationally designed antipeptide peptides, for example see Hurby et al., "Application of Synthetic Peptides: Antisense Peptides", In: *Synthetic*

*Peptides, A User's Guide*, W.H. Freeman, NY, pp. 289–307 (1992), and Kaspczak et al., Biochemistry 28:9230–8 (1989).

One embodiment for carrying out the diagnostic assay of the invention on a biological sample containing a PNS SCP, comprises:

(a) contacting a detectably labeled PNS SCP-specific antibody with a solid support to effect immobilization of said PNS SCP-specific antibody or a fragment thereof;

(b) contacting a sample suspected of containing a PNS SCP with said solid support;

(c) incubating said detectably labeled PNS SCP-specific antibody with said support for a time sufficient to allow the immobilized PNS SCP-specific antibody to bind to the PNS SCP;

(d) separating the solid phase support from the incubation mixture obtained in step (c); and (e) detecting the bound label and thereby detecting and quantifying PNS SCP.

The specific concentrations of detectably labeled antibody and PNS SCP, the temperature and time of incubation, as well as other assay conditions can be varied, depending on various factors including the concentration of a PNS SCP in the sample, the nature of the sample, and the like. The binding activity of a given lot of anti-PNS SCP antibody can be determined according to well known methods. Those skilled in the ant will be able to determine operative and optimal assay conditions for each determination by employing routine experimentation. Other such steps as washing, stirring, shaking, filtering and the like can be added to the assays as is customary or necessary for the particular situation.

Detection can be accomplished using any of a variety of assays. For example, by radioactively labeling the PNS SCP-specific antibodies or antibody fragments, it is possible to detect PNS SCP through the use of radioimmune assays. A good description of a radioimmune assay can be found in Colligan, infra, and Ausubel, infra, entirely incorporated by reference herein. Preferably, the detection of cells which express a PNS SCP can be accomplished by in vivo imaging techniques, in which the labeled antibodies (or fragments thereof) are provided to a subject, and the presence of the PNS SCP is detected without the prior removal of any tissue sample. Such in vivo detection procedures have the advantage of being less invasive than other detection methods, and are, moreover, capable of detecting the presence of PNS SCP in tissue which cannot be easily removed from the patient, such as brain tissue.

There are many different in vivo labels and methods of labeling known to those of ordinary skill in the art. Examples of the types of labels which can be used in the invention include radioactive isotopes and paramagnetic isotopes. Those of ordinary skill in the art will know of other suitable labels for binding to the antibodies used in the invention, or will be able to ascertain such, using routine experimentation. Furthermore, the binding of these labels to the antibodies can be done using standard techniques common to those of ordinary skill in the art.

For diagnostic in vivo imaging, the type of detection instrument available is a major factor in selecting a given radionuclide. The radionuclide chosen must have a type of decay which is detectable for a given type of instrument. In general, any conventional method for visualizing diagnostic imaging can be utilized in accordance with this invention. For example, positron emission tomography (PET), gamma, beta, and magnetic resonance imaging (MRI) detectors can be used to visualize diagnostic imagining.

The antibodies useful in the invention can also be labeled with paramagnetic isotopes for purposes of in vivo diagnosis. Elements which are particularly useful, as in Magnetic Resonance Imaging (MRI), include $^{157}$Gd, $^{55}$Mn, $^{162}$Dy, and $^{56}$Fe.

The antibodies (or fragments thereof) useful in the invention are also particularly suited for use in in vitro immunoassays to detect the presence of a PNS SCP in body tissue, fluids (such as CSF), or cellular extracts. In such immunoassays, the antibodies (or antibody fragments) can be utilized in liquid phase or, preferably, bound to a solid-phase carrier, as described above.

In situ detection can be accomplished by removing a histological specimen from a patient, and providing the combination of labeled antibodies of the invention to such a specimen. The antibody (or fragment) is preferably provided by applying or by overlaying the labeled antibody (or fragment) to a biological sample. Through the use of such a procedure, it is possible to determine not only the presence of a PNS SCP, but also the distribution of a PNS SCP on the examined tissue. Using the invention, those of ordinary skill will readily perceive that any of a wide variety of histological methods (such as staining procedures) can be modified in order to achieve such in situ detection.

As used herein, an effective amount of a diagnostic reagent (such as an antibody or antibody fragment) is one capable of achieving the desired diagnostic discrimination and will vary depending on such factors as age, condition, sex, the extent of disease of the subject, counter-indications, if any, and other variables to be adjusted by the physician. The amount of such materials which are typically used in a diagnostic test are generally between 0.1 to 5 mg, and preferably between 0.1 to 0.5 mg.

The assay of the invention is also ideally suited for the preparation of a kit. Such a kit can comprise a carrier means being compartmentalized to receive in close confinement therewith one or more container means such as vials, tubes and the like, each of said container means comprising the separate elements of the immunoassay.

For example, there can be a container means containing a first antibody immobilized on a solid phase support, and a further container means containing a second detectably labeled antibody in solution. Further container means can contain standard solutions comprising serial dilutions of the PNS SCP to be detected. The standard solutions of a PNS SCP can be used to prepare a standard curve with the concentration of PNS SCP plotted on the abscissa and the detection signal on the ordinate. The results obtained from a sample containing a PNS SCP can be interpolated from such a plot to give the concentration of the PNS SCP.

Diagnostic Screening and Treatment. It is to be understood that although the following discussion is specifically directed to human patients, the teachings are also applicable to any animal that expresses at least one PNS SC. The diagnostic and screening methods of the invention are especially useful for a patient suspected of being at risk for developing a disease associated with an altered expression level of PNS SCP based on family history, or a patient in which it is desired to diagnose a PNS SCP-related disease.

According to the invention, presymptomatic screening of an individual in need of such screening is now possible using DNA encoding the PNS SCP protein of the invention. The screening method of the invention allows a presymptomatic diagnosis, including prenatal diagnosis, of the presence of a missing or aberrant PNS SC gene in individuals, and thus an opinion concerning the likelihood that such individual would develop or has developed a PNS SC-associated disease. This is especially valuable for the identification of carriers of altered or missing PNS SC genes, for example, from individuals with a family history of a PNS SC-related pathology. Early diagnosis is also desired to maximize appropriate timely intervention.

In one preferred embodiment of the method of screening, a tissue sample would be taken from such individual, and screened for (1) the presence of the "normal" PNS SCP gene; (2) the presence of PNS SCP mRNA and/or (3) the presence of PNS SCP protein. The normal human gene can be characterized based upon, for example, detection of restriction digestion patterns in "normal" versus the patient's DNA, including RFLP analysis, using DNA probes prepared against the PNS SCP sequence (or a functional fragment thereof) taught in the invention. Similarly, PNS SCP mRNA can be characterized and compared to normal PNS SCP mRNA (a) levels and/or (b) size as found in a human population not at risk of developing PNS SCP-associated disease using similar probes. Lastly, PNS SCP protein can be (a) detected and/or (b) quantitated using a biological assay for PNS SCP activity or using an immunological assay and PNS SCP antibodies. When assaying PNS SCP protein, the immunological assay is preferred for its speed. An (I) aberrant PNS SCP DNA size pattern, and/or (2) aberrant PNS SCP mRNA sizes or levels and/or (3) aberrant PNS SCP protein levels would indicate that the patient is at risk for developing a PNS SCP-associated disease.

The screening and diagnostic methods of the invention do not require that the entire PNS SCP DNA coding sequence be used for the probe. Rather, it is only necessary to use a fragment or length of nucleic acid that is sufficient to detect the presence of the PNS SCP gene in a DNA preparation from a normal or affected individual, the absence of such gene, or an altered physical property of such gene (such as a change in electrophoretic migration pattern).

Prenatal diagnosis can be performed when desired, using any known method to obtain fetal cells, including amniocentesis, chorionic villous sampling (CVS), and fetoscopy. Prenatal chromosome analysis can be used to determine if the portion of the chromosome possessing the normal PNS SCP gene is present in a heterozygous state.

Overview of PNS SCP Purification and Crystallization Methods. In general, a PNS SCP as a membrane protein, is purified in soluble form using detergents (e.g., octyglucosides) or other suitable amphiphillic molecules. The resulting PNS SCP is in sufficient purity and concentration for crystallization. The purified PNS SCP is then isolated and assayed for biological activity and for lack of aggregation (which interferes with crystallization). The purified and cleaved PNS SCP preferably runs as a single band under reducing or nonreducing polyacrylamide gel electrophoresis (PAGE) (nonreducing is used to evaluate the presence of cysteine bridges). The purified PNS SCP is preferably crystallized under varying conditions of at least one of the following: pH, buffer type, buffer concentration, salt type, polymer type, polymer concentration, other precipitating ligands and concentration of purified and cleaved PNS SCP by known methods. See, e.g., Michel, *Trends in Biochem. Sci.* 8:56–59 (1983); Deisenhofer et al *J. Mol. Biol* 180:385–398 (1984); Weiss et al. *FEBS Let.* 267:268–272 (1990). Blundell, et al. *Protein Crystallography* Academic Press, London (1976); Oxender et al. eds., *Protein Engineering* Liss, New York (1986); McPherson; *The Preparation and Analysis of Protein Crystals* Wiley, N.Y. (1982); or the methods provided in a commercial kit, such as CRYS-TAL SCREEN (Hampton Research, Riverside, Calif.). The crystallized protein is also tested for at least one SC activity and differently sized and shaped crystals are further tested for suitability in X-ray diffraction. Generally, larger crystals provide better crystallography than smaller crystals, and thicker crystals provide better crystallography than thinner crystals. See, e.g., Blundell., infra; Oxender, infra; McPherson, infra; Wyckoff et al, eds., *Diffraction Methods for Biological Macromolecules*, Vols. 114–115. *Methods in Enzymology*, Orlando, Fla. Academic Press (1985).

Protein Crystallization Methods. The hanging drop method is preferably used to crystallize a purified soluble, PNS SCP protein. See, e.g., Tayloretal., *J. Mol. Biol.* 226:1287–1290 (1992); Takimoto et al. (1992), infra; CRYSTAL SCREEN, Hampton Research. A mixture of the protein and precipitant can include the following: • pH (e.g., 4–10); • buffer type (e.g., tromethamine (TRIZMA), sodium azide, phosphate, sodium, or cacodylate acetates, imidazole, Tris HCl, sodium hepes); • buffer concentration (e.g., 0.1–100 mM); • salt type (e.g., sodium azide, calcium chloride, sodium citrate, magnesium chloride, ammonium acetate, ammonium sulfate, potassium phosphate, magnesium acetate, zinc acetate; calcium acetate); • polymer type and concentration: (e.g., polyethylene glycol (PEG) 1–50%, type 6000–10,000); • other precipitating ligands (salts: potassium, sodium, tartrate, ammonium sulfate, sodium acetate, lithium sulfate, sodium formate, sodium citrate, magnesium formate, sodium phosphate, potassium phosphage; organics: 2-propanol; non-volatile: 2-methyl-2,4-pentanediol); and • concentration of purified PNS SCP (e.g., 0.1–100 mg/ml, with added amphiphillic molecules (detergents such as octylgluosides)). See, e.g. CRYSTAL SCREEN, Hampton Research.

The above mixtures are used and screened by varying at least one of pH, buffer type; buffer concentration, precipitating salt type or concentration, PEG type, PEG concentration, and cleaved protein concentration. Crystals ranging in size from 0.1–1.5 mm are formed in 1–14 days. These crystals diffract X-rays to at least 10 Å resolution, such as 1.5–10.0 Å, or any range of value therein, such as 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5 or 3, with 3.5 Å or less being preferred for the highest resolution. In addition to diffraction patterns having this highest resolution, lower resolution, such as 25–3.5 Å can further be used.

Protein Crystals. Crystals appear after 1–14 days and continue to grow on subsequent days. Some of the crystals are removed, washed, and assayed for biological activity, which activity is preferred for using in further characterizations. Other washed crystals are preferably run on a stained gel and those that migrate in the same position as the purified cleaved PNS SCP are preferably used. From two to one hundred crystals are observed in one drop and crystal forms can occur, such as, but not limited to, bipyramidal, rhomboid, and cubic. Initial X-ray analyses are expected to indicate that such crystals diffract at moderately high to high resolution. When fewer crystals are produced in a drop, they can be much larger size, e.g., 0.2–1.5 mm.

PNS SCP X-ray Crystallography Methods. The crystals so produced for a PNS SCP are X-ray analyzed using a suitable X-ray source. A suitable number of diffraction patterns are obtained. Crystals are preferably stable for at least 10 hrs in the X-ray beam. Frozen crystals (e.g., −220 to −50° C.) are optionally used for longer X-ray exposures (e.g., 4–72 hrs), the crystals being relatively more stable to the X-rays in the frozen state. To collect the maximum number of useful reflections, multiple frames are optionally collected as the crystal is rotated in the X-ray beam, e.g., for 12–96 hrs. Larger crystals (>0.2 mm) are preferred, to increase the resolution of the X-ray diffraction. Crystals are preferably analyzed using a synchrotron high energy X-ray source. Using frozen crystals, X-ray diffraction data is collected on crystals that diffract to a resolution of 10–1.5 Å, with lower resolutions also useful, such as 25–10 Å, sufficient to solve the three-dimensional structure of a PNS SCP in considerable detail, as presented herein.

Computer Related Embodiments. An amino acid sequence of a PNS SCP and/or x-ray diffraction data, useful for computer molecular modeling of a PNS SCP or a portion thereof, can be "provided" in a variety of mediums to facilitate use thereof. As used herein, provided refers to a manufacture, which contains a PNS SCP amino acid sequence and/or x-ray diffraction data of the present invention, e.g., the amino sequence provided in FIGS. 1, 8, 10 or 11, a representative fragment thereof, or an amino acid sequence having at least 80–100% overall identity to a 5–2005 amino acid fragment of an amino acid sequence of FIGS. 11A–F or a variant thereof. Such a method provides the amino acid sequence and/or x-ray diffraction data in a form which allows a skilled artisan to analyze and molecular model the three dimension structure of a PNS SCP or subdomain thereof.

In one application of this embodiment, PNS SCP, or at least one subdomain thereof, amino acid sequence and/or x-ray diffraction data of the present invention is recorded on computer readable medium. As used herein, "computer readable medium" refers to any medium which can be read and accessed directly by a computer. Such media include, but are not limited to: magnetic storage media, such as floppy discs, hard disc storage medium, and magnetic tape; optical storage media such as optical discs or CD-ROM; electrical storage media such as RAM and ROM; and hybrids of these categories such as magnetic/optical storage media. A skilled artisan can readily appreciate how any of the presently known computer readable mediums can be used to create a manufacture comprising computer readable medium having recorded thereon a n amino acid sequence and/or x-ray diffraction data of the present invention.

As used herein, "recorded" refers to a process for storing information on computer readable medium. A skilled artisan can readily adopt any of the presently know methods for recording information on computer readable medium to generate manufactures comprising an amino acid sequence and/or x-ray diffraction data information of the present invention.

A variety of data storage structures are available to a skilled artisan for creating a computer readable medium having recorded thereon an amino acid sequence and/or x-ray diffraction data of the present invention. The choice of the data storage structure will generally be based on the means chosen to access the stored information. In addition, a variety of data processor programs and formats can be used to store the sequence and x-ray data information of the present invention on computer readable medium. The sequence information can be represented in a word processing text file, formatted in commercially-available software such as WordPerfect and MicroSoft Word, or represented in the form of an ASCII file, stored in a database application, such as DB2, Sybase, Oracle, or the like. A skilled artisan can readily adapt any number of dataprocessor structuring formats (e.g. text file or database) in order to obtain computer readable medium having recorded thereon the information of the present invention.

By providing the PNS SCP sequence and/or x-ray diffraction data on computer readable medium, a skilled artisan can routinely access the sequence and x-ray diffraction data to model a PNS SCP, a subdomain thereof, or a ligand thereof. Computer algorythms are publicly and commercially available which allow a skilled artisan to access this data provided in a computer readable medium and analyze it for molecular modeling and/or RDD.

The present invention further provides systems, particularly computer-based systems, which contain the sequence and/or diffraction data described herein. Such systems are designed to do molecular modeling and RDD for a PNS SCP or at least one subdomain thereof.

As used herein, "a computer-based system" refers to the hardware means, software means, and data storage means used to analyze the sequence and/or x-ray diffraction data of the present invention. The minimum hardware means of the computer-based systems of the present invention comprises a central processing unit (CPU), input means, output means, and data storage means. A skilled artisan can readily appreciate which of the currently available computer-based system are suitable for use in the present invention.

As stated above, the computer-based systems of the present invention comprise a data storage means having stored therein a PNS SCP or fragment sequence and/or x-ray diffraction data of the present invention and the necessary hardware means and software means for supporting and implementing an analysis means. As used herein, "data storage means" refers to memory which can store sequence or x-ray diffraction data of the present invention, or a memory access means which can access manufactures having recorded thereon the sequence or x-ray data of the present invention.

As used herein, "search means" or "analysis means" refers to one or more programs which are implemented on the computer-based system to compare a target sequence or target structural motif with the sequence or x-ray data stored within the data storage means. Search means are used to identify fragments or regions of a PNS SCP which match a particular target sequence or target motif. A variety of known algorithms are disclosed publicly and a variety of commercially available software for conducting search means are and can be used in the computer-based systems of the present invention. A skilled artisan can readily recognize that any one of the available algorithms or implementing software packages for conducting computer analyses that can be adapted for use in the present computer-based systems.

As used herein, "a target structural motif," or "target motif," refers to any rationally selected sequence or combination of sequences in which the sequence(s) are chosen based on a three-dimensional configuration or electron density map which is formed upon the folding of the target motif. There are a variety of target motifs known in the art. Protein target motifs include, but are not limited to, enzymic active sites, structural subdomains, epitopes, functional domains and signal sequences. A variety of structural formats for the input and output means can be used to input and output the information in the computer-based systems of the present invention.

A variety of comparing means can be used to compare a target sequence or target motif with the data storage means to identify structural motifs or electron density maps. A skilled artisan can readily recognize that any one of the publicly available computer modeling programs can be used as the search means for the computer-based systems of the present invention.

Figure 12:
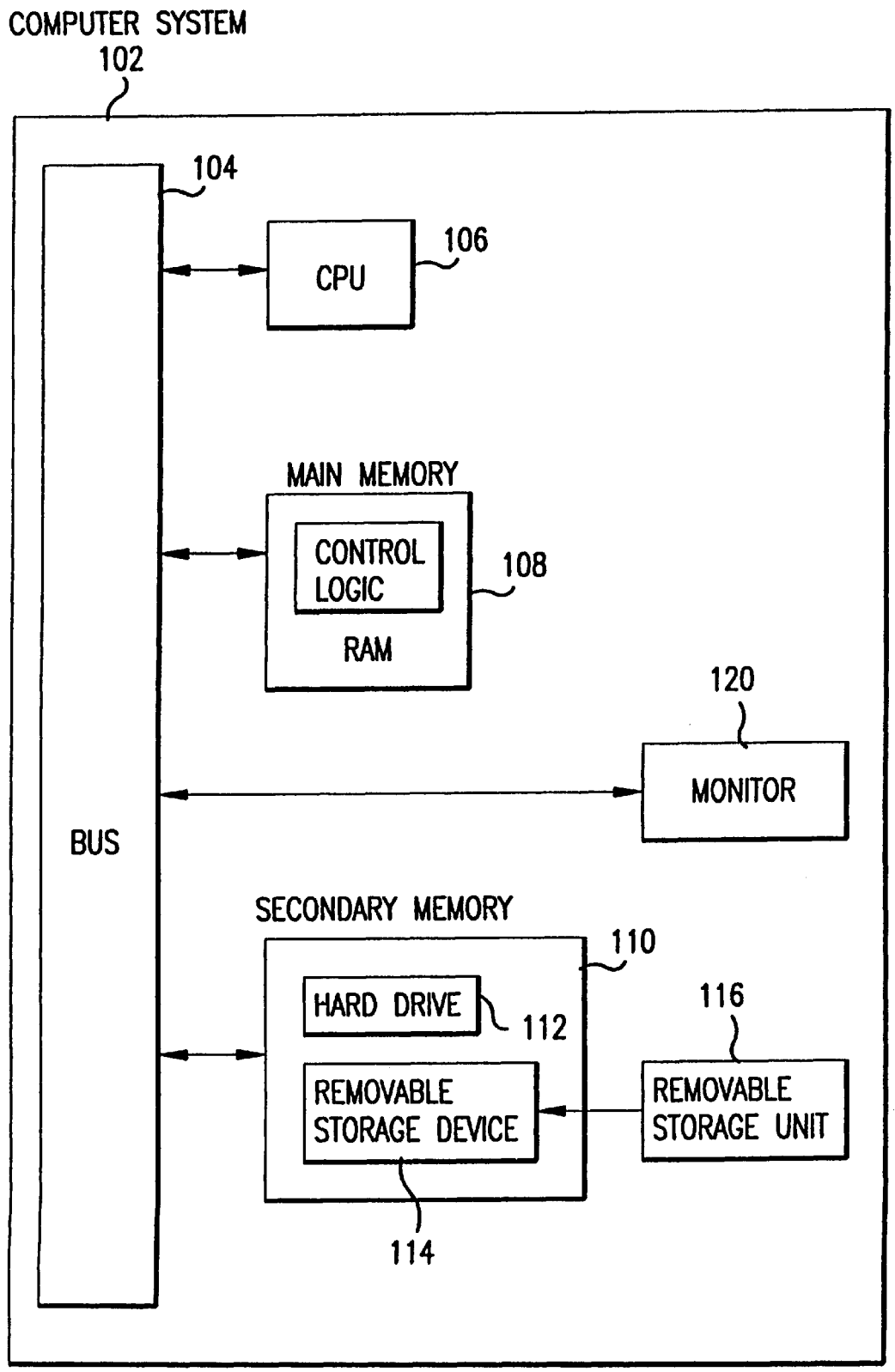
FIG. 12 shows a computer system suitable for three dimensional structure determination and/or rational drug design.

One application of this embodiment is provided in FIG. 12. FIG. 12 provides a block diagram of a computer system 102 that can be used to implement the present invention. The computer system 102 includes a processor 106 connected to a bus 104. Also connected to the bus 104 are a main memory 108 (preferably implemented as random access memory, RAM) and a variety of secondary storage memory 110, such as a hard drive 112 and a removable storage medium 114. The removable medium storage device 114 may represent, for example, a floppy disk drive, a CD-ROM drive, a magnetic tape drive, etc. A removable storage medium 116 (such as a floppy disk, a compact disk, a magnetic tape, etc.) containing control logic and/or data recorded therein may be inserted into the removable medium storage medium 114. The computer system 102 includes appropriate software for reading the control logic and/or the data from the removable medium storage device 114 once inserted in the removable medium storage device 114. A monitor 120 can be used as connected to the bus 104 to visualize the structure determination data.

Amino acid, encoding nucleotide or other sequence and/or x-ray diffraction data of the present invention may be stored in a well known manner in the main memory 108, any of the secondary storage devices 110, and/or a removable storage device 116. Software for accessing and processing the amino acid sequence and/or x-ray diffraction data (such as search tools, comparing tools, etc.) reside in main memory 108 during execution.

Three Dimensional Structure Determination. One or more computer modeling steps and/or computer algorythms are used to provide a molecular 3-D model of a cleaved PNS SCP, using amino acid sequence data from FIGS. 1, 8, 10 or 11 (or variants thereof) and/or x-ray diffraction data. If only the amino acid sequence is used, for three-dimensional structure determination then a suitable modeling program can be used, e.g., LINUS (Rose et. al. *Proteins: Structure, Function and Genetics* (June, 1995) and references cited herein. It is preferred that the PNS SCP model has no or Ala-substituted (for surface) residues in disallowed regions of the Ramachandran plot, and gives a positive 3D–1D profile (Luthy et al, *Nature* 356:83–85 (1992)), suggesting that all the residues are in acceptable environments (Kraulis (1991), infoa). Alternatively, the dissallowed regions can be corrected by the use of suitable algorithms, such as the RAVE program described herein. Phase determination is optionally used for solving the three-dimensional structure of a cleaved PNS SCP. This structure can then be used for RDD of modulators of PNS SCP neuraminidase, endothelin cathepsin A or other biological activity, e.g., which is relevant to a PNS SCP related pathology.

Density Modification and Map Interpretation. Electron density maps can be calculated using such programs as those from the CCP4 computing package (SERC (UK) Collaborative Computing Project 4, Daresbury Laboratory, UK, 1979). Cycles of two-fold averaging can further be used, such as with the program RAVE (Kleywegt & Jones, Bailey et al, eds., *First Map to Final Model*, SERC Daresbury Laboratory, UK, pp 59–66 (1994)) and gradual model expansion. For map visualization and model building a program usch as "O" (Jones (1991), infra) can be used.

Refinement and Model Validation. Rigid body and positional refinement can be carried out using a program such as X-PLOR (Brunger (1992), infra), e.g., with the stereochemical parameters of Engh and Huber (*Acta Cryst.* A47:392–400 (1991)). If the model at this stage in the averaged maps still misses residues (e.g., at least 5–10 per subunit), the some or all of the missing residues can be incorporated in the model during additional cycles of positional refinement and model building. The refinement procedure can start using data from lower resolution (e.g., 25–10 Å to 10–3.0 Å and then gradually extended to include data from 12–6 Å to 3.0–1.5 Å). β-values for individual atoms can be refined once data between 2.9 and 1.5 Å has been added. Subsequently waters can be gradually added. A program such as ARP (Lamzin and Wilson, *Acta Cryst* D49: 129–147 (1993)) can be used to add crystallographic waters and as a tool to check for bad areas in the model. Programs such as PROCHECK (Lackowski et al, *J. Appl. Cryst.* 26:283–291 (1993)), WHATIF(Vriend, *J. Mol. Graph.* 8:52–56 (1990)) and PROFILE 3D (Liuthy et al., *Nature* 356:83–85 (1992)), as well as the geometrical analysis generated by X-PLOR can be been used to check the structure for errors. For the final refinement cycle, 20–5% of the weakest data can be rejected using a $IF_{obs}I/\sigma$ cutoff and anisotropic scaling between $F_{obs}$ and $F_{calc}$ applied after careful assessment of the quality and completeness of the data Structure Analysis. A program such as DSSP can be used to assign the secondary structure elements (Kabsch and Sander (1983), infra). A program such as SUPPOS (from the BIOMOL crystallographic computing package) can be used to for some or all of the least-squares superpositions of various models and parts of models. Solvent accessible surfaces and electrostatic potentials can be calculated using such programs as GRASP (Nicholls et al (1991), infra).

Structure Determination. The structure of a PNS SCP can thus be solved with the molecular replacement procedure such as by using X-PLOR (Brunger (1992), infra). A partial search model for the monomer can be constructed using a related protein, such as wheat serine carboxypeptidase structure (Liao et al. (1992), infra). The rotation and translation function can be used to yield two or more orientations and positions for two subunits to form a physiological dimer as determined based on their interactions. Cyclical two-fold density averaging can also be done using the RAVE program and model expansion can also be used to add missing residues for each monomer, resulting in a model with 95–99.9% of the total number residues. The model can be refined in a program such as X-PLOR (Brühnger (1992), supra), to a suitable crystallographic $R_{factor}$. The model data is then saved on computer readable medium for use in further analysis, such as rational drug design.

Rational Design of Drugs that Interact with the PNS SCP. The determination of the three dimensional structure of a cleaved PNS SCP, as described herein, provides a basis for the design of new and specific ligands for the diagnosis and/or treatment of at least one PNS SCP-related pathology. Several approaches can be taken for the use of the crystal structure of a PNS SCP in the rational design of ligands of this protein. A computer-assisted, manual examination of the active site structure is optionally done. The use of software such as GRID (Goodford, *J. Med. Chem.* 28:849–857 (1985)) a program that determines probable interaction sites between probes with various functional group characteristics and the enzyme surface—is used to analyze the active site to determine structures of inhibiting compounds. The program calculations, with suitable inhibiting groups on molecules (e.g., protonated primary amines) as the probe, are used to identify potential hotspots around accessible positions at suitable energy contour levels. Suitable ligands, as inhibiting or stimulating modulating compounds or compositions, are then tested for modulating activities of at least one PNS SCP.

A diagnostic or therapeutic PNS SCP modulating ligand of the present invention can be, but is not limited to, at least one selected from a nucleic acid, a compound, a protein, an element, a lipid, an antibody, a saccharide, an isotope, a carbohydrate, an imaging agent, a lipoprotein, a glycoprotein, an enzyme, a detectable probe, and antibody or fragment thereof, or any combination thereof, which can be detectably labeled as for labeling antibodies. Such labels include, but are not limited to, enzymatic labels, radioisotope or radioactive compounds or elements, fluorescent compounds or metals, chemiluminescent compounds and bioluminescent compounds. Alternatively, any other known diagnostic or therapeutic agent can be used in a method of the invention.

After preliminary experiments are done to determine the $K_m$ of the substrate with each enzyme activity of a PNS SCP, the time-dependent nature of modulation of ligand $K_i$ values are determined, (e.g., by the method of Henderson (*Biochem. J.* 127:321–333 (1972)). For example, the substrate (or blank where appropriate) and enzyme are pre-incubated in buffer. Reactions are initiated by the addition of substrate. Aliquots are removed over a suitable time course and each quenched by addition into the aliquots of suitable quenching solution (e.g., sodium hydroxide in aqueous ethanol). The concentration of product is determined, e.g., fluorometrically, using a spectrometer. Plots of fluorescence against time can be close to linear over the assay period, and are used to obtain values for the initial velocity in the presence ($V_i$) or absence ($V_o$) of ligand. Error is present in both axes in a Henderson plot, making it inappropriate for standard regression analysis (Leatherbarrow, *Trends Biochem. Sci.* 15:455–458 (1990)). Therefore, $K_i$ values is obtained from the data by fitting to a modified version of the Henderson equation for competitive inhibition:

$$Qr^2 + (E_t - Q - I_t)r - E_t = 0$$

where (using the notation of Henderson (*Biochem. J.* 127:321–333 (1972)):

$$Q = K_i\left(\frac{A_t + K_a}{K_a}\right) \text{ and } r = \frac{V_o}{V_i}$$

This equation is solved for the positive root with the constraint that $$Q = K_i((A_t + K_a)/K_a)$$

using PROCNLIN from SAS (SAS Institute Inc., Cary, N.C., USA) which performs nonlinear regression using least-square techniques. The iterative method used is optionally the multivariate secant method, similar to the Gauss-Newton method, except that the derivatives in the Taylor series are estimated from the histogram of iterations rather than supplied analytically. A suitable convergence criterion is optionally used, e.g., where there is a change in loss function of less than $10^{-8}$.

Once modulating ligands are found and isolated or synthesized, crystallographic studies of the compounds complexed to a PNS SCP are performed. As a non-limiting example, PNS SCP crystals are soaked for 2 days in 0.01–100 mM ligand and X-ray diffraction data are collected on an area detector and/or an image plate detector (e.g., a Mar image plate detector) using a rotating anode X-ray source. Data are collected to as high a resolution as possible, e.g., 1.5–3.5 Å, and merged with an R-factor on suitable intensities. An atomic model of the inhibitor is built into the difference Fourier map ($F_{inhibitor\ complex} - F_{native}$). The model can be refined to a solution in a cycle of simulated annealing (Branger (1987), infra) involving 10–500 cycles of energy refinement, 100–10,000 1-FS steps of room temperature dynamics and/or 10–500 more cycles of energy refinement. Harmonic restraints are also used for the atom refinement, except for atoms within a 10–15 Å radius of the inhibitor. An R-factor is selected for the model for both the r.m.s. deviations from the ideal bond lengths, as well as for the angles, respectively. Direct measurements of enzyme inhibition provide further confirmation that the modeled ligands are modulators of at least one biological activity of a PNS SC.

Ligands of a PNS SCP, based on the crystal structure of this enzyme, are thus also provided by the present invention. Demonstration of clinically useful levels, e.g., in vivo activity is also important. In evaluating PNS SCP inhibitors for biological activity in animal models (e.g., rat, mouse, rabbit) using various oral and parenteral routes of administration are evaluated. Using this approach, it is expected that modulation of a PNS SCP occurs in suitable animal models, using the ligands discovered by molecular modeling and x-ray crystallography.

Diagnostic and/or Therapeutic Agents. A diagnostic or therapeutic PNS SCP modulating agent or ligand of the present invention can be, but is not limited to, at least one selected from a nucleic acid, a compound, a protein, an element, a lipid, an antibody, a saccharide, an isotope, a carbohydrate, an imaging agent, a lipoprotein, a glycoprotein, an enzyme, a detectable probe, and antibody or fragment thereof, or any combination thereof, which can be detectably labeled as for labeling antibodies, as described herein. Such labels include, but are not limited to, enzymatic labels, radioisotope or radioactive compounds or elements, fluorescent compounds or metals, chemiluminescent compounds and bioluminescent compounds. Alternatively, any other known diagnostic or therapeutic agent can be used in a method of the invention.

A therapeutic agent used in the invention can have a therapeutic effect on the target cell as a cell or neuron of the peripheral nervous system, the effect selected from, but not limited to: correcting a defective gene or protein, a drug action, a toxic effect, a growth stimulating effect, a growth inhibiting effect, a metabolic effect, a catabolic affect, an anabolic effect, a neurohumoral effect, a cell differentiation stimulatory effect, a cell differentiation inhibitory effect, a neuromodulatory effect, a pluripotent stem cell stimulating effect, and any other known therapeutic effects that modulates at least one SC in a cell of the peripheral nervous system can be provided by a therapeutic agent delivered to a target cell via pharmaceutical administration or via a delivery vector according to the invention.

A therapeutic nucleic acid as a therapeutic agent can have, but is not limited to, at least one of the following therapeutic effects on a target cell: inhibiting transcription of a DNA sequence; inhibiting translation of an RNA sequence; inhibiting reverse transcription of an RNA or DNA sequence; inhibiting a post-translational modification of a protein; inducing transcription of a DNA sequence; inducing translation of an RNA sequence; inducing reverse transcription of an RNA or DNA sequence; inducing a post-translational modification of a protein; transcription of the nucleic acid as an RNA; translation of the nucleic acid as a protein or enzyme; and incorporating the nucleic acid into a chromosome of a target cell for constitutive or transient expression of the therapeutic nucleic acid.

Therapeutic effects of therapeutic nucleic acids can include, but are not limited to: turning off a defective gene or processing the expression thereof, such as antisense RNA or DNA; inhibiting viral replication or synthesis; gene therapy as expressing a heterologous nucleic acid encoding a therapeutic protein or correcting a defective protein; modifying a defective or underexpression of an RNA such as an hnRNA, an mRNA, a tRNA, or an rRNA; encoding a drug or prodrug, or an enzyme that generates a compound as a drug or prodrug in pathological or normal cells expressing the chimeric receptor; and any other known therapeutic effects.

A therapeutic nucleic acid of the invention which encodes, or provides the therapeutic effect any known toxin, prodrug or gene drug for delivery to pathogenic nervous cells can also include genes under the control of a tissue specific transcriptional regulatory sequence (TRSs) specific for pathogenic SC containing cells. Such TRSs would further limit the expression of the therapeutic agent in the target cell, according to known methods.

Non-limiting examples of such PNS SCP modulating agents or ligands of the present invention and methods thereof include methyl/halophenyl-substituted piperizine compounds, such as lidoflazine (see, e.g., Merck Index Monograph 5311 and U.S. Pat. No. 3,267,104, both entirely incoporated herein by reference). Such compounds were tested and found to inhibit sodium channel activity of at least one PNS SCP of the present invention in cell lines expressing at least one PNS SCP, such as PC 12, PK 1–4 and other isolated or recombinant cells expressing at least one PNS SCP of the present invention. Accordingly, the present invention provides PNS SCP modulating agents or ligands as methyl/halophenyl-substituted piperizines. The substitutions can include alkyl- and/or halophenyl-substituted piperizines.

Pharmaceutical/Diagnostic Administration. Using PNS SCP modulating compounds or compositions (including antagonists and agonists as described above) the present invention further provides a method for modulating the activity of the PNS SCP protein in a cell. In general, agents (antagonists or agonists) which have been identified to inhibit or enhance the activity of PNS SCP can be formulated so that the agent can be contacted with a cell expressing a PNS SCP protein in vivo. The contacting of such a cell with such an agent results in the in vivo modulation of the activity of the PNS SCP proteins. So long as a formulation barrier or toxicity barrier does not exist, agents identified in the assays described above will be effective for in vivo use.

In another embodiment, the invention relates to a method of administering PNS SCP or a PNS SCP modulating compound or composition (including PNS SCP antagonists and agonists) to an animal (preferably, a mammal (specifically, a human)) in an amount sufficient to effect an altered level of PNS SCP in the animal. The administered PNS SC or PNS SCP modulating compound or composition could specifically effect PNS SCP associated functions. Further, since PNS SCP is expressed in peripheral nervous system tissue, administration of PNS SC or PNS SCP modulating compound or composition could be used to alter PNS SCP levels in the peripheral nervous system.

PNS SCP antagonists can be used to treat pain due to trauma or pathology involving the central or peripheral nervous system, or pathologies related to the abnormally high levels of expression of at least one naturally occurring nervous system specific (NS) sodium channel (SC), where a PNS SCP antagonist also inhibits at least one NS SC, or where the pain is mediated to some extent by PN SC. Such pathologies, include, but are not limited to; inflammatory diseases, neuropathies (e.g., diabetic neuropathy), dystrophies (e.g., reflex sympathetic dystrophy, post-herpetic neuralgia); trauma (tissue damage by any cause); focal pain by any cause.

Inflammatory diseases can include, but are not limited to, chronic inflammatory pathologies and vascular inflammatory pathologies. Chronic inflammatory pathologies include, but are not limited to sarcoidosis, chronic inflammatory bowel disease, ulcerative colitis, and Crohn's pathology and vascular inflammatory pathologies, such as, but not limited to, disseminated intravascular coagulation, atherosclerosis, and Kawasaki's pathology.

PNS SCP agonists can be used to treat pathologies involving the central or peripheral nervous system, or pathologies related to the abnormally low levels of expression of at least one naturally occurring nervous system specific (NS) sodium channel (SC), where a PNS SCP agonist also enhances or stimulates at least one NS SC. Such pathologies, include, but are not limited to, neurodegenerative diseases, diseases of the gastrointestinal tract due to dysfunction of the enteric nervous system (e.g., colitis, ileitis, inflammatory bowel syndrome); diseases of the cardiovascular system (e.g., hypertension and congestive heart failure); diseases of the genitourinary tract involving sympathetic and parasympathetic innervation (e.g., benign prostrate hyperplasia, impotence); diseases of the neuromuscular system (e.g., muscular dystrophy, multiple sclerosis, epilepsy).

Neurodegenerative diseases can include, but are not limited to, demyelinating diseases, such as multiple sclerosis and acute transverse myelitis; hyperkinetic movement disorders, such as Huntington's Chorea and senile chorea; hypokinetic movement disorders, such as Parkinson's disease; progressive supranucleo palsy; spinocerebellar degenerations, such as spinal ataxia, Friedreich's ataxia; multiple systems degenerations (Mencel, Dejerine-Thomas, Shi-Drager, and Machado-Joseph); and systemic disorders (Refsum's disease, abetalipoprotemia, ataxia, telangiectasia, and mitochondrial multi-system disorder); demyelinating core disorders, such as multiple sclerosis. acute transverse myelitis; disorders of the motor unit, such as neurogenic muscular atrophies (anterior horn cell degeneration, such as amyotrophic lateral sclerosis, infantile spinal muscular atrophy and juvenile spinal muscular atrophy); or any subset thereof.

Pharmaceutical/diagnostic administration of diagnostic/pharmaceutical compound or composition of the invention, for a PNS SC related pathology can be administered by any means that achieve its intended purpose, for example, to treat or prevent a cancer or precancerous condition.

The term "protection", as in "protection from infection or disease", as used herein, encompasses "prevention," "suppression" or "treatment." "Prevention" involves administration of a Pharmaceutical composition prior to the induction of the disease. "Suppression" involves administration of the composition prior to the clinical appearance of the disease. "Treatment" involves administration of the protective composition after the appearance of the disease. It will be understood that in human and veterinary medicine, it is not always possible to distinguish between "preventing" and "suppressing" since the ultimate inductive event or events can be unknown, latent, or the patient is not ascertained until well after the occurrence of the event or events. Therefore, it is common to use the term "prophylaxis" as distinct from "treatment" to encompass both "preventing" and "suppressing" as defined herein. The term "protection," as used herein, is meant to include "prophylaxis." See, e.g., Berker, infra, Goodman, infra, Avery, infra and Katzung, infra, which are entirely incorporated herein by reference, including all references cited therein. The "protection" provided need not be absolute, i.e., the disease need not be totally prevented or eradicated, provided that there is a statistically significant improvement relative to a control population. Protection can be limited to mitigating the severity or rapidity of onset of symptoms of the disease.

At least one PNS SC modulating compound or composition of the invention can be administered by any means that achieve the intended purpose, using a pharmaceutical composition as previously described.

For example, administration can be by various parenteral routes such as subcutaneous, intravenous, intradermal, intramuscular, intraperitoneal, intranasal, intracranial, transdermal, or buccal routes. Alternatively, or concurrently, administration can be by the oral route. Parenteral administration can be by bolus injection or by gradual perfusion over time.

An additional mode of using of a diagnostic/pharmaceutical compound or composition of the invention is by topical application. A diagnostic/pharmaceutical compound or composition of the invention can be incorporated into topically applied vehicles such as salves or ointments.

For topical applications, it is preferred to administer an effective amount of a diagnostic/pharmaceutical compound or composition according to the invention to target area, e.g., skin surfaces, mucous membranes, and the like, which are adjacent to peripheral neurons which are to be treated. This amount will generally range from about 0.0001 mg to about 1 g of a PNS SC modulating compound per application, depending upon the area to be treated, whether the use is diagnostic, prophylactic or therapeutic, the severity of the symptoms, and the nature of the topical vehicle employed. A preferred topical preparation is an ointment, wherein about 0.001 to about 50 mg of active ingredient is used per cc of ointment base.

A typical regimen for treatment or prophylaxis comprises administration of an effective amount over a period of one or several days, up to and including between one week and about six months.

It is understood that the dosage of a diagnostic/pharmaceutical compound or composition of the invention administered in vivo or in vitro will be dependent upon the age, sex, health, and weight of the recipient, kind of concurrent treatment, if any, frequency of treatment, and the nature of the diagnostic/pharmaceutical effect desired. The ranges of effective doses provided herein are not intended to be limiting and represent preferred dose ranges. However, the most preferred dosage will be tailored to the individual subject, as is understood and determinable by one skilled in the relevant arts. See, e.g., Berkow et al, eds., *The Merck Manual.* 16th edition, Merck and Co., Rahway, N.J., 1992, Goodman et al., eds., *Goodman and Gilman's The Pharmacological Basis of Therapeutics,* 8th edition, Pergamon Press, Inc., Elmsford, N.Y., (1990); *Avery's Drug Treatment: Principles and Practice of Clinical Pharmacology and Therapeutics,* 3rd edition, ADIS Press, LTD., Williams and Wilkins, Baltimore, Md. (1987), Ebadi, *Pharmacology,* Little, Brown and Co., Boston, (1985); Osol et al., eds. *Remington's Pharmaceutical Sciences,* 18th edition, Mack Publishing Co., Easton, Pa. (1990); Katzung, *Basic and Clinical Pharmacology,* Appleton and Lange, Norwalk, Conn. (1992), which references are entirely incorporated herein by reference.

The total dose required for each treatment can be administered by multiple doses or in a single dose. The diagnostic/pharmaceutical compound or composition can be administered alone or in conjunction with other diagnostics and/or pharmaceuticals directed to the pathology, or directed to other symptoms of the pathology.

Effective amounts of a diagnostic/pharmaceutical compound or composition of the invention are from about 0.1 µg to about 100 mg/kg body weight, administered at intervals of 4–72 hours, for a period of 2 hours to 1 year, and/or any range or value therein, such as 0.0001–1.0, 1–10, 10–50 and 50–100, 0.0001–0.001, 0.001–0.01, 0.01–0.1, 0.1–1.0, 1.0–1 0, 5–10, 10–20, 20–50 and 50–100 mg/kg, at intervals of 1–4, 4–10, 10–16, 16–24, 24–36, 36–48,48–72 hours, for a period of 1–14, 14–28, or 30–44 days, or 1–24 weeks, or any range or value therein.

The recipients of administration of compounds and/or compositions of the invention can be any vertebrate animal, such as mammals, birds, bony fish, frogs and toads. Among mammals, the preferred recipients are mammals of the Orders Primata (including humans, apes and monkeys), Arteriodactyla (including horses, goats, cows, sheep, pigs), Rodenta (including mice, rats, rabbits, and hamsters), and Carnivora (including cats, and dogs). Among birds, the preferred recipients are turkeys, chickens and other members of the same order. The most preferred recipients are humans.

Gene Therapy. A delivery vector of the present invention can be, but is not limited to, a viral vector, a liposome, an anti-PNS SCP or anti-SC antibody, or a SC ligand, one or more of which delivery vectors is associated with a diagnostic or therapeutic agent.

The delivery vector can comprise any diagnostic or therapeutic agent which has a therapeutic or diagnostic effect on the target cell. The target cell specificity of the delivery vector is thus provided by use of a target cell specific delivery vector.

The delivery vector can also be a recombinant viral vector comprising at least one binding domain selected from the group consisting of an antibody or fragment, a chimeric binding site antibody or fragment, a target cell or specific ligand, a receptor which binds a target cell ligand, an anti-idiotypic antibody, a liposome or other component which is specific for the target cell. A PNS SCP can be already associated with the target cell, or the delivery vector can bind the target cell via a ligand to a target cell receptor or vice versa.

Thus, the therapeutic or diagnostic agent, such as a therapeutic or diagnostic nucleic acid, protein, drug, compound composition and the like, is delivered preferentially to the target cell, e.g., where the nucleic acid is preferably incorporated into the chromosome of the target cell, to the partial or complete exclusion of non-target cells.

The invention is thus intended to provide delivery vectors, containing one or more therapeutic and/or diagnostic agents, including vectors suitable for gene therapy.

In a method of treating a PNS SCP-associated disease in a patient in need of such treatment, functional PNS SCP DNA can be provided to the PNS cells of such patient in a manner and amount that permits the expression of the PNS SCP protein provided by such gene, for a time and in a quantity sufficient to treat such patient, such as a suitable delivery vector. Many vector systems are known in the art to provide such delivery to human patients in need of a gene or protein missing from the cell. For example, retrovirus systems can be used, especially modified retrovirus systems and especially herpes simplex virus systems. Such methods are provided for, in, for example, the teachings of Breakefield, et al., *The New Biologist* 3:203–218 (1991); Huang, Q. et al., *Experimental Neurology* 115:303–316 (1992), WO93/03743 and WO90/09441. Delivery of a DNA sequence encoding a functional PNS SCP protein will effectively replace the missing or mutated PNS SCP gene of the invention.

In another embodiment of this invention, the PNS SCP modulating compound or composition is expressed as a recombinant gene in a cell, so that the cells can be transplanted into a mammal, preferably a human in need of gene therapy. To provide gene therapy to an individual, a genetic sequence which encodes for all or part of the PNS SCP modulating compound or composition is added into a vector and introduced into a host cell. Examples of diseases that can be suitable for gene therapy include, but are not limited to, neurodegenerative diseases or disorders, Alzheimer's, schizophrenia, epilepsy, neoplasms and cancer. Examples of vectors that can be used in gene therapy include, but are not limited to, defective retroviral, adenoviral, or other viral vectors (Mulligan, R. C., Science 260:926–932 (1993)). See Anderson, Gene Therapy, 246 J. Amer. Med. Assn. 2737 (1980); Friedmann, Progress toward human gene therapy, 244 Science 1275 (1989); Anderson, 256 Science 808 (1992); human gene therapy protocols published in Human Gene Therapy, Mary Ann Liebert Publishers, N.Y. (1990–1994); Bank et al., 565 Ann. N.Y. Acad. Sci. 37 (1989); LTR-Vectors (U.S. Pat. No. 4,405,712); Ausubel , infra, §§ 9.10–9.17; Jon A. Wolff., ed, Gene Therapeutics: methods and applications of direct gene transfer, Birkhäuser, Boston (1994).

The means by which the vector carrying the gene can be introduced into the cell include but is not limited to, microinjection, electroporation, transduction, or transfection using DEAE-Dextran, lipofection, calcium phosphate or other procedures known to one skilled in the art (Sambrook infra; Ausubel, infra).

Preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose and sodium chloride, lactated Ringer's, or fixed oils. Intravenous vehicles include fluid and nutrient replenishers, electrolyte replenishers, such as those based on Ringer's dextrose, and the like. Preservatives and other additives can also be present, such as, for example, antimicrobials, antioxidants, chelating agents, inert gases and the like. See, generally, Osol et al., eds. Remington's Pharmaceutical Science, 16th Ed., (1980).

In another embodiment, the invention relates to a pharmaceutical composition comprising PNS SC or PNS SCP modulating compound or composition in an amount sufficient to alter PNS SCP associated activity, and a pharmaceutically acceptable diluent, carrier, or excipient. Appropriate concentrations and dosage unit sizes can be readily determined by one skilled in the art (See, e.g., Osol et al. ed., Remington's Pharmaceutical Sciences, 16th Ed., Mack, Easton Pa. (1980) and WO 91/19008).

Included as well in the invention are pharmaceutical compositions comprising an effective amount of at least one PNS SCP antisense oligonucleotide, in combination with a pharmaceutically acceptable carrier. Such antisense oligos include, but are not limited to, at least one nucleotide sequence of 12–500 bases in length which is complementary to a DNA sequence of SEQ ID NO:1, or a DNA sequence encoding at least 4 amino acids of SEQ ID NO:2 or FIGS. 11A–11E.

Alternatively, the PNS SCP nucleic acid can be combined with a lipophilic carrier such as any one of a number of sterols including cholesterol, cholate and deoxycholic acid. A preferred sterol is cholesterol.

The PNS SCP gene therapy nucleic acids and the pharmaceutical compositions of the invention can be administered by any means that achieve their intended purpose. For example, administration can be by parenteral, subcutaneous, intravenous, intramuscular, intra-peritoneal, or transdermal routes. The dosage administered will be dependent upon the age, health, and weight of the recipient, kind of concurrent treatment, if any, frequency of treatment, and the nature of the effect desired.

Compositions within the scope of this invention include all compositions wherein the PNS SCP antisense oligonucleotide is contained in an amount effective to achieve enhanced expression of at least one PNS SCP in a peripheral nervous system neuron or ganglion. While individual needs vary, determination of optimal ranges of effective amounts of each component is with the skill of the art. Typically, the PNS SCP nucleic acid can be administered to mammals, e.g. humans, at a dose of 0.005 to 1 mg/kg/day, or an equivalent amount of the pharmaceutically acceptable salt thereof, per day of the body weight of the mammal being treated.

Suitable formulations for parenteral administration include aqueous solutions of the PNS SCP nucleic acid in water-soluble form, for example, water-soluble salts. In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides. Aqueous injection suspensions can contain substances which increase the viscosity of the suspension include, for example, sodium carboxymethyl cellulose, sorbitol, and/or dextran. Optionally, the suspension can also contain stabilizers.

Alternatively, at least one PNS SCP can be coded by DNA constructs which are administered in the form of virions, which are preferably incapable of replicating in vivo (see, for example, Taylor, WO 92/06693). For example, such DNA constructs can be administered using herpes-based viruses (Gage et al., U.S. Pat. No. 5,082,670). Alternatively, PNS SCP antisense RNA sequences, PNS SCP ribozymes, and PNS SCP EGS can be coded by RNA constructs which are administered in the form of virions, such as recombinant, replication deficient retroviruses or adenoviruses. The preparation of retroviral vectors is well known in the art (see, for example, Brown et al., "Retroviral Vectors," in DNA Cloning. A Practical Approach, Volume 3, IRL Press, Washington, D.C. (1987)).

Specificity for gene expression in the peripheral nervous system can be conferred by using appropriate cell-specific regulatory sequences, such as cell-specific enhancers and promoters. Since protein phosphorylation is critical for neuronal regulation (Kennedy, "Second Messengers and Neuronal Function," in An Introduction to Molecular Neurobiology, Hall, Ed., Sinauer Associates, Inc. (1992)), protein kinase promoter sequences can be used to achieve sufficient levels of PNS SCP gene expression.

Thus, gene therapy can be used to alleviate sodium channel related pathology by inhibiting the inappropriate expression of a particular form of PNS SC. Moreover, gene therapy can be used to alleviate such pathologies by providing the appropriate expression level of a particular form of PNS SCP. In this case, particular PNS SCP nucleic acid sequences can be coded by DNA or RNA constructs which are administered in the form of viruses, as described above.

Having now generally described the invention, the same will be more readily understood through reference to the following Examples which are provided by way of illustration, and are not intended to be limiting of the invention, unless specified.

EXAMPLE 1

Cloning and Sequencing of a PNS SC Encoding Nucleic Acid

Materials and Methods

Cell Culture. PC12 cells and PKI-4 PC12 subclones were grown as previously described (Mandel et al., 1988). NGF (2.5 S subunit, kindly supplied by Dr. S. Halegoua, SUNY at Stony Brook), was added to the culture medium at final concentration of 110 ng/ml. The PKI-4 PC12 subclone which expresses the cAMP-dependent kinase inhibitor protein (PKI) was also provided by Dr. S. Halegoua (see D'Arcangelo et al., *J. Cell Biol.* 122:915–921 (1993)).

PCR Amplification. Total cellular RNA was isolated, according to the method of Cathala et al. *DNA* 2:329–335 (1983), from a PC12 subclone (PKI-4) which expresses high levels of the cAMP-dependent protein kinase inhibitor protein. Two µg of total RNA prepared time NGF-treated PKI-4 cells was used to synthesize first strand cDNA using random hexamer primers for the reverse transcriptase reaction. The cDNA then served as template for the PCR amplification, using a pair of degenerate oligonucleotide primers that specified a 400 base pair region within repeat domain III of the sodium channel α subunit gene. The 5' primer (designated YJ1:GCG AAGCTT(TC)TIATITT(TC)I(GATC)IAT(ATC)ATGGG (SEQ ID NO:3), underline indicates a HindIII restriction site), corresponded to amino acids FWLIFSIM (SEQ ID NO:4) at positions 1347–1354 in the type 11 sodium channel gene. The 3' primer (designated YO1C: GCAGGATCC (AG)TT(AG)AAA(AG)TT(AG)TC(AGT)AT(AGT)AT (AGCT)AC(AGCT)CC (SEQ ID NO:5), underline indicates a BamH1 restriction site) corresponded to amino acids GVIIDNFN (SEQ ID NO:6) at positions 1470–1447 in the type II gene. The amplification reaction mixture consisted of 5% of the cDNA, 1 mM $MgCl_2$, 0.2 mM dNTPSs, 0.5 µM each primer, Taq polymerase (Perkin-Elmer) in a buffer consisting of 0.1 M KCl, 0.1 M TRIS HCl (pH 8.3) and gelatin (1 mg/ml). The reaction was performed in a Perkin-Elmer thermocycler as follows: 5 cycles of denaturation (94° C., 1 min.), annealing (37° C., 1 min.), and extension (72° C., 1 min) followed by 25 cycles of denaturation (94° C., 1 min.), annealing (50° C., 1 min.) and extension (72° C., 1 min.). The PCR products were excised from a low melt agarose gel (SEAPLAQUE GTG, FMC BIOPRODUCTS) and subcloned into a Bluescript II SK plasmid vector previously restricted with HindIII and BamH1. The clones were screened for cDNA inserts by miniprep (Sambrook et al., infra) and sequenced in both directions by dideoxy chain termination (Sequenase 2.0 kit, UNITED STATES BIOCHEMICAL). Sequence data was compiled and analyzed using GENWORKS software (INTELLIGENETICS, INC., Mountain View, Calif.).

cDNA Library Construction and Screening. Poly(A)+ mRNA from the PKI-4 PC12 subclone was purified (mRNA purification kit, PHARMACIA) and used to construct a random- and oligo (dT)-primed Lambda ZAP II cDNA library (STRATAGENE CORP., La Jolla, Calif.). The library consisted of $5.6 \times 10^6$ independent clones prior to amplification. Screening of approximately $4 \times 10^6$ recombinants using the cloned PCR product pPC 12-1 labeled by random primers (PHARMACIA kit) resulted in isolation of 5 cDNAs ranging in size from 1–3 kb. Sequence analysis and comparison to published sequences established that the two of the cDNAs together encoded 3033 bp of the novel sodium channel α subunit, PN 1.

Northern blot analysis and ribonuclease protection assays. Total cellular RNA was isolated from adult Sprague-Dawley rat brain, spinal cord, superior cervical ganglion, dorsal root ganglion, skeletal muscle, cardiac muscle, and adrenal gland using the standard method of Chirgwin, *Biochemistry* 18:5294–5299 (1979). RNA was electrophoresed and transferred to nylon membrane as previously described (Cooperman et al., *Proc. Nat'l Acad Sci. USA* 84:8721 (1987)) (DURALON-UV; STRATAGENE CORP.). RNA blots were cross-linked to the nylon using Stratalinker UV crosslinker (STRATAGENE CORP.) and hybridized to $^{32}$P-UTP-labeled antisense RNA probes generated from the following linearized templates: pPC 12-1, pRB211 (Cooperman, infra, 1987), p1B15 (cyclophilin; Danielson et al., *DNA* 7:261–267 (1988)), and rat brain type 1, which contains 51 bp of intron, 5' untranslated sequence and 267 bp of coding sequence of the type I sodium channel. RNA probes were transcribed with either T3 (pPC12-1), T7, (pNach1), or SP6 (pRB211, p1B15) RNA polymerase according to the manufacturer's instructions (PROMEGA CORP, Madison, Wis.). The blots were washed once in 2× SSC, 0.1% $NaDodSO_4$ for 15 min. at 68° C., followed by two washes in 0.2× SSC, 0.1% $NaDodSO_4$ for 15 min. at 68° C. Autoradiography with preflashed XAR-5 film (EASTMAN KODAK CO., Rochester, N.Y.) was used for quantitation of mRNA by densitometry.

Ribonuclease protections assays were performed by use of a kit (RPA II, AMBION INC., Austin, Tex.). Total RNA was hybridized with $10^4$ cpm of antisense RNA probe generated from pPC12-1. To control for differences in the amount of total RNA between samples, we included an antisense RNA probe for β actin, transcribed from pTRI-β-actin (AMBION, INC.).

In situ hybridization. Tissue preparation and hybridization were performed using a modification of the procedure described by Yokouchi et al., *Develop.* 113:431–444 (1991). SCG and DRG were dissected from adult Sprague-Dawley rats and fixed in 4% paraformaldehyde (in 0.1 M PBS) for 2–6 hrs. at 4° C. The tissue was then rinsed ≈5 min. in 0.1 M PBS (pH 7.3), cryoprotected in 30% sucrose (in 0.1 M PBS) for 2 hrs. at 4° C. and embedded in O.C.T. (TISSUE-TEK). Cryostat sections (14 µM) were collected on SUPERFROST/Plus slides (FISHER SCIENTIFIC), dried ≈2 hrs. at room temp., and then stored at −80° C.

Immediately before prehybridization, sections were brought to room temp. and rehydrated in 0.1M PBS (pH 7.3) containing 0.3% Triton X-100 for 5 min. Sections were then treated with 0.2 N HCl for 20 min., washed in 0.1 M PBS for 5 min., and digested with proteinase K (5 µg/ml in 0.1 M PBS) for 40 min. at 37° C. Sections were then postfixed with 4% paraformaldehyde (in 0.1 M PBS), rinsed with 0.1 M PBS containing 0.1 M glycine for 15 min., and equilibrated in 50% formamide, 2× SSC for 1 hr. (room temp.).

Sections were hybridized with antisense digoxigenin-labeled RNA probes transcribed from pPC12-1 or pNach2 (Cooperman et al., *Proc. Nat'l Acad Sci. USA* 84:8721 (1987)) according to the manufacturer's instructions for RNA labeling with digoxigenin-UTP (BOEHRINGER MANNHEIM). Unlabeled probes were synthesized by replacing digoxigenin-UTP with rUTP. Each section was covered with ≈100 µl of hybridization solution containing 20 mM TRIS HCl (pH 8.0), 2.5 mM EDTA, 50% formamide, 0.3 M NaCl, 1× Denhardt's, 10% dextran sulfate, 1 mg/ml tRNA, and probe at a concentration of 0.7 µg/ml. Sections were then covered with PARAFILM coverslips and incubated in a humid chamber overnight at 45° C. After hybridization, sections were washed in 50% formamide, 2× SSC at 45° C. for 1 hr., followed by RNase digestion in 0.5M NaCl, 10 mM TRIS HCl (pH 8.0), and 20 µg/ml RNase A (BOEHRINGER MANNHEIM). Sections were subsequently washed at 45° C. in 50% formamide, 2× SSC for 1 hr., and 50% formamide, 1× SSC for 1 hr.

Immunological detection was performed using a kit (GENIUS 3 KIT, BOEHRINGER MANNHEIM), according to the manufacturer's instructions. In most experiments, the sections were incubated in the color solution for ≈3–5 hrs. at room temp. Sections were then coverslipped with AQUA-MOUNT (Lerner Laboratories) and stored in the dark.

Densitometry. Levels of sodium channel mRNA were determined by densitometric analysis of the autoradiograms using Bio Image software (Millipore Corp., Ann Arbor, Mich.). Levels of RNA were normalized to the quantitated levels of cyclophilin mRNA.

Results

Isolation of a cDNA expressed preferentially in peripheral nerve. D'Arcangelo et al., *J. Cell Biol.* 122:915–921 (1993) showed previously that NGF treatment of PC12 cells increase the level of an ≈11 kb sodium channel gene transcript which did not hybridize to probes specific for any of the known sodium channel genes. A transcript identical in size was also detected in mRNA from adult rat sympathetic and sensory ganglia, but not in mRNA from brain. These results suggested that the transcript encoded a new member of the sodium channel gene family (termed Peripheral Nerve type 1 (PN1)).

To confirm the identity of the PN1 gene, cDNAs from an NGF-treated PC12 subclone which preferentially expresses PN1 mRNA (PKI-4 cells) D'Arcangelo et al. were amplified by the polymerase chain reaction (PCR), using a pair of degenerate oligonucleotide primers that specify a 400 base pair (bp) region of the sodium channel α subunit gene (see Methods, FIG. 1). Both primers specified putative membrane-spanning regions within repeat domain III, which are highly conserved among voltage-gated sodium channels. The amplified regions between the primers include the strictly-conserved pore-lining residues, as well as residues which are divergent among the different mammalian a subunits. Sequence analysis of the PCR products revealed a cDNA, pPCI2-1, which encoded a portion of a novel putative sodium channel α subunit (FIG. 1). Additional cDNAs were further isolated which encapsulated the entire PN1 coding region.

To determine whether pPC12-1 encode part of the PN1 gene, the cDNA was used to generate antisense RNA probes for Northern blot analysis of mRNA from control and NGF-treated PC12 cells (FIG. 2B). For comparison, a duplicate blot (FIG. 2A) was hybridized with an antisense probe pRB211, which encode a highly-conserved region of the sodium channel a subunit (Cooperman et al., *Proc. Nat'l Acad Sci. USA* 84:8721 (1987)) and which cross-hybridizes with the PN1 transcript, and that, as shown by D'Arcangelo et al, *J. Cell Biol.* 122:915–921 (1993), levels of the detected transcript should increase rapidly and transiently following NGF treatment (maximal≈5 hrs). Comparison of FIGS. 2A and 2B shows that pPC12-1 fulfilled both of these criteria. Also, consistent with D'Arcangelo et al., *J. Cell Biol.* 122:915–921 (1993), we found that NGF induction of the transcript detected by pPC12-1 is independent of cAMP-dependent protein kinase activity.

To isolate additional cDNAs encoding PN1, a random- and oligo (dT)-primed Lambda ZAP II cDNA library (STRATAGENE, 5.6×10$^6$ independent clones) was prepared from poly(A)+mRNA isolated from the same PC12 subclone from which pPC12-1 was isolated. Screening 4×10$^4$ recombinants with a probe generated from pPC12-1 resulted in isolation of 2 additional, overlapping cDNAs which are joined to give a 3033 bp cDNA (FIG. 7). Additional cDNAs were further isolated which encapsulated the entire PN1 coding region.

Analysis of the deduced primary structure of PN1. As shown in FIG. 8, the deduced primary structure of PN1 encodes repeat domain II of the sodium channel α subunit gene. Comparison with the type II sodium channel shows that the PN1 sequence contains all of the structural motifs characteristic of voltage-gated sodium channels, including six putative transmembrane domains (IIIS1–IIIS6). The S4 domain, thought to serve as the voltage sensor, exhibits the highly-conserved pattern of a positively-charged residue (lysine or arginine) at every third position. Furthermore, the putative pore-lining segments (IIISS1–IIISS2) contain residues shown to be involved in sodium-selective permeation (laeinemann et al., *Nature* 356:441–443 (1992)) as well as TTX afftnity (Terlaue et al., *FEBS Lett.* 293:93–96 (1991)).

In addition to such highly-conserved structural features, the sodium channel αsubunit undergoes several characteristic post-translational modifications. All sodium channels sequenced to date exhibit a distinctive pattern of asparagine-linked (N-linked) glycosylation sites, which are found almost exclusively in the extracellular loops joining the S5 and S6 transmembrane helices. The N-linked glycosylation sites of PN1 are in good agreement with this pattern; three potential extracellular glycosylation sites are located between IIIS5 and IIIS6. Two of the sites are also found in the types I, II and III sodium channels.

The α subunit is phosphorylated by protein kinase C (PKC), and deduced PN1 sequence contains the highly-conserved consensus PKC phosphorylation site FIGS. 1A–B. This residue is located in the cytoplasmic loop joining domains III and IV that has been implicated in channel inactivation, and mutational analysis has shown that this serine is required for PKC modulation of channel inactivation (West et al, 1991).

The entire DNA (FIGS. 9A–C) and amino acid (FIG. 10) sequences were determined. The rat PN1 amino acid sequence was compared with new human sequences (FIGS. 11A–F) presented in Example 2.

In sum, the deduced primary structure of PN1 contains all of the hallmark structural and functional domains characteristics a ce subunit the voltage-gated sodium channel.

Figure 3A:
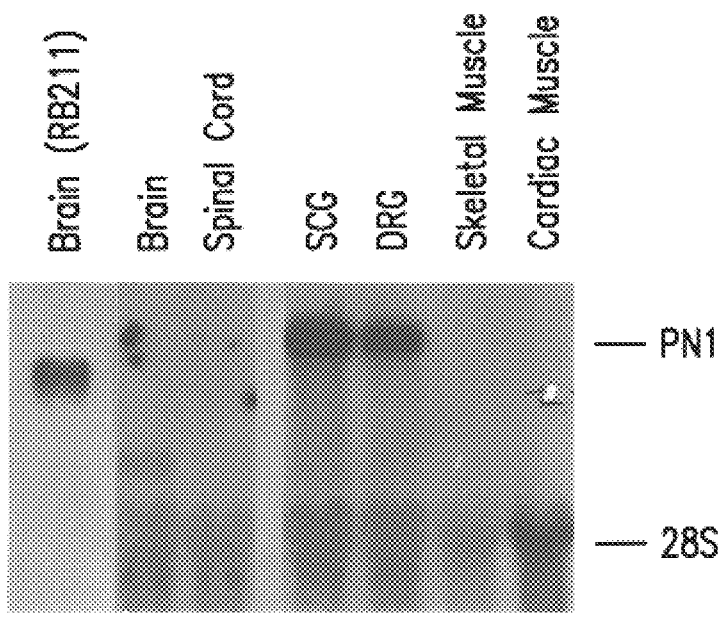
FIGS. 3A–B shows an example of tissue-specific distribution of PN1 mRNA.
Figure 3B:
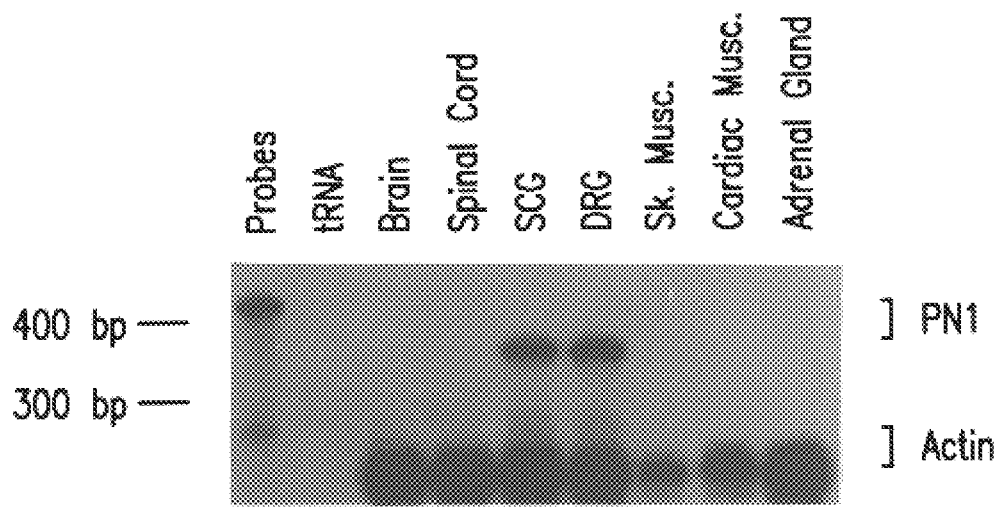

The PN1 gene is expressed preferentially in the PNS. To determine whether the PN1 gene was expressed preferentially in the PNS, total RNA was isolated from adult rat brain, spinal cord, SCG, DRG, skeletal muscle, and cardiac muscle and subjected to Northern blot analysis. Blots were hybridized with the PN1-specific anti sense probe generated from pPC12-1. As shown in FIG. 3A, we found high levels of hybridization to an ≈11 kb transcript in both SCG and DRG. Much lower, but detectable levels hybridization were seen to transcripts in both spinal cord and brain. No detectable hybridization was observed to mRNA from skeletal muscle, cardiac muscle, or liver.

Ribonuclease (RNase) protection analyses were also prepared. Total RNA was isolated from the same tissues used in Northern blot analysis, as well as adrenal gland, and hybridized to PN1-specific antisense probe (pPC12-1). mRNA from SCG, DRG, brain, spinal cord, and adrenal gland protected a 343 bp fragment of the PN1 probe (FIG. 4B). The non-protected bases represent oligonucleotide primer and plasmid sequences. The PN1 probe was not protected by mRNA from either skeletal muscle or cardiac muscle.

To determine the relative amounts of PN1 mRNA in the various tissues, autoradiographs from three separate RNase protection experiments were analyzed by densitometry. To control for small differences in the amount of total RNA between samples, we included a probe for a β actin. PN1 mRNA levels in both SCG and DRG are approximately 40-fold greater than in spinal cord, adrenal gland and brain.

The PN1 gene is expressed in sympathetic and sensory neurons. To determine whether the PN1 gene is expressed in neurons of peripheral ganglia, in situ hybridization was used to examine the cellular distribution of PN1 mRNA in adult rat SCG and DRG. Cryostat sections were hybridized with a PN1-specific digoxigenin-labeled RNA probe (pPC12-1), which was visualized using an anti-digoxigenin antibody conjugated to alkaline phosphatase. As shown in FIG. 4A, B the PN1 antisense probe labeled most neuronal cell bodies in both SCG and DRG. To confirm that the hybridization signal was due to binding of the probe specifically to PN mRNA, we performed two different negative controls: (1) Sections were hybridized with the digoxigenin-labeled probe in the presence of a 100-fold excess of unlabeled PN1 antisense probe. (2) Previous experiments have shown that SCG and DRG contain extremely low levels of type II sodium channel mRNA (Beckh, S., FEBS Lett. 262:317–322 (1990)). Therefore, we also hybridized sections with a type II-specific antisense probe. As shown, in FIGS. 4C–F, both of these control experiments greatly reduced the hybridization signal. Also, consistent with the results of Northern blot and RNase protection analyses, we found that hybridization of the labeled PN1 probe to sections of adult rat cerebral cortex yielded no detectable staining.

Although the PN1 probe stained most neuronal cell bodies in both SCG and DRG, we found that cell-to-cell variability in PN1 mRNA levels differed between the two ganglia. SCG neurons were fairly homogeneous, in that the intensity of reaction product was relatively constant between different cells. DRG neurons, however, were quite heterogeneous in that the staining intensity varied considerably from cell to cell. For example, in FIG. 4B, arrows indicate two DRG neurons of approximately the same diameter which differ markedly in staining intensity.

Finally, we found that the PN2 probe did not stain non-neuronal cells such as satellite cells and Schwann cells. However, it is possible that these cells contain very low levels of PN1 mRNA which are not detectable by this method.

SCG neurons also express the type I sodium channel gene. Earlier Northern blot analysis has shown that mRNA from SCG contains two distinct sodium channel gene transcripts. As we have demonstrated, the larger, 11 kb transcript encodes the PN1 sodium channel. The smaller transcript, however, has not yet been identified. We hypothesized that this smaller transcript encoded the type I sodium channel, because moderate levels of type I mRNA have been found in other PNS tissues (Beckh, S., FEBS Lett. 262:317–322 (1990)). To test this hypothesis, Northern blots of SCG mRNA isolated from adult rats were hybridized with an antisense probe specific for the type I sodium channel gene (pNach1, see Methods above). As shown in FIG. 5, the type I-specific probe hybridized specifically to the smaller transcript. Furthermore, we have found that SCG mRNA protects the type I probe in an RNas protection assay.

Figure 6A:
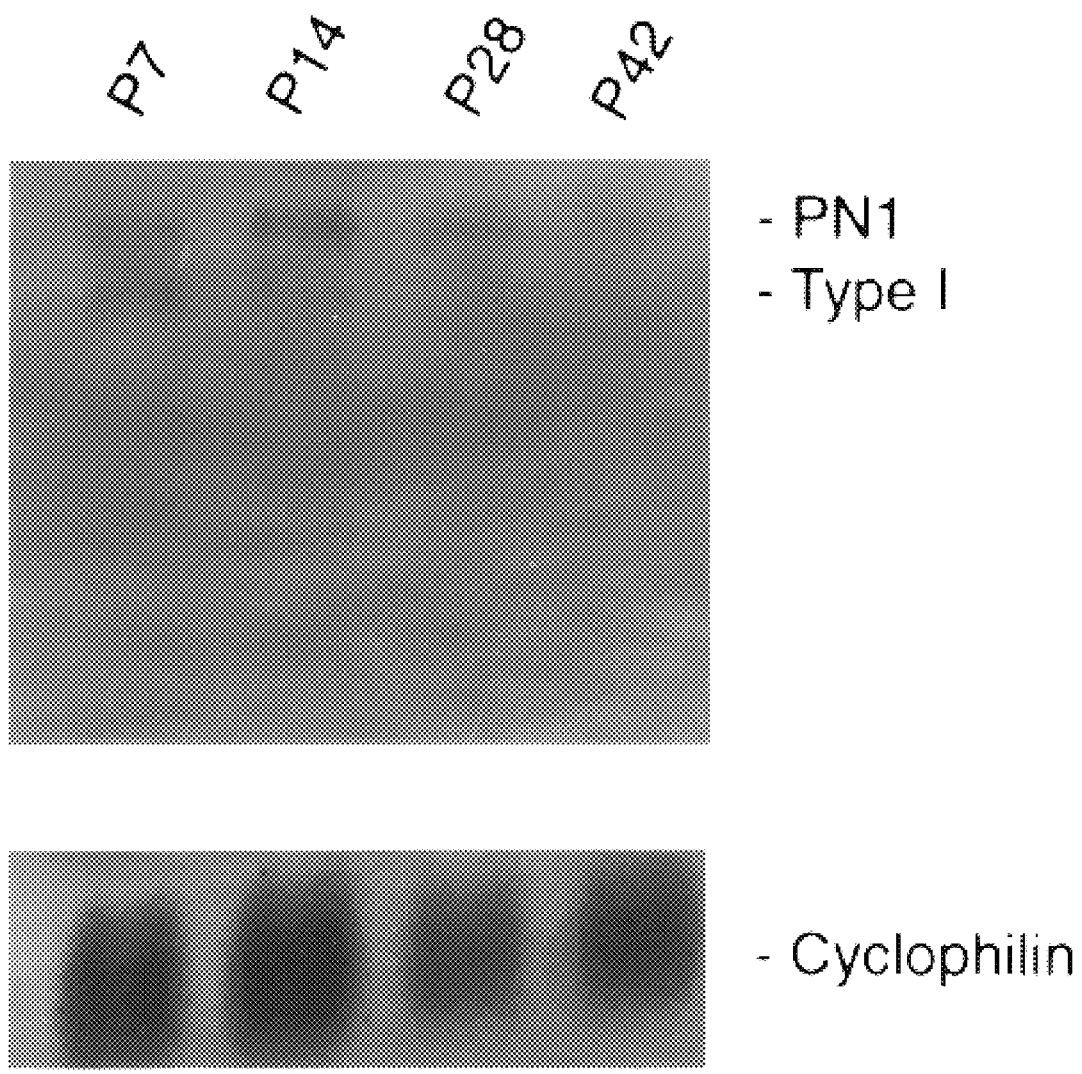
FIGS. 6A–B shows a Northern blot analysis which reveals differential expression of PN1 and type I sodium channel mRNAs during postnatal rat development.

The putative PN1α subunit and type Iα subunit genes are differentially regulated during development. Several studies have shown that the types I, II and III sodium channel genes are differentially regulated during development in both the central and peripheral nervous systems. To determine whether the PN1 and type I genes are also independently regulated during development, we measured their relative mRNA levels in SCG isolated from rats of different postnatal ages. To visualize both transcripts simultaneously, Northern blots were hybridized with the conserved sodium channel gene probe pRB2 11. As shown in FIG. 6A, in SCG removed on postnatal day 7 (P7), the levels of PN1 and type I mRNA are approximately equal. However, by P14, their relative abundance has shifted such that level of PN1 mRNA exceeds that of type I by ≈*-fold. This increase in ratio of PN1 to type I mRNA levels continues for at least the next four postnatal weeks. By P42, PN1 is the predominant sodium channel gene transcript, with levels of PN1 mRNA several-fold greater than that of type I.

Figure 6B:
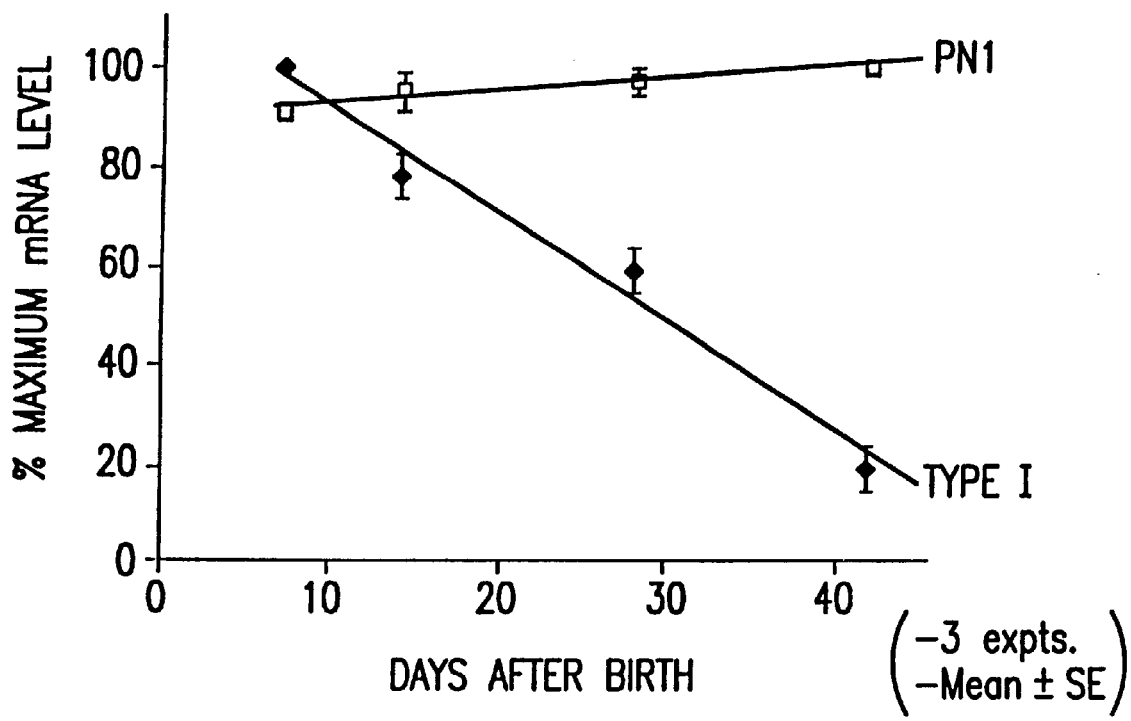

To quantitate the development changes in mRNA levels, autoradiographs from three separate experiments were analyzed by densitometry. To control for differences in the amount of total RNA between lanes, blots were subsequently hybridizing blots with a probe for the internal control cyclophilin. As shown in FIG. 6B, in which percent maximum mRNA is plotted versus postnatal age, the shift in relative abundance of the two transcripts in largely due to a developmental decrease in level of type I sodium channel mRNA. From P7 to P42, the level of type I mRNA decreases by approximately 80%.

EXAMPLE 2

Drug Screening for PN-1 Antagonists

The ability of a PNS SCP-ligand (e.g., antagonists and agonists) to inhibit or enhance the activity of a PNS SCP is be evaluated with cells expressing at least one PNS SCP. An assay for PNS SCP activity in such cells is used to determine the functionality of the PNS SCP protein in the presence of at least one agent which can act as antagonist or agonist, and thus, agents that interfere or enhance the activity of PNS SCP are identified. Two or more cell lines (each expressing a different PNS SCP) are used, as well as optionally using one or more cell lines expressing a CNS specific sodium channel as a control.

These agents are selected and screened (1) at random; (2) by a rational selection; and or (3) by design using for example, computer modeling techniques.

There are numerous variations of assays which can be used by a skilled artisan without the need for undue experimentation in order to isolate, modulating agents or ligands of a PNS SCP. Agent determination methods include Computer Assisted Molecular Design (CAMD), PNS SCP-agent binding, sophisticated chemical synthesis and testing, targeted screening, peptide combinatorial library technology, antisense technology and/or biological assays, according to known methods. See, e.g., Rapaka et al., eds., *Medications Development: Drug Discovery, Databases, and Computer-Aided Drug Design*, NIDA Research Monograph 134, NIH Publication No. 93–3638, U.S. Dept. of Health and Human Services, Rockville, Md. (1993); Langone, *Methods in Enzymology*, Volume 203, *Molecular Design and Modeling:Concepts and Applications, Part B, Antibodies and Antigens, Nucleic Acids, Polysaccharides and Drugs*, Section III, pp 587–702, Academic Press, New York (1991)).

Alternatively, cell expression libraries, or other cells are used to that have been selected or genetically engineered to express and display a PNS SCP via the use of the PNS SCP nucleic acids of the invention are preferred in such methods, as host cell lines may be chosen which are devoid of related receptors. Rapaka, infra, (1993), at pages 58–65.

A PNS SCP agent in the context of the present invention refers to any chemical or biological molecule that associates with a PNS SCP in vitro, in situ or in vivo, and can be, but is not limited to, synthetic, recombinant or naturally derived chemical compounds and compositions, e.g., organic compounds, nucleic acids, peptides, carbohydrates, vitamin derivatives, hormones, neurotransmitters, viruses or receptor binding domains thereof, opsins, rhodopsins, nucleosides, nucleotides, coagulation cascade factors, odorants or pheremones, toxins, growth factors, platelet activating factors, neuroactive peptides, neurohumors, or any biologically active compound, such as drugs or naturally occurring compounds.

The agents are selected and screened at random or rationally selected or designed using computer modeling techniques. For random screening, potential agents are selected and assayed for their ability to bind to the PNS SCP, or a fragment thereof. Alternatively, agents may be rationally selected or designed. As used herein, a agent is said to be "rationally selected or designed" when the agent is chosen based on the configuration of at least one specific PNS SCP (e.g., as presented in FIG. 11). For example, one skilled in the art can readily adapt currently available procedures to generate agents capable of binding to a specific peptide sequence in order to generate rationally designed compounds, such as chemical compounds, nucleic acids or peptides. See, e.g., Rapaka, infra, (1993); Hurby et al., "Application of Synthetic Peptides: Antisense Peptides," in Synthetic Peptides: A User's Guide, W.H. Freeman, New York (1992), pp. 289–307; and Kaspczak et al, Biochemistry 28:9230–2938 (1989).

A method of screening for an agent that modulates the activity of at least one PNS SCP comprising:
  (a) incubating at least one cell line expressing at least one PNS SCP with an agent to be tested; and
  (b) assaying the at least one cell for the activity of the at least one PNS SCP protein by measuring the agents effect on PNS SCP binding or PNS SCP activity preferably the or assay distinguishes the agent's effect on alternative PNS SCP and determines that the agent has little or no effect on CNS sodium channels, or has relatively less effect on CNS sodium channels.

Any cell can be used in the above assay so long as it expresses a functional form of PNS SCP protein and the PNS SCP activity can be measured. The preferred expression cells are eukaryotic cells or organisms. Such cells can be modified to contain DNA sequences encoding the PNS SCP protein using routine procedures known in the art. Alternatively, one skilled in the art can introduce mRNA encoding the PNS SCP protein directly into the cell.

In an alternative embodiment stem cell populations for either neuronal or glial cells can be genetically engineered to express a functional PNS SCP ion channel. Such cells expressing the PNS SCP ion channel, can be transplanted to the diseased or injured region of the mammal's neurological system (Neural Transplantation. A Practical Approach, Donnet & Djorklund, eds., Oxford University Press, New York, N.Y. (1992)). In another embodiment, embryonic tissue or fetal neurons can be genetically engineered to express functional PNS SCP ion channel and transplanted to the diseased or injured region of the mammal's limbic system. The feasibility of transplanting fetal dopamine neurons into Parkinsonian patients has been demonstrated. (Lindvall el al., Archives of Neurology 46:615–631 (1989)).

At least two types of approaches are currently used to express voltage-dependent sodium channel clones in order to generate functional channel proteins. In one approach, mRNA encoding the cloned cDNA is expressed in Xenopus oocytes. The sodium channel cDNA is cloned into a bacterial expression vector such as the pGEM recombinant plasmid (Melton, et al., 1984). Transcription of the cloned cDNA is carried out using an RNA polymerase such as SP6 polymerase or T7 polymerase with a capping analog such as $M^7G(5')ppp(5')G$. The resulting RNA (e.g., about 50 nl, corresponding to 2–5 ng) is injected into stage V and stage VI oocytes isolated from Xenopus, and incubated for 3–5 days at 19° C. Oocytes axe tested for sodium channel expression with a two-microelectrode voltage clamp (Trimmer et al, Neuron 3:33–49 1989).

In an alternative approach, cDNAs encoding a voltage-dependent sodium channel is cloned into any one of a number of mammalian expression vectors, and transfected into mammalian cells which do not express endogenous voltage-dependent sodium channels (such as fibroblast cell lines). Transfected clones are selected expressing the cloned, transfected cDNA. Sodium channel expression is measured with a whole cell voltage clamp technique using a patch electrode (D'Arcangelo et al., J. Cell. Biol. 122:915–921 (1993)).

Sources of PNS SCPs and Cell Lines Useful for Drug Screening. Any cell line expressing (Naturally, by induction or due to recombinant expression of a PNS SCP) can be used for drug screening. As a non-limiting example, PCI2 cells express both PNI and Type II sodium channels. A126-1B2 cells are mutants deficient in Protein Kinase A (PKA) activity and which express PN1, but are now discovered to not express Type II sodium channels. PKI-4 is a PC 12 cell line transfected with a cDNA encoding a peptide inhibitor of PKA. Each of these cell lines can be used as one source of a PNS SCP of the present invention, or as a cell line itself to use in drug screening. Treatment of PC12 cells with NGF reduces both a PNS SCP (PN1) and type II sodium channels, while NGF induces only PN1 in A126–182 cells. PKI-4 cells express a PNS SCP (PN1) without NGF treatment. (D'Arcangelo el al., J. Cell Biol. 122:915–921 (1993)).

Additionally or alternatively, heterologous expression systems can also be used in which cell lines (such as Chinese Hamster Ovary cells (CHO)) are stably transfected with a cDNA encoding PN-1. Method steps for transfecting and stably expressing cDNA to form heterologous cell lines, are well known in the art. An advantage of using transfected cells is that clones are obtained that express very high levels of a PNS SCP, such as PN-1.

To screen for PNS SCP modulators, as antagonists or agonists, drugs are examined for their ability to:
  (a) inhibit or enhance the binding of radioligands to a PNS SCP (labeled ligand binding reaction), and/or
  (b) to inhibit or enhance ion flux through the channel of the PNS SCP in a cell line that expresses a PNS SCP.

Labeled ligand binding neurotoxins can be used to characterize PNS sodium channels. For example previous studies have identified at least six distinct neurotoxin binding sites on previously characterized non-PNS sodium channels (reviewed in Lombert et al, FEB 219(2):355–359 (1987)). Many of these sites are thought to be allosterically coupled to one another (for review, see Strichartz et al., Ann. Rev. Neurosci. 10:237–267 (1987), and references cited therein). In other words, binding of a drug or toxin to a particular neurotoxin site can be sensitive to drug binding at not only that site, but other sites on the channel as well. This is advantageous for a drug screening program in that for a given labeled ligand, the likelihood of identifying agents that preferrentially bind to a PNS SCP is increased.

The techniques described herein for measuring labeled ligand binding to a PNS SCP of the invention in intact cells (e.g., PC12 PKI or PNS SCP expressing heterologous cell lines) in suspension are similar to those described previously for radioligand binding to other sodium channels in brain synaptosomal preparations (see, e.g., Catterall et al, J. Biol. Chem. 256(17):8922–8927 (198 1)). However, it is well recognized by those skilled in the art that these techniques are routinely modified for the use of substrate-attached cells or broken cell preparations, based on the teaching and guidance presented herein.

A126-1B2, PC12, PK1–4 or other cells expressing a PNS SCP cells are grown using standard techniques, and optionally treated with NGF for 1–2 days to induce PN-1 expression. Cells are harvested and tested for ion flux activity with alternative potential agents.

For both radioligands, binding reactions are conducted e.g., at 37° C., then stopped. Samples are quickly filtered with vacuum washed with ice-cold buffer, and bound radioactivity determined by scintillation counting.

Ion Flux directly tests the ability of a potential PNS SCP agent to inhibit or enhance the activity of a PNS SCP function, by their ability to inhibit or enhance the influx of ion tracers through a PNS SCP.

Most previous sodium channel studies have employed $^{22}$Na as a tracer (for example, see Catterall et al., *J. Biol. Chem.* 256(17):8922–8927 (1981)). However, the high toxicity of $^{22}$Na can be a disadvantage for its use in high-throughput drug screening. A less toxic alternative is ($^{14}$C) guanidimium ion, influx of which has been shown to be a reliable indicator of sodium channel opening (Reith, *Europ. J. Pharmacol.* 188:33–41 (1990)). Accordingly, routine methods can be used to screen compounds for modulating PNS SCP ion channel activity, e.g., ($^{14}$C) guanidimium ion flux using intact cells expressing at least one PNS SCP. Additionally these methods are well known to be easily modified for use with $^{22}$Na. Similarly, these known method steps could be modified for use with substrate-attached cells or vesicles prepared from broken cells, according to known method steps.

For a guanidinium flux assay the methods for $^2$Na are modified from those of Reith (Europ. *J. Pharmacol.* 188:33–41 (1990) for brain synaptosomes), e.g., as described in Example 2 below. Aliquots of a cell suspension containing heterologous cells expressing at least one PNS SCP are incubated for 10 minutes at 37° C. in the presence of channel openers (typically, 100 µM veratridine) and test drugs in a total volume of 100 µM (0.20–0.25 mg protein). Ion flux is initiated by the addition of HEPESITRIS solution also containing 4 mM guanidine HCl (final) and 1000 dpm/nmol ($^{14}$C) guanidine. The reaction is continued for 30 seconds and is stopped by the addition of ice-cold incubation buffer, followed by rapid filtration under vacuum over Whatman GF/C filter. The filters are washed rapidly with ice-cold incubation buffer and radioactivity determined by scintillation counting. Nonspecific uptake is determined in parallel by the inclusion of 1 mM tetrodotoxin during both preincubation and uptake.

Using the guanidinium flux assay several methyl/halophenyl substituted compounds, such as lidoflazine (see, e.g., Merck Index Monograph 5311 and U.S. Pat. No. 3,267,104, both entirely incoporated herein by reference), were tested and found to inhibit sodium channel activity of at least one PNS SCP of the present invention in cell lines expressing at least one PNS SCP, with a pIC50 of 6.51 for lidoflazine on PK1–4 cells. Accordingly, the present invention provides PNS SCP modulating agents as methyl/halophenyl-substituted piperizines.

EXAMPLE 3

Identification of Human PNS SCP Sequence from a Human Peripheral Nervous System cDNA Library Similar to the procedures provided in Example 1, a human peripheral nervous system cDNA library (as a human DRG library) was used for polymerase chain reaction (PCR) amplification. The PCR used a 5' primer corresponding to DNA encoding amino acids 604–611 of SEQ ID NO:2, and a corresponding 3' primer encoding amino acids 723–731 of SEQ ID NO:2.

The PCR reaction mixture consisted of 5% of the cDNA, 1 mM MgCl$_2$, 0.2 mM dNTPSs, 0.5 mM, each primer, Taq polymerase (Perkin-Elmer) in a buffer consisting of 0.1 M KCl, 0.1 M TRIS HCl (pH 8.3) and gelatin (1 mg/ml). The reaction was performed in a Perkin-Elmer thermocycler as follows: five cycles of denaturations (94° C., 1 min.), annealing (37° C., 1 min), and extension (72° C., 1 min.), followed by 25 cycles of denaturation (94° C., 1 min.), annealing (50° C., 1 min.), and extension (72° C., 1 min.).

The resulting PCR products provided a human amplified cDNA which encoded amino acids 646–658 of SEQ ID NO:2, as presented in FIGS. 11A–F.

EXAMPLE 4

Cloning and Sequencing of Human PN-1 Sequence from Human Dorsal Root Ganglion cDNA Library As in Examples 1 and 3 above, additional PCR primers corresponding to SEQ ID NO:1 are used to isolate clones from the human DRG cDNA library which encompass the entire coding region of one or more human PNS SCPs of the present invention. A 5' primer includes the sequence 5'TTTGTGCCCCACAGACCCCAG3' (SEQ ID NO:17) and a 3' primer includes the sequence 5' ACACAAATTCT-TGATCTGGAATTGCT3' (SEQ ID NO:18) or 5'CAAC-CTC AGACAGAGAG CAATGA 3' (SEQ ID NO:19), which are used for nested PCR. According to Examples 1 and 3 above, PCR is performed to obtain cDNAs encoding a human PNS SCP.

Additional PCR is performed by "walking" 5' or 3' of the sequence corresponding to the above PCR product. In this way cDNAs encompassing the entire coding region of one or more human PNS SCPs are provided.

The resulting additional cDNA clones or PCR products, encoding the entire human PNS SCP, are subcloned into a plasmid vector previously restricted with suitable restriction sites. The clones are screened for cDNA inserts by miniprep (Sambrook et al., infra) and sequenced in both directions by dideoxy chain termination (Sequenase 2.0 kit, United States Biochemical). Sequence data is compiled and analyzed using GeneWorks software (IntelliGenetics, Inc., Mountain View, Calif.). The expected alternative amino acid sequences for a human PN1 sequence or presented in FIGS. 11A–F and as SEQ ID NOS:7, 11 and 12, where Xaa represents 0, 1, 2 or 3 amino acids.

Transcripts of the size of the resulting human PNS SCP are then confirmed to be present in human PNS mRNA or cDNA (encoding a 1970–1990 amino acid sequence of FIGS. 11A–F). However, as in Example 1, such transcripts are not expected to be detected in mRNA from brain. This expected result confirms new human members of the sodium channel gene family (termed Human Peripheral Nerve type 1 HUMPNIA and HUMPN1B of FIGS. 11A–F, where X is 0, 1, 2 or 3 of the same or different amino acid).

Complete DNA and amino acid sequences of novel human PN1s are then confirmed and are expected to contain all of the structural and functional domain characteristics of an α subunit of a mammalian voltage-gated sodium channel.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. An isolated nucleic acid molecule comprising:
   (a) a polynucleotide sequence encoding the polypeptide of SEQ ID NO:10; or
   (b) a polynucleotide sequence that is complementary to a polynucleotide sequence set forth in (a).

2. A method of making a recombinant vector comprising inserting the nucleic acid molecule of claim 1 into a vector.

3. A recombinant vector comprising the nucleic acid of claim 1.

4. A method of making a cultured recombinant host cell comprising introducing the recombinant vector of claim 3 into a cultured host cell.

5. A cultured host cell comprising the vector of claim 3.

6. A recombinant virion comprising the isolated nucleic acid molecule of claim 1.

7. An isolated nucleic acid molecule comprising:
   (a) a polynucleotide sequence encoding the polypeptide of SEQ ID NO:2; or
   (b) a polynucleotide sequence that is complementary to a polynucleotide sequence set forth in (a).

8. A method of making a recombinant vector comprising inserting the nucleic acid molecule of claim 7 into a vector.

9. A recombinant vector comprising the nucleic acid of claim 7.

10. A method of making a cultured host cell comprising introducing the recombinant vector of claim 9 into a cultured host cell.

11. A cultured host cell comprising the vector of claim 9.

12. A recombinant virion comprising, the isolated nucleic acid molecule of claim 7.

13. An isolated nucleic acid molecule which encodes a polypeptide comprising amino acids selected from the group consisting of:
   (a) amino acids 18–214 of SEQ ID NO:2;
   (b) amino acids 229–258 of SEQ ID NO:2;
   (c) amino acids 268–297 of SEQ ID NO:2;
   (d) amino acids 300–325 of SEQ ID NO:2;
   (e) amino acids 326–351 of SEQ ID NO:2;
   (f) amino acids 474–504 of SEQ ID NO:2;
   (g) amino acids 501–554 of SEQ ID NO:2;
   (h) amino acids 553–583 of SEQ ID NO:2;
   (i) amino acids 589–615 of SEQ ID NO:2;
   (j) amino acids 619–646 of SEQ ID NO:2;
   (k) amino acids 233–555 of SEQ ID NO:2;
   (l) amino acids 554–945 of SEQ ID NO:2.

14. The nucleic acid molecule of claim 13, wherein said molecule is a detectably labeled probe.

15. A method of detecting PNS SCP encoding nucleic acid in a sample comprising:
   (a) contacting said sample with the labeled probe of claim 14; and
   (b) detecting the presence of said labeled probe bound to PNS SCP nucleic acid.

* * * * *

```
                              SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
        (A) LENGTH: 3033 base pairs
        (B) TYPE: nucleic acid
        (C) STRANDEDNESS: both
        (D) TOPOLOGY: both (ii) MOLECULE TYPE: DNA (genomic)

(ix) FEATURE:
        (A) NAME/KEY: CDS
        (B) LOCATION: 1..3033

(xi) SEQUENCE DESCRIPTION: SEQ ID NO:1:

AGG AAC CTT GTG GTC CTG AAC CTG TTT CTG GCT CTT TTG CTG AGT TCC      48
Arg Asn Leu Val Val Leu Asn Leu Phe Leu Ala Leu Leu Leu Ser Ser
 1               5                  10                  15

TTT AGT TCT GAC AAT CTT ACA GCA ATT GAG GAA GAC ACC GAT GCA AAC      96
Phe Ser Ser Asp Asn Leu Thr Ala Ile Glu Glu Asp Thr Asp Ala Asn
             20                  25                  30

AAC CTC CAG ATC GCA GTG GCC AGA ATT AAG AGG GGA ATC AAT TAC GTG     144
Asn Leu Gln Ile Ala Val Ala Arg Ile Lys Arg Gly Ile Asn Tyr Val
         35                  40                  45

AAA CAG ACC CTG CGT GAA TTC ATT CTA AAA TCA TTT TCC AAA AAG CCA     192
Lys Gln Thr Leu Arg Glu Phe Ile Leu Lys Ser Phe Ser Lys Lys Pro
     50                  55                  60

AAG GGC TCC AAG GAC ACA AAA CGA ACA GCA GAT CCC AAC AAC AAG AAA     240
Lys Gly Ser Lys Asp Thr Lys Arg Thr Ala Asp Pro Asn Asn Lys Lys
 65                  70                  75                  80

GAA AAC TAT ATT TCA AAC CGT ACC CTT GCG GAG ATG AGC AAG GAT CAC     288
Glu Asn Tyr Ile Ser Asn Arg Thr Leu Ala Glu Met Ser Lys Asp His
                 85                  90                  95

AAT TTC CTC AAA GAA AAG GAT AGG ATC AGT GGT TAT GGC AGC AGT CTA     336
Asn Phe Leu Lys Glu Lys Asp Arg Ile Ser Gly Tyr Gly Ser Ser Leu
            100                 105                 110

GAC AAA AGC TTT ATG GAT GAA AAT GAT TAC CAG TCC TTT ATC CAT AAC     384
Asp Lys Ser Phe Met Asp Glu Asn Asp Tyr Gln Ser Phe Ile His Asn
        115                 120                 125

CCC AGC CTC ACA GTG ACA GTG CCA ATT GCA CCT GGG GAG TCT GAT TTG     432
Pro Ser Leu Thr Val Thr Val Pro Ile Ala Pro Gly Glu Ser Asp Leu
    130                 135                 140

GAG ATT ATG AAC ACA GAA GAG CTT AGC AGT GAC TCA GAC AGT GAC TAC     480
Glu Ile Met Asn Thr Glu Glu Leu Ser Ser Asp Ser Asp Ser Asp Tyr
145                 150                 155                 160

AGC AAA GAG AAA CGG AAC CGA TCA AGC TCT TCT GAG TGC AGC ACT GTT     528
Ser Lys Glu Lys Arg Asn Arg Ser Ser Ser Glu Cys Ser Thr Val
                165                 170                 175
```

-continued

```
GAC AAC CCT CTG CCA GGA GAA GAG GAG GCT GAA GCA GAG CCC GTA AAC         576
Asp Asn Pro Leu Pro Gly Glu Glu Glu Ala Glu Ala Glu Pro Val Asn
            180                 185                 190

GCA GAT GAG CCT GAA GCC TGC TTT ACA GAT GGT TGT GTG AGG AGA TTT         624
Ala Asp Glu Pro Glu Ala Cys Phe Thr Asp Gly Cys Val Arg Arg Phe
        195                 200                 205

CCA TGC TGC CAA GTT AAT GTA GAC TCT GGG AAA GGG AAA GTT TGG TGG         672
Pro Cys Cys Gln Val Asn Val Asp Ser Gly Lys Gly Lys Val Trp Trp
    210                 215                 220

ACC ATC AGG AAG ACG TGC TAC AGG ATA GTT GAA CAC AGC TGG TTT GAA         720
Thr Ile Arg Lys Thr Cys Tyr Arg Ile Val Glu His Ser Trp Phe Glu
225                 230                 235                 240

AGC TTC ATC GTT CTC ATG ATC CTG CTC AGC AGT GGA GCT CTG GCT TTT         768
Ser Phe Ile Val Leu Met Ile Leu Leu Ser Ser Gly Ala Leu Ala Phe
            245                 250                 255

GAA GAT ATC TAT ATT GAA AAG AAA AAG ACC ATT AAG ATT ATC CTG GAG         816
Glu Asp Ile Tyr Ile Glu Lys Lys Lys Thr Ile Lys Ile Ile Leu Glu
            260                 265                 270

TAT GCT GAC AAG ATA TTC ACC TAC ATC TTC ATT CTG GAA ATG CTT CTA         864
Tyr Ala Asp Lys Ile Phe Thr Tyr Ile Phe Ile Leu Glu Met Leu Leu
        275                 280                 285

AAA TGG GTC GCA TAT GGG TAT AAA ACA TAT TTC ACT AAT GCC TGG TGT         912
Lys Trp Val Ala Tyr Gly Tyr Lys Thr Tyr Phe Thr Asn Ala Trp Cys
    290                 295                 300

TGG CTG GAC TTC TTA ATT GTT GAT GTG TCT CTA GTT ACT TTA GTA GCC         960
Trp Leu Asp Phe Leu Ile Val Asp Val Ser Leu Val Thr Leu Val Ala
305                 310                 315                 320

AAC ACT CTT GGC TAC TCA GAC CTT GGC CCC ATT AAA TCT CTA CGG ACA        1008
Asn Thr Leu Gly Tyr Ser Asp Leu Gly Pro Ile Lys Ser Leu Arg Thr
            325                 330                 335

CTG AGG GCC CTA AGA CCC CTA AGA GCC TTG TCT AGA TTT GAA GGA ATG        1056
Leu Arg Ala Leu Arg Pro Leu Arg Ala Leu Ser Arg Phe Glu Gly Met
            340                 345                 350

AGG GTA GTG GTC AAC GCA CTC ATA GGA GCA ATC CCT TCC ATC ATG AAC        1104
Arg Val Val Val Asn Ala Leu Ile Gly Ala Ile Pro Ser Ile Met Asn
        355                 360                 365

GTG CTT CTC GTG TGC CTT ATA TTC TGG CTA ATA TTT AGC ATC ATG GGA        1152
Val Leu Leu Val Cys Leu Ile Phe Trp Leu Ile Phe Ser Ile Met Gly
    370                 375                 380

GTC AAT CTG TTT GCT GGC AAG TTC TAT GAG TGT GTC AAC ACC ACC GAT        1200
Val Asn Leu Phe Ala Gly Lys Phe Tyr Glu Cys Val Asn Thr Thr Asp
385                 390                 395                 400

GGG TCA CGA TTT CCT ACA TCT CAA GTT GCA AAC CGT TCT GAG TGT TTT        1248
Gly Ser Arg Phe Pro Thr Ser Gln Val Ala Asn Arg Ser Glu Cys Phe
            405                 410                 415

GCC CTG ATG AAC GTT AGT GGA AAT GTG CGA TGG AAA AAC CTG AAA GTA        1296
Ala Leu Met Asn Val Ser Gly Asn Val Arg Trp Lys Asn Leu Lys Val
            420                 425                 430

AAC TTC GAC AAC GTT GGG CTT GGT TAC CTG TCG CTG CTT CAA GTT GCA        1344
Asn Phe Asp Asn Val Gly Leu Gly Tyr Leu Ser Leu Leu Gln Val Ala
        435                 440                 445

ACA TTC AAG GGC TGG ATG GAT ATT ATG TAT GCA GCA GTT GAC TCT GTT        1392
Thr Phe Lys Gly Trp Met Asp Ile Met Tyr Ala Ala Val Asp Ser Val
    450                 455                 460

AAT GTA AAT GAA CAG CCG AAA TAC GAA TAC AGT CTC TAC ATG TAC ATT        1440
Asn Val Asn Glu Gln Pro Lys Tyr Glu Tyr Ser Leu Tyr Met Tyr Ile
465                 470                 475                 480

TAC TTT GTC ATC TTC ATC ATC TTC GGC TCA TTC TTC ACG TTG AAC CTG        1488
Tyr Phe Val Ile Phe Ile Ile Phe Gly Ser Phe Phe Thr Leu Asn Leu
            485                 490                 495
```

```
TTC ATT GGT GTC ATC ATA GAT AAT TTC AAC CAA CAG AAA AAA AAG CTT      1536
Phe Ile Gly Val Ile Ile Asp Asn Phe Asn Gln Gln Lys Lys Lys Leu
            500                 505                 510

GGA GGT CAA GAT ATC TTT ATG ACA GAA GAA CAG AAG AAA TAC TAT AAT      1584
Gly Gly Gln Asp Ile Phe Met Thr Glu Glu Gln Lys Lys Tyr Tyr Asn
            515                 520                 525

GCA ATG AAG AAG CTT GGG TCC AAA AAA CCA CAA AAA CCA ATT CCA AGG      1632
Ala Met Lys Lys Leu Gly Ser Lys Lys Pro Gln Lys Pro Ile Pro Arg
            530                 535                 540

CCA GGG AAC AAA TTC CAA GGA TGT ATA TTT GAC TTA GTG ACA AAC CAA      1680
Pro Gly Asn Lys Phe Gln Gly Cys Ile Phe Asp Leu Val Thr Asn Gln
545                 550                 555                 560

GCT TTT GAT ATC ACC ATC ATG GTT CTT ATA TGC CTC AAC ATG GTA ACC      1728
Ala Phe Asp Ile Thr Ile Met Val Leu Ile Cys Leu Asn Met Val Thr
                565                 570                 575

ATG ATG GTA GAA AAA GAG GGG CAA ACT GAG TAC ATG GAT TAT GTT TTA      1776
Met Met Val Glu Lys Glu Gly Gln Thr Glu Tyr Met Asp Tyr Val Leu
            580                 585                 590

CAC TGG ATC AAC ATG GTC TTC ATT ATC CTG TTC ACT GGG GAG TGT GTG      1824
His Trp Ile Asn Met Val Phe Ile Ile Leu Phe Thr Gly Glu Cys Val
            595                 600                 605

CTG AAG CTA ATC TCC CTC AGA CAT TAC TAC TTC ACT GTG GGT TGG AAC      1872
Leu Lys Leu Ile Ser Leu Arg His Tyr Tyr Phe Thr Val Gly Trp Asn
610                 615                 620

ATT TTG TAT TTT GTG GTA GTG ATC CTC TCC ATT GTA GGA ATG TTT CTC      1920
Ile Leu Tyr Phe Val Val Val Ile Leu Ser Ile Val Gly Met Phe Leu
625                 630                 635                 640

GCT GAG ATG ATA GAG AAG TAT TTC GTG TCC CCT ACC CTG TTC CGA GTC      1968
Ala Glu Met Ile Glu Lys Tyr Phe Val Ser Pro Thr Leu Phe Arg Val
                645                 650                 655

ATC CGC CTG GCC AGG ATT GGA CGA ATC CTA CGC CTG ATC AAA GGC GCC      2016
Ile Arg Leu Ala Arg Ile Gly Arg Ile Leu Arg Leu Ile Lys Gly Ala
            660                 665                 670

AAG GGG ATC CGC ACT CTG CTC TTT GCT TTG ATG ATG TCC CTT CCT GCG      2064
Lys Gly Ile Arg Thr Leu Leu Phe Ala Leu Met Met Ser Leu Pro Ala
            675                 680                 685

CTG TTC AAC ATC GGC CTC CTG CTT TTC CTG GTC ATG TTC ATC TAC GCC      2112
Leu Phe Asn Ile Gly Leu Leu Leu Phe Leu Val Met Phe Ile Tyr Ala
690                 695                 700

ATC TTT GGG ATG TCC AAC TTT GCC TAC GTT AAA AAG GAG GCT GGA ATT      2160
Ile Phe Gly Met Ser Asn Phe Ala Tyr Val Lys Lys Glu Ala Gly Ile
705                 710                 715                 720

AAT GAC ATG TTC AAC TTT GAG ACT TTT GGC AAC AGC ATG ATC TGC TTG      2208
Asn Asp Met Phe Asn Phe Glu Thr Phe Gly Asn Ser Met Ile Cys Leu
                725                 730                 735

TTC CAA ATC ACC ACC TCT GCC GGC TGG GAC GGA CTG CTG GCC CCC ATC      2256
Phe Gln Ile Thr Thr Ser Ala Gly Trp Asp Gly Leu Leu Ala Pro Ile
            740                 745                 750

CTC AAC AGC GCA CCT CCC GAC TGT GAC CCT AAA AAA GTT CAC CCA GGA      2304
Leu Asn Ser Ala Pro Pro Asp Cys Asp Pro Lys Lys Val His Pro Gly
            755                 760                 765

AGT TCA GTG GAA GGG GAC TGT GGG AAC CCA TCC GTG GGG ATT TTT TAC      2352
Ser Ser Val Glu Gly Asp Cys Gly Asn Pro Ser Val Gly Ile Phe Tyr
770                 775                 780

TTT GTC AGC TAC ATC ATC ATA TCC TTC CTG GTG GTG GTG AAC ATG TAC      2400
Phe Val Ser Tyr Ile Ile Ile Ser Phe Leu Val Val Val Asn Met Tyr
785                 790                 795                 800

ATC GCT GTC ATC CTG GAG AAC TTC AGC GTC GCC ACC GAA GAG AGC ACT      2448
Ile Ala Val Ile Leu Glu Asn Phe Ser Val Ala Thr Glu Glu Ser Thr
```

```
                    805                 810                 815
GAG CCT CTG AGT GAG GAC GAC TTT GAG ATG TTC TAC GAG GTC TGG GAG     2496
Glu Pro Leu Ser Glu Asp Asp Phe Glu Met Phe Tyr Glu Val Trp Glu
            820                 825                 830

AAG TTC GAC CCT GAC GCC ACT CAG TTC ATA GAG TTC TGC AAG CTC TCT     2544
Lys Phe Asp Pro Asp Ala Thr Gln Phe Ile Glu Phe Cys Lys Leu Ser
            835                 840                 845

GAC TTT GCA GCT GCC CTG GAT CCT CCC CTC CTC ATC GCA AAG CCA AAC     2592
Asp Phe Ala Ala Ala Leu Asp Pro Pro Leu Leu Ile Ala Lys Pro Asn
    850                 855                 860

AAA GTC CAG CTC ATT GCC ATG GAC CTG CCC ATG GTG AGT GGA GAC CGC     2640
Lys Val Gln Leu Ile Ala Met Asp Leu Pro Met Val Ser Gly Asp Arg
865                 870                 875                 880

ATC CAC TGC CTG GAC ATC TTG TTT GCT TTT ACA AAG CGG GTC CTG GGT     2688
Ile His Cys Leu Asp Ile Leu Phe Ala Phe Thr Lys Arg Val Leu Gly
                885                 890                 895

GAG GGT GGA GAG ATG GAT TCT CTT CGT TCA CAG ATG GAA GAA AGG TTC     2736
Glu Gly Gly Glu Met Asp Ser Leu Arg Ser Gln Met Glu Glu Arg Phe
            900                 905                 910

ATG TCA GCC AAT CCT TCT AAA GTG TCC TAT GAA CCC ATC ACG ACC ACA     2784
Met Ser Ala Asn Pro Ser Lys Val Ser Tyr Glu Pro Ile Thr Thr Thr
            915                 920                 925

CTG AAG AGA AAA CAA GAG GAG GTG TCC GCG ACT ATC ATT CAG CGT GCT     2832
Leu Lys Arg Lys Gln Glu Glu Val Ser Ala Thr Ile Ile Gln Arg Ala
        930                 935                 940

TAC AGA CGG TAT CGC CTC AGA CAA CAC GTC AAG AAT ATA TCG AGT ATA     2880
Tyr Arg Arg Tyr Arg Leu Arg Gln His Val Lys Asn Ile Ser Ser Ile
945                 950                 955                 960

TAC ATA AAA GAT GGA GAC AGG GAT GAT GAT TTG CCC AAT AAA GAA GAT     2928
Tyr Ile Lys Asp Gly Asp Arg Asp Asp Asp Leu Pro Asn Lys Glu Asp
                965                 970                 975

ACA GTT TTT GAT AAC GTG AAC GAG AAC TCA AGT CCG GAA AAG ACA GAT     2976
Thr Val Phe Asp Asn Val Asn Glu Asn Ser Ser Pro Glu Lys Thr Asp
            980                 985                 990

GTA ACT GCC TCA ACC ATC TCG CCA CCT TCC TAT GAC AGT GTC ACA AAG     3024
Val Thr Ala Ser Thr Ile Ser Pro Pro Ser Tyr Asp Ser Val Thr Lys
            995                 1000                1005

CCA GAT CAA                                                         3033
Pro Asp Gln
    1010

(2) INFORMATION FOR SEQ ID NO:2:

(i) SEQUENCE CHARACTERISTICS:
        (A) LENGTH: 1011 amino acids
        (B) TYPE: amino acid
        (D) TOPOLOGY: linear (ii) MOLECULE TYPE: protein (xi) SEQUENCE DESCRIPTION: SEQ ID NO:2:

Arg Asn Leu Val Val Leu Asn Leu Phe Leu Ala Leu Leu Leu Ser Ser
 1               5                  10                  15

Phe Ser Ser Asp Asn Leu Thr Ala Ile Glu Glu Asp Thr Asp Ala Asn
                20                  25                  30

Asn Leu Gln Ile Ala Val Ala Arg Ile Lys Arg Gly Ile Asn Tyr Val
            35                  40                  45

Lys Gln Thr Leu Arg Glu Phe Ile Leu Lys Ser Phe Ser Lys Lys Pro
        50                  55                  60

Lys Gly Ser Lys Asp Thr Lys Arg Thr Ala Asp Pro Asn Asn Lys Lys
```

-continued

```
            65                  70                  75                  80
Glu Asn Tyr Ile Ser Asn Arg Thr Leu Ala Glu Met Ser Lys Asp His
                    85                  90                  95
Asn Phe Leu Lys Glu Lys Asp Arg Ile Ser Gly Tyr Gly Ser Ser Leu
                100                 105                 110
Asp Lys Ser Phe Met Asp Glu Asn Asp Tyr Gln Ser Phe Ile His Asn
                115                 120                 125
Pro Ser Leu Thr Val Thr Val Pro Ile Ala Pro Gly Glu Ser Asp Leu
                130                 135                 140
Glu Ile Met Asn Thr Glu Glu Leu Ser Ser Asp Ser Asp Ser Asp Tyr
145                 150                 155                 160
Ser Lys Glu Lys Arg Asn Arg Ser Ser Ser Glu Cys Ser Thr Val
                165                 170                 175
Asp Asn Pro Leu Pro Gly Glu Glu Ala Glu Ala Glu Pro Val Asn
                180                 185                 190
Ala Asp Glu Pro Glu Ala Cys Phe Thr Asp Gly Cys Val Arg Arg Phe
                195                 200                 205
Pro Cys Cys Gln Val Asn Val Asp Ser Gly Lys Gly Lys Val Trp Trp
                210                 215                 220
Thr Ile Arg Lys Thr Cys Tyr Arg Ile Val Glu His Ser Trp Phe Glu
225                 230                 235                 240
Ser Phe Ile Val Leu Met Ile Leu Ser Ser Gly Ala Leu Ala Phe
                245                 250                 255
Glu Asp Ile Tyr Ile Glu Lys Lys Lys Thr Ile Lys Ile Ile Leu Glu
                260                 265                 270
Tyr Ala Asp Lys Ile Phe Thr Tyr Ile Phe Ile Leu Glu Met Leu Leu
                275                 280                 285
Lys Trp Val Ala Tyr Gly Tyr Lys Thr Tyr Phe Thr Asn Ala Trp Cys
290                 295                 300
Trp Leu Asp Phe Leu Ile Val Asp Val Ser Leu Val Thr Leu Val Ala
305                 310                 315                 320
Asn Thr Leu Gly Tyr Ser Asp Leu Gly Pro Ile Lys Ser Leu Arg Thr
                325                 330                 335
Leu Arg Ala Leu Arg Pro Leu Arg Ala Leu Ser Arg Phe Glu Gly Met
                340                 345                 350
Arg Val Val Asn Ala Leu Ile Gly Ala Ile Pro Ser Ile Met Asn
                355                 360                 365
Val Leu Leu Val Cys Leu Ile Phe Trp Leu Ile Phe Ser Ile Met Gly
                370                 375                 380
Val Asn Leu Phe Ala Gly Lys Phe Tyr Glu Cys Val Asn Thr Thr Asp
385                 390                 395                 400
Gly Ser Arg Phe Pro Thr Ser Gln Val Ala Asn Arg Ser Glu Cys Phe
                405                 410                 415
Ala Leu Met Asn Val Ser Gly Asn Val Arg Trp Lys Asn Leu Lys Val
                420                 425                 430
Asn Phe Asp Asn Val Gly Leu Gly Tyr Leu Ser Leu Leu Gln Val Ala
                435                 440                 445
Thr Phe Lys Gly Trp Met Asp Ile Met Tyr Ala Ala Val Asp Ser Val
                450                 455                 460
Asn Val Asn Glu Gln Pro Lys Tyr Glu Tyr Ser Leu Tyr Met Tyr Ile
465                 470                 475                 480
Tyr Phe Val Ile Phe Ile Ile Phe Gly Ser Phe Phe Thr Leu Asn Leu
                485                 490                 495
```

-continued

```
Phe Ile Gly Val Ile Ile Asp Asn Phe Asn Gln Gln Lys Lys Lys Leu
            500                 505                 510
Gly Gly Gln Asp Ile Phe Met Thr Glu Glu Gln Lys Lys Tyr Tyr Asn
            515                 520                 525
Ala Met Lys Lys Leu Gly Ser Lys Lys Pro Gln Lys Pro Ile Pro Arg
            530                 535                 540
Pro Gly Asn Lys Phe Gln Gly Cys Ile Phe Asp Leu Val Thr Asn Gln
545                 550                 555                 560
Ala Phe Asp Ile Thr Ile Met Val Leu Ile Cys Leu Asn Met Val Thr
                565                 570                 575
Met Met Val Glu Lys Glu Gly Gln Thr Glu Tyr Met Asp Tyr Val Leu
            580                 585                 590
His Trp Ile Asn Met Val Phe Ile Ile Leu Phe Thr Gly Glu Cys Val
            595                 600                 605
Leu Lys Leu Ile Ser Leu Arg His Tyr Tyr Phe Thr Val Gly Trp Asn
            610                 615                 620
Ile Leu Tyr Phe Val Val Ile Leu Ser Ile Val Gly Met Phe Leu
625                 630                 635                 640
Ala Glu Met Ile Glu Lys Tyr Phe Val Ser Pro Thr Leu Phe Arg Val
                645                 650                 655
Ile Arg Leu Ala Arg Ile Gly Arg Ile Leu Arg Leu Ile Lys Gly Ala
            660                 665                 670
Lys Gly Ile Arg Thr Leu Leu Phe Ala Leu Met Met Ser Leu Pro Ala
            675                 680                 685
Leu Phe Asn Ile Gly Leu Leu Leu Phe Leu Val Met Phe Ile Tyr Ala
            690                 695                 700
Ile Phe Gly Met Ser Asn Phe Ala Tyr Val Lys Lys Glu Ala Gly Ile
705                 710                 715                 720
Asn Asp Met Phe Asn Phe Glu Thr Phe Gly Asn Ser Met Ile Cys Leu
                725                 730                 735
Phe Gln Ile Thr Thr Ser Ala Gly Trp Asp Gly Leu Leu Ala Pro Ile
            740                 745                 750
Leu Asn Ser Ala Pro Pro Asp Cys Asp Pro Lys Lys Val His Pro Gly
            755                 760                 765
Ser Ser Val Glu Gly Asp Cys Gly Asn Pro Ser Val Gly Ile Phe Tyr
            770                 775                 780
Phe Val Ser Tyr Ile Ile Ile Ser Phe Leu Val Val Val Asn Met Tyr
785                 790                 795                 800
Ile Ala Val Ile Leu Glu Asn Phe Ser Val Ala Thr Glu Glu Ser Thr
                805                 810                 815
Glu Pro Leu Ser Glu Asp Asp Phe Glu Met Phe Tyr Glu Val Trp Glu
            820                 825                 830
Lys Phe Asp Pro Asp Ala Thr Gln Phe Ile Glu Phe Cys Lys Leu Ser
            835                 840                 845
Asp Phe Ala Ala Ala Leu Asp Pro Pro Leu Leu Ile Ala Lys Pro Asn
            850                 855                 860
Lys Val Gln Leu Ile Ala Met Asp Leu Pro Met Val Ser Gly Asp Arg
865                 870                 875                 880
Ile His Cys Leu Asp Ile Leu Phe Ala Phe Thr Lys Arg Val Leu Gly
                885                 890                 895
Glu Gly Gly Glu Met Asp Ser Leu Arg Ser Gln Met Glu Glu Arg Phe
            900                 905                 910
```

-continued

```
Met Ser Ala Asn Pro Ser Lys Val Ser Tyr Glu Pro Ile Thr Thr Thr
            915                 920                 925

Leu Lys Arg Lys Gln Glu Val Ser Ala Thr Ile Ile Gln Arg Ala
        930                 935                 940

Tyr Arg Arg Tyr Arg Leu Arg Gln His Val Lys Asn Ile Ser Ser Ile
945                 950                 955                 960

Tyr Ile Lys Asp Gly Asp Arg Asp Asp Leu Pro Asn Lys Glu Asp
                965                 970                 975

Thr Val Phe Asp Asn Val Asn Glu Asn Ser Ser Pro Glu Lys Thr Asp
            980                 985                 990

Val Thr Ala Ser Thr Ile Ser Pro Pro Ser Tyr Asp Ser Val Thr Lys
            995                 1000                1005

Pro Asp Gln
    1010
```

(2) INFORMATION FOR SEQ ID NO:3:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 12
        (D) OTHER INFORMATION: /note= "Base is Inosine"

(ix) FEATURE:
        (A) NAME/KEY: misc_feature
        (B) LOCATION: 15
        (D) OTHER INFORMATION: /note= "Base is Inosine"

(ix) FEATURE:
        (A) NAME/KEY: misc_feature
        (B) LOCATION: 19
        (D) OTHER INFORMATION: /note= "Base is Inosine"

(ix) FEATURE:
        (A) NAME/KEY: misc_feature
        (B) LOCATION: 21
        (D) OTHER INFORMATION: /note= "Base is Inosine"

(xi) SEQUENCE DESCRIPTION: SEQ ID NO:3:

GCGAAGCTTY TNATNTTYNN NATHATGGG                                      29

(2) INFORMATION FOR SEQ ID NO:4:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Phe Trp Leu Ile Phe Ser Ile Met
1               5
```

(2) INFORMATION FOR SEQ ID NO:5:

(i) SEQUENCE CHARACTERISTICS:
        (A) LENGTH: 34 base pairs
        (B) TYPE: nucleic acid
        (C) STRANDEDNESS: single (D) TOPOLOGY: linear (ii) MOLECULE TYPE: cDNA (xi) SEQUENCE DESCRIPTION: SEQ ID NO:5:

GCAGGATCCR TTRAAARTTR TCDATDATNA CNCC                34

(2) INFORMATION FOR SEQ ID NO:6:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Gly Val Ile Ile Asp Asn Phe Asn
1               5

(2) INFORMATION FOR SEQ ID NO:7:

(i) SEQUENCE CHARACTERISTICS:
        (A) LENGTH: 2005 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Met Ala Arg Ser Val Leu Val Pro Pro Gly Pro Asp Ser Phe Arg Phe
1               5                   10                  15

Phe Thr Arg Glu Ser Leu Ala Ala Ile Glu Gln Arg Ile Ala Glu Glu
                20                  25                  30

Lys Ala Lys Arg Pro Lys Gln Glu Arg Lys Asp Glu Asp Asp Glu Asn
            35                  40                  45

Gly Pro Lys Pro Asn Ser Asp Leu Glu Ala Gly Lys Ser Leu Pro Phe
50                  55                  60

Ile Tyr Gly Asp Ile Pro Pro Glu Met Val Ser Glu Pro Leu Glu Asp
65                  70                  75                  80

Leu Asp Pro Tyr Tyr Ile Asn Lys Lys Thr Phe Ile Val Leu Asn Lys
                85                  90                  95

Gly Lys Ala Ile Ser Arg Phe Ser Ala Thr Ser Ala Leu Tyr Ile Leu
            100                 105                 110

Thr Pro Phe Asn Pro Ile Arg Lys Leu Ala Ile Lys Ile Leu Val His
            115                 120                 125

Ser Leu Phe Asn Val Leu Ile Met Cys Thr Ile Leu Thr Asn Cys Val
130                 135                 140

Phe Met Thr Met Ser Asn Pro Pro Asp Trp Thr Lys Asn Val Glu Tyr
145                 150                 155                 160

Thr Phe Thr Gly Ile Tyr Thr Phe Glu Ser Leu Ile Lys Ile Leu Ala
                165                 170                 175

Arg Gly Phe Cys Leu Glu Asp Phe Thr Phe Leu Arg Asn Pro Trp Asn
            180                 185                 190

Trp Leu Asp Phe Thr Val Ile Thr Phe Ala Tyr Val Thr Glu Phe Val
            195                 200                 205

Asn Leu Gly Asn Val Ser Ala Leu Arg Thr Phe Arg Val Leu Arg Ala
210                 215                 220

-continued

```
Leu Lys Thr Ile Ser Val Ile Pro Gly Leu Lys Thr Ile Val Gly Ala
225                 230                 235                 240

Leu Ile Gln Ser Val Lys Lys Leu Ser Asp Val Met Ile Leu Thr Val
            245                 250                 255

Phe Cys Leu Ser Val Phe Ala Leu Ile Gly Leu Gln Leu Phe Met Gly
                260                 265                 270

Asn Leu Arg Asn Lys Cys Leu Gln Trp Pro Pro Asp Asn Ser Thr Phe
            275                 280                 285

Glu Ile Asn Ile Thr Ser Phe Phe Asn Asn Ser Leu Asp Trp Asn Gly
        290                 295                 300

Thr Ala Phe Asn Arg Thr Val Asn Met Phe Asn Trp Asp Glu Tyr Ile
305                 310                 315                 320

Glu Asp Lys Ser His Phe Tyr Phe Leu Glu Gly Gln Asn Asp Ala Leu
                325                 330                 335

Leu Cys Gly Asn Ser Ser Asp Ala Gly Gln Cys Pro Glu Gly Tyr Ile
                340                 345                 350

Cys Val Lys Ala Gly Arg Asn Pro Asn Tyr Gly Tyr Thr Ser Phe Asp
            355                 360                 365

Thr Phe Ser Trp Ala Phe Leu Ser Leu Phe Arg Leu Met Thr Gln Asp
        370                 375                 380

Phe Trp Glu Asn Leu Tyr Gln Leu Thr Leu Arg Ala Ala Gly Lys Thr
385                 390                 395                 400

Tyr Met Ile Phe Phe Val Leu Val Ile Phe Leu Gly Ser Phe Tyr Leu
                405                 410                 415

Ile Asn Leu Ile Leu Ala Val Val Ala Met Ala Tyr Glu Glu Gln Asn
            420                 425                 430

Gln Ala Thr Leu Glu Glu Ala Glu Gln Lys Glu Ala Glu Phe Gln Gln
        435                 440                 445

Met Leu Glu Gln Leu Lys Lys Gln Gln Glu Glu Ala Gln Ala Ala Ala
    450                 455                 460

Ala Ala Ala Ser Ala Glu Ser Arg Asp Phe Ser Gly Ala Gly Gly Ile
465                 470                 475                 480

Gly Val Phe Ser Glu Ser Ser Ser Val Ala Ser Lys Leu Ser Ser Lys
                485                 490                 495

Ser Glu Lys Glu Leu Lys Asn Arg Arg Lys Lys Lys Gln Lys Glu
            500                 505                 510

Gln Ala Gly Glu Glu Glu Lys Glu Asp Ala Val Arg Lys Ser Ala Ser
        515                 520                 525

Glu Asp Ser Ile Arg Lys Lys Gly Phe Gln Phe Ser Leu Glu Gly Ser
    530                 535                 540

Arg Leu Thr Tyr Glu Lys Arg Phe Ser Ser Pro His Gln Ser Leu Leu
545                 550                 555                 560

Ser Ile Arg Gly Ser Leu Phe Ser Pro Arg Arg Asn Ser Arg Ala Ser
                565                 570                 575

Leu Phe Asn Phe Lys Gly Arg Val Lys Asp Ile Gly Ser Glu Asn Asp
            580                 585                 590

Phe Ala Asp Asp Glu His Ser Thr Phe Glu Asp Asn Asp Ser Arg Arg
        595                 600                 605

Asp Ser Leu Phe Val Pro His Arg His Gly Glu Arg Arg Pro Ser Asn
    610                 615                 620

Val Ser Gln Ala Ser Arg Ala Ser Arg Gly Ile Pro Thr Leu Pro Met
625                 630                 635                 640

Asn Gly Lys Met His Ser Ala Val Asp Cys Asn Gly Val Val Ser Leu
```

-continued

```
                    645                 650                 655
    Val Gly Gly Pro Ser Ala Leu Thr Ser Pro Val Gly Gln Leu Leu Pro
                660                 665                 670

Glu Gly Thr Thr Thr Glu Thr Glu Ile Arg Lys Arg Arg Ser Ser Ser
                675                 680                 685

Tyr His Val Ser Met Asp Leu Leu Glu Asp Pro Ser Arg Gln Arg Ala
                690                 695                 700

Met Ser Met Ala Ser Ile Leu Thr Asn Thr Met Glu Glu Leu Glu Glu
    705                 710                 715                 720

Ser Arg Gln Lys Cys Pro Pro Cys Trp Tyr Lys Phe Ala Asn Met Cys
                        725                 730                 735

Leu Ile Trp Asp Cys Cys Lys Pro Trp Leu Lys Val Lys His Val Val
                        740                 745                 750

Asn Leu Val Val Met Asp Pro Phe Val Asp Leu Ala Ile Thr Ile Cys
                        755                 760                 765

Ile Val Leu Asn Thr Leu Phe Met Ala Met Glu His Tyr Pro Met Thr
                770                 775                 780

Glu Gln Phe Ser Ser Val Leu Ser Val Gly Asn Leu Val Phe Thr Gly
    785                 790                 795                 800

Ile Phe Thr Ala Glu Met Phe Leu Lys Ile Ile Ala Met Asp Pro Tyr
                        805                 810                 815

Tyr Tyr Phe Gln Glu Gly Trp Asn Ile Phe Asp Gly Phe Ile Val Ser
                        820                 825                 830

Leu Ser Leu Met Glu Leu Gly Leu Ala Asn Val Glu Gly Leu Ser Val
                835                 840                 845

Leu Arg Ser Phe Arg Leu Leu Arg Val Phe Lys Leu Ala Lys Ser Trp
    850                 855                 860

Pro Thr Leu Asn Met Leu Ile Lys Ile Ile Gly Asn Ser Val Gly Ala
    865                 870                 875                 880

Leu Gly Asn Leu Thr Leu Val Leu Ala Ile Ile Val Phe Ile Phe Ala
                        885                 890                 895

Val Val Gly Met Gln Leu Phe Gly Lys Ser Tyr Lys Glu Cys Val Cys
                900                 905                 910

Lys Ile Ser Asn Asp Cys Glu Leu Pro Arg Trp His Met His Asp Phe
                915                 920                 925

Phe His Ser Phe Leu Ile Val Phe Arg Val Leu Cys Gly Glu Trp Ile
                930                 935                 940

Glu Thr Met Trp Asp Cys Met Glu Val Ala Gly Gln Thr Met Cys Leu
    945                 950                 955                 960

Thr Val Phe Met Met Val Met Val Ile Gly Asn Leu Val Val Leu Asn
                        965                 970                 975

Leu Phe Leu Ala Leu Leu Leu Ser Ser Phe Ser Ser Asp Asn Leu Ala
                980                 985                 990

Ala Thr Asp Asp Asp Asn Glu Met Asn Asn Leu Gln Ile Ala Val Gly
                995                 1000                1005

Arg Met Gln Lys Gly Ile Asp Phe Val Lys Arg Lys Ile Arg Glu Phe
                1010                1015                1020

Ile Gln Lys Ala Phe Val Arg Lys Gln Lys Ala Leu Asp Glu Ile Lys
    1025                1030                1035                1040

Pro Leu Glu Asp Leu Asn Asn Lys Lys Asp Ser Cys Ile Ser Asn His
                        1045                1050                1055

Thr Thr Ile Glu Ile Gly Lys Asp Leu Asn Tyr Leu Lys Asp Gly Asn
                1060                1065                1070
```

-continued

```
Gly Thr Thr Ser Gly Ile Gly Ser Ser Val Glu Lys Tyr Val Asp
        1075            1080            1085

Glu Ser Asp Tyr Met Ser Phe Ile Asn Asn Pro Ser Leu Thr Val Thr
    1090            1095            1100

Val Pro Ile Ala Leu Gly Glu Ser Asp Phe Glu Asn Leu Asn Thr Glu
1105            1110            1115            1120

Glu Phe Ser Ser Glu Ser Asp Met Glu Glu Ser Lys Glu Lys Leu Asn
            1125            1130            1135

Ala Thr Ser Ser Ser Glu Gly Ser Thr Val Asp Ile Gly Ala Pro Ala
            1140            1145            1150

Glu Gly Glu Gln Pro Glu Ala Glu Pro Glu Gly Ser Leu Glu Pro Glu
            1155            1160            1165

Ala Cys Phe Thr Glu Asp Cys Val Arg Lys Phe Lys Cys Cys Gln Ile
            1170            1175            1180

Ser Ile Glu Glu Gly Lys Gly Lys Leu Trp Trp Asn Leu Arg Lys Thr
1185            1190            1195            1200

Cys Tyr Lys Ile Val Glu His Asn Trp Phe Glu Ile Phe Ile Val Phe
            1205            1210            1215

Met Ile Leu Leu Ser Ser Gly Ala Leu Ala Phe Glu Asp Ile Tyr Ile
            1220            1225            1230

Glu Gln Arg Lys Thr Ile Lys Thr Met Leu Glu Tyr Ala Asp Lys Val
            1235            1240            1245

Phe Thr Tyr Ile Phe Ile Leu Glu Met Leu Leu Lys Trp Val Ala Tyr
            1250            1255            1260

Gly Phe Gln Met Tyr Phe Thr Asn Ala Trp Cys Trp Leu Asp Phe Leu
1265            1270            1275            1280

Ile Val Asp Val Ser Leu Val Ser Leu Thr Ala Asn Ala Leu Gly Tyr
            1285            1290            1295

Ser Glu Leu Gly Ala Ile Lys Ser Leu Arg Thr Leu Arg Ala Leu Arg
            1300            1305            1310

Pro Leu Arg Ala Leu Ser Arg Phe Glu Gly Met Arg Val Val Val Asn
            1315            1320            1325

Ala Leu Leu Gly Ala Ile Pro Ser Ile Met Asn Val Leu Leu Val Cys
            1330            1335            1340

Leu Ile Phe Trp Leu Ile Phe Ser Ile Met Gly Val Asn Leu Phe Ala
1345            1350            1355            1360

Gly Lys Phe Tyr His Cys Ile Asn Tyr Thr Ile Gly Glu Met Phe Asp
            1365            1370            1375

Val Ser Val Val Asn Asn Tyr Ser Glu Cys Gln Ala Leu Ile Glu Ser
            1380            1385            1390

Asn Gln Thr Ala Arg Trp Lys Asn Val Lys Val Asn Phe Asp Asn Val
            1395            1400            1405

Gly Leu Gly Tyr Leu Ser Leu Leu Gln Val Ala Thr Phe Lys Gly Trp
            1410            1415            1420

Met Asp Ile Met Tyr Ala Ala Val Asp Ser Arg Asn Val Glu Leu Gln
1425            1430            1435            1440

Pro Lys Tyr Glu Asp Asn Leu Tyr Met Tyr Leu Tyr Phe Val Ile Phe
            1445            1450            1455

Ile Ile Phe Gly Ser Phe Phe Thr Leu Asn Leu Phe Ile Gly Val Ile
            1460            1465            1470

Ile Asp Asn Phe Asn Gln Gln Lys Lys Lys Phe Gly Gly Gln Asp Ile
            1475            1480            1485
```

-continued

Phe Met Thr Glu Glu Gln Lys Lys Tyr Tyr Asn Ala Met Lys Lys Leu
    1490                1495                1500

Gly Ser Lys Lys Pro Gln Lys Pro Ile Pro Arg Pro Ala Asn Lys Phe
1505                1510                1515                1520

Gln Gly Met Val Phe Asp Phe Val Thr Lys Gln Val Phe Asp Ile Ser
            1525                1530                1535

Ile Met Ile Leu Ile Cys Leu Asn Met Val Thr Met Met Val Glu Thr
        1540                1545                1550

Asp Asp Gln Ser Gln Glu Met Thr Asn Ile Leu Tyr Trp Ile Asn Leu
            1555                1560                1565

Val Phe Ile Val Leu Phe Thr Gly Glu Cys Val Leu Lys Leu Ile Ser
    1570                1575                1580

Leu Arg His Tyr Tyr Phe Thr Ile Gly Trp Asn Ile Phe Asp Phe Val
1585                1590                1595                1600

Val Val Ile Leu Ser Ile Val Gly Met Phe Leu Ala Glu Leu Ile Glu
            1605                1610                1615

Lys Tyr Phe Val Ser Pro Thr Leu Phe Arg Val Ile Arg Leu Ala Arg
        1620                1625                1630

Ile Gly Arg Ile Leu Arg Leu Ile Lys Gly Ala Lys Gly Ile Arg Thr
        1635                1640                1645

Leu Leu Phe Ala Leu Met Met Ser Leu Pro Ala Leu Phe Asn Ile Gly
        1650                1655                1660

Leu Leu Leu Phe Leu Val Met Phe Ile Tyr Ala Ile Phe Gly Met Ser
1665                1670                1675                1680

Asn Phe Ala Tyr Val Lys Arg Glu Val Gly Ile Asp Asp Met Phe Asn
            1685                1690                1695

Phe Glu Thr Phe Gly Asn Ser Met Ile Cys Leu Phe Gln Ile Thr Thr
            1700                1705                1710

Ser Ala Gly Trp Asp Gly Leu Leu Ala Pro Ile Leu Asn Ser Gly Pro
        1715                1720                1725

Pro Asp Cys Asp Pro Glu Lys Asp His Pro Gly Ser Ser Val Lys Gly
        1730                1735                1740

Asp Cys Gly Asn Pro Ser Val Gly Ile Phe Phe Phe Val Ser Tyr Ile
1745                1750                1755                1760

Ile Ile Ser Phe Leu Val Val Val Asn Met Tyr Ile Ala Val Ile Leu
            1765                1770                1775

Glu Asn Phe Ser Val Ala Thr Glu Glu Ser Ala Glu Pro Leu Ser Glu
            1780                1785                1790

Asp Asp Phe Glu Met Phe Tyr Glu Val Trp Glu Lys Phe Asp Pro Asp
        1795                1800                1805

Ala Thr Gln Phe Ile Glu Phe Cys Lys Leu Ser Asp Phe Ala Ala Ala
        1810                1815                1820

Leu Asp Pro Pro Leu Leu Ile Ala Lys Pro Asn Lys Val Gln Leu Ile
1825                1830                1835                1840

Ala Met Asp Leu Pro Met Val Ser Gly Asp Arg Ile His Cys Leu Asp
            1845                1850                1855

Ile Leu Phe Ala Phe Thr Lys Arg Val Leu Gly Glu Ser Gly Glu Met
        1860                1865                1870

Asp Ala Leu Arg Ile Gln Met Glu Glu Arg Phe Met Ala Ser Asn Pro
        1875                1880                1885

Ser Lys Val Ser Tyr Glu Pro Ile Thr Thr Thr Leu Lys Arg Lys Gln
        1890                1895                1900

Glu Glu Val Ser Ala Ile Val Ile Gln Arg Ala Tyr Arg Arg Tyr Leu

```
                1905                1910                1915                1920
Leu Lys Gln Lys Val Lys Val Ser Ser Ile Tyr Lys Lys Asp Lys
                    1925                1930                1935

Gly Lys Glu Asp Glu Gly Thr Pro Ile Lys Glu Asp Ile Ile Thr Asp
                1940                1945                1950

Lys Leu Asn Glu Asn Ser Thr Pro Glu Lys Thr Asp Val Thr Pro Ser
                1955                1960                1965

Thr Thr Ser Pro Pro Ser Tyr Asp Ser Val Thr Lys Pro Glu Lys Glu
        1970                1975                1980

Lys Phe Glu Lys Asp Lys Ser Glu Lys Glu Asp Lys Gly Lys Asp Ile
1985                1990                1995                2000

Arg Glu Ser Lys Lys
                2005

(2) INFORMATION FOR SEQ ID NO:8:

(i) SEQUENCE CHARACTERISTICS:
        (A) LENGTH: 813 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Asn Leu Val Val Leu Asn Leu Phe Leu Ala Leu Leu Ser Ser Phe
1               5                   10                  15

Ser Ser Asp Asn Leu Ala Asp Asn Asn Leu Gln Ile Ala Val Arg Gly
                20                  25                  30

Ile Val Lys Arg Glu Phe Ile Lys Phe Lys Lys Asp Asn Asn Lys
            35                  40                  45

Lys Ile Ser Asn Thr Glu Lys Asp Asn Leu Lys Ser Gly Gly Ser Ser
        50                  55                  60

Lys Asp Glu Asp Tyr Ser Phe Ile Asn Pro Ser Leu Thr Val Thr Val
65                  70                  75                  80

Pro Ile Ala Gly Glu Ser Asp Glu Asn Thr Glu Glu Ser Ser Ser Asp
                85                  90                  95

Ser Lys Glu Lys Asn Ser Ser Glu Ser Thr Val Asp Pro Glu Glu
            100                 105                 110

Glu Ala Glu Pro Glu Pro Glu Ala Cys Phe Thr Cys Val Arg Phe Cys
            115                 120                 125

Cys Gln Gly Lys Gly Lys Trp Trp Arg Lys Thr Cys Tyr Ile Val Glu
        130                 135                 140

His Trp Phe Glu Phe Ile Val Met Ile Leu Leu Ser Ser Gly Ala Leu
145                 150                 155                 160

Ala Phe Glu Asp Ile Tyr Ile Glu Lys Thr Ile Lys Leu Glu Tyr Ala
                165                 170                 175

Asp Lys Phe Thr Tyr Ile Phe Ile Leu Glu Met Leu Leu Lys Trp Val
            180                 185                 190

Ala Tyr Gly Tyr Phe Thr Asn Ala Trp Cys Trp Leu Asp Phe Leu Ile
            195                 200                 205

Val Asp Val Ser Leu Val Leu Ala Asn Leu Gly Tyr Ser Leu Gly Ile
        210                 215                 220

Lys Ser Leu Arg Thr Leu Arg Ala Leu Arg Pro Leu Arg Ala Leu Ser
225                 230                 235                 240

Arg Phe Glu Gly Met Arg Val Val Val Asn Ala Leu Gly Ala Ile Pro
```

-continued

```
                245                 250                 255
Ser Ile Met Asn Val Leu Leu Val Cys Leu Ile Phe Trp Leu Ile Phe
                260                 265                 270

Ser Ile Met Gly Val Asn Leu Phe Ala Gly Lys Phe Tyr Cys Asn Thr
                275                 280                 285

Gly Phe Ser Val Asn Ser Glu Cys Ala Leu Arg Trp Lys Asn Lys Val
                290                 295                 300

Asn Phe Asp Asn Val Gly Leu Gly Tyr Leu Ser Leu Gln Val Ala
305                 310                 315                 320

Thr Phe Lys Gly Trp Met Asp Ile Met Tyr Ala Ala Val Asp Ser Asn
                    325                 330                 335

Val Gln Pro Lys Tyr Glu Leu Tyr Met Tyr Tyr Phe Val Ile Phe Ile
                    340                 345                 350

Ile Phe Gly Ser Phe Phe Thr Leu Asn Leu Phe Ile Gly Val Ile Ile
                    355                 360                 365

Asp Asn Phe Asn Gln Gln Lys Lys Lys Gly Gly Gln Asp Ile Phe Met
    370                 375                 380

Thr Glu Glu Gln Lys Lys Tyr Tyr Asn Ala Met Lys Lys Leu Gly Ser
385                 390                 395                 400

Lys Lys Pro Gln Lys Pro Ile Pro Arg Pro Asn Lys Phe Gln Gly Phe
                    405                 410                 415

Asp Val Thr Gln Phe Asp Ile Ile Met Leu Ile Cys Leu Asn Met Val
                    420                 425                 430

Thr Met Met Val Glu Gln Met Leu Trp Ile Asn Val Phe Ile Leu Phe
            435                 440                 445

Thr Gly Glu Cys Val Leu Lys Leu Ile Ser Leu Arg His Tyr Tyr Phe
    450                 455                 460

Thr Gly Trp Asn Ile Phe Val Val Ile Leu Ser Ile Val Gly Met
465                 470                 475                 480

Phe Leu Ala Glu Ile Glu Lys Tyr Phe Val Ser Pro Thr Leu Phe Arg
                    485                 490                 495

Val Ile Arg Leu Ala Arg Ile Gly Arg Ile Leu Arg Leu Ile Lys Gly
                    500                 505                 510

Ala Lys Gly Ile Arg Thr Leu Leu Phe Ala Leu Met Met Ser Leu Pro
    515                 520                 525

Ala Leu Phe Asn Ile Gly Leu Leu Phe Leu Val Met Phe Ile Tyr
530                 535                 540

Ala Ile Phe Gly Met Ser Asn Phe Ala Tyr Val Lys Glu Gly Ile Asp
545                 550                 555                 560

Met Phe Asn Phe Glu Thr Phe Gly Asn Ser Met Ile Cys Leu Phe Gln
                    565                 570                 575

Ile Thr Thr Ser Ala Gly Trp Asp Gly Leu Leu Ala Pro Ile Leu Asn
                    580                 585                 590

Ser Pro Pro Asp Cys Asp Pro Lys His Pro Gly Ser Ser Val Gly Asp
        595                 600                 605

Cys Gly Asn Pro Ser Val Gly Ile Phe Phe Val Ser Tyr Ile Ile Ile
    610                 615                 620

Ser Phe Leu Val Val Val Asn Met Tyr Ile Ala Val Ile Leu Glu Asn
625                 630                 635                 640

Phe Ser Val Ala Thr Glu Glu Ser Glu Pro Leu Ser Glu Asp Asp Phe
                    645                 650                 655

Glu Met Phe Tyr Glu Val Trp Glu Lys Phe Asp Pro Asp Ala Thr Gln
                    660                 665                 670
```

```
Phe Ile Glu Phe Cys Lys Leu Ser Asp Phe Ala Ala Leu Asp Pro
            675                 680                 685
Pro Leu Leu Ile Ala Lys Pro Asn Lys Val Gln Leu Ile Ala Met Asp
        690                 695                 700
Leu Pro Met Val Ser Gly Asp Arg Ile His Cys Leu Asp Ile Leu Phe
705                 710                 715                 720
Ala Phe Thr Lys Arg Val Leu Gly Glu Gly Glu Met Asp Leu Arg Gln
                725                 730                 735
Met Glu Glu Arg Phe Met Asn Pro Ser Lys Val Ser Tyr Glu Pro Ile
            740                 745                 750
Thr Thr Thr Leu Lys Arg Lys Gln Glu Glu Val Ser Ala Ile Gln Arg
            755                 760                 765
Ala Tyr Arg Arg Tyr Leu Gln Val Lys Ser Ser Ile Tyr Lys Asp Asp
        770                 775                 780
Pro Lys Glu Asp Asp Asn Glu Asn Ser Pro Glu Lys Thr Asp Val Thr
785                 790                 795                 800
Ser Thr Ser Pro Pro Ser Tyr Asp Ser Val Thr Lys Pro
                805                 810

(2) INFORMATION FOR SEQ ID NO:9:

(i) SEQUENCE CHARACTERISTICS:
        (A) LENGTH: 6452 base pairs
        (B) TYPE: nucleic acid
        (C) STRANDEDNESS: double
        (D) TOPOLOGY: both (ii) MOLECULE TYPE: DNA (genomic)

(ix) FEATURE:
        (A) NAME/KEY: CDS
        (B) LOCATION: 326..6277

(xi) SEQUENCE DESCRIPTION: SEQ ID NO:9:

GTCGCCTCAT CCTGAGCAGA CTGGAAACAG ACTCCGTGCA GGCCTCGCCC GCGCTCCAGT      60

TGCGACTGTA GGGTTTTCAT TCCTGCCCAC TGCGCAGACT GGGCTGAGCT AGCCTGGGTA     120

TCCACGATTC GCGACTCGTA GTAACAGGCA CTCTGAGCAA CAGGATTTCA GAGAAAGAAG     180

CAGAGGCAAG AAAGAAGCCT GGGGAGAGAG GAAGACTTTC CTTGGATCAG ACTCCGCAGG     240

TGCACACACC GGGTGGGCAT GATCCGTGGG GCCAGGCCTC TTAGGTAAGG AGTCAAAGGG     300

GAAATAAAAC ATACAGGATG AAAAG ATG GCG ATG CTG CCT CCT CCA GGA CCT      352
                            Met Ala Met Leu Pro Pro Pro Gly Pro
                                         1015                1020

CAG AGT TTC GTT CAC TTC ACA AAA CAG TCC CTT GCC CTC ATT GAA CAG      400
Gln Ser Phe Val His Phe Thr Lys Gln Ser Leu Ala Leu Ile Glu Gln
                1025                1030                1035

CGT ATT TCT GAA GAA AAA GCC AAG GAA CAC AAA GAC GAA AAG AAA GAT      448
Arg Ile Ser Glu Glu Lys Ala Lys Glu His Lys Asp Glu Lys Lys Asp
        1040                1045                1050

GAT GAG GAA GAA GGC CCC AAG CCC AGC AGT GAC TTG GAA GCT GGG AAA      496
Asp Glu Glu Glu Gly Pro Lys Pro Ser Ser Asp Leu Glu Ala Gly Lys
    1055                1060                1065

CAG CTC CCC TTC ATC TAT GGA GAC ATT CCC CCT GGA ATG GTG TCA GAG      544
Gln Leu Pro Phe Ile Tyr Gly Asp Ile Pro Pro Gly Met Val Ser Glu
    1070                1075                1080

CCC CTG GAG GAC CTG GAC CCA TAC TAT GCT GAC AAA AAA ACT TTT ATA      592
Pro Leu Glu Asp Leu Asp Pro Tyr Tyr Ala Asp Lys Lys Thr Phe Ile
1085                1090                1095                1100
```

```
GTA TTG AAC AAA GGG AAA GCA ATC TTC CGT TTC AAC GCC ACC CCT GCT          640
Val Leu Asn Lys Gly Lys Ala Ile Phe Arg Phe Asn Ala Thr Pro Ala
            1105                1110                1115

TTG TAC ATG CTG TCT CCC TTC AGT CCT CTA AGA AGA ATA TCT ATT AAG          688
Leu Tyr Met Leu Ser Pro Phe Ser Pro Leu Arg Arg Ile Ser Ile Lys
            1120                1125                1130

ATC TTA GTG CAC TCC TTA TTC AGC ATG CTA ATC ATG TGC ACA ATT CTG          736
Ile Leu Val His Ser Leu Phe Ser Met Leu Ile Met Cys Thr Ile Leu
            1135                1140                1145

ACG AAC TGC ATA TTC ATG ACC TTG AGC AAC CCT CCA GAA TGG ACC AAA          784
Thr Asn Cys Ile Phe Met Thr Leu Ser Asn Pro Pro Glu Trp Thr Lys
            1150                1155                1160

AAT GTA GAG TAC ACT TTT ACT GGG ATA TAT ACT TTT GAA TCA CTC ATA          832
Asn Val Glu Tyr Thr Phe Thr Gly Ile Tyr Thr Phe Glu Ser Leu Ile
1165                1170                1175                1180

AAA ATC CTT GCA AGA GGC TTT TGC GTG GGA GAA TTC ACC TTC CTC CGT          880
Lys Ile Leu Ala Arg Gly Phe Cys Val Gly Glu Phe Thr Phe Leu Arg
            1185                1190                1195

GAC CCT TGG AAC TGG CTG GAC TTT GTT GTC ATT GTT TTT GCG TAT TTA          928
Asp Pro Trp Asn Trp Leu Asp Phe Val Val Ile Val Phe Ala Tyr Leu
            1200                1205                1210

ACA GAA TTT GTA AAC CTA GGC AAT GTT TCA GCT CTT CGA ACT TTC AGA          976
Thr Glu Phe Val Asn Leu Gly Asn Val Ser Ala Leu Arg Thr Phe Arg
            1215                1220                1225

GTC TTG AGA GCT TTG AAA ACT ATT TCT GTA ATC CCA GGA CTA AAG ACC         1024
Val Leu Arg Ala Leu Lys Thr Ile Ser Val Ile Pro Gly Leu Lys Thr
            1230                1235                1240

ATC GTG GGG GCC CTG ATC CAG TCA GTG AAG AAG CTC TCT GAC GTC ATG         1072
Ile Val Gly Ala Leu Ile Gln Ser Val Lys Lys Leu Ser Asp Val Met
1245                1250                1255                1260

ATC CTC ACT GTG TTC TGT CTC AGT GTG TTT GCA CTA ATT GGA CTA CAG         1120
Ile Leu Thr Val Phe Cys Leu Ser Val Phe Ala Leu Ile Gly Leu Gln
            1265                1270                1275

CTG TTT ATG GGC AAC TTG AAG CAT AAA TGT TTC AGG AAG GAA CTC GAA         1168
Leu Phe Met Gly Asn Leu Lys His Lys Cys Phe Arg Lys Glu Leu Glu
            1280                1285                1290

GAG AAT GAA ACA TTA GAA AGT ATC ATG AAT ACT GCT GAG AGT GAA GAA         1216
Glu Asn Glu Thr Leu Glu Ser Ile Met Asn Thr Ala Glu Ser Glu Glu
            1295                1300                1305

GAA TTG AAA AAA TAT TTT TAT TAC TTG GAG GGA TCC AAA GAT GCT CTA         1264
Glu Leu Lys Lys Tyr Phe Tyr Tyr Leu Glu Gly Ser Lys Asp Ala Leu
            1310                1315                1320

CTC TGC GGC TTC AGC ACA GAT TCA GGG CAG TGT CCA GAA GGC TAC ATC         1312
Leu Cys Gly Phe Ser Thr Asp Ser Gly Gln Cys Pro Glu Gly Tyr Ile
1325                1330                1335                1340

TGT GTG AAG GCT GGC AGA AAC CCG GAT TAT GGC TAC ACG AGC TTT GAC         1360
Cys Val Lys Ala Gly Arg Asn Pro Asp Tyr Gly Tyr Thr Ser Phe Asp
            1345                1350                1355

ACA TTC AGC TGG GCC TTC TTG GCC TTG TTT CGG CTA ATG ACT CAG GAC         1408
Thr Phe Ser Trp Ala Phe Leu Ala Leu Phe Arg Leu Met Thr Gln Asp
            1360                1365                1370

TAC TGG GAG AAC CTT TAC CAA CAG ACT CTG CGT GCT GCT GGC AAA ACC         1456
Tyr Trp Glu Asn Leu Tyr Gln Gln Thr Leu Arg Ala Ala Gly Lys Thr
            1375                1380                1385

TAC ATG ATT TTC TTT GTC GTG GTT ATT TTT CTG GGC TCC TTT TAC CTG         1504
Tyr Met Ile Phe Phe Val Val Val Ile Phe Leu Gly Ser Phe Tyr Leu
            1390                1395                1400

ATA AAC TTG ATC CTG GCT GTG GTA GCC ATG GCG TAT GAG GAA CAG AAC         1552
Ile Asn Leu Ile Leu Ala Val Val Ala Met Ala Tyr Glu Glu Gln Asn
1405                1410                1415                1420
```

```
CAG GCC AAC ATC GAA GAA GCT AAA CAG AAA GAG TTA GAA TTT CAG CAG      1600
Gln Ala Asn Ile Glu Glu Ala Lys Gln Lys Glu Leu Glu Phe Gln Gln
            1425                1430                1435

ATG TTA GAC CGA CTC AAA AAG GAG CAG GAA GAA GCT GAG GCG ATC GCT      1648
Met Leu Asp Arg Leu Lys Lys Glu Gln Glu Glu Ala Glu Ala Ile Ala
            1440                1445                1450

GCA GCT GCT GCT GAG TTC ACG AGT ATA GGG CGG AGC AGG ATC ATG GGA      1696
Ala Ala Ala Ala Glu Phe Thr Ser Ile Gly Arg Ser Arg Ile Met Gly
            1455                1460                1465

CTC TCT GAG AGC TCT TCA GAA ACC TCC AGG CTG AGC TCA AAG AGT GCC      1744
Leu Ser Glu Ser Ser Ser Glu Thr Ser Arg Leu Ser Ser Lys Ser Ala
            1470                1475                1480

AAG GAG AGA AGA AAC CGA AGA AAG AAA AAG CAG AAG ATG TCC AGT          1792
Lys Glu Arg Arg Asn Arg Arg Lys Lys Lys Gln Lys Met Ser Ser
1485                1490                1495                1500

GGC GAG GAA AAG GGT GAC GAT GAG AAG CTG TCC AAG TCA GGA TCA GAG      1840
Gly Glu Glu Lys Gly Asp Asp Glu Lys Leu Ser Lys Ser Gly Ser Glu
            1505                1510                1515

GAA AGC ATC CGA AAG AAA AGC TTC CAT CTC GGT GTG GAA GGG CAC CAC      1888
Glu Ser Ile Arg Lys Lys Ser Phe His Leu Gly Val Glu Gly His His
            1520                1525                1530

CGG ACC CGG GAA AAG AGG CTG TCC ACC CCC AAC CAG TCG CCA CTC AGC      1936
Arg Thr Arg Glu Lys Arg Leu Ser Thr Pro Asn Gln Ser Pro Leu Ser
            1535                1540                1545

ATT CGC GGG TCC CTG TTT TCT GCC AGG CGC AGC AGC AGG ACG AGT CTC      1984
Ile Arg Gly Ser Leu Phe Ser Ala Arg Arg Ser Ser Arg Thr Ser Leu
            1550                1555                1560

TTC AGT TTT AAG GGG CGA GGA AGA GAT CTG GGA TCT GAG ACA GAA TTC      2032
Phe Ser Phe Lys Gly Arg Gly Arg Asp Leu Gly Ser Glu Thr Glu Phe
1565                1570                1575                1580

GCT GAT GAT GAG CAT AGC ATT TTT GGA GAC AAC GAG AGC AGA AGG GGT      2080
Ala Asp Asp Glu His Ser Ile Phe Gly Asp Asn Glu Ser Arg Arg Gly
            1585                1590                1595

TCA CTA TTC GTA CCC CAT AGA CCC CGG GAG CGG CGC AGC AGT AAC ATC      2128
Ser Leu Phe Val Pro His Arg Pro Arg Glu Arg Arg Ser Ser Asn Ile
            1600                1605                1610

AGT CAG GCC AGT AGG TCC CCG CCA GTG CTA CCG GTG AAC GGG AAG ATG      2176
Ser Gln Ala Ser Arg Ser Pro Pro Val Leu Pro Val Asn Gly Lys Met
            1615                1620                1625

CAC AGT GCA GTG GAC TGC AAT GGA GTC GTG TCG CTT GTT GAT GGA CCC      2224
His Ser Ala Val Asp Cys Asn Gly Val Val Ser Leu Val Asp Gly Pro
            1630                1635                1640

TCA GCC CTC ATG CTC CCC AAT GGA CAG CTT CTT CCA GAG GTG ATA ATA      2272
Ser Ala Leu Met Leu Pro Asn Gly Gln Leu Leu Pro Glu Val Ile Ile
1645                1650                1655                1660

GAT AAG GCA ACT TCC GAC GAC AGC GGC ACG ACT AAT CAG ATG CGC AAA      2320
Asp Lys Ala Thr Ser Asp Asp Ser Gly Thr Thr Asn Gln Met Arg Lys
            1665                1670                1675

AAA AGG CTC TCT AGT TCT TAC TTC TTG TCT GAG GAC ATG CTG AAT GAC      2368
Lys Arg Leu Ser Ser Ser Tyr Phe Leu Ser Glu Asp Met Leu Asn Asp
            1680                1685                1690

CCG CAT CTC AGG CAA AGG GCC ATG AGC AGG GCG AGC ATA CTG ACC AAC      2416
Pro His Leu Arg Gln Arg Ala Met Ser Arg Ala Ser Ile Leu Thr Asn
            1695                1700                1705

ACT GTG GAA GAA CTT GAA GAA TCT AGA CAA AAA TGT CCA CCA TGG TGG      2464
Thr Val Glu Glu Leu Glu Glu Ser Arg Gln Lys Cys Pro Pro Trp Trp
            1710                1715                1720

TAC AGA TTT GCT CAC ACA TTT TTA ATC TGG AAT TGC TCT CCA TAT TGG      2512
Tyr Arg Phe Ala His Thr Phe Leu Ile Trp Asn Cys Ser Pro Tyr Trp
```

-continued

```
       1725                1730                1735                1740
ATA AAA TTC AAA AAG CTC ATC TAT TTT ATT GTG ATG GAT CCT TTT GTA       2560
Ile Lys Phe Lys Lys Leu Ile Tyr Phe Ile Val Met Asp Pro Phe Val
            1745                1750                1755

GAT CTT GCA ATT ACC ATT TGC ATA GTT TTA AAC ACC TTA TTT ATG GCT       2608
Asp Leu Ala Ile Thr Ile Cys Ile Val Leu Asn Thr Leu Phe Met Ala
                1760                1765                1770

ATG GAG CAC CAC CCA ATG ACT GAA GAA TTC AAA AAT GTC CTT GCA GTG       2656
Met Glu His His Pro Met Thr Glu Glu Phe Lys Asn Val Leu Ala Val
            1775                1780                1785

GGG AAC TTG ATC TTT ACA GGG ATC TTC GCA GCT GAA ATG GTA CTG AAG       2704
Gly Asn Leu Ile Phe Thr Gly Ile Phe Ala Ala Glu Met Val Leu Lys
        1790                1795                1800

TTA ATA GCC ATG GAC CCC TAT GAG TAT TTC CAA GTA GGG TGG AAT ATT       2752
Leu Ile Ala Met Asp Pro Tyr Glu Tyr Phe Gln Val Gly Trp Asn Ile
1805                1810                1815                1820

TTT GAC AGC CTA ATT GTG ACG CTG AGT TTG ATA GAG CTT TTC CTA GCA       2800
Phe Asp Ser Leu Ile Val Thr Leu Ser Leu Ile Glu Leu Phe Leu Ala
                1825                1830                1835

GAT GTG GAA GGA TTA TCA GTT CTG CGG TCA TTC AGA TTG CTC CGA GTC       2848
Asp Val Glu Gly Leu Ser Val Leu Arg Ser Phe Arg Leu Leu Arg Val
            1840                1845                1850

TTC AAG TTG GCA AAG TCC TGG CCC ACA CTG AAC ATG CTC ATT AAG ATC       2896
Phe Lys Leu Ala Lys Ser Trp Pro Thr Leu Asn Met Leu Ile Lys Ile
        1855                1860                1865

ATC GGC AAC TCG GTG GGC GCA CTG GGC AAC CTG ACC CTG GTG CTG GCC       2944
Ile Gly Asn Ser Val Gly Ala Leu Gly Asn Leu Thr Leu Val Leu Ala
    1870                1875                1880

ATC ATC GTC TTC ATT TTT GCC GTG GTC GGC ATG CAG CTG TTT GGA AAG       2992
Ile Ile Val Phe Ile Phe Ala Val Val Gly Met Gln Leu Phe Gly Lys
1885                1890                1895                1900

AGC TAC AAG GAG TGT GTC TGC AAG ATC AAT GTG GAC TGC AAG CTG CCG       3040
Ser Tyr Lys Glu Cys Val Cys Lys Ile Asn Val Asp Cys Lys Leu Pro
                1905                1910                1915

CGC TGG CAC ATG AAC GAC TTC TTC CAC TCC TTC CTC ATC GTG TTC CGA       3088
Arg Trp His Met Asn Asp Phe Phe His Ser Phe Leu Ile Val Phe Arg
            1920                1925                1930

GTG CTG TGT GGG GAG TGG ATA GAG ACC ATG TGG GAC TGC ATG GAG GTC       3136
Val Leu Cys Gly Glu Trp Ile Glu Thr Met Trp Asp Cys Met Glu Val
        1935                1940                1945

GCG GGC CAG ACC ATG TGC CTT ATT GTT TAC ATG ATG GTC ATG GTG ATT       3184
Ala Gly Gln Thr Met Cys Leu Ile Val Tyr Met Met Val Met Val Ile
    1950                1955                1960

GGG AAC CTT GTG GTC CTG AAC CTG TTT CTG GCT CTT TTG CTG AGT TCC       3232
Gly Asn Leu Val Val Leu Asn Leu Phe Leu Ala Leu Leu Leu Ser Ser
1965                1970                1975                1980

TTT AGT TCT GAC AAT CTT ACA GCA ATT GAG GAA GAC ACC GAT GCA AAC       3280
Phe Ser Ser Asp Asn Leu Thr Ala Ile Glu Glu Asp Thr Asp Ala Asn
                1985                1990                1995

AAC CTC CAG ATC GCA GTG GCC AGA ATT AAG AGG GGA ATC AAT TAC GTG       3328
Asn Leu Gln Ile Ala Val Ala Arg Ile Lys Arg Gly Ile Asn Tyr Val
            2000                2005                2010

AAA CAG ACC CTG CGT GAA TTC ATT CTA AAA TCA TTT TCC AAA AAG CCA       3376
Lys Gln Thr Leu Arg Glu Phe Ile Leu Lys Ser Phe Ser Lys Lys Pro
        2015                2020                2025

AAG GGC TCC AAG GAC ACA AAA CGA ACA GCA GAT CCC AAC AAC AAG AAA       3424
Lys Gly Ser Lys Asp Thr Lys Arg Thr Ala Asp Pro Asn Asn Lys Lys
    2030                2035                2040

GAA AAC TAT ATT TCA AAC CGT ACC CTT GCG GAG ATG AGC AAG GAT CAC       3472
```

```
                                                                -continued

Glu Asn Tyr Ile Ser Asn Arg Thr Leu Ala Glu Met Ser Lys Asp His
2045                2050                2055                2060

AAT TTC CTC AAA GAA AAG GAT AGG ATC AGT GGT TAT GGC AGC AGT CTA    3520
Asn Phe Leu Lys Glu Lys Asp Arg Ile Ser Gly Tyr Gly Ser Ser Leu
                2065                2070                2075

GAC AAA AGC TTT ATG GAT GAA AAT GAT TAC CAG TCC TTT ATC CAT AAC    3568
Asp Lys Ser Phe Met Asp Glu Asn Asp Tyr Gln Ser Phe Ile His Asn
            2080                2085                2090

CCC AGC CTC ACA GTG ACA GTG CCA ATT GCA CCT GGG GAG TCT GAT TTG    3616
Pro Ser Leu Thr Val Thr Val Pro Ile Ala Pro Gly Glu Ser Asp Leu
        2095                2100                2105

GAG ATT ATG AAC ACA GAA GAG CTT AGC AGT GAC TCA GAC AGT GAC TAC    3664
Glu Ile Met Asn Thr Glu Glu Leu Ser Ser Asp Ser Asp Ser Asp Tyr
    2110                2115                2120

AGC AAA GAG AAA CGG AAC CGA TCA AGC TCT TCT GAG TGC AGC ACT GTT    3712
Ser Lys Glu Lys Arg Asn Arg Ser Ser Ser Ser Glu Cys Ser Thr Val
2125                2130                2135                2140

GAC AAC CCT CTG CCA GGA GAA GAG GAG GCT GAA GCA GAG CCC GTA AAC    3760
Asp Asn Pro Leu Pro Gly Glu Glu Glu Ala Glu Ala Glu Pro Val Asn
                2145                2150                2155

GCA GAT GAG CCT GAA GCC TGC TTT ACA GAT GGT TGT GTG AGG AGA TTT    3808
Ala Asp Glu Pro Glu Ala Cys Phe Thr Asp Gly Cys Val Arg Arg Phe
            2160                2165                2170

CCA TGC TGC CAA GTT AAT GTA GAC TCT GGG AAA GGG AAA GTT TGG TGG    3856
Pro Cys Cys Gln Val Asn Val Asp Ser Gly Lys Gly Lys Val Trp Trp
        2175                2180                2185

ACC ATC AGG AAG ACG TGC TAC AGG ATA GTT GAA CAC AGC TGG TTT GAA    3904
Thr Ile Arg Lys Thr Cys Tyr Arg Ile Val Glu His Ser Trp Phe Glu
    2190                2195                2200

AGC TTC ATC GTT CTC ATG ATC CTG CTC AGC AGT GGA GCT CTG GCT TTT    3952
Ser Phe Ile Val Leu Met Ile Leu Leu Ser Ser Gly Ala Leu Ala Phe
2205                2210                2215                2220

GAA GAT ATC TAT ATT GAA AAG AAA AAG ACC ATT AAG ATT ATC CTG GAG    4000
Glu Asp Ile Tyr Ile Glu Lys Lys Lys Thr Ile Lys Ile Ile Leu Glu
                2225                2230                2235

TAT GCT GAC AAG ATA TTC ACC TAC ATC TTC ATT CTG GAA ATG CTT CTA    4048
Tyr Ala Asp Lys Ile Phe Thr Tyr Ile Phe Ile Leu Glu Met Leu Leu
            2240                2245                2250

AAA TGG GTC GCA TAT GGG TAT AAA ACA TAT TTC ACT AAT GCC TGG TGT    4096
Lys Trp Val Ala Tyr Gly Tyr Lys Thr Tyr Phe Thr Asn Ala Trp Cys
        2255                2260                2265

TGG CTG GAC TTC TTA ATT GTT GAT GTG TCT CTA GTT ACT TTA GTA GCC    4144
Trp Leu Asp Phe Leu Ile Val Asp Val Ser Leu Val Thr Leu Val Ala
    2270                2275                2280

AAC ACT CTT GGC TAC TCA GAC CTT GGC CCC ATT AAA TCT CTA CGG ACA    4192
Asn Thr Leu Gly Tyr Ser Asp Leu Gly Pro Ile Lys Ser Leu Arg Thr
2285                2290                2295                2300

CTG AGG GCC CTA AGA CCC CTA AGA GCC TTG TCT AGA TTT GAA GGA ATG    4240
Leu Arg Ala Leu Arg Pro Leu Arg Ala Leu Ser Arg Phe Glu Gly Met
                2305                2310                2315

AGG GTA GTG GTC AAC GCA CTC ATA GGA GCA ATC CCT TCC ATC ATG AAC    4288
Arg Val Val Val Asn Ala Leu Ile Gly Ala Ile Pro Ser Ile Met Asn
            2320                2325                2330

GTG CTT CTC GTG TGC CTT ATA TTC TGG CTA ATA TTT AGC ATC ATG GGA    4336
Val Leu Leu Val Cys Leu Ile Phe Trp Leu Ile Phe Ser Ile Met Gly
        2335                2340                2345

GTC AAT CTG TTT GCT GGC AAG TTC TAT GAG TGT GTC AAC ACC ACC GAT    4384
Val Asn Leu Phe Ala Gly Lys Phe Tyr Glu Cys Val Asn Thr Thr Asp
    2350                2355                2360
```

```
GGG TCA CGA TTT CCT ACA TCT CAA GTT GCA AAC CGT TCT GAG TGT TTT    4432
Gly Ser Arg Phe Pro Thr Ser Gln Val Ala Asn Arg Ser Glu Cys Phe
2365             2370             2375             2380

GCC CTG ATG AAC GTT AGT GGA AAT GTG CGA TGG AAA AAC CTG AAA GTA    4480
Ala Leu Met Asn Val Ser Gly Asn Val Arg Trp Lys Asn Leu Lys Val
             2385             2390             2395

AAC TTC GAC AAC GTT GGG CTT GGT TAC CTG TCG CTG CTT CAA GTT GCA    4528
Asn Phe Asp Asn Val Gly Leu Gly Tyr Leu Ser Leu Leu Gln Val Ala
         2400             2405             2410

ACA TTC AAG GGC TGG ATG GAT ATT ATG TAT GCA GCA GTT GAC TCT GTT    4576
Thr Phe Lys Gly Trp Met Asp Ile Met Tyr Ala Ala Val Asp Ser Val
     2415             2420             2425

AAT GTA AAT GAA CAG CCG AAA TAC GAA TAC AGT CTC TAC ATG TAC ATT    4624
Asn Val Asn Glu Gln Pro Lys Tyr Glu Tyr Ser Leu Tyr Met Tyr Ile
 2430             2435             2440

TAC TTT GTC ATC TTC ATC ATC TTC GGC TCA TTC TTC ACG TTG AAC CTG    4672
Tyr Phe Val Ile Phe Ile Ile Phe Gly Ser Phe Phe Thr Leu Asn Leu
2445             2450             2455             2460

TTC ATT GGT GTC ATC ATA GAT AAT TTC AAC CAA CAG AAA AAA AAG CTT    4720
Phe Ile Gly Val Ile Ile Asp Asn Phe Asn Gln Gln Lys Lys Lys Leu
             2465             2470             2475

GGA GGT CAA GAT ATC TTT ATG ACA GAA GAA CAG AAG AAA TAC TAT AAT    4768
Gly Gly Gln Asp Ile Phe Met Thr Glu Glu Gln Lys Lys Tyr Tyr Asn
         2480             2485             2490

GCA ATG AAG AAG CTT GGG TCC AAA AAA CCA CAA AAA CCA ATT CCA AGG    4816
Ala Met Lys Lys Leu Gly Ser Lys Lys Pro Gln Lys Pro Ile Pro Arg
     2495             2500             2505

CCA GGG AAC AAA TTC CAA GGA TGT ATA TTT GAC TTA GTG ACA AAC CAA    4864
Pro Gly Asn Lys Phe Gln Gly Cys Ile Phe Asp Leu Val Thr Asn Gln
 2510             2515             2520

GCT TTT GAT ATC ACC ATC ATG GTT CTT ATA TGC CTC AAC ATG GTA ACC    4912
Ala Phe Asp Ile Thr Ile Met Val Leu Ile Cys Leu Asn Met Val Thr
2525             2530             2535             2540

ATG ATG GTA GAA AAA GAG GGG CAA ACT GAG TAC ATG GAT TAT GTT TTA    4960
Met Met Val Glu Lys Glu Gly Gln Thr Glu Tyr Met Asp Tyr Val Leu
             2545             2550             2555

CAC TGG ATC AAC ATG GTC TTC ATT ATC CTG TTC ACT GGG GAG TGT GTG    5008
His Trp Ile Asn Met Val Phe Ile Ile Leu Phe Thr Gly Glu Cys Val
         2560             2565             2570

CTG AAG CTA ATC TCC CTC AGA CAT TAC TAC TTC ACT GTG GGT TGG AAC    5056
Leu Lys Leu Ile Ser Leu Arg His Tyr Tyr Phe Thr Val Gly Trp Asn
     2575             2580             2585

ATT TTT GAT TTT GTG GTA GTG ATC CTC TCC ATT GTA GGA ATG TTT CTC    5104
Ile Phe Asp Phe Val Val Val Ile Leu Ser Ile Val Gly Met Phe Leu
 2590             2595             2600

GCT GAG ATG ATA GAG AAG TAT TTC GTG TCC CCT ACC CTG TTC CGA GTC    5152
Ala Glu Met Ile Glu Lys Tyr Phe Val Ser Pro Thr Leu Phe Arg Val
2605             2610             2615             2620

ATC CGC CTG GCC AGG ATT GGA CGA ATC CTA CGC CTG ATC AAA GGC GCC    5200
Ile Arg Leu Ala Arg Ile Gly Arg Ile Leu Arg Leu Ile Lys Gly Ala
             2625             2630             2635

AAG GGG ATC CGC ACT CTG CTC TTT GCT TTG ATG ATG TCC CTT CCT GCG    5248
Lys Gly Ile Arg Thr Leu Leu Phe Ala Leu Met Met Ser Leu Pro Ala
         2640             2645             2650

CTG TTC AAC ATC GGC CTC CTG CTT TTC CTG GTC ATG TTC ATC TAC GCC    5296
Leu Phe Asn Ile Gly Leu Leu Leu Phe Leu Val Met Phe Ile Tyr Ala
     2655             2660             2665

ATC TTT GGG ATG TCC AAC TTT GCC TAC GTT AAA AAG GAG GCT GGA ATT    5344
Ile Phe Gly Met Ser Asn Phe Ala Tyr Val Lys Lys Glu Ala Gly Ile
 2670             2675             2680
```

```
AAT GAC ATG TTC AAC TTT GAG ACT TTT GGC AAC AGC ATG ATC TGC TTG     5392
Asn Asp Met Phe Asn Phe Glu Thr Phe Gly Asn Ser Met Ile Cys Leu
2685                2690                2695                2700

TTC CAA ATC ACC ACC TCT GCC GGC TGG GAC GGA CTG CTG GCC CCC ATC     5440
Phe Gln Ile Thr Thr Ser Ala Gly Trp Asp Gly Leu Leu Ala Pro Ile
                    2705                2710                2715

CTC AAC AGC GCA CCT CCC GAC TGT GAC CCT AAA AAA GTT CAC CCA GGA     5488
Leu Asn Ser Ala Pro Pro Asp Cys Asp Pro Lys Lys Val His Pro Gly
            2720                2725                2730

AGT TCA GTG GAA GGG GAC TGT GGG AAC CCA TCC GTG GGG ATT TTT TAC     5536
Ser Ser Val Glu Gly Asp Cys Gly Asn Pro Ser Val Gly Ile Phe Tyr
        2735                2740                2745

TTT GTC AGC TAC ATC ATC ATA TCC TTC CTG GTG GTG GTG AAC ATG TAC     5584
Phe Val Ser Tyr Ile Ile Ile Ser Phe Leu Val Val Val Asn Met Tyr
    2750                2755                2760

ATC GCT GTC ATC CTG GAG AAC TTC AGC GTC GCC ACC GAA GAG AGC ACT     5632
Ile Ala Val Ile Leu Glu Asn Phe Ser Val Ala Thr Glu Glu Ser Thr
2765                2770                2775                2780

GAG CCT CTG AGT GAG GAC GAC TTT GAG ATG TTC TAC GAG GTC TGG GAG     5680
Glu Pro Leu Ser Glu Asp Asp Phe Glu Met Phe Tyr Glu Val Trp Glu
                2785                2790                2795

AAG TTC GAC CCT GAC GCC ACT CAG TTC ATA GAG TTC TGC AAG CTC TCT     5728
Lys Phe Asp Pro Asp Ala Thr Gln Phe Ile Glu Phe Cys Lys Leu Ser
            2800                2805                2810

GAC TTT GCA GCT GCC CTG GAT CCT CCC CTC CTC ATC GCA AAG CCA AAC     5776
Asp Phe Ala Ala Ala Leu Asp Pro Pro Leu Leu Ile Ala Lys Pro Asn
        2815                2820                2825

AAA GTC CAG CTC ATT GCC ATG GAC CTG CCC ATG GTG AGT GGA GAC CGC     5824
Lys Val Gln Leu Ile Ala Met Asp Leu Pro Met Val Ser Gly Asp Arg
    2830                2835                2840

ATC CAC TGC CTG GAC ATC TTG TTT GCT TTT ACA AAG CGG GTC CTG GGT     5872
Ile His Cys Leu Asp Ile Leu Phe Ala Phe Thr Lys Arg Val Leu Gly
2845                2850                2855                2860

GAG GGT GGA GAG ATG GAT TCT CTT CGT TCA CAG ATG GAA GAA AGG TTC     5920
Glu Gly Gly Glu Met Asp Ser Leu Arg Ser Gln Met Glu Glu Arg Phe
                2865                2870                2875

ATG TCA GCC AAT CCT TCT AAA GTG TCC TAT GAA CCC ATC ACG ACC ACA     5968
Met Ser Ala Asn Pro Ser Lys Val Ser Tyr Glu Pro Ile Thr Thr Thr
            2880                2885                2890

CTG AAG AGA AAA CAA GAG GAG GTG TCC GCG ACT ATC ATT CAG CGT GCT     6016
Leu Lys Arg Lys Gln Glu Glu Val Ser Ala Thr Ile Ile Gln Arg Ala
        2895                2900                2905

TAC AGA CGG TAT CGC CTC AGA CAA CAC GTC AAG AAT ATA TCG AGT ATA     6064
Tyr Arg Arg Tyr Arg Leu Arg Gln His Val Lys Asn Ile Ser Ser Ile
    2910                2915                2920

TAC ATA AAA GAT GGA GAC AGG GAT GAT GAT TTG CCC AAT AAA GAA GAT     6112
Tyr Ile Lys Asp Gly Asp Arg Asp Asp Asp Leu Pro Asn Lys Glu Asp
2925                2930                2935                2940

ACA GTT TTT GAT AAC GTG AAC GAG AAC TCA AGT CCG GAA AAG ACA GAT     6160
Thr Val Phe Asp Asn Val Asn Glu Asn Ser Ser Pro Glu Lys Thr Asp
                2945                2950                2955

GTA ACT GCC TCA ACC ATC TCG CCA CCT TCC TAT GAC AGT GTC ACA AAG     6208
Val Thr Ala Ser Thr Ile Ser Pro Pro Ser Tyr Asp Ser Val Thr Lys
            2960                2965                2970

CCA GAT CAA GAG AAA TAT GAA ACA GAC AAA ACA GAG AAG GAA GAC AAA     6256
Pro Asp Gln Glu Lys Tyr Glu Thr Asp Lys Thr Glu Lys Glu Asp Lys
        2975                2980                2985

GAG AAA GAT GAA AGC AGG AAA TAGAGCTTTG GTTTTGATAC ACTGTTGACA        6307
Glu Lys Asp Glu Ser Arg Lys
```

```
                                    2990                2995
GCCTGTGAAG GTTGACTCAC TCGTGTTAGT AAGACTCTTT TACGGAGGTC TATCCAAACT        6367

CTTTTATCAA AAATTCTCAA GGCAGCACAG CCATTAGCTC TGATCCAACG AGGCAGAGGG        6427

CAGCATTTAC ACATGGCTAT GTTTT                                              6452
```

(2) INFORMATION FOR SEQ ID NO:10:

(i) SEQUENCE CHARACTERISTICS:
        (A) LENGTH: 1984 amino acids
        (B) TYPE: amino acid
        (D) TOPOLOGY: linear (ii) MOLECULE TYPE: protein (xi) SEQUENCE DESCRIPTION: SEQ ID NO:10:

```
Met Ala Met Leu Pro Pro Gly Pro Gln Ser Phe Val His Phe Thr
 1               5                  10                  15

Lys Gln Ser Leu Ala Leu Ile Glu Gln Arg Ile Ser Glu Glu Lys Ala
                20                  25                  30

Lys Glu His Lys Asp Glu Lys Asp Asp Glu Glu Glu Gly Pro Lys
            35                  40                  45

Pro Ser Ser Asp Leu Glu Ala Gly Lys Gln Leu Pro Phe Ile Tyr Gly
        50                  55                  60

Asp Ile Pro Pro Gly Met Val Ser Glu Pro Leu Glu Asp Leu Asp Pro
65                  70                  75                  80

Tyr Tyr Ala Asp Lys Lys Thr Phe Ile Val Leu Asn Lys Gly Lys Ala
                85                  90                  95

Ile Phe Arg Phe Asn Ala Thr Pro Ala Leu Tyr Met Leu Ser Pro Phe
                100                 105                 110

Ser Pro Leu Arg Arg Ile Ser Ile Lys Ile Leu Val His Ser Leu Phe
            115                 120                 125

Ser Met Leu Ile Met Cys Thr Ile Leu Thr Asn Cys Ile Phe Met Thr
        130                 135                 140

Leu Ser Asn Pro Pro Glu Trp Thr Lys Asn Val Glu Tyr Thr Phe Thr
145                 150                 155                 160

Gly Ile Tyr Thr Phe Glu Ser Leu Ile Lys Ile Leu Ala Arg Gly Phe
                165                 170                 175

Cys Val Gly Glu Phe Thr Phe Leu Arg Asp Pro Trp Asn Trp Leu Asp
            180                 185                 190

Phe Val Val Ile Val Phe Ala Tyr Leu Thr Glu Phe Val Asn Leu Gly
        195                 200                 205

Asn Val Ser Ala Leu Arg Thr Phe Arg Val Leu Arg Ala Leu Lys Thr
    210                 215                 220

Ile Ser Val Ile Pro Gly Leu Lys Thr Ile Val Gly Ala Leu Ile Gln
225                 230                 235                 240

Ser Val Lys Lys Leu Ser Asp Val Met Ile Leu Thr Val Phe Cys Leu
                245                 250                 255

Ser Val Phe Ala Leu Ile Gly Leu Gln Leu Phe Met Gly Asn Leu Lys
            260                 265                 270

His Lys Cys Phe Arg Lys Glu Leu Glu Glu Asn Glu Thr Leu Glu Ser
        275                 280                 285

Ile Met Asn Thr Ala Glu Ser Glu Glu Glu Leu Lys Lys Tyr Phe Tyr
    290                 295                 300

Tyr Leu Glu Gly Ser Lys Asp Ala Leu Leu Cys Gly Phe Ser Thr Asp
305                 310                 315                 320
```

-continued

```
Ser Gly Gln Cys Pro Glu Gly Tyr Ile Cys Val Lys Ala Gly Arg Asn
                325                 330                 335

Pro Asp Tyr Gly Tyr Thr Ser Phe Asp Thr Phe Ser Trp Ala Phe Leu
            340                 345                 350

Ala Leu Phe Arg Leu Met Thr Gln Asp Tyr Trp Glu Asn Leu Tyr Gln
        355                 360                 365

Gln Thr Leu Arg Ala Ala Gly Lys Thr Tyr Met Ile Phe Phe Val Val
    370                 375                 380

Val Ile Phe Leu Gly Ser Phe Tyr Leu Ile Asn Leu Ile Leu Ala Val
385                 390                 395                 400

Val Ala Met Ala Tyr Glu Glu Gln Asn Gln Ala Asn Ile Glu Glu Ala
                405                 410                 415

Lys Gln Lys Glu Leu Glu Phe Gln Gln Met Leu Asp Arg Leu Lys Lys
            420                 425                 430

Glu Gln Glu Glu Ala Glu Ala Ile Ala Ala Ala Ala Ala Glu Phe Thr
        435                 440                 445

Ser Ile Gly Arg Ser Arg Ile Met Gly Leu Ser Glu Ser Ser Ser Glu
    450                 455                 460

Thr Ser Arg Leu Ser Ser Lys Ser Ala Lys Glu Arg Arg Asn Arg Arg
465                 470                 475                 480

Lys Lys Lys Lys Gln Lys Met Ser Ser Gly Glu Glu Lys Gly Asp Asp
                485                 490                 495

Glu Lys Leu Ser Lys Ser Gly Ser Glu Glu Ser Ile Arg Lys Lys Ser
            500                 505                 510

Phe His Leu Gly Val Glu Gly His His Arg Thr Arg Glu Lys Arg Leu
        515                 520                 525

Ser Thr Pro Asn Gln Ser Pro Leu Ser Ile Arg Gly Ser Leu Phe Ser
    530                 535                 540

Ala Arg Arg Ser Ser Arg Thr Ser Leu Phe Ser Phe Lys Gly Arg Gly
545                 550                 555                 560

Arg Asp Leu Gly Ser Glu Thr Glu Phe Ala Asp Asp Glu His Ser Ile
                565                 570                 575

Phe Gly Asp Asn Glu Ser Arg Arg Gly Ser Leu Phe Val Pro His Arg
            580                 585                 590

Pro Arg Glu Arg Arg Ser Ser Asn Ile Ser Gln Ala Ser Arg Ser Pro
        595                 600                 605

Pro Val Leu Pro Val Asn Gly Lys Met His Ser Ala Val Asp Cys Asn
    610                 615                 620

Gly Val Val Ser Leu Val Asp Gly Pro Ser Ala Leu Met Leu Pro Asn
625                 630                 635                 640

Gly Gln Leu Leu Pro Glu Val Ile Ile Asp Lys Ala Thr Ser Asp Asp
                645                 650                 655

Ser Gly Thr Thr Asn Gln Met Arg Lys Lys Arg Leu Ser Ser Ser Tyr
            660                 665                 670

Phe Leu Ser Glu Asp Met Leu Asn Asp Pro His Leu Arg Gln Arg Ala
        675                 680                 685

Met Ser Arg Ala Ser Ile Leu Thr Asn Thr Val Glu Glu Leu Glu Glu
    690                 695                 700

Ser Arg Gln Lys Cys Pro Pro Trp Trp Tyr Arg Phe Ala His Thr Phe
705                 710                 715                 720

Leu Ile Trp Asn Cys Ser Pro Tyr Trp Ile Lys Phe Lys Lys Leu Ile
                725                 730                 735
```

```
Tyr Phe Ile Val Met Asp Pro Phe Val Asp Leu Ala Ile Thr Ile Cys
                740                 745                 750

Ile Val Leu Asn Thr Leu Phe Met Ala Met Glu His His Pro Met Thr
            755                 760                 765

Glu Glu Phe Lys Asn Val Leu Ala Val Gly Asn Leu Ile Phe Thr Gly
        770                 775                 780

Ile Phe Ala Ala Glu Met Val Leu Lys Leu Ile Ala Met Asp Pro Tyr
785                 790                 795                 800

Glu Tyr Phe Gln Val Gly Trp Asn Ile Phe Asp Ser Leu Ile Val Thr
                805                 810                 815

Leu Ser Leu Ile Glu Leu Phe Leu Ala Asp Val Glu Gly Leu Ser Val
            820                 825                 830

Leu Arg Ser Phe Arg Leu Leu Arg Val Phe Lys Leu Ala Lys Ser Trp
        835                 840                 845

Pro Thr Leu Asn Met Leu Ile Lys Ile Ile Gly Asn Ser Val Gly Ala
        850                 855                 860

Leu Gly Asn Leu Thr Leu Val Leu Ala Ile Ile Val Phe Ile Phe Ala
865                 870                 875                 880

Val Val Gly Met Gln Leu Phe Gly Lys Ser Tyr Lys Glu Cys Val Cys
                885                 890                 895

Lys Ile Asn Val Asp Cys Lys Leu Pro Arg Trp His Met Asn Asp Phe
            900                 905                 910

Phe His Ser Phe Leu Ile Val Phe Arg Val Leu Cys Gly Glu Trp Ile
        915                 920                 925

Glu Thr Met Trp Asp Cys Met Glu Val Ala Gly Gln Thr Met Cys Leu
        930                 935                 940

Ile Val Tyr Met Met Val Met Val Ile Gly Asn Leu Val Val Leu Asn
945                 950                 955                 960

Leu Phe Leu Ala Leu Leu Leu Ser Ser Phe Ser Ser Asp Asn Leu Thr
                965                 970                 975

Ala Ile Glu Glu Asp Thr Asp Ala Asn Asn Leu Gln Ile Ala Val Ala
            980                 985                 990

Arg Ile Lys Arg Gly Ile Asn Tyr Val Lys Gln Thr Leu Arg Glu Phe
        995                 1000                1005

Ile Leu Lys Ser Phe Ser Lys Pro Lys Gly Ser Lys Asp Thr Lys
    1010                1015                1020

Arg Thr Ala Asp Pro Asn Asn Lys Lys Glu Asn Tyr Ile Ser Asn Arg
1025                1030                1035                1040

Thr Leu Ala Glu Met Ser Lys Asp His Asn Phe Leu Lys Glu Lys Asp
                1045                1050                1055

Arg Ile Ser Gly Tyr Gly Ser Ser Leu Asp Lys Ser Phe Met Asp Glu
            1060                1065                1070

Asn Asp Tyr Gln Ser Phe Ile His Asn Pro Ser Leu Thr Val Thr Val
        1075                1080                1085

Pro Ile Ala Pro Gly Glu Ser Asp Leu Glu Ile Met Asn Thr Glu Glu
        1090                1095                1100

Leu Ser Ser Asp Ser Asp Ser Asp Tyr Ser Lys Glu Lys Arg Asn Arg
1105                1110                1115                1120

Ser Ser Ser Ser Glu Cys Ser Thr Val Asp Asn Pro Leu Pro Gly Glu
                1125                1130                1135

Glu Glu Ala Glu Ala Glu Pro Val Asn Ala Asp Glu Pro Glu Ala Cys
            1140                1145                1150

Phe Thr Asp Gly Cys Val Arg Arg Phe Pro Cys Cys Gln Val Asn Val
```

-continued

```
                1155                1160                1165

Asp Ser Gly Lys Gly Lys Val Trp Trp Thr Ile Arg Lys Thr Cys Tyr
             1170                1175                1180

Arg Ile Val Glu His Ser Trp Phe Glu Ser Phe Ile Val Leu Met Ile
1185                1190                1195                1200

Leu Leu Ser Ser Gly Ala Leu Ala Phe Glu Asp Ile Tyr Ile Glu Lys
                 1205                1210                1215

Lys Lys Thr Ile Lys Ile Ile Leu Glu Tyr Ala Asp Lys Ile Phe Thr
             1220                1225                1230

Tyr Ile Phe Ile Leu Glu Met Leu Leu Lys Trp Val Ala Tyr Gly Tyr
             1235                1240                1245

Lys Thr Tyr Phe Thr Asn Ala Trp Cys Trp Leu Asp Phe Leu Ile Val
1250                1255                1260

Asp Val Ser Leu Val Thr Leu Val Ala Asn Thr Leu Gly Tyr Ser Asp
1265                1270                1275                1280

Leu Gly Pro Ile Lys Ser Leu Arg Thr Leu Arg Ala Leu Arg Pro Leu
                 1285                1290                1295

Arg Ala Leu Ser Arg Phe Glu Gly Met Arg Val Val Val Asn Ala Leu
             1300                1305                1310

Ile Gly Ala Ile Pro Ser Ile Met Asn Val Leu Leu Val Cys Leu Ile
             1315                1320                1325

Phe Trp Leu Ile Phe Ser Ile Met Gly Val Asn Leu Phe Ala Gly Lys
             1330                1335                1340

Phe Tyr Glu Cys Val Asn Thr Thr Asp Gly Ser Arg Phe Pro Thr Ser
1345                1350                1355                1360

Gln Val Ala Asn Arg Ser Glu Cys Phe Ala Leu Met Asn Val Ser Gly
             1365                1370                1375

Asn Val Arg Trp Lys Asn Leu Lys Val Asn Phe Asp Asn Val Gly Leu
             1380                1385                1390

Gly Tyr Leu Ser Leu Leu Gln Val Ala Thr Phe Lys Gly Trp Met Asp
                 1395                1400                1405

Ile Met Tyr Ala Ala Val Asp Ser Val Asn Val Asn Glu Gln Pro Lys
             1410                1415                1420

Tyr Glu Tyr Ser Leu Tyr Met Tyr Ile Tyr Phe Val Ile Phe Ile Ile
1425                1430                1435                1440

Phe Gly Ser Phe Phe Thr Leu Asn Leu Phe Ile Gly Val Ile Ile Asp
                 1445                1450                1455

Asn Phe Asn Gln Gln Lys Lys Lys Leu Gly Gly Gln Asp Ile Phe Met
                 1460                1465                1470

Thr Glu Glu Gln Lys Lys Tyr Tyr Asn Ala Met Lys Lys Leu Gly Ser
             1475                1480                1485

Lys Lys Pro Gln Lys Pro Ile Pro Arg Pro Gly Asn Lys Phe Gln Gly
             1490                1495                1500

Cys Ile Phe Asp Leu Val Thr Asn Gln Ala Phe Asp Ile Thr Ile Met
1505                1510                1515                1520

Val Leu Ile Cys Leu Asn Met Val Thr Met Met Val Glu Lys Glu Gly
                 1525                1530                1535

Gln Thr Glu Tyr Met Asp Tyr Val Leu His Trp Ile Asn Met Val Phe
             1540                1545                1550

Ile Ile Leu Phe Thr Gly Glu Cys Val Leu Lys Leu Ile Ser Leu Arg
                 1555                1560                1565

His Tyr Tyr Phe Thr Val Gly Trp Asn Ile Phe Asp Phe Val Val Val
             1570                1575                1580
```

```
Ile Leu Ser Ile Val Gly Met Phe Leu Ala Glu Met Ile Glu Lys Tyr
1585                1590                1595                1600

Phe Val Ser Pro Thr Leu Phe Arg Val Ile Arg Leu Ala Arg Ile Gly
                1605                1610                1615

Arg Ile Leu Arg Leu Ile Lys Gly Ala Lys Gly Ile Arg Thr Leu Leu
                1620                1625                1630

Phe Ala Leu Met Met Ser Leu Pro Ala Leu Phe Asn Ile Gly Leu Leu
            1635                1640                1645

Leu Phe Leu Val Met Phe Ile Tyr Ala Ile Phe Gly Met Ser Asn Phe
        1650                1655                1660

Ala Tyr Val Lys Lys Glu Ala Gly Ile Asn Asp Met Phe Asn Phe Glu
1665                1670                1675                1680

Thr Phe Gly Asn Ser Met Ile Cys Leu Phe Gln Ile Thr Thr Ser Ala
                1685                1690                1695

Gly Trp Asp Gly Leu Leu Ala Pro Ile Leu Asn Ser Ala Pro Pro Asp
                1700                1705                1710

Cys Asp Pro Lys Lys Val His Pro Gly Ser Ser Val Glu Gly Asp Cys
            1715                1720                1725

Gly Asn Pro Ser Val Gly Ile Phe Tyr Phe Val Ser Tyr Ile Ile Ile
        1730                1735                1740

Ser Phe Leu Val Val Val Asn Met Tyr Ile Ala Val Ile Leu Glu Asn
1745                1750                1755                1760

Phe Ser Val Ala Thr Glu Glu Ser Thr Glu Pro Leu Ser Glu Asp Asp
                1765                1770                1775

Phe Glu Met Phe Tyr Glu Val Trp Glu Lys Phe Asp Pro Asp Ala Thr
                1780                1785                1790

Gln Phe Ile Glu Phe Cys Lys Leu Ser Asp Phe Ala Ala Ala Leu Asp
            1795                1800                1805

Pro Pro Leu Leu Ile Ala Lys Pro Asn Lys Val Gln Leu Ile Ala Met
        1810                1815                1820

Asp Leu Pro Met Val Ser Gly Asp Arg Ile His Cys Leu Asp Ile Leu
1825                1830                1835                1840

Phe Ala Phe Thr Lys Arg Val Leu Gly Glu Gly Gly Glu Met Asp Ser
                1845                1850                1855

Leu Arg Ser Gln Met Glu Glu Arg Phe Met Ser Ala Asn Pro Ser Lys
            1860                1865                1870

Val Ser Tyr Glu Pro Ile Thr Thr Thr Leu Lys Arg Lys Gln Glu Glu
        1875                1880                1885

Val Ser Ala Thr Ile Ile Gln Arg Ala Tyr Arg Arg Tyr Arg Leu Arg
    1890                1895                1900

Gln His Val Lys Asn Ile Ser Ser Ile Tyr Ile Lys Asp Gly Asp Arg
1905                1910                1915                1920

Asp Asp Asp Leu Pro Asn Lys Glu Asp Thr Val Phe Asp Asn Val Asn
                1925                1930                1935

Glu Asn Ser Ser Pro Glu Lys Thr Asp Val Thr Ala Ser Thr Ile Ser
            1940                1945                1950

Pro Pro Ser Tyr Asp Ser Val Thr Lys Pro Asp Gln Glu Lys Tyr Glu
        1955                1960                1965

Thr Asp Lys Thr Glu Lys Glu Asp Lys Glu Lys Asp Glu Ser Arg Lys
    1970                1975                1980

(2) INFORMATION FOR SEQ ID NO:11:
```

(i) SEQUENCE CHARACTERISTICS:
 (A) LENGTH: 1989 amino acids
 (B) TYPE: amino acid
 (C) STRANDEDNESS: Not Relevant
 (D) TOPOLOGY: Not Relevant (ii) MOLECULE TYPE: protein (xi) SEQUENCE DESCRIPTION: SEQ ID NO:11:

```
Met Ala Met Leu Pro Pro Gly Pro Gln Ser Phe Val His Phe Thr
 1               5                  10                  15

Lys Gln Ser Leu Ala Leu Ile Glu Gln Arg Ile Xaa Glu Xaa Lys Xaa
                 20                  25                  30

Lys Glu Xaa Lys Xaa Glu Lys Lys Asp Asp Xaa Glu Glu Xaa Pro Lys
             35                  40                  45

Pro Ser Ser Asp Leu Glu Ala Gly Lys Gln Leu Pro Phe Ile Tyr Gly
 50                  55                  60

Asp Ile Pro Pro Gly Met Val Ser Glu Pro Leu Glu Asp Leu Asp Pro
 65                  70                  75                  80

Tyr Tyr Ala Asp Lys Lys Thr Phe Ile Val Leu Asn Lys Gly Lys Xaa
                 85                  90                  95

Ile Phe Arg Phe Asn Ala Thr Pro Ala Leu Tyr Met Leu Ser Pro Phe
                100                 105                 110

Ser Pro Leu Arg Arg Ile Ser Ile Lys Ile Leu Val His Ser Leu Phe
            115                 120                 125

Ser Met Leu Ile Met Cys Thr Ile Leu Thr Asn Cys Ile Phe Met Thr
        130                 135                 140

Xaa Xaa Asn Pro Pro Xaa Trp Thr Lys Asn Val Xaa Tyr Thr Phe Thr
145                 150                 155                 160

Gly Ile Tyr Thr Phe Glu Ser Leu Xaa Lys Ile Leu Ala Arg Gly Phe
                165                 170                 175

Cys Val Gly Glu Phe Thr Phe Leu Arg Asp Pro Trp Asn Trp Leu Asp
            180                 185                 190

Phe Val Val Ile Val Phe Ala Tyr Leu Thr Glu Phe Val Asn Leu Gly
        195                 200                 205

Asn Val Ser Ala Leu Arg Thr Phe Arg Val Leu Arg Ala Leu Lys Thr
210                 215                 220

Ile Ser Val Ile Pro Gly Leu Lys Thr Ile Val Gly Ala Leu Ile Gln
225                 230                 235                 240

Ser Val Lys Lys Leu Ser Asp Val Met Ile Leu Thr Val Phe Cys Leu
                245                 250                 255

Ser Val Phe Ala Leu Ile Gly Leu Gln Leu Phe Met Gly Asn Leu Lys
            260                 265                 270

His Lys Cys Phe Arg Xaa Xaa Leu Glu Xaa Asn Glu Thr Leu Glu Ser
        275                 280                 285

Ile Met Asn Thr Xaa Glu Ser Glu Glu Xaa Xaa Xaa Lys Tyr Phe Tyr
        290                 295                 300

Tyr Leu Glu Gly Ser Lys Asp Ala Leu Leu Cys Gly Phe Ser Thr Asp
305                 310                 315                 320

Ser Gly Gln Cys Pro Glu Gly Tyr Xaa Cys Val Lys Xaa Gly Arg Asn
                325                 330                 335

Pro Asp Tyr Gly Tyr Thr Ser Phe Asp Thr Phe Ser Trp Ala Phe Leu
            340                 345                 350

Ala Leu Phe Arg Leu Met Thr Gln Asp Tyr Trp Glu Asn Leu Tyr Gln
        355                 360                 365
```

```
Gln Thr Leu Arg Ala Ala Gly Lys Thr Tyr Met Ile Phe Phe Val Val
    370                 375                 380

Val Ile Phe Leu Gly Ser Phe Tyr Leu Ile Asn Leu Ile Leu Ala Val
385                 390                 395                 400

Val Ala Met Ala Tyr Glu Glu Gln Asn Gln Ala Asn Ile Glu Glu Ala
                405                 410                 415

Lys Gln Lys Glu Leu Glu Phe Gln Gln Met Leu Asp Arg Leu Lys Lys
                420                 425                 430

Glu Gln Glu Glu Ala Glu Ala Ile Ala Ala Ala Ala Glu Xaa Thr
                435                 440                 445

Ser Ile Xaa Arg Ser Arg Ile Met Gly Leu Ser Glu Ser Ser Ser Glu
    450                 455                 460

Thr Ser Xaa Leu Ser Ser Lys Ser Ala Lys Glu Arg Arg Asn Arg Arg
465                 470                 475                 480

Lys Lys Lys Xaa Gln Lys Lys Xaa Ser Ser Gly Glu Glu Lys Gly Asp
                485                 490                 495

Xaa Glu Lys Leu Ser Lys Ser Xaa Ser Glu Xaa Ser Ile Arg Xaa Lys
                500                 505                 510

Ser Phe His Leu Gly Val Glu Gly His Xaa Arg Xaa Xaa Glu Lys Arg
                515                 520                 525

Leu Ser Thr Pro Asn Gln Ser Pro Leu Ser Ile Arg Gly Ser Leu Phe
    530                 535                 540

Ser Ala Arg Arg Ser Ser Arg Thr Ser Leu Phe Ser Phe Lys Gly Arg
545                 550                 555                 560

Gly Arg Asp Xaa Gly Ser Glu Thr Glu Phe Ala Asp Asp Glu His Ser
                565                 570                 575

Ile Phe Gly Asp Asn Glu Ser Arg Arg Gly Ser Leu Phe Val Pro His
                580                 585                 590

Arg Pro Xaa Glu Arg Arg Ser Ser Asn Ile Ser Gln Ala Ser Arg Ser
    595                 600                 605

Pro Pro Xaa Leu Pro Val Asn Gly Lys Met His Ser Ala Val Asp Cys
    610                 615                 620

Asn Gly Val Val Ser Leu Val Asp Gly Xaa Ser Ala Leu Met Leu Pro
625                 630                 635                 640

Asn Gly Gln Leu Leu Pro Glu Xaa Xaa Xaa Xaa Xaa Xaa Xaa Xaa Xaa
                645                 650                 655

Xaa Xaa Gly Thr Thr Asn Gln Xaa Xaa Lys Lys Arg Xaa Xaa Ser Ser
                660                 665                 670

Tyr Xaa Leu Ser Glu Asp Met Leu Asn Asp Pro Xaa Leu Arg Gln Arg
                675                 680                 685

Ala Met Ser Arg Ala Ser Ile Leu Thr Asn Thr Val Glu Glu Leu Glu
    690                 695                 700

Glu Ser Arg Gln Lys Cys Xaa Xaa Xaa Xaa Tyr Arg Phe Ala His Xaa
705                 710                 715                 720

Phe Leu Ile Trp Asn Cys Ser Pro Tyr Trp Ile Lys Phe Lys Lys Xaa
                725                 730                 735

Ile Tyr Phe Ile Val Met Asp Pro Phe Val Asp Leu Ala Ile Thr Ile
                740                 745                 750

Cys Ile Val Leu Asn Thr Leu Phe Met Ala Met Glu His His Pro Met
                755                 760                 765

Thr Glu Glu Phe Lys Asn Val Leu Ala Xaa Gly Asn Leu Xaa Phe Thr
    770                 775                 780

Gly Ile Phe Ala Ala Glu Met Val Leu Lys Leu Ile Ala Met Asp Pro
```

-continued

```
              785                 790                 795                 800

Tyr Glu Tyr Phe Gln Val Gly Trp Asn Ile Phe Asp Ser Leu Ile Val
                            805                 810                 815

Thr Leu Ser Leu Xaa Glu Leu Phe Leu Ala Asp Val Glu Gly Leu Ser
                            820                 825                 830

Val Leu Arg Ser Phe Arg Leu Leu Arg Val Phe Lys Leu Ala Lys Ser
                            835                 840                 845

Trp Pro Thr Leu Asn Met Leu Ile Lys Ile Ile Gly Asn Ser Val Gly
                            850                 855                 860

Ala Leu Gly Asn Leu Thr Leu Val Leu Ala Ile Ile Val Phe Ile Phe
        865                 870                 875                 880

Ala Val Val Gly Met Gln Leu Phe Gly Lys Ser Tyr Lys Glu Cys Val
                            885                 890                 895

Cys Lys Ile Asn Xaa Asp Cys Xaa Leu Pro Arg Trp His Met Asn Asp
                            900                 905                 910

Phe Phe His Ser Phe Leu Ile Val Phe Arg Val Leu Cys Gly Glu Trp
                            915                 920                 925

Ile Glu Thr Met Trp Asp Cys Met Glu Val Ala Gly Gln Xaa Met Cys
                            930                 935                 940

Leu Ile Val Tyr Met Met Val Met Val Ile Gly Asn Leu Val Val Leu
        945                 950                 955                 960

Asn Leu Phe Leu Ala Leu Leu Leu Ser Ser Phe Ser Ser Asp Asn Leu
                            965                 970                 975

Thr Ala Ile Glu Glu Asp Xaa Asp Ala Asn Asn Leu Gln Ile Ala Val
                            980                 985                 990

Xaa Arg Ile Lys Xaa Gly Ile Asn Tyr Val Lys Gln Thr Leu Arg Glu
                            995                 1000                1005

Phe Ile Leu Lys Xaa Phe Ser Lys Lys Pro Lys Xaa Ser Xaa Xaa Xaa
                            1010                1015                1020

Xaa Xaa Xaa Xaa Asp Xaa Asn Xaa Lys Lys Glu Asn Tyr Ile Ser Asn
        1025                1030                1035                1040

Xaa Thr Leu Ala Glu Met Ser Lys Xaa His Asn Phe Leu Lys Glu Lys
                            1045                1050                1055

Asp Xaa Ile Ser Gly Xaa Gly Ser Ser Xaa Asp Lys Xaa Xaa Met Xaa
                            1060                1065                1070

Xaa Xaa Asp Xaa Gln Ser Phe Ile His Asn Pro Ser Leu Thr Val Thr
                            1075                1080                1085

Val Pro Ile Ala Pro Gly Glu Ser Asp Leu Glu Xaa Met Asn Xaa Glu
                            1090                1095                1100

Glu Leu Ser Ser Asp Ser Asp Ser Xaa Tyr Ser Lys Xaa Xaa Xaa Asn
        1105                1110                1115                1120

Arg Ser Ser Ser Glu Cys Ser Thr Val Asp Asn Pro Leu Pro Gly
                            1125                1130                1135

Glu Gly Glu Glu Ala Glu Ala Glu Pro Xaa Asn Xaa Asp Glu Pro Glu
                            1140                1145                1150

Ala Cys Phe Thr Asp Gly Cys Val Arg Arg Phe Xaa Cys Cys Gln Val
                            1155                1160                1165

Asn Xaa Xaa Ser Gly Lys Gly Lys Xaa Trp Trp Xaa Ile Arg Lys Thr
                            1170                1175                1180

Cys Tyr Xaa Ile Val Glu His Ser Trp Phe Glu Ser Phe Ile Val Leu
        1185                1190                1195                1200

Met Ile Leu Leu Ser Ser Gly Ala Leu Ala Phe Glu Asp Ile Tyr Ile
                            1205                1210                1215
```

-continued

```
Glu Xaa Lys Lys Thr Ile Lys Ile Ile Leu Glu Tyr Ala Asp Lys Ile
    1220            1225                1230
Phe Thr Tyr Ile Phe Ile Leu Glu Met Leu Leu Lys Trp Xaa Ala Tyr
    1235            1240                1245
Gly Tyr Lys Thr Tyr Phe Thr Asn Ala Trp Cys Trp Leu Asp Phe Leu
    1250            1255                1260
Ile Val Asp Val Ser Leu Val Thr Leu Val Ala Asn Thr Leu Gly Tyr
1265            1270            1275                1280
Ser Asp Leu Gly Pro Ile Lys Ser Leu Arg Thr Leu Arg Ala Leu Arg
                1285            1290                1295
Pro Leu Arg Ala Leu Ser Arg Phe Glu Gly Met Arg Val Val Val Asn
                1300            1305                1310
Ala Leu Ile Gly Ala Ile Pro Ser Ile Met Asn Val Leu Leu Val Cys
                1315            1320                1325
Leu Ile Phe Trp Leu Ile Phe Ser Ile Met Gly Val Asn Leu Phe Ala
                1330            1335                1340
Gly Lys Phe Tyr Glu Cys Xaa Asn Thr Thr Asp Gly Ser Arg Phe Pro
1345            1350            1355                1360
Xaa Ser Gln Val Xaa Asn Arg Ser Glu Cys Phe Ala Leu Met Asn Val
                1365            1370                1375
Ser Xaa Asn Val Arg Trp Lys Asn Leu Lys Val Asn Phe Asp Asn Val
                1380            1385                1390
Gly Leu Gly Tyr Leu Ser Leu Leu Gln Val Ala Thr Phe Lys Gly Trp
                1395            1400                1405
Xaa Xaa Ile Met Tyr Ala Ala Val Asp Ser Val Asn Val Xaa Xaa Gln
    1410            1415                1420
Pro Lys Tyr Glu Tyr Ser Leu Tyr Met Tyr Ile Tyr Phe Val Xaa Phe
1425            1430            1435                1440
Ile Ile Phe Gly Ser Phe Phe Thr Leu Asn Leu Phe Ile Gly Val Ile
                1445            1450                1455
Ile Asp Asn Phe Asn Gln Gln Lys Lys Lys Leu Gly Gly Gln Asp Ile
                1460            1465                1470
Phe Met Thr Glu Glu Gln Lys Lys Tyr Tyr Asn Ala Met Lys Lys Leu
                1475            1480                1485
Gly Ser Lys Lys Pro Gln Lys Pro Ile Pro Arg Pro Gly Asn Lys Xaa
                1490            1495                1500
Gln Gly Cys Ile Phe Asp Leu Val Thr Asn Gln Ala Phe Asp Ile Xaa
1505            1510            1515                1520
Ile Met Val Leu Ile Cys Leu Asn Met Val Thr Met Met Val Glu Lys
                1525            1530                1535
Glu Gly Gln Xaa Xaa Xaa Met Xaa Xaa Val Leu Xaa Trp Ile Asn Xaa
                1540            1545                1550
Val Phe Ile Ile Leu Phe Thr Gly Glu Cys Val Leu Lys Leu Ile Ser
    1555            1560                1565
Leu Arg His Tyr Tyr Phe Thr Val Gly Trp Asn Ile Xaa Xaa Phe Val
    1570            1575                1580
Val Val Ile Xaa Ser Ile Val Gly Met Phe Leu Ala Xaa Xaa Ile Glu
1585            1590            1595                1600
Xaa Tyr Phe Val Ser Pro Thr Leu Phe Arg Val Ile Arg Leu Ala Arg
                1605            1610                1615
Ile Gly Arg Ile Leu Arg Leu Xaa Lys Gly Ala Lys Gly Ile Arg Thr
                1620            1625                1630
```

-continued

```
Leu Leu Phe Ala Leu Met Met Ser Leu Pro Ala Leu Phe Asn Ile Gly
            1635                1640                1645

Leu Leu Leu Phe Leu Val Met Phe Ile Tyr Ala Ile Phe Gly Met Ser
            1650                1655                1660

Asn Phe Ala Tyr Val Lys Lys Glu Xaa Gly Ile Asn Asp Met Phe Asn
1665                1670                1675                1680

Phe Glu Thr Phe Gly Asn Ser Met Ile Cys Leu Phe Gln Ile Thr Thr
            1685                1690                1695

Ser Ala Gly Trp Asp Gly Leu Leu Ala Pro Ile Leu Asn Ser Xaa Pro
            1700                1705                1710

Pro Asp Cys Asp Pro Lys Lys Val His Pro Gly Ser Ser Val Glu Gly
            1715                1720                1725

Asp Cys Gly Asn Pro Ser Val Gly Ile Phe Tyr Phe Val Ser Tyr Ile
            1730                1735                1740

Ile Ile Ser Phe Leu Val Val Val Asn Met Tyr Ile Ala Val Ile Leu
1745                1750                1755                1760

Glu Asn Phe Ser Val Ala Thr Glu Glu Ser Thr Glu Pro Leu Ser Glu
            1765                1770                1775

Asp Asp Phe Glu Met Phe Tyr Glu Val Trp Glu Lys Phe Asp Pro Asp
            1780                1785                1790

Ala Thr Gln Phe Ile Glu Phe Xaa Lys Leu Ser Asp Phe Ala Ala Ala
            1795                1800                1805

Leu Asp Pro Pro Leu Leu Ile Ala Lys Pro Asn Lys Val Gln Leu Ile
            1810                1815                1820

Ala Met Asp Leu Pro Met Val Ser Gly Asp Arg Ile His Cys Leu Asp
1825                1830                1835                1840

Ile Leu Phe Ala Phe Thr Lys Arg Val Leu Gly Glu Xaa Gly Glu Met
            1845                1850                1855

Asp Ser Leu Arg Ser Gln Met Glu Glu Arg Phe Met Ser Ala Asn Pro
            1860                1865                1870

Ser Lys Val Ser Tyr Glu Pro Ile Thr Thr Thr Leu Lys Arg Lys Gln
            1875                1880                1885

Glu Xaa Val Ser Ala Thr Xaa Ile Gln Arg Ala Tyr Arg Arg Tyr Arg
            1890                1895                1900

Leu Arg Gln Xaa Val Lys Asn Ile Ser Ser Ile Tyr Ile Lys Asp Gly
1905                1910                1915                1920

Asp Arg Asp Asp Asp Leu Xaa Asn Lys Xaa Asp Xaa Xaa Phe Asp Asn
            1925                1930                1935

Val Asn Glu Asn Ser Ser Pro Glu Lys Thr Asp Xaa Thr Xaa Ser Thr
            1940                1945                1950

Xaa Ser Pro Pro Ser Tyr Asp Ser Val Thr Lys Pro Asp Xaa Glu Lys
            1955                1960                1965

Tyr Glu Xaa Asp Xaa Thr Glu Leu Glu Asp Lys Xaa Lys Asp Ser Lys
            1970                1975                1980

Glu Ser Xaa Lys Xaa
1985

(2) INFORMATION FOR SEQ ID NO:12:

(i) SEQUENCE CHARACTERISTICS:
        (A) LENGTH: 1989 amino acids
        (B) TYPE: amino acid
        (C) STRANDEDNESS: Not Relevant
        (D) TOPOLOGY: Not Relevant (ii) MOLECULE TYPE: protein
```

(xi) SEQUENCE DESCRIPTION: SEQ ID NO:12:

Met Ala Met Leu Pro Pro Gly Pro Gln Ser Phe Val His Phe Thr
1               5                   10                  15

Lys Gln Ser Leu Ala Leu Ile Glu Gln Arg Ile Ser Glu Glu Lys Ala
                20                  25                  30

Lys Glu His Lys Asp Glu Lys Lys Asp Asp Glu Glu Gly Pro Lys
            35                  40                  45

Pro Ser Ser Asp Leu Glu Ala Gly Lys Gln Leu Pro Phe Ile Tyr Gly
        50                  55                  60

Asp Ile Pro Pro Gly Met Val Ser Glu Pro Leu Glu Asp Leu Asp Pro
65                  70                  75                  80

Tyr Tyr Ala Asp Lys Lys Thr Phe Ile Val Leu Asn Lys Gly Lys Ala
                85                  90                  95

Ile Phe Arg Phe Asn Ala Thr Pro Ala Leu Tyr Met Leu Ser Pro Phe
            100                 105                 110

Ser Pro Leu Arg Arg Ile Ser Ile Lys Ile Leu Val His Ser Leu Phe
        115                 120                 125

Ser Met Leu Ile Met Cys Thr Ile Leu Thr Asn Cys Ile Phe Met Thr
130                 135                 140

Leu Ser Asn Pro Pro Glu Trp Thr Lys Asn Val Gly Tyr Thr Phe Thr
145                 150                 155                 160

Gly Ile Tyr Thr Phe Glu Ser Leu Ile Lys Ile Leu Ala Arg Gly Phe
                165                 170                 175

Cys Val Gly Glu Phe Thr Phe Leu Arg Asp Pro Trp Asn Trp Leu Asp
            180                 185                 190

Phe Val Val Ile Val Phe Ala Tyr Leu Thr Glu Phe Val Asn Leu Gly
        195                 200                 205

Asn Val Ser Ala Leu Arg Thr Phe Arg Val Leu Arg Ala Leu Lys Thr
210                 215                 220

Ile Ser Val Ile Pro Gly Leu Lys Thr Ile Val Gly Ala Leu Ile Gln
225                 230                 235                 240

Ser Val Lys Lys Leu Ser Asp Val Met Ile Leu Thr Val Phe Cys Leu
                245                 250                 255

Ser Val Phe Ala Leu Ile Gly Leu Gln Leu Phe Met Gly Asn Leu Lys
            260                 265                 270

His Lys Cys Phe Arg Lys Glu Leu Glu Glu Asn Glu Thr Leu Glu Ser
        275                 280                 285

Ile Met Asn Thr Ala Glu Ser Glu Glu Leu Lys Lys Tyr Phe Tyr
290                 295                 300

Tyr Leu Glu Gly Ser Lys Asp Ala Leu Leu Cys Gly Phe Ser Thr Asp
305                 310                 315                 320

Ser Gly Gln Cys Pro Glu Gly Tyr Ile Cys Val Lys Ala Gly Arg Asn
                325                 330                 335

Pro Asp Tyr Gly Tyr Thr Ser Phe Asp Thr Phe Ser Trp Ala Phe Leu
            340                 345                 350

Ala Leu Phe Arg Leu Met Thr Gln Asp Tyr Trp Glu Asn Leu Tyr Gln
        355                 360                 365

Gln Thr Leu Arg Ala Ala Gly Lys Thr Tyr Met Ile Phe Phe Val Val
        370                 375                 380

Val Ile Phe Leu Gly Ser Phe Tyr Leu Ile Asn Leu Ile Leu Ala Val
385                 390                 395                 400

Val Ala Met Ala Tyr Glu Glu Gln Asn Gln Ala Asn Ile Glu Glu Ala

```
                    405                 410                 415
Lys Gln Lys Glu Leu Glu Phe Gln Gln Met Leu Asp Arg Leu Lys Lys
                420                 425                 430
Glu Gln Glu Ala Glu Ala Ile Ala Ala Ala Ala Glu Phe Thr
        435                 440                 445
Ser Ile Arg Arg Ser Arg Ile Met Gly Leu Ser Glu Ser Ser Ser Glu
        450                 455                 460
Thr Ser Arg Leu Ser Ser Lys Ser Ala Lys Glu Arg Arg Asn Arg Arg
465                 470                 475                 480
Lys Lys Lys Lys Gln Lys Xaa Met Ser Ser Gly Glu Lys Gly Asp
                485                 490                 495
Asp Glu Lys Leu Ser Lys Ser Gly Ser Glu Glu Ser Ile Arg Lys Lys
            500                 505                 510
Ser Phe His Leu Gly Val Glu Gly His His Arg Thr Arg Glu Lys Arg
        515                 520                 525
Leu Ser Thr Pro Asn Gln Ser Pro Leu Ser Ile Arg Gly Ser Leu Phe
        530                 535                 540
Ser Ala Arg Arg Ser Ser Arg Thr Ser Leu Phe Ser Phe Lys Gly Arg
545                 550                 555                 560
Gly Arg Asp Leu Gly Ser Glu Thr Glu Phe Ala Asp Glu His Ser
            565                 570                 575
Ile Phe Gly Asp Asn Glu Ser Arg Arg Gly Ser Leu Phe Val Pro His
            580                 585                 590
Arg Pro Arg Glu Arg Arg Ser Ser Asn Ile Ser Gln Ala Ser Arg Ser
        595                 600                 605
Pro Pro Val Leu Pro Val Asn Gly Lys Met His Ser Ala Val Asp Cys
        610                 615                 620
Asn Gly Val Val Ser Leu Val Asp Gly Pro Ser Ala Leu Met Leu Pro
625                 630                 635                 640
Asn Gly Gln Leu Leu Pro Glu Val Ile Ile Asp Lys Ala Thr Ser Asp
            645                 650                 655
Asp Ser Gly Thr Thr Asn Gln Met Arg Lys Lys Arg Leu Ser Ser Ser
            660                 665                 670
Tyr Phe Leu Ser Glu Asp Met Leu Asn Asp Pro His Leu Arg Gln Arg
            675                 680                 685
Ala Met Ser Arg Ala Ser Ile Leu Thr Asn Thr Val Glu Glu Leu Glu
            690                 695                 700
Glu Ser Arg Gln Lys Cys His Gln Leu Leu Tyr Arg Phe Ala His Thr
705                 710                 715                 720
Phe Leu Ile Trp Asn Cys Ser Pro Tyr Trp Ile Lys Phe Lys Lys Leu
                725                 730                 735
Ile Tyr Phe Ile Val Met Asp Pro Phe Val Asp Leu Ala Ile Thr Ile
            740                 745                 750
Cys Ile Val Leu Asn Thr Leu Phe Met Ala Met Glu His His Pro Met
        755                 760                 765
Thr Glu Glu Phe Lys Asn Val Leu Ala Val Gly Asn Leu Ile Phe Thr
        770                 775                 780
Gly Ile Phe Ala Ala Glu Met Val Leu Lys Leu Ile Ala Met Asp Pro
785                 790                 795                 800
Tyr Glu Tyr Phe Gln Val Gly Trp Asn Ile Phe Asp Ser Leu Ile Val
                805                 810                 815
Thr Leu Ser Leu Ile Glu Leu Phe Leu Ala Asp Val Glu Gly Leu Ser
            820                 825                 830
```

-continued

```
Val Leu Arg Ser Phe Arg Leu Arg Val Phe Lys Leu Ala Lys Ser
    835                 840                 845
Trp Pro Thr Leu Asn Met Leu Ile Lys Ile Ile Gly Asn Ser Val Gly
850                 855                 860
Ala Leu Gly Asn Leu Thr Leu Val Leu Ala Ile Ile Val Phe Ile Phe
865                 870                 875                 880
Ala Val Val Gly Met Gln Leu Phe Gly Lys Ser Tyr Lys Glu Cys Val
                885                 890                 895
Cys Lys Ile Asn Val Asp Cys Lys Leu Pro Arg Trp His Met Asn Asp
                900                 905                 910
Phe Phe His Ser Phe Leu Ile Val Phe Arg Val Leu Cys Gly Glu Trp
            915                 920                 925
Ile Glu Thr Met Trp Asp Cys Met Glu Val Ala Gly Gln Thr Met Cys
    930                 935                 940
Leu Ile Val Tyr Met Met Val Met Val Ile Gly Asn Leu Val Val Leu
945                 950                 955                 960
Asn Leu Phe Leu Ala Leu Leu Leu Ser Ser Phe Ser Ser Asp Asn Leu
                965                 970                 975
Thr Ala Ile Glu Glu Asp Thr Asp Ala Asn Asn Leu Gln Ile Ala Val
                980                 985                 990
Ala Arg Ile Lys Arg Gly Ile Asn Tyr Val Lys Gln Thr Leu Arg Glu
            995                 1000                1005
Phe Ile Leu Lys Ser Phe Ser Lys Lys Pro Lys Gly Ser Lys Asp Thr
    1010                1015                1020
Lys Arg Thr Ala Asp Pro Asn Asn Lys Lys Glu Asn Tyr Ile Ser Asn
1025                1030                1035                1040
Arg Thr Leu Ala Glu Met Ser Lys Asp His Asn Phe Leu Lys Glu Lys
                1045                1050                1055
Asp Arg Ile Ser Gly Tyr Gly Ser Ser Leu Asp Lys Ser Phe Met Asp
                1060                1065                1070
Glu Asn Asp Tyr Gln Ser Phe Ile His Asn Pro Ser Leu Thr Val Thr
            1075                1080                1085
Val Pro Ile Ala Pro Gly Glu Ser Asp Leu Glu Ile Met Asn Thr Glu
    1090                1095                1100
Glu Leu Ser Ser Asp Ser Asp Ser Asp Tyr Ser Lys Glu Lys Arg Asn
1105                1110                1115                1120
Arg Ser Ser Ser Ser Glu Cys Ser Thr Val Asp Asn Pro Leu Pro Gly
                1125                1130                1135
Glu Xaa Glu Glu Ala Glu Ala Glu Pro Val Asn Ala Asp Glu Pro Glu
                1140                1145                1150
Ala Cys Phe Thr Asp Gly Cys Val Arg Arg Phe Pro Cys Cys Gln Val
            1155                1160                1165
Asn Val Asp Ser Gly Lys Gly Lys Val Trp Trp Thr Ile Arg Lys Thr
    1170                1175                1180
Cys Tyr Arg Ile Val Glu His Ser Trp Phe Glu Ser Phe Ile Val Leu
1185                1190                1195                1200
Met Ile Leu Leu Ser Ser Gly Ala Leu Ala Phe Glu Asp Ile Tyr Ile
                1205                1210                1215
Glu Lys Lys Lys Thr Ile Lys Ile Ile Leu Glu Tyr Ala Asp Lys Ile
                1220                1225                1230
Phe Thr Tyr Ile Phe Ile Leu Glu Met Leu Leu Lys Trp Val Ala Tyr
            1235                1240                1245
```

-continued

```
Gly Tyr Lys Thr Tyr Phe Thr Asn Ala Trp Cys Trp Leu Asp Phe Leu
    1250                1255                1260
Ile Val Asp Val Ser Leu Val Thr Leu Val Ala Asn Thr Leu Gly Tyr
1265            1270                1275                1280
Ser Asp Leu Gly Pro Ile Lys Ser Leu Arg Thr Leu Arg Ala Leu Arg
                1285                1290                1295
Pro Leu Arg Ala Leu Ser Arg Phe Glu Gly Met Arg Val Val Val Asn
            1300                1305                1310
Ala Leu Ile Gly Ala Ile Pro Ser Ile Met Asn Val Leu Leu Val Cys
        1315                1320                1325
Leu Ile Phe Trp Leu Ile Phe Ser Ile Met Gly Val Asn Leu Phe Ala
    1330                1335                1340
Gly Lys Phe Tyr Glu Cys Val Asn Thr Thr Asp Gly Ser Arg Phe Pro
1345                1350                1355                1360
Thr Ser Gln Val Ala Asn Arg Ser Glu Cys Phe Ala Leu Met Asn Val
                1365                1370                1375
Ser Gly Asn Val Arg Trp Lys Asn Leu Lys Val Asn Phe Asp Asn Val
            1380                1385                1390
Gly Leu Gly Tyr Leu Ser Leu Leu Gln Val Ala Thr Phe Lys Gly Trp
        1395                1400                1405
Met Asp Ile Met Tyr Ala Ala Val Asp Ser Val Asn Val Asn Glu Gln
    1410                1415                1420
Pro Lys Tyr Glu Tyr Ser Leu Tyr Met Tyr Ile Tyr Phe Val Ile Phe
1425                1430                1435                1440
Ile Ile Phe Gly Ser Phe Phe Thr Leu Asn Leu Phe Ile Gly Val Ile
                1445                1450                1455
Ile Asp Asn Phe Asn Gln Gln Lys Lys Lys Leu Gly Gly Gln Asp Ile
            1460                1465                1470
Phe Met Thr Glu Glu Gln Lys Lys Tyr Tyr Asn Ala Met Lys Lys Leu
        1475                1480                1485
Gly Ser Lys Lys Pro Gln Lys Pro Ile Pro Arg Pro Gly Asn Lys Phe
    1490                1495                1500
Gln Gly Cys Ile Phe Asp Leu Val Thr Asn Gln Ala Phe Asp Ile Thr
1505                1510                1515                1520
Ile Met Val Leu Ile Cys Leu Asn Met Val Thr Met Met Val Glu Lys
                1525                1530                1535
Glu Gly Gln Thr Glu Tyr Met Asp Tyr Val Leu His Trp Ile Asn Met
            1540                1545                1550
Val Phe Ile Ile Leu Phe Thr Gly Glu Cys Val Leu Lys Leu Ile Ser
        1555                1560                1565
Leu Arg His Tyr Tyr Phe Thr Val Gly Trp Asn Ile Leu Tyr Phe Val
    1570                1575                1580
Val Val Ile Leu Ser Ile Val Gly Met Phe Leu Ala Glu Met Ile Glu
1585                1590                1595                1600
Lys Tyr Phe Val Ser Pro Thr Leu Phe Arg Val Ile Arg Leu Ala Arg
                1605                1610                1615
Ile Gly Arg Ile Leu Arg Leu Ile Lys Gly Ala Lys Gly Ile Arg Thr
            1620                1625                1630
Leu Leu Phe Ala Leu Met Met Ser Leu Pro Ala Leu Phe Asn Ile Gly
        1635                1640                1645
Leu Leu Leu Phe Leu Val Met Phe Ile Tyr Ala Ile Phe Gly Met Ser
    1650                1655                1660
Asn Phe Ala Tyr Val Lys Lys Glu Ala Gly Ile Asn Asp Met Phe Asn
```

```
1665                1670                1675                1680

Phe Glu Thr Phe Gly Asn Ser Met Ile Cys Leu Phe Gln Ile Thr Thr
                    1685                1690                1695

Ser Ala Gly Trp Asp Gly Leu Leu Ala Pro Ile Leu Asn Ser Ala Pro
            1700                1705                1710

Pro Asp Cys Asp Pro Lys Lys Val His Pro Gly Ser Ser Val Glu Gly
        1715                1720                1725

Asp Cys Gly Asn Pro Ser Val Gly Ile Phe Tyr Phe Val Ser Tyr Ile
    1730                1735                1740

Ile Ile Ser Phe Leu Val Val Asn Met Tyr Ile Ala Val Ile Leu
1745                1750                1755                1760

Glu Asn Phe Ser Val Ala Thr Glu Glu Ser Thr Glu Pro Leu Ser Glu
                1765                1770                1775

Asp Asp Phe Glu Met Phe Tyr Glu Val Trp Glu Lys Phe Asp Pro Asp
            1780                1785                1790

Ala Thr Gln Phe Ile Glu Phe Cys Lys Leu Ser Asp Phe Ala Ala Ala
        1795                1800                1805

Leu Asp Pro Pro Leu Leu Ile Ala Lys Pro Asn Lys Val Gln Leu Ile
    1810                1815                1820

Ala Met Asp Leu Pro Met Val Ser Gly Asp Arg Ile His Cys Leu Asp
1825                1830                1835                1840

Ile Leu Phe Ala Phe Thr Lys Arg Val Leu Gly Glu Gly Gly Glu Met
                1845                1850                1855

Asp Ser Leu Arg Ser Gln Met Glu Glu Arg Phe Met Ser Ala Asn Pro
            1860                1865                1870

Ser Lys Val Ser Tyr Glu Pro Ile Thr Thr Thr Leu Lys Arg Lys Gln
        1875                1880                1885

Glu Glu Val Ser Ala Thr Ile Ile Gln Arg Ala Tyr Arg Arg Tyr Arg
    1890                1895                1900

Leu Arg Gln His Val Lys Asn Ile Ser Ser Ile Tyr Ile Lys Asp Gly
1905                1910                1915                1920

Asp Arg Asp Asp Asp Leu Pro Asn Lys Glu Asp Thr Val Phe Asp Asn
                1925                1930                1935

Val Asn Glu Asn Ser Ser Pro Glu Lys Thr Asp Val Thr Ala Ser Thr
            1940                1945                1950

Ile Ser Pro Pro Ser Tyr Asp Ser Val Thr Lys Pro Asp Gln Glu Lys
        1955                1960                1965

Tyr Glu Thr Asp Lys Thr Glu Lys Glu Asp Lys Glu Lys Asp Xaa Xaa
    1970                1975                1980

Glu Ser Arg Lys Xaa
1985

(2) INFORMATION FOR SEQ ID NO:13:

(i) SEQUENCE CHARACTERISTICS:
        (A) LENGTH: 6371 base pairs
        (B) TYPE: nucleic acid
        (C) STRANDEDNESS: both
        (D) TOPOLOGY: both (ii) MOLECULE TYPE: DNA (genomic)

(xi) SEQUENCE DESCRIPTION: SEQ ID NO:13:

CTCTTATGTG AGGAGCTGAA GAGGAATTAA AATATACAGG ATGAAAAGAT GGCAATGTTG    60

CCTCCCCCAG GACCTCAGAG CTTTGTCCAT TTCACAAAAC AGTCTCTTGC CCTCATTGAA    120
```

```
CAACGCATTG CTGAAAGAAA ATCAAAGGAA CCCAAAGAAG AAAAGAAAGA TGATGATGAA      180

GAAGCCCCAA AGCCAAGCAG TGACTTGGAA GCTGGCAAAC AACTGCCCTT CATCTATGGG      240

GACATTCCTC CCGGCATGGT GTCAGAGCCC CTGGAGGACT TGGACCCCTA CTATGCAGAC      300

AAAAAGACTT TCATAGTATT GAACAAAGGG AAAACAATCT TCCGTTTCAA TGCCACACCT      360

GCTTTATATA TGCTTTCTCC TTTCAGTCCT CTAAGAAGAA TATCTATTAA GATTTTAGTA      420

CACTCCTTAT TCAGCATGCT CATCATGTGC ACTATTCTGA CAAACTGCAT ATTTATGACC      480

ATGAATAACC CGCCGGACTG GACCAAAAAT GTCGAGTACA CTTTTACTGG AATATATACT      540

TTTGAATCAC TTGTAAAAAT CCTTGCAAGA GGCTTCTGTG TAGGAGAATT CACTTTTCTT      600

CGTGACCCGT GGAACTGGCT GGATTTTGTC GTCATTGTTT TTGCGTATTT AACAGAATTT      660

GTAAACCTAG GCAATGTTTC AGCTCTTCGA ACTTTCAGAG TATTGAGAGC TTTGAAAACT      720

ATTTCTGTAA TCCAGGCCT GAAGACAATT GTAGGGCTT TGATCCAGTC AGTGAAGAAG        780

CTTTCTGATG TCATGATCCT GACTGTGTTC TGTCTGAGTG TGTTTGCACT AATTGGACTA      840

CAGCTGTTCA TGGGAAACCT GAAGCATAAA TGTTTTCGAA ATTCACTTGA AAATAATGAA      900

ACATTAGAAA GCATAATGAA TACCCTAGAG AGTGAAGAAG ACTTTAGAAA ATATTTTTAT      960

TACTTGGAAG GATCCAAAGA TGCTCTCCTT TGTGGTTTCA GCACAGATTC AGGTCAGTGT     1020

CCAGAGGGGT ACACCTGTGT GAAAATTGGC AGAAACCCTG ATTATGGCTA CACGAGCTTT     1080

GACACTTTCA GCTGGGCCTT CTTAGCCTTG TTTAGGCTAA TGACCCAAGA TTACTGGGAA     1140

AACCTTTACC AACAGACGCT GCGTGCTGCT GGCAAAACCT ACATGATCTT CTTTGTCGTA     1200

GTGATTTTCC TGGGCTCCTT TTATCTAATA AACTTGATCC TGGCTGTGGT TGCCATGGCA     1260

TATGAAGAAC AGAACCAGGC AAACATTGAA GAAGCTAAAC AGAAAGAATT AGAATTTCAA     1320

CAGATGTTAG ACCGTCTTAA AAAAGAGCAA GAAGAAGCTG AGGCAATTGC AGCGGCAGCG     1380

GCTGAATATA CAAGTATTAG GAGAAGCAGA ATTATGGGCC TCTCAGAGAG TTCTTCTGAA     1440

ACATCCAAAC TGAGCTCTAA AAGTGCTAAA GAAAGAAGAA ACAGAAGAAA GAAAAAGAAT     1500

CAAAAGAAGC TCTCCAGTGG AGAGGAAAAG GGAGATGCTG AGAAATTGTC GAAATCAGAA     1560

TCAGAGGACA GCATCAGAAG AAAAAGTTTC CACCTTGGTG TCGAAGGGCA TAGGCGAGCA     1620

CATGAAAAGA GGTTGTCTAC CCCCAATCAG TCACCACTCA GCATTCGTGG CTCCTTGTTT     1680

TCTGCAAGGC GAAGCAGCAG AACAAGTCTT TTTAGTTTCA AAGGCAGAGG AAGAGATATA     1740

GGATCTGAGA CTGAATTTGC CGATGATGAG CACAGCATTT TTGGAGACAA TGAGAGCAGA     1800

AGGGGCTCAC TGTTTGTGCC CCACAGACCC CAGGAGCGAC GCAGCAGTAA CATCAGCCAA     1860

GCCAGTAGGT CCCCACCAAT GCTGCCGGTG AACGGGAAAA TGCACAGTGC TGTGGACTGC     1920

AACGGTGTGG TCTCCCTGGT TGATGGACGC TCAGCCCTCA TGCTCCCCAA TGGACAGCTT     1980

CTGCCAGAGG GCACGACCAA TCAAATACAC AAGAAAAGGC GTTGTAGTTC CTATCTCCTT     2040

TCAGAGGATA TGCTGAATGA TCCCAACCTC AGACAGAGAG CAATGAGTAG AGCAAGCATA     2100

TTAACAAACA CTGTGGAAGA ACTTGAAGAG TCCAGACAAA AATGTCCACC TTGGTGGTAC     2160

AGATTTGCAC ACAAATTCTT GATCTGGAAT TGCTCTCCAT ATTGGATAAA ATTCAAAAAG     2220

TGTATCTATT TTATTGTAAT GGATCCTTTT GTAGATCTTG CAATTACCAT TTGCATAGTT     2280

TTAAACACAT TATTTATGGC TATGGAACAC CACCCAATGA CTGAGGAATT CAAAAATGTA     2340

CTTGCTATAG GAAATTTGGT CTTTACTGGA ATCTTTGCAG CTGAAATGGT ATTAAAACTG     2400

ATTGCCATGG ATCCATATGA GTATTTCCAA GTAGGCTGGA ATATTTTTGA CAGCCTTATT     2460

GTGACTTTAA GTTTAGTGGA GCTCTTTCTA GCAGATGTGG AAGGATTGTC AGTTCTGCGA     2520
```

```
TCATTCAGAC TGCTCCGAGT CTTCAAGTTG GCAAAATCCT GGCCAACATT GAACATGCTG   2580

ATTAAGATCA TTGGTAACTC AGTAGGGGCT CTAGGTAACC TCACCTTAGT GTTGGCCATC   2640

ATCGTCTTCA TTTTTGCTGT GGTCGGCATG CAGCTCTTTG GTAAGAGCTA CAAAGAATGT   2700

GTCTGCAAGA TCAATGATGA CTGTACGCTC CCACGGTGGC ACATGAACGA CTTCTTCCAC   2760

TCCTTCCTGA TTGTGTTCCG CGTGCTGTGT GGAGAGTGGA TAGAGACCAT GTGGGACTGT   2820

ATGGAGGTCG CTGGTCAAGC TATGTGCCTT ATTGTTTACA TGATGGTCAT GGTCATTGGA   2880

AACCTGGTGG TCCTAAACCT ATTTCTGGCC TTATTATTGA GCTCATTTAG TTCAGACAAT   2940

CTTACAGCAA TTGAAGAAGA CCCTGATGCA AACAACCTCC AGATTGCAGT GACTAGAATT   3000

AAAAAGGGAA TAAATTATGT GAAACAAACC TTACGTGAAT TTATTCTAAA AGCATTTTCC   3060

AAAAAGCCAA AGATTTCCAG GGAGATAAGA CAAGCAGAAG ATCTGAATAC TAAGAAGGAA   3120

AACTATATTT CTAACCATAC ACTTGCTGAA ATGAGCAAAG GTCACAATTT CCTCAAGGAA   3180

AAAGATAAAA TCAGTGGTTT TGGAAGCAGC GTGGACAAAC ACTTGATGGA AGACAGTGAT   3240

GGTCAATCAT TTATTCACAA TCCCAGCCTC ACAGTGACAG TGCCAATTGC ACCTGGGGAA   3300

TCCGATTTGG AAAATATGAA TGCTGAGGAA CTTAGCAGTG ATTCGGATAG TGAATACAGC   3360

AAAGTGAGAT TAAACCGGTC AAGCTCCTCA GAGTGCAGCA CAGTTGATAA CCCTTTGCCT   3420

GGAGAAGGAG AAGAAGCAGA GGCTGAACCT ATGAATTCCG ATGAGCCAGA GGCCTGTTTC   3480

ACAGATGGTT GTGTACGGAG GTTCTCATGC TGCCAAGTTA ACATAGAGTC AGGGAAAGGA   3540

AAAATCTGGT GGAACATCAG GAAAACCTGC TACAAGATTG TTGAACACAG TTGGTTTGAA   3600

AGCTTCATTG TCCTCATGAT CCTGCTCAGC AGTGGTGCCC TGGCTTTTGA AGATATTTAT   3660

ATTGAAAGGA AAAAGACCAT TAAGATTATC CTGGAGTATG CAGACAAGAT CTTCACTTAC   3720

ATCTTCATTC TGGAAATGCT TCTAAAATGG ATAGCATATG GTTATAAAAC ATATTTCACC   3780

AATGCCTGGT GTTGGCTGGA TTTCCTAATT GTTGATGTTT CTTTGGTTAC TTTAGTGGCA   3840

AACACTCTTG GCTACTCAGA TCTTGGCCCC ATTAAATCCC TTCGGACACT GAGAGCTTTA   3900

AGACCTCTAA GAGCCTTATC TAGATTTGAA GGAATGAGGG TCGTTGTGAA TGCACTCATA   3960

GGAGCAATTC CTTCCATCAT GAATGTGCTA CTTGTGTGTC TTATATTCTG GCTGATATTC   4020

AGCATCATGG GAGTAAATTT GTTTGCTGGC AAGTTCTATG AGTGTATTAA CACCACAGAT   4080

GGGTCACGGT TCCTGCAAG TCAAGTTCCA AATCGTTCCG AATGTTTTGC CCTTATGAAT   4140

GTTAGTCAAA ATGTGCGATG GAAAAACCTG AAAGTGAACT TTGATAATGT CGGACTTGGT   4200

TACCTATCTC TGCTTCAAGT TGCAACTTTT AAGGGATGGA CGATTATTAT GTATGCAGCA   4260

GTGGATTCTG TTAATGTAGA CAAGCAGCCC AAATATGAAT ATAGCCTCTA CATGTATATT   4320

TATTTTGTCG TCTTTATCAT CTTTGGGTCA TTCTTCACTT TGAACTTGTT CATTGGTGTC   4380

ATCATAGATA ATTTCAACCA ACAGAAAAAG AAGCTTGGAG GTCAAGACAT CTTTATGACA   4440

GAAGAACAGA AGAAATACTA TAATGCAATG AAAAAGCTGG GGTCCAAGAA GCCACAAAAG   4500

CCAATTCCTC GACCAGGGAA CAAAATCCAA GGATGTATAT TTGACCTAGT GACAAATCAA   4560

GCCTTTGATA TTAGTATCAT GGTTCTTATC TGTCTCAACA TGGTAACCAT GATGGTAGAA   4620

AAGGAGGGTC AAAGTCAACA TATGACTGAA GTTTTATATT GGATAAATGT GGTTTTTATA   4680

ATCCTTTTCA CTGGAGAATG TGTGCTAAAA CTGATCTCCC TCAGACACTA CTACTTCACT   4740

GTAGGATGGA ATATTTTTGA TTTTGTGGTT GTGATTATCT CCATTGTAGG TATGTTTCTA   4800

GCTGATTTGA TTGAAACGTA TTTTGTGTCC CCTACCCTGT TCCGAGTGAT CCGTCTTGCC   4860
```

```
AGGATTGGCC GAATCCTACG TCTAGTCAAA GGAGCAAAGG GGATCCGCAC GCTGCTCTTT    4920

GCTTTGATGA TGTCCCTTCC TGCGTTGTTT AACATCGGCC TCCTGCTCTT CCTGGTCATG    4980

TTCATCTACG CCATCTTTGG AATGTCCAAC TTTGCCTATG TTAAAAAGGA AGATGGAATT    5040

AATGACATGT TCAATTTTGA GACCTTTGGC AACAGTATGA TTTGCCTGTT CCAAATTACA    5100

ACCTCTGCTG GCTGGGATGG ATTGCTAGCA CCTATTCTTA ACAGTAAGCC ACCCGACTGT    5160

GACCCAAAAA AAGTTCATCC TGGAAGTTCA GTTGAAGGAG ACTGTGGTAA CCCATCTGTT    5220

GGAATATTCT ACTTTGTTAG TTATATCATC ATATCCTTCC TGGTTGTGGT GAACATGTAC    5280

ATTGCAGTCA TACTGGAGAA TTTTAGTGTT GCCACTGAAG AAAGTACTGA ACCTCTGAGT    5340

GAGGATGACT TTGAGATGTT CTATGAGGTT TGGGAGAAGT TGATCCCGA TGCGACCCAG    5400

TTTATAGAGT TCTCTAAACT CTCTGATTTT GCAGCTGCCC TGGATCCTCC TCTTCTCATA    5460

GCAAACCCA ACAAAGTCCA GCTCATTGCC ATGGATCTGC CCATGGTTAG TGGTGACCGG    5520

ATCCATTGTC TTGACATCTT ATTTGCTTTT ACAAAGCGTG TTTTGGGTGA GAGTGGGGAG    5580

ATGGATTCTC TTCGTTCACA GATGGAAGAA AGGTTCATGT CTGCAAATCC TTCCAAAGTG    5640

TCCTATGAAC CCATCACAAC CACACTAAAA CGGAAACAAG AGGATGTGTC TGCTACTGTC    5700

ATTCAGCGTG CTTATAGACG TTACCGCTTA AGGCAAAATG TCAAAAATAT ATCAAGTATA    5760

TACATAAAAG ATGGAGACAG AGATGATGAT TTACTCAATA AAAAGATAT GGCTTTTGAT    5820

AATGTTAATG AGAACTCAAG TCCAGAAAAA ACAGATGCCA CTTCATCCAC CACCTCTCCA    5880

CCTTCATATG ATAGTGTAAC AAAGCCAGAC AAAGAGAAAT ATGAACAAGA CAGAACAGAA    5940

AAGGAAGACA AAGGGAAAGA CAGCAAGGAA AGCAAAAAAT AGAGCTTCAT TTTTGATATA    6000

TTGTTTACAG CCTGTGAAAG TGATTTATTT GTGTTAATAA AACTCTTTTG AGGAAGTCTA    6060

TGCCAAAATC CTTTTTATCA AAATATTCTC GAAGGCAGTG CAGTCACTAA CTCTGATTTC    6120

CTAAGAAAGG TGGGCAGCAT TAGCAGATGG TTATTTTTGC ACTGATGATT CTTTAAGAAT    6180

CGTAAGAGAA CTCTGTAGGA ATTATTGATT ATAGCATACA AAAGTGATTG ATTCAGTTTT    6240

TTGGTTTTTA ATAAATCAGA AGACCATGTA GAAAACTTTT ACATCTGCCT TGTCATCTTT    6300

TCACAGGATT GTAATTAGTC TTGTTTCCCA TGTAAATAAA CAACACACGC ATACAGAAAA    6360

AAAAAAAAA A                                                          6371

(2) INFORMATION FOR SEQ ID NO:14:

(i) SEQUENCE CHARACTERISTICS:
        (A) LENGTH: 6404 base pairs
        (B) TYPE: nucleic acid
        (C) STRANDEDNESS: both
        (D) TOPOLOGY: both (ii) MOLECULE TYPE: DNA (genomic)

(xi) SEQUENCE DESCRIPTION: SEQ ID NO:14:

CTCTTATGTG AGGAGCTGAA GAGGAATTAA AATATACAGG ATGAAAAGAT GGCAATGTTG     60

CCTCCCCCAG GACCTCAGAG CTTTGTCCAT TTCACAAAAC AGTCTCTTGC CCTCATTGAA    120

CAACGCATTG CTGAAAGAAA ATCAAAGGAA CCCAAAGAAG AAAAGAAAGA TGATGATGAA    180

GAAGCCCCAA AGCCAAGCAG TGACTTGGAA GCTGGCAAAC AACTGCCCTT CATCTATGGG    240

GACATTCCTC CCGGCATGGT GTCAGAGCCC CTGGAGGACT TGGACCCCTA CTATGCAGAC    300

AAAAAGACTT TCATAGTATT GAACAAAGGG AAAACAATCT TCCGTTTCAA TGCCACACCT    360

GCTTTATATA TGCTTTCTCC TTTCAGTCCT CTAAGAAGAA TATCTATTAA GATTTTAGTA    420
```

```
CACTCCTTAT TCAGCATGCT CATCATGTGC ACTATTCTGA CAAACTGCAT ATTTATGACC      480
ATGAATAACC CGCCGGACTG GACCAAAAAT GTCGAGTACA CTTTTACTGG AATATATACT      540
TTTGAATCAC TTGTAAAAAT CCTTGCAAGA GGCTTCTGTG TAGGAGAATT CACTTTTCTT      600
CGTGACCCGT GGAACTGGCT GGATTTTGTC GTCATTGTTT TTGCGTATTT AACAGAATTT      660
GTAAACCTAG GCAATGTTTC AGCTCTTCGA ACTTTCAGAG TATTGAGAGC TTTGAAAACT      720
ATTTCTGTAA TCCCAGGCCT GAAGACAATT GTAGGGCTT TGATCCAGTC AGTGAAGAAG       780
CTTTCTGATG TCATGATCCT GACTGTGTTC TGTCTGAGTG TGTTTGCACT AATTGGACTA      840
CAGCTGTTCA TGGGAAACCT GAAGCATAAA TGTTTTCGAA ATTCACTTGA AAATAATGAA      900
ACATTAGAAA GCATAATGAA TACCCTAGAG AGTGAAGAAG ACTTTAGAAA ATATTTTTAT      960
TACTTGGAAG GATCCAAAGA TGCTCTCCTT TGTGGTTTCA GCACAGATTC AGGTCAGTGT     1020
CCAGAGGGGT ACACCTGTGT GAAAATTGGC AGAAACCCTG ATTATGGCTA CACGAGCTTT     1080
GACACTTTCA GCTGGGCCTT CTTAGCCTTG TTTAGGCTAA TGACCCAAGA TTACTGGGAA     1140
AACCTTTACC AACAGACGCT GCGTGCTGCT GGCAAAACCT ACATGATCTT CTTTGTCGTA     1200
GTGATTTTCC TGGGCTCCTT TTATCTAATA AACTTGATCC TGGCTGTGGT TGCCATGGCA     1260
TATGAAGAAC AGAACCAGGC AAACATTGAA GAAGCTAAAC AGAAAGAATT AGAATTTCAA     1320
CAGATGTTAG ACCGTCTTAA AAAAGAGCAA GAAGAAGCTG AGGCAATTGC AGCGGCAGCG     1380
GCTGAATATA CAAGTATTAG GAGAAGCAGA ATTATGGGCC TCTCAGAGAG TTCTTCTGAA     1440
ACATCCAAAC TGAGCTCTAA AAGTGCTAAA GAAAGAAGAA ACAGAAGAAA GAAAAAGAAT     1500
CAAAAGAAGC TCTCCAGTGG AGAGGAAAAG GGAGATGCTG AGAAATTGTC GAAATCAGAA     1560
TCAGAGGACA GCATCAGAAG AAAAAGTTTC CACCTTGGTG TCGAAGGGCA TAGGCGAGCA     1620
CATGAAAAGA GGTTGTCTAC CCCCAATCAG TCACCACTCA GCATTCGTGG CTCCTTGTTT     1680
TCTGCAAGGC GAAGCAGCAG AACAAGTCTT TTTAGTTTCA AAGGCAGAGG AAGAGATATA     1740
GGATCTGAGA CTGAATTTGC CGATGATGAG CACAGCATTT TTGGAGACAA TGAGAGCAGA     1800
AGGGGCTCAC TGTTTGTGCC CCACAGACCC CAGGAGCGAC GCAGCAGTAA CATCAGCCAA     1860
GCCAGTAGGT CCCCACCAAT GCTGCCGGTG AACGGGAAAA TGCACAGTGC TGTGGACTGC     1920
AACGGTGTGG TCTCCCTGGT TGATGGACGC TCAGCCCTCA TGCTCCCCAA TGGACAGCTT     1980
CTGCCAGAGG TGATAATAGA TAAGACAACT TCTGATGACA GCGGCACGAC CAATCAAATA     2040
CACAAGAAAA GGCGTTGTAG TTCCTATCTC CTTTCAGAGG ATATGCTGAA TGATCCCAAC     2100
CTCAGACAGA GAGCAATGAG TAGAGCAAGC ATATTAACAA ACACTGTGGA AGAACTTGAA     2160
GAGTCCAGAC AAAAATGTCC ACCTTGGTGG TACAGATTTG CACACAAATT CTTGATCTGG     2220
AATTGCTCTC CATATTGGAT AAAATTCAAA AAGTGTATCT ATTTTATTGT AATGGATCCT     2280
TTTGTAGATC TTGCAATTAC CATTTGCATA GTTTTAAACA CATTATTTAT GGCTATGGAA     2340
CACCACCCAA TGACTGAGGA ATTCAAAAAT GTACTTGCTA TAGGAAATTT GGTCTTTACT     2400
GGAATCTTTG CAGCTGAAAT GGTATTAAAA CTGATTGCCA TGGATCCATA TGAGTATTTC     2460
CAAGTAGGCT GGAATATTTT TGACAGCCTT ATTGTGACTT TAAGTTTAGT GGAGCTCTTT     2520
CTAGCAGATG TGGAAGGATT GTCAGTTCTG CGATCATTCA GACTGCTCCG AGTCTTCAAG     2580
TTGGCAAAAT CCTGGCCAAC ATTGAACATG CTGATTAAGA TCATTGGTAA CTCAGTAGGG     2640
GCTCTAGGTA ACCTCACCTT AGTGTTGGCC ATCATCGTCT TCATTTTTGC TGTGGTCGGC     2700
ATGCAGCTCT TTGGTAAGAG CTACAAAGAA TGTGTCTGCA AGATCAATGA TGACTGTACG     2760
CTCCCACGGT GGCACATGAA CGACTTCTTC CACTCCTTCC TGATTGTGTT CCGCGTGCTG     2820
```

```
TGTGGAGAGT GGATAGAGAC CATGTGGGAC TGTATGGAGG TCGCTGGTCA AGCTATGTGC       2880

CTTATTGTTT ACATGATGGT CATGGTCATT GGAAACCTGG TGGTCCTAAA CCTATTTCTG       2940

GCCTTATTAT TGAGCTCATT TAGTTCAGAC AATCTTACAG CAATTGAAGA AGACCCTGAT       3000

GCAAACAACC TCCAGATTGC AGTGACTAGA ATTAAAAAGG GAATAAATTA TGTGAAACAA       3060

ACCTTACGTG AATTTATTCT AAAAGCATTT TCCAAAAAGC CAAAGATTTC CAGGGAGATA       3120

AGACAAGCAG AAGATCTGAA TACTAAGAAG GAAAACTATA TTTCTAACCA TACACTTGCT       3180

GAAATGAGCA AAGGTCACAA TTTCCTCAAG GAAAAAGATA AAATCAGTGG TTTTGGAAGC       3240

AGCGTGGACA AACACTTGAT GGAAGACAGT GATGGTCAAT CATTTATTCA CAATCCCAGC       3300

CTCACAGTGA CAGTGCCAAT TGCACCTGGG GAATCCGATT TGGAAAATAT GAATGCTGAG       3360

GAACTTAGCA GTGATTCGGA TAGTGAATAC AGCAAAGTGA GATTAAACCG GTCAAGCTCC       3420

TCAGAGTGCA GCACAGTTGA TAACCCTTTG CCTGGAGAAG GAGAAGAAGC AGAGGCTGAA       3480

CCTATGAATT CCGATGAGCC AGAGGCCTGT TTCACAGATG GTTGTGTACG GAGGTTCTCA       3540

TGCTGCCAAG TTAACATAGA GTCAGGGAAA GGAAAAATCT GGTGGAACAT CAGGAAAACC       3600

TGCTACAAGA TTGTTGAACA CAGTTGGTTT GAAAGCTTCA TTGTCCTCAT GATCCTGCTC       3660

AGCAGTGGTG CCCTGGCTTT TGAAGATATT TATATTGAAA GGAAAAAGAC CATTAAGATT       3720

ATCCTGGAGT ATGCAGACAA GATCTTCACT TACATCTTCA TTCTGGAAAT GCTTCTAAAA       3780

TGGATAGCAT ATGGTTATAA AACATATTTC ACCAATGCCT GGTGTTGGCT GGATTTCCTA       3840

ATTGTTGATG TTTCTTTGGT TACTTTAGTG GCAAACACTC TTGGCTACTC AGATCTTGGC       3900

CCCATTAAAT CCCTTCGGAC ACTGAGAGCT TTAAGACCTC TAAGAGCCTT ATCTAGATTT       3960

GAAGGAATGA GGGTCGTTGT GAATGCACTC ATAGGAGCAA TTCCTTCCAT CATGAATGTG       4020

CTACTTGTGT GTCTTATATT CTGGCTGATA TTCAGCATCA TGGGAGTAAA TTTGTTTGCT       4080

GGCAAGTTCT ATGAGTGTAT TAACACCACA GATGGGTCAC GGTTTCCTGC AAGTCAAGTT       4140

CCAAATCGTT CCGAATGTTT TGCCCTTATG AATGTTAGTC AAAATGTGCG ATGGAAAAAC       4200

CTGAAAGTGA ACTTTGATAA TGTCGGACTT GGTTACCTAT CTCTGCTTCA AGTTGCAACT       4260

TTTAAGGGAT GGACGATTAT TATGTATGCA GCAGTGGATT CTGTTAATGT AGACAAGCAG       4320

CCCAAATATG AATATAGCCT CTACATGTAT ATTTATTTTG TCGTCTTTAT CATCTTTGGG       4380

TCATTCTTCA CTTTGAACTT GTTCATTGGT GTCATCATAG ATAATTTCAA CCAACAGAAA       4440

AAGAAGCTTG GAGGTCAAGA CATCTTTATG ACAGAAGAAC AGAAGAAATA CTATAATGCA       4500

ATGAAAAAGC TGGGGTCCAA GAAGCCACAA AAGCCAATTC CTCGACCAGG GAACAAAATC       4560

CAAGGATGTA TATTTGACCT AGTGACAAAT CAAGCCTTTG ATATTAGTAT CATGGTTCTT       4620

ATCTGTCTCA ACATGGTAAC CATGATGGTA GAAAAGGAGG GTCAAAGTCA ACATATGACT       4680

GAAGTTTTAT ATTGGATAAA TGTGGTTTTT ATAATCCTTT TCACTGGAGA ATGTGTGCTA       4740

AAACTGATCT CCCTCAGACA CTACTACTTC ACTGTAGGAT GGAATATTTT TGATTTTGTG       4800

GTTGTGATTA TCTCCATTGT AGGTATGTTT CTAGCTGATT TGATTGAAAC GTATTTTGTG       4860

TCCCCTACCC TGTTCCGAGT GATCCGTCTT GCCAGGATTG GCCGAATCCT ACGTCTAGTC       4920

AAAGGAGCAA AGGGGATCCG CACGCTGCTC TTTGCTTTGA TGATGTCCCT TCCTGCGTTG       4980

TTTAACATCG GCCTCCTGCT CTTCCTGGTC ATGTTCATCT ACGCCATCTT TGGAATGTCC       5040

AACTTTGCCT ATGTTAAAAA GGAAGATGGA ATTAATGACA TGTTCAATTT TGAGACCTTT       5100

GGCAACAGTA TGATTTGCCT GTTCCAAATT ACAACCTCTG CTGGCTGGGA TGGATTGCTA       5160
```

```
GCACCTATTC TTAACAGTAA GCCACCCGAC TGTGACCCAA AAAAAGTTCA TCCTGGAAGT      5220

TCAGTTGAAG GAGACTGTGG TAACCCATCT GTTGGAATAT TCTACTTTGT TAGTTATATC      5280

ATCATATCCT TCCTGGTTGT GGTGAACATG TACATTGCAG TCATACTGGA GAATTTTAGT      5340

GTTGCCACTG AAGAAAGTAC TGAACCTCTG AGTGAGGATG ACTTTGAGAT GTTCTATGAG      5400

GTTTGGGAGA AGTTTGATCC CGATGCGACC CAGTTTATAG AGTTCTCTAA ACTCTCTGAT      5460

TTTGCAGCTG CCCTGGATCC TCCTCTTCTC ATAGCAAAAC CCAACAAAGT CCAGCTCATT      5520

GCCATGGATC TGCCCATGGT TAGTGGTGAC CGGATCCATT GTCTTGACAT CTTATTTGCT      5580

TTTACAAAGC GTGTTTTGGG TGAGAGTGGG GAGATGGATT CTCTTCGTTC ACAGATGGAA      5640

GAAAGGTTCA TGTCTGCAAA TCCTTCCAAA GTGTCCTATG AACCCATCAC AACCACACTA      5700

AAACGGAAAC AAGAGGATGT GTCTGCTACT GTCATTCAGC GTGCTTATAG ACGTTACCGC      5760

TTAAGGCAAA ATGTCAAAAA TATATCAAGT ATATACATAA AAGATGGAGA CAGAGATGAT      5820

GATTTACTCA ATAAAAAAGA TATGGCTTTT GATAATGTTA ATGAGAACTC AAGTCCAGAA      5880

AAAACAGATG CCACTTCATC CACCACCTCT CCACCTTCAT ATGATAGTGT AACAAAGCCA      5940

GACAAAGAGA AATATGAACA AGACAGAACA GAAAAGGAAG ACAAAGGGAA AGACAGCAAG      6000

GAAAGCAAAA AATAGAGCTT CATTTTTGAT ATATTGTTTA CAGCCTGTGA AAGTGATTTA      6060

TTTGTGTTAA TAAAACTCTT TTGAGGAAGT CTATGCCAAA ATCCTTTTTA TCAAAATATT      6120

CTCGAAGGCA GTGCAGTCAC TAACTCTGAT TTCCTAAGAA AGGTGGGCAG CATTAGCAGA      6180

TGGTTATTTT TGCACTGATG ATTCTTTAAG AATCGTAAGA GAACTCTGTA GGAATTATTG      6240

ATTATAGCAT ACAAAAGTGA TTGATTCAGT TTTTTGGTTT TTAATAAATC AGAAGACCAT      6300

GTAGAAAACT TTTACATCTG CCTTGTCATC TTTTCACAGG ATTGTAATTA GTCTTGTTTC      6360

CCATGTAAAT AAACAACACA CGCATACAGA AAAAAAAAAA AAAA                      6404

(2) INFORMATION FOR SEQ ID NO:15:

(i) SEQUENCE CHARACTERISTICS:
        (A) LENGTH: 1835 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:15:

Met Ala Met Leu Pro Pro Gly Pro Gln Ser Phe Val His Phe Thr
1               5                   10                  15

Lys Gln Ser Leu Ala Leu Ile Glu Gln Arg Ile Glu Lys Glu Lys
                20                  25                  30

Glu Lys Lys Asp Asp Glu Glu Pro Lys Pro Ser Ser Asp Leu Glu Ala
            35                  40                  45

Gly Lys Gln Leu Pro Phe Ile Tyr Gly Asp Ile Pro Pro Gly Met Val
        50                  55                  60

Ser Glu Pro Leu Glu Asp Leu Asp Pro Tyr Tyr Ala Asp Lys Lys Thr
65                  70                  75                  80

Phe Ile Val Leu Asn Lys Gly Lys Ile Phe Arg Phe Asn Ala Thr Pro
                85                  90                  95

Ala Leu Tyr Met Leu Ser Pro Phe Ser Pro Leu Arg Arg Ile Ser Ile
                100                 105                 110

Lys Ile Leu Val His Ser Leu Phe Ser Met Leu Ile Met Cys Thr Ile
            115                 120                 125
```

-continued

```
Leu Thr Asn Cys Ile Phe Met Thr Asn Pro Pro Trp Thr Lys Asn Val
    130                 135                 140

Tyr Thr Phe Thr Gly Ile Tyr Thr Phe Glu Ser Leu Lys Ile Leu Ala
145                 150                 155                 160

Arg Gly Phe Cys Val Gly Glu Phe Thr Phe Leu Arg Asp Pro Trp Asn
                165                 170                 175

Trp Leu Asp Phe Val Val Ile Val Phe Ala Tyr Leu Thr Glu Phe Val
                180                 185                 190

Asn Leu Gly Asn Val Ser Ala Leu Arg Thr Phe Arg Val Leu Arg Ala
            195                 200                 205

Leu Lys Thr Ile Ser Val Ile Pro Gly Leu Lys Thr Ile Val Gly Ala
    210                 215                 220

Leu Ile Gln Ser Val Lys Lys Leu Ser Asp Val Met Ile Leu Thr Val
225                 230                 235                 240

Phe Cys Leu Ser Val Phe Ala Leu Ile Gly Leu Gln Leu Phe Met Gly
                245                 250                 255

Asn Leu Lys His Lys Cys Phe Arg Leu Glu Asn Glu Thr Leu Glu Ser
            260                 265                 270

Ile Met Asn Thr Glu Ser Glu Glu Lys Tyr Phe Tyr Leu Glu Gly
    275                 280                 285

Ser Lys Asp Ala Leu Leu Cys Gly Phe Ser Thr Asp Ser Gly Gln Cys
290                 295                 300

Pro Glu Gly Tyr Cys Val Lys Gly Arg Asn Pro Asp Tyr Gly Tyr Thr
305                 310                 315                 320

Ser Phe Asp Thr Phe Ser Trp Ala Phe Leu Ala Leu Phe Arg Leu Met
                325                 330                 335

Thr Gln Asp Tyr Trp Glu Asn Leu Tyr Gln Gln Thr Leu Arg Ala Ala
            340                 345                 350

Gly Lys Thr Tyr Met Ile Phe Phe Val Val Ile Phe Leu Gly Ser
    355                 360                 365

Phe Tyr Leu Ile Asn Leu Ile Leu Ala Val Val Ala Met Ala Tyr Glu
370                 375                 380

Glu Gln Asn Gln Ala Asn Ile Glu Glu Ala Lys Gln Lys Glu Leu Glu
385                 390                 395                 400

Phe Gln Gln Met Leu Asp Arg Leu Lys Lys Glu Gln Glu Glu Ala Glu
                405                 410                 415

Ala Ile Ala Ala Ala Ala Ala Glu Thr Ser Ile Arg Ser Arg Ile Met
            420                 425                 430

Gly Leu Ser Glu Ser Ser Ser Glu Thr Ser Leu Ser Ser Lys Ser Ala
    435                 440                 445

Lys Glu Arg Arg Asn Arg Arg Lys Lys Gln Lys Lys Ser Ser Gly
    450                 455                 460

Glu Glu Lys Gly Asp Glu Lys Leu Ser Lys Ser Ser Glu Ser Ile Arg
465                 470                 475                 480

Lys Ser Phe His Leu Gly Val Glu Gly His Arg Glu Lys Arg Leu Ser
                485                 490                 495

Thr Pro Asn Gln Ser Pro Leu Ser Ile Arg Gly Ser Leu Phe Ser Ala
            500                 505                 510

Arg Arg Ser Ser Arg Thr Ser Leu Phe Ser Phe Lys Gly Arg Gly Arg
    515                 520                 525

Asp Gly Ser Glu Thr Glu Phe Ala Asp Asp Glu His Ser Ile Phe Gly
    530                 535                 540

Asp Asn Glu Ser Arg Arg Gly Ser Leu Phe Val Pro His Arg Pro Glu
```

-continued

```
545                 550                 555                 560
Arg Arg Ser Ser Asn Ile Ser Gln Ala Ser Arg Ser Pro Pro Leu Pro
                565                 570                 575
Val Asn Gly Lys Met His Ser Ala Val Asp Cys Asn Gly Val Val Ser
                580                 585                 590
Leu Val Asp Gly Ser Ala Leu Met Leu Pro Asn Gly Gln Leu Leu Pro
                595                 600                 605
Glu Gly Thr Thr Asn Gln Lys Lys Arg Ser Ser Tyr Leu Ser Glu Asp
                610                 615                 620
Met Leu Asn Asp Pro Leu Arg Gln Arg Ala Met Ser Arg Ala Ser Ile
625                 630                 635                 640
Leu Thr Asn Thr Val Glu Glu Leu Glu Glu Ser Arg Gln Lys Cys Tyr
                645                 650                 655
Arg Phe Ala His Phe Leu Ile Trp Asn Cys Ser Pro Tyr Trp Ile Lys
                660                 665                 670
Phe Lys Lys Ile Tyr Phe Ile Val Met Asp Pro Phe Val Asp Leu Ala
                675                 680                 685
Ile Thr Ile Cys Ile Val Leu Asn Thr Leu Phe Met Ala Met Glu His
                690                 695                 700
His Pro Met Thr Glu Glu Phe Lys Asn Val Leu Ala Gly Asn Leu Phe
705                 710                 715                 720
Thr Gly Ile Phe Ala Ala Glu Met Val Leu Lys Leu Ile Ala Met Asp
                725                 730                 735
Pro Tyr Glu Tyr Phe Gln Val Gly Trp Asn Ile Phe Asp Ser Leu Ile
                740                 745                 750
Val Thr Leu Ser Leu Glu Leu Phe Leu Ala Asp Val Glu Gly Leu Ser
                755                 760                 765
Val Leu Arg Ser Phe Arg Leu Leu Arg Val Phe Lys Leu Ala Lys Ser
                770                 775                 780
Trp Pro Thr Leu Asn Met Leu Ile Lys Ile Ile Gly Asn Ser Val Gly
785                 790                 795                 800
Ala Leu Gly Asn Leu Thr Leu Val Leu Ala Ile Ile Val Phe Ile Phe
                805                 810                 815
Ala Val Val Gly Met Gln Leu Phe Gly Lys Ser Tyr Lys Glu Cys Val
                820                 825                 830
Cys Lys Ile Asn Asp Cys Leu Pro Arg Trp His Met Asn Asp Phe Phe
                835                 840                 845
His Ser Phe Leu Ile Val Phe Arg Val Leu Cys Gly Glu Trp Ile Glu
                850                 855                 860
Thr Met Trp Asp Cys Met Glu Val Ala Gly Gln Met Cys Leu Ile Val
865                 870                 875                 880
Tyr Met Met Val Met Val Ile Gly Asn Leu Val Val Leu Asn Leu Phe
                885                 890                 895
Leu Ala Leu Leu Leu Ser Ser Phe Ser Ser Asp Asn Leu Thr Ala Ile
                900                 905                 910
Glu Glu Asp Asp Ala Asn Asn Leu Gln Ile Ala Val Arg Ile Lys Gly
                915                 920                 925
Ile Asn Tyr Val Lys Gln Thr Leu Arg Glu Phe Ile Leu Lys Phe Ser
                930                 935                 940
Lys Lys Pro Lys Ser Asp Asn Lys Glu Asn Tyr Ile Ser Asn Thr
945                 950                 955                 960
Leu Ala Glu Met Ser Lys His Asn Phe Leu Lys Glu Lys Asp Ile Ser
                965                 970                 975
```

-continued

```
Gly Gly Ser Ser Asp Lys Met Asp Gln Ser Phe Ile His Asn Pro Ser
            980                 985                 990

Leu Thr Val Thr Val Pro Ile Ala Pro Gly Glu Ser Asp Leu Glu Met
            995                1000                1005

Asn Glu Glu Leu Ser Ser Asp Ser Asp Ser Tyr Ser Lys Asn Arg Ser
           1010                1015                1020

Ser Ser Ser Glu Cys Ser Thr Val Asp Asn Pro Leu Pro Gly Glu Gly
1025                1030                1035                1040

Glu Glu Ala Glu Ala Glu Pro Asn Asp Glu Pro Glu Ala Cys Phe Thr
                1045                1050                1055

Asp Gly Cys Val Arg Arg Phe Cys Cys Gln Val Asn Ser Gly Lys Gly
                1060                1065                1070

Lys Trp Trp Ile Arg Lys Thr Cys Tyr Ile Val Glu His Ser Trp Phe
           1075                1080                1085

Glu Ser Phe Ile Val Leu Met Ile Leu Leu Ser Ser Gly Ala Leu Ala
           1090                1095                1100

Phe Glu Asp Ile Tyr Ile Glu Lys Lys Thr Ile Lys Ile Ile Leu Glu
1105                1110                1115                1120

Tyr Ala Asp Lys Ile Phe Thr Tyr Ile Phe Ile Leu Glu Met Leu Leu
                1125                1130                1135

Lys Trp Ala Tyr Gly Tyr Lys Thr Tyr Phe Thr Asn Ala Trp Cys Trp
                1140                1145                1150

Leu Asp Phe Leu Ile Val Asp Val Ser Leu Val Thr Leu Val Ala Asn
           1155                1160                1165

Thr Leu Gly Tyr Ser Asp Leu Gly Pro Ile Lys Ser Leu Arg Thr Leu
           1170                1175                1180

Arg Ala Leu Arg Pro Leu Arg Ala Leu Ser Arg Phe Glu Gly Met Arg
1185                1190                1195                1200

Val Val Val Asn Ala Leu Ile Gly Ala Ile Pro Ser Ile Met Asn Val
                1205                1210                1215

Leu Leu Val Cys Leu Ile Phe Trp Leu Ile Phe Ser Ile Met Gly Val
                1220                1225                1230

Asn Leu Phe Ala Gly Lys Phe Tyr Glu Cys Asn Thr Thr Asp Gly Ser
           1235                1240                1245

Arg Phe Pro Ser Gln Val Asn Arg Ser Glu Cys Phe Ala Leu Met Asn
           1250                1255                1260

Val Ser Asn Val Arg Trp Lys Asn Leu Val Asn Phe Asp Asn Val
1265                1270                1275                1280

Gly Leu Gly Tyr Leu Ser Leu Leu Gln Val Ala Thr Phe Lys Gly Trp
           1285                1290                1295

Ile Met Tyr Ala Ala Val Asp Ser Val Asn Val Gln Pro Lys Tyr Glu
                1300                1305                1310

Tyr Ser Leu Tyr Met Tyr Ile Tyr Phe Val Phe Ile Ile Phe Gly Ser
           1315                1320                1325

Phe Phe Thr Leu Asn Leu Phe Ile Gly Val Ile Ile Asp Asn Phe Asn
           1330                1335                1340

Gln Gln Lys Lys Lys Leu Gly Gly Gln Asp Ile Phe Met Thr Glu Glu
1345                1350                1355                1360

Gln Lys Lys Tyr Tyr Asn Ala Met Lys Lys Leu Gly Ser Lys Pro
                1365                1370                1375

Gln Lys Pro Ile Pro Arg Pro Gly Asn Lys Gln Gly Cys Ile Phe Asp
           1380                1385                1390
```

-continued

```
Leu Thr Asn Gln Ala Phe Asp Ile Ile Met Val Leu Ile Cys Leu Asn
        1395                1400                1405

Met Val Thr Met Met Val Glu Lys Glu Gly Gln Met Val Leu Trp Ile
    1410                1415                1420

Asn Val Phe Ile Ile Leu Phe Thr Gly Glu Cys Val Leu Lys Leu Ile
1425                1430                1435                1440

Ser Leu Arg His Tyr Tyr Phe Thr Val Gly Trp Asn Ile Phe Val Val
            1445                1450                1455

Val Ile Ser Ile Val Gly Met Phe Leu Ala Ile Glu Tyr Phe Val Ser
                1460                1465                1470

Pro Thr Leu Phe Arg Val Ile Arg Leu Ala Arg Ile Gly Arg Ile Leu
            1475                1480                1485

Arg Leu Lys Gly Ala Lys Gly Ile Arg Thr Leu Leu Phe Ala Leu Met
        1490                1495                1500

Met Ser Leu Pro Ala Leu Phe Asn Ile Gly Leu Leu Leu Phe Leu Val
1505                1510                1515                1520

Met Phe Ile Tyr Ala Ile Phe Gly Met Ser Asn Phe Ala Tyr Val Lys
            1525                1530                1535

Lys Glu Gly Ile Asn Asp Met Phe Asn Phe Glu Thr Phe Gly Asn Ser
            1540                1545                1550

Met Ile Cys Leu Phe Gln Ile Thr Thr Ser Ala Gly Trp Asp Gly Leu
        1555                1560                1565

Leu Ala Pro Ile Leu Asn Ser Pro Pro Asp Cys Asp Pro Lys Lys Val
    1570                1575                1580

His Pro Gly Ser Ser Val Glu Gly Asp Cys Gly Asn Pro Ser Val Gly
1585                1590                1595                1600

Ile Phe Tyr Phe Val Ser Tyr Ile Ile Ile Ser Phe Leu Val Val Val
            1605                1610                1615

Asn Met Tyr Ile Ala Val Ile Leu Glu Asn Phe Ser Val Ala Thr Glu
            1620                1625                1630

Glu Ser Thr Glu Pro Leu Ser Glu Asp Asp Phe Glu Met Phe Tyr Glu
        1635                1640                1645

Val Trp Glu Lys Phe Asp Pro Asp Ala Thr Gln Phe Ile Glu Phe Lys
    1650                1655                1660

Leu Ser Asp Phe Ala Ala Ala Leu Asp Pro Pro Leu Leu Ile Ala Lys
1665                1670                1675                1680

Pro Asn Lys Val Gln Leu Ile Ala Met Asp Leu Pro Met Val Ser Gly
            1685                1690                1695

Asp Arg Ile His Cys Leu Asp Ile Leu Phe Ala Phe Thr Lys Arg Val
            1700                1705                1710

Leu Gly Glu Gly Glu Met Asp Ser Leu Arg Ser Gln Met Glu Glu Arg
        1715                1720                1725

Phe Met Ser Ala Asn Pro Ser Lys Val Ser Tyr Glu Pro Ile Thr Thr
    1730                1735                1740

Thr Leu Lys Arg Lys Gln Glu Val Ser Ala Thr Ile Gln Arg Ala Tyr
1745                1750                1755                1760

Arg Arg Tyr Arg Leu Arg Gln Val Lys Asn Ile Ser Ser Ile Tyr Ile
            1765                1770                1775

Lys Asp Gly Asp Arg Asp Asp Leu Asn Lys Asp Phe Asp Asn Val
            1780                1785                1790

Asn Glu Asn Ser Ser Pro Glu Lys Thr Asp Thr Ser Thr Ser Pro Pro
        1795                1800                1805

Ser Tyr Asp Ser Val Thr Lys Pro Asp Glu Lys Tyr Glu Asp Thr Glu
```

```
                  1810                1815                1820
Lys Glu Asp Lys Lys Asp Ser Lys Glu Ser Lys
1825                1830                1835
```

(2) INFORMATION FOR SEQ ID NO:16:

(i) SEQUENCE CHARACTERISTICS:
        (A) LENGTH: 1969 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:16:

```
Met Ala Met Leu Pro Pro Gly Pro Gln Ser Phe Val His Phe Thr
1               5                   10                  15

Lys Gln Ser Leu Ala Leu Ile Glu Gln Arg Ile Ala Glu Arg Lys Ser
            20                  25                  30

Lys Glu Pro Lys Glu Glu Lys Lys Asp Asp Asp Glu Glu Ala Pro Lys
            35                  40                  45

Pro Ser Ser Asp Leu Glu Ala Gly Lys Gln Leu Pro Phe Ile Tyr Gly
        50                  55                  60

Asp Ile Pro Pro Gly Met Val Ser Glu Pro Leu Glu Asp Leu Asp Pro
65                  70                  75                  80

Tyr Tyr Ala Asp Lys Lys Thr Phe Ile Val Leu Asn Lys Gly Lys Ala
                85                  90                  95

Ile Phe Arg Phe Asn Ala Thr Pro Ala Leu Tyr Met Leu Ser Pro Phe
                100                 105                 110

Ser Pro Leu Arg Arg Ile Ser Ile Lys Ile Leu Val His Ser Leu Phe
            115                 120                 125

Ser Met Leu Ile Met Cys Thr Ile Leu Thr Asn Cys Ile Phe Met Thr
        130                 135                 140

Met Asn Asn Pro Pro Asp Trp Thr Lys Asn Val Gly Tyr Thr Phe Thr
145                 150                 155                 160

Gly Ile Tyr Thr Phe Glu Ser Leu Val Lys Ile Leu Ala Arg Gly Phe
                165                 170                 175

Cys Val Gly Glu Phe Thr Phe Leu Arg Asp Pro Trp Asn Trp Leu Asp
                180                 185                 190

Phe Val Val Ile Val Phe Ala Tyr Leu Thr Glu Phe Val Asn Leu Gly
            195                 200                 205

Asn Val Ser Ala Leu Arg Thr Phe Arg Val Leu Arg Ala Leu Lys Thr
        210                 215                 220

Ile Ser Val Ile Pro Gly Leu Lys Thr Ile Val Gly Ala Leu Ile Gln
225                 230                 235                 240

Ser Val Lys Lys Leu Ser Asp Val Met Ile Leu Thr Val Phe Cys Leu
                245                 250                 255

Ser Val Phe Ala Leu Ile Gly Leu Gln Leu Phe Met Gly Asn Leu Lys
                260                 265                 270

His Lys Cys Phe Arg Asn Ser Leu Glu Asn Asn Glu Thr Leu Glu Ser
            275                 280                 285

Ile Met Asn Thr Leu Glu Ser Glu Glu Asp Phe Arg Lys Tyr Phe Tyr
        290                 295                 300

Tyr Leu Glu Gly Ser Lys Asp Ala Leu Leu Cys Gly Phe Ser Thr Asp
305                 310                 315                 320

Ser Gly Gln Cys Pro Glu Gly Tyr Thr Cys Val Lys Ile Gly Arg Asn
```

```
                    325                 330                 335
Pro Asp Tyr Gly Tyr Thr Ser Phe Asp Thr Phe Ser Trp Ala Phe Leu
                340                 345                 350
Ala Leu Phe Arg Leu Met Thr Gln Asp Tyr Trp Glu Asn Leu Tyr Gln
                355                 360                 365
Gln Thr Leu Arg Ala Ala Gly Lys Thr Tyr Met Ile Phe Phe Val Val
            370                 375                 380
Val Ile Phe Leu Gly Ser Phe Tyr Leu Ile Asn Leu Ile Leu Ala Val
385                 390                 395                 400
Val Ala Met Ala Tyr Glu Glu Gln Asn Gln Ala Asn Ile Glu Glu Ala
                405                 410                 415
Lys Gln Lys Glu Leu Glu Phe Gln Gln Met Leu Asp Arg Leu Lys Lys
                420                 425                 430
Glu Gln Glu Glu Ala Glu Ala Ile Ala Ala Ala Ala Glu Tyr Thr
            435                 440                 445
Ser Ile Arg Arg Ser Arg Ile Met Gly Leu Ser Glu Ser Ser Ser Glu
            450                 455                 460
Thr Ser Lys Leu Ser Ser Lys Ser Ala Lys Glu Arg Arg Asn Arg Arg
465                 470                 475                 480
Lys Lys Lys Asn Gln Lys Lys Leu Ser Ser Gly Glu Glu Lys Gly Asp
                485                 490                 495
Ala Glu Lys Leu Ser Lys Ser Glu Ser Glu Asp Ser Ile Arg Arg Lys
                500                 505                 510
Ser Phe His Leu Gly Val Glu Gly His Arg Arg Ala His Glu Lys Arg
                515                 520                 525
Leu Ser Thr Pro Asn Gln Ser Pro Leu Ser Ile Arg Gly Ser Leu Phe
            530                 535                 540
Ser Ala Arg Arg Ser Ser Arg Thr Ser Leu Phe Ser Phe Lys Gly Arg
545                 550                 555                 560
Gly Arg Asp Xaa Gly Ser Glu Thr Glu Phe Ala Asp Asp Glu His Ser
                565                 570                 575
Ile Phe Gly Asp Asn Glu Ser Arg Arg Gly Ser Leu Phe Val Pro His
                580                 585                 590
Arg Pro Xaa Glu Arg Arg Ser Ser Asn Ile Ser Gln Ala Ser Arg Ser
            595                 600                 605
Pro Pro Met Leu Pro Val Asn Gly Lys Met His Ser Ala Val Asp Cys
            610                 615                 620
Asn Gly Val Val Ser Leu Val Asp Gly Xaa Ser Ala Leu Met Leu Pro
625                 630                 635                 640
Asn Gly Gln Leu Leu Pro Glu Gly Thr Thr Asn Gln Ile His Lys Lys
                645                 650                 655
Arg Arg Cys Ser Ser Tyr Leu Leu Ser Glu Asp Met Leu Asn Asp Pro
            660                 665                 670
Asn Leu Arg Gln Arg Ala Met Ser Arg Ala Ser Ile Leu Thr Asn Thr
            675                 680                 685
Val Glu Glu Leu Glu Glu Ser Arg Gln Lys Cys Pro Pro Trp Trp Tyr
            690                 695                 700
Arg Phe Ala His Lys Phe Leu Ile Trp Asn Cys Ser Pro Tyr Trp Ile
705                 710                 715                 720
Lys Phe Lys Lys Cys Ile Tyr Phe Ile Val Met Asp Pro Phe Val Asp
                725                 730                 735
Leu Ala Ile Thr Ile Cys Ile Val Leu Asn Thr Leu Phe Met Ala Met
            740                 745                 750
```

-continued

```
Glu His His Pro Met Thr Glu Phe Lys Asn Val Leu Ala Ile Gly
    755                 760                 765

Asn Leu Val Phe Thr Gly Ile Phe Ala Ala Glu Met Val Leu Lys Leu
    770                 775                 780

Ile Ala Met Asp Pro Tyr Glu Tyr Phe Gln Val Gly Trp Asn Ile Phe
785                 790                 795                 800

Asp Ser Leu Ile Val Thr Leu Ser Leu Val Glu Leu Phe Leu Ala Asp
                805                 810                 815

Val Glu Gly Leu Ser Val Leu Arg Ser Phe Arg Leu Leu Arg Val Phe
                820                 825                 830

Lys Leu Ala Lys Ser Trp Pro Thr Leu Asn Met Leu Ile Lys Ile Ile
                835                 840                 845

Gly Asn Ser Val Gly Ala Leu Gly Asn Leu Thr Leu Val Leu Ala Ile
    850                 855                 860

Ile Val Phe Ile Phe Ala Val Val Gly Met Gln Leu Phe Gly Lys Ser
865                 870                 875                 880

Tyr Lys Glu Cys Val Cys Lys Ile Asn Asp Asp Cys Thr Leu Pro Arg
                885                 890                 895

Trp His Met Asn Asp Phe Phe His Ser Phe Leu Ile Val Phe Arg Val
                900                 905                 910

Leu Cys Gly Glu Trp Ile Glu Thr Met Trp Asp Cys Met Glu Val Ala
                915                 920                 925

Gly Gln Ala Met Cys Leu Ile Val Tyr Met Met Val Met Val Ile Gly
    930                 935                 940

Asn Leu Val Val Leu Asn Leu Phe Leu Ala Leu Leu Leu Ser Ser Phe
945                 950                 955                 960

Ser Ser Asp Asn Leu Thr Ala Ile Glu Glu Asp Pro Asp Ala Asn Asn
                965                 970                 975

Leu Gln Ile Ala Val Thr Arg Ile Lys Lys Gly Ile Asn Tyr Val Lys
                980                 985                 990

Gln Thr Leu Arg Glu Phe Ile Leu Lys Ala Phe Ser Lys Lys Pro Lys
                995                 1000                1005

Ile Ser Arg Glu Ile Arg Gln Ala Glu Asp Leu Asn Thr Lys Lys Glu
    1010                1015                1020

Asn Tyr Ile Ser Asn Met Thr Leu Ala Glu Met Ser Lys Gly His Asn
1025                1030                1035                1040

Phe Leu Lys Glu Lys Asp Lys Ile Ser Gly Phe Gly Ser Ser Xaa Asp
                1045                1050                1055

Lys His Leu Met Glu Asp Ser Asp Gly Gln Ser Phe Ile His Asn Pro
                1060                1065                1070

Ser Leu Thr Val Thr Val Pro Ile Ala Pro Gly Glu Ser Asp Leu Glu
                1075                1080                1085

Met Asn Glu Glu Leu Ser Ser Asp Ser Asp Ser Tyr Ser Lys Asn Arg
    1090                1095                1100

Ser Ser Ser Ser Glu Cys Ser Thr Val Asp Asn Pro Leu Pro Gly Glu
1105                1110                1115                1120

Gly Glu Glu Ala Glu Ala Glu Pro Asn Asp Glu Pro Glu Ala Cys Phe
                1125                1130                1135

Thr Asp Gly Cys Val Arg Arg Phe Ser Cys Cys Gln Val Asn Ile Glu
                1140                1145                1150

Ser Gly Lys Gly Lys Ile Trp Trp Asn Ile Arg Lys Thr Cys Tyr Lys
                1155                1160                1165
```

-continued

```
Ile Val Glu His Ser Trp Phe Glu Ser Phe Ile Val Leu Met Ile Leu
    1170                1175                1180

Leu Ser Ser Gly Ala Leu Ala Phe Glu Asp Ile Tyr Ile Glu Arg Lys
1185                1190                1195                1200

Lys Thr Ile Lys Ile Ile Leu Glu Tyr Ala Asp Lys Ile Phe Thr Tyr
                1205                1210                1215

Ile Phe Ile Leu Glu Met Leu Leu Lys Trp Ile Ala Tyr Gly Tyr Lys
            1220                1225                1230

Thr Tyr Phe Thr Asn Ala Trp Cys Trp Leu Asp Phe Leu Ile Val Asp
        1235                1240                1245

Val Ser Leu Val Thr Leu Val Ala Asn Thr Leu Gly Tyr Ser Asp Leu
    1250                1255                1260

Gly Pro Ile Lys Ser Leu Arg Thr Leu Arg Ala Leu Arg Pro Leu Arg
1265                1270                1275                1280

Ala Leu Ser Arg Phe Glu Gly Met Arg Val Val Val Asn Ala Leu Ile
                1285                1290                1295

Gly Ala Ile Pro Ser Ile Met Asn Val Leu Leu Val Cys Leu Ile Phe
            1300                1305                1310

Trp Leu Ile Phe Ser Ile Met Gly Val Asn Leu Phe Ala Gly Lys Phe
        1315                1320                1325

Tyr Glu Cys Ile Asn Thr Thr Asp Gly Ser Arg Phe Pro Ala Ser Gln
    1330                1335                1340

Val Pro Asn Arg Ser Glu Cys Phe Ala Leu Met Asn Val Ser Gln Asn
1345                1350                1355                1360

Val Arg Trp Lys Asn Leu Lys Val Asn Phe Asp Asn Val Gly Leu Gly
                1365                1370                1375

Tyr Leu Ser Leu Leu Gln Val Ala Thr Phe Lys Gly Trp Thr Ile Ile
            1380                1385                1390

Met Tyr Ala Ala Val Asp Ser Val Asn Val Asp Lys Gln Pro Lys Tyr
        1395                1400                1405

Glu Tyr Ser Leu Tyr Met Tyr Ile Tyr Phe Val Val Phe Ile Ile Phe
    1410                1415                1420

Gly Ser Phe Phe Thr Leu Asn Leu Phe Ile Gly Val Ile Ile Asp Asn
1425                1430                1435                1440

Phe Asn Gln Gln Lys Lys Lys Leu Gly Gly Gln Asp Ile Phe Met Thr
                1445                1450                1455

Glu Glu Gln Lys Lys Tyr Tyr Asn Ala Met Lys Lys Leu Gly Ser Lys
            1460                1465                1470

Lys Pro Gln Lys Pro Ile Pro Arg Pro Gly Asn Lys Ile Gln Gly Cys
        1475                1480                1485

Ile Phe Asp Leu Val Thr Asn Gln Ala Phe Asp Ile Ser Ile Met Val
    1490                1495                1500

Leu Ile Cys Leu Asn Met Val Thr Met Met Val Glu Lys Glu Gly Gln
1505                1510                1515                1520

Ser Gln His Met Thr Glu Val Leu Tyr Trp Ile Asn Val Val Phe Ile
                1525                1530                1535

Ile Leu Phe Thr Gly Glu Cys Val Leu Lys Leu Ile Ser Leu Arg His
            1540                1545                1550

Tyr Tyr Phe Thr Val Gly Trp Asn Ile Phe Asp Phe Val Val Val Ile
        1555                1560                1565

Ile Ser Ile Val Gly Met Phe Leu Ala Asp Leu Ile Glu Thr Tyr Phe
    1570                1575                1580

Val Ser Pro Thr Leu Phe Arg Val Ile Arg Leu Ala Arg Ile Gly Arg
```

```
                1585                1590                1595                1600
Ile Leu Arg Leu Val Lys Gly Ala Lys Gly Ile Arg Thr Leu Leu Phe
                    1605                1610                1615

Ala Leu Met Met Ser Leu Pro Ala Leu Phe Asn Ile Gly Leu Leu Leu
            1620                1625                1630

Phe Leu Val Met Phe Ile Tyr Ala Ile Phe Gly Met Ser Asn Phe Ala
        1635                1640                1645

Tyr Val Lys Lys Glu Asp Gly Ile Asn Asp Met Phe Asn Phe Glu Thr
    1650                1655                1660

Phe Gly Asn Ser Met Ile Cys Leu Phe Gln Ile Thr Thr Ser Ala Gly
1665                1670                1675                1680

Trp Asp Gly Leu Leu Ala Pro Ile Leu Asn Ser Lys Pro Pro Asp Cys
                    1685                1690                1695

Asp Pro Lys Lys Val His Pro Gly Ser Ser Val Glu Gly Asp Cys Gly
            1700                1705                1710

Asn Pro Ser Val Gly Ile Phe Tyr Phe Val Ser Tyr Ile Ile Ile Ser
        1715                1720                1725

Phe Leu Val Val Val Asn Met Tyr Ile Ala Val Ile Leu Glu Asn Phe
    1730                1735                1740

Ser Val Ala Thr Glu Glu Ser Thr Glu Pro Leu Ser Glu Asp Asp Phe
1745                1750                1755                1760

Glu Met Phe Tyr Glu Val Trp Glu Lys Phe Asp Pro Asp Ala Thr Gln
                    1765                1770                1775

Phe Ile Glu Phe Ser Lys Leu Ser Asp Phe Ala Ala Ala Leu Asp Pro
            1780                1785                1790

Pro Leu Leu Ile Ala Lys Pro Asn Lys Val Gln Leu Ile Ala Met Asp
        1795                1800                1805

Leu Pro Met Val Ser Gly Asp Arg Ile His Cys Leu Asp Ile Leu Phe
    1810                1815                1820

Ala Phe Thr Lys Arg Val Leu Gly Glu Ser Gly Glu Met Asp Ser Leu
1825                1830                1835                1840

Arg Ser Gln Met Glu Glu Arg Phe Met Ser Ala Asn Pro Ser Lys Val
                    1845                1850                1855

Ser Tyr Glu Pro Ile Thr Thr Thr Leu Lys Arg Lys Gln Glu Xaa Val
            1860                1865                1870

Ser Ala Thr Val Ile Gln Arg Ala Tyr Arg Arg Tyr Arg Leu Arg Gln
        1875                1880                1885

Asn Val Lys Asn Ile Ser Ser Ile Tyr Ile Lys Asp Gly Asp Arg Asp
    1890                1895                1900

Asp Asp Leu Leu Asn Lys Glu Asp Met Ala Phe Asp Asn Val Asn Glu
1905                1910                1915                1920

Asn Ser Ser Pro Glu Lys Thr Asp Ala Thr Ser Ser Thr Thr Ser Pro
                    1925                1930                1935

Pro Ser Tyr Asp Ser Val Thr Lys Pro Asp Lys Glu Lys Tyr Glu Xaa
            1940                1945                1950

Asp Gln Thr Glu Lys Glu Asp Lys Gly Lys Asp Ser Lys Glu Ser Lys
        1955                1960                1965

Lys (2) INFORMATION FOR SEQ ID NO:17:

(i) SEQUENCE CHARACTERISTICS:
        (A) LENGTH: 21 base pairs
        (B) TYPE: nucleic acid
```

-continued

```
        (C) STRANDEDNESS: single
        (D) TOPOLOGY: linear (ii) MOLECULE TYPE: cDNA (xi) SEQUENCE DESCRIPTION: SEQ ID NO:17:

TTTGTGCCCC ACAGACCCCA G                                              21

(2) INFORMATION FOR SEQ ID NO:18:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

ACACAAATTC TTGATCTGGA ATTGCT                                         26

(2) INFORMATION FOR SEQ ID NO:19:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

CAACCTCAGA CAGAGAGCAA TGA                                            23
```